US011039053B2

(12) United States Patent
Wexler et al.

(10) Patent No.: US 11,039,053 B2
(45) Date of Patent: Jun. 15, 2021

(54) REMOTELY IDENTIFYING A LOCATION OF A WEARABLE APPARATUS

(71) Applicant: ORCAM TECHNOLOGIES LTD., Jerusalem (IL)

(72) Inventors: Yonatan Wexler, Jerusalem (IL); Amnon Shashua, Mevaseret Zion (IL)

(73) Assignee: OrCam Technologies Ltd., Jerusalem (IL)

( * ) Notice: Subject to any disclaimer, the term of this patent is extended or adjusted under 35 U.S.C. 154(b) by 0 days.

(21) Appl. No.: 16/659,190

(22) Filed: Oct. 21, 2019

(65) Prior Publication Data

US 2020/0051271 A1 Feb. 13, 2020

Related U.S. Application Data

(63) Continuation of application No. PCT/IB2018/000474, filed on Apr. 23, 2018.
(Continued)

(51) Int. Cl.
*H04N 5/225* (2006.01)
*G06T 7/70* (2017.01)
(Continued)

(52) U.S. Cl.
CPC .......... *H04N 5/2257* (2013.01); *G06F 1/163* (2013.01); *G06F 3/16* (2013.01); *G06F 16/951* (2019.01); *G06F 16/9532* (2019.01); *G06K 9/00288* (2013.01); *G06K 9/00355* (2013.01); *G06K 9/00671* (2013.01); *G06K 9/00677* (2013.01); *G06K 9/209* (2013.01); *G06T 7/0002* (2013.01); *G06T 7/70* (2017.01); *G10L 15/08* (2013.01);
(Continued)

(58) Field of Classification Search
CPC .. H04N 5/2257; H04N 5/232941; G06T 7/70; G06F 16/9532; G06F 16/951; G06F 1/163
USPC ........................................................ 348/158
See application file for complete search history.

(56) References Cited

U.S. PATENT DOCUMENTS 8,542,118 B2 9/2013 Al-Kadi et al.
2005/0256720 A1 11/2005 Iorio
(Continued)

FOREIGN PATENT DOCUMENTS

WO WO 2016/012865 1/2016

OTHER PUBLICATIONS

PCT International Search Report and Written Opinion of PCT Application PCT/162018/00474 filed Apr. 23, 2018 (9 pages).

*Primary Examiner* — Chikaodili E Anyikire
(74) *Attorney, Agent, or Firm* — Finnegan, Henderson, Farabow, Garrett & Dunner, LLP

(57) ABSTRACT

A wearable apparatus and methods may analyze images. In one implementation, a wearable apparatus for capturing and processing images may comprise a wearable image sensor configured to capture a plurality of images from an environment of a user of the wearable apparatus and at least one processing device. The at least one processing device may be programmed to: analyze the plurality of images to identify a plurality of people; analyze the plurality of images to determine an affinity level between the user and each of the plurality of people; obtain an image representation of each of the plurality of people; and generate, based on the affinity levels, a visualization comprising the image representations.

20 Claims, 84 Drawing Sheets

Related U.S. Application Data

(60) Provisional application No. 62/503,034, filed on May 8, 2017, provisional application No. 62/488,791, filed on Apr. 23, 2017, provisional application No. 62/488,789, filed on Apr. 23, 2017.

(51) Int. Cl.

| | |
|---|---|
| *H04N 5/232* | (2006.01) |
| *G06T 7/00* | (2017.01) |
| *G06F 1/16* | (2006.01) |
| *G06K 9/00* | (2006.01) |
| *G10L 15/08* | (2006.01) |
| *G10L 15/22* | (2006.01) |
| *G10L 15/30* | (2013.01) |
| *G06K 9/20* | (2006.01) |
| *G10L 15/18* | (2013.01) |
| *G06F 3/16* | (2006.01) |
| *G06F 16/9532* | (2019.01) |
| *G06F 16/951* | (2019.01) |

(52) U.S. Cl.
CPC .......... G10L 15/1822 (2013.01); G10L 15/22 (2013.01); G10L 15/30 (2013.01); H04N 5/2253 (2013.01); H04N 5/23203 (2013.01); H04N 5/232941 (2018.08); *G06T 2207/30196* (2013.01); *G06T 2207/30244* (2013.01); *G10L 2015/088* (2013.01); *G10L 2015/223* (2013.01)

(56) References Cited

U.S. PATENT DOCUMENTS

2010/0273452 A1\* 10/2010 Rajann ................ H04W 4/029
                                                                                      455/411
2014/0369595 A1\* 12/2014 Pavlidis ............. G06K 9/00637
                                                                                      382/154

\* cited by examiner

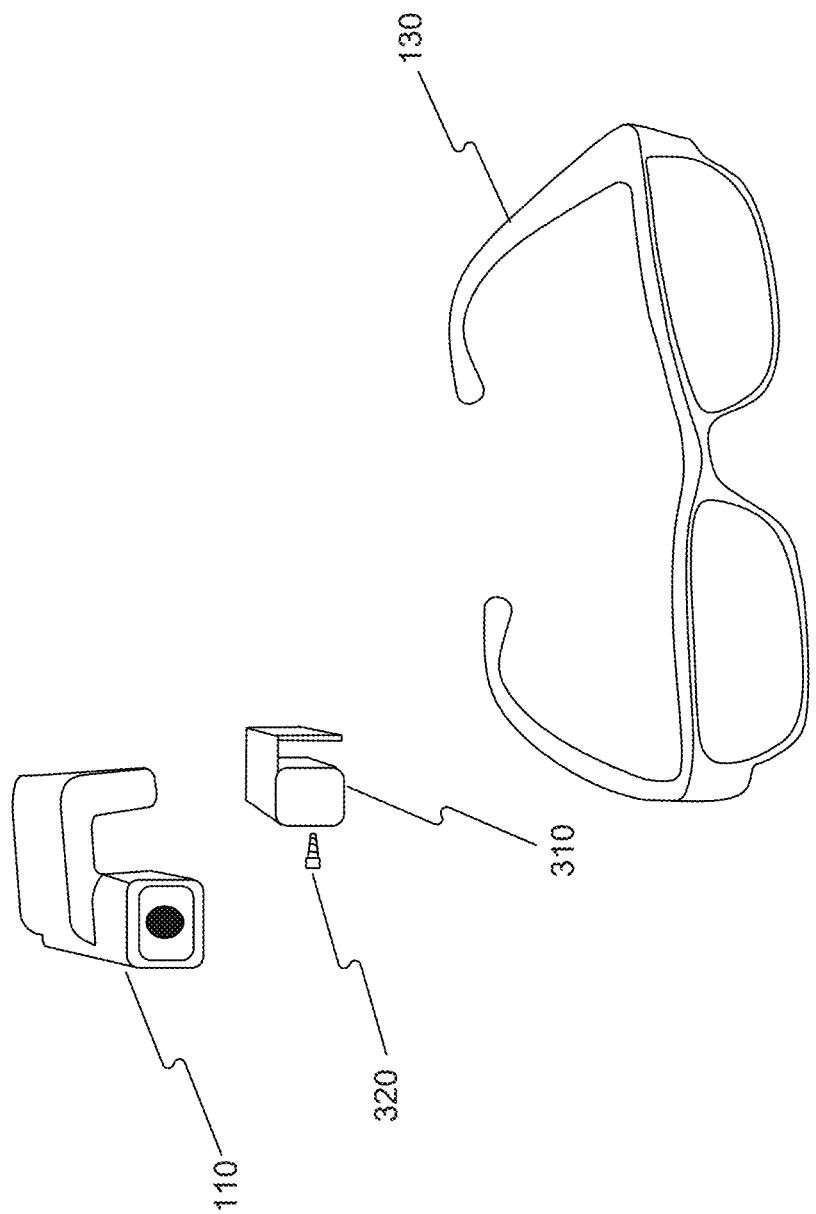

| Key Words | Interaction Frequency |
|---|---|
| "coffee" 2701a | 1 2703a |
| "client" "paperwork" 2701b | 2 2703b |
| "love" "wife" "movie" "television" "dinner" 2701c | 4 2703c |

REMOTELY IDENTIFYING A LOCATION OF A WEARABLE APPARATUS

CROSS REFERENCES TO RELATED APPLICATIONS

This application is a continuation of PCT Application No. PCT/IB2018/000474, filed Apr. 23, 2018, which claims the benefit of priority of U.S. Provisional Patent Application No. 62/488,789, filed Apr. 23, 2017; U.S. Provisional Patent Application No. 62/488,791, filed Apr. 23, 2017; and U.S. Provisional Patent Application No. 62/503,034, filed May 8, 2017. All of the foregoing applications are incorporated herein by reference in their entirety.

BACKGROUND

Technical Field

This disclosure generally relates to devices and methods for capturing and processing images from an environment of a user, and using information derived from captured images.

Background Information

Today, technological advancements make it possible for wearable devices to automatically capture images and store information that is associated with the captured images. Certain devices have been used to digitally record aspects and personal experiences of one's life in an exercise typically called "lifelogging." Some individuals log their life so they can retrieve moments from past activities, for example, social events, trips, etc. Lifelogging may also have significant benefits in other fields (e.g., business, fitness and healthcare, and social research). Lifelogging devices, while useful for tracking daily activities, may be improved with capability to enhance one's interaction in his environment with feedback and other advanced functionality based on the analysis of captured image data.

Even though users can capture images with their smartphones and some smartphone applications can process the captured images, smartphones may not be the best platform for serving as lifelogging apparatuses in view of their size and design. Lifelogging apparatuses should be small and light, so they can be easily worn and would not require intensive attention and operation from the user. Moreover, with improvements in image capture devices, including wearable apparatuses, additional functionality may be provided to assist users in navigating in and around an environment, identifying persons and objects they encounter, and providing feedback to the users about their surroundings and activities. Therefore, there is a need for apparatuses and methods for automatically capturing and processing images to provide useful information to users of the apparatuses, and for systems and methods to process and leverage information gathered by the apparatuses.

SUMMARY

Embodiments consistent with the present disclosure provide devices and methods for automatically capturing and processing images from an environment of a user, and systems and methods for processing information related to images captured from the environment of the user.

In one embodiment, a wearable apparatus for capturing and processing images may comprise a wearable image sensor configured to capture a plurality of images from an environment of a user of the wearable apparatus; and at least one processing device. The at least one processing device may be programmed to: analyze the plurality of images to identify a plurality of people; analyze the plurality of images to determine an affinity level between the user and each of the plurality of people; obtain an image representation of each of the plurality of people; and generate, based on the affinity levels, a visualization comprising the image representations.

In one embodiment, a wearable apparatus may comprise a wearable image sensor configured to capture a plurality of images from an environment of a user of the wearable apparatus; and at least one processing device. The at least one processing device may be programmed to: receive from the wearable image sensor a plurality of facial images of individuals with whom the user interacted; store, in association with each of the plurality of facial images, at least one linking attribute, the at least one linking attribute including at least one of an environmental characteristic, a geographical location, an associated word, a social interconnection, or a temporal indicator; and cause a visual representation to be displayed. The visual representation may include the plurality of facial images, and the plurality of facial images may be arranged based on the at least one linking attribute.

In one embodiment, a non-transitory computer-readable medium for use in a system employing a wearable image sensor pairable with a mobile communications device, the computer readable medium containing instructions. The instructions, when executed by at least one processor, may cause the at least one processor to perform steps, comprising: receiving, from the wearable image sensor worn by a user, a plurality of facial images of individuals with whom the user interacted; storing, in a manner associated with each of the plurality of facial images, at least one linking attribute, the at least one linking attribute including at least one of an environmental characteristic, a geographical location, an associated word, a social interconnection, or a temporal indicator; and displaying, in a face cloud, the plurality of facial images. The plurality of facial images may be arranged based on the at least one linking attribute.

In one embodiment, a non-transitory computer-readable medium contains instructions. The instructions, when executed by at least one processor may cause the at least one processor to perform steps, comprising: receiving from a wearable image sensor worn by a user a plurality of facial images of individuals with whom the user has interacted; receiving a list of words parsed from a sound file captured during a time period associated with detection of a presence of the plurality of individuals in a vicinity of the wearer; associating in memory, the list of parsed words with a corresponding individual; and presenting on a screen of a display a subset of the plurality of facial images of individuals whose word lists contain overlapping common words.

In one embodiment, a non-transitory computer-readable medium may contain instructions that, when executed by at least one processor cause the at least one processor to perform steps. The steps may comprise receiving facial images of a plurality of individuals with whom a user interacted; receiving at least one linking attribute for each of the plurality of facial images; associating in memory each of the plurality of facial images with the at least one linking attribute received for a corresponding one of the plurality of facial images; and for a selected linking attribute, presenting on a screen of a display a set of the plurality of facial images that share the selected linking attribute.

In one embodiment, a non-transitory computer-readable medium may contain instructions that, when executed by at least one processor cause the at least one processor to perform steps. The steps may comprise receiving from a wearable image sensor worn by a user at least one image captured in a time window; receiving a file of sound captured in a vicinity of the image sensor during the time window; processing the sound file to identify at least one word in the sound file; storing in memory an association between the word and the object image; receiving at a time remote from the time window a search input of the at least one key word; accessing the memory to locate the association between the at least one key word and the at least one object image; and causing a display of the object image on a mobile communications device of the user, separate from the wearable image sensor.

In one embodiment, a non-transitory computer-readable medium may contain instructions that, when executed by at least one processor cause the at least one processor to perform steps. The steps may comprise receiving from a wearable image sensor worn by a user a first plurality of facial images of individuals with whom the user interacted on a first calendar date; storing an indicator of the first calendar date in association with each of the first plurality of individuals; receiving from the wearable image sensor worn by the user a second plurality of facial images of individuals with whom the user interacted on a second calendar date; storing an indicator of the second calendar date in association with each of the second plurality of individuals; receiving a first input request by the user for recall of interactions on the first calendar date; in response to the first input, displaying to the user images of at least some of the first plurality of individuals; receiving a second input request by the user for recall of interactions on the second calendar date; and in response to the second input, displaying to the user images of at least some of the second plurality of individuals.

In one embodiment, a wearable apparatus for capturing and processing images may comprise a wearable image sensor configured to capture a plurality of images from an environment of a user of the wearable apparatus and at least one processing device. The at least one processing device may be programmed to analyze the plurality of images to detect at least one person; select at least one record associated with the detected person; analyze the plurality of images to identify contextual information associated with the detected person; and update the at least one record based on the contextual information.

In one embodiment, a wearable apparatus for capturing and processing images may comprise a wearable image sensor configured to capture a plurality of images from an environment of a user of the wearable apparatus and at least one processing device. The at least one processing device may be programmed to analyze the plurality of images to detect at least one person; determine contextual category based on the detected person; analyze the plurality of images to identify a visual context indicator; and associate the visual context indicator with the determined contextual category.

In one embodiment, a wearable apparatus may comprise a wearable image sensor configured to capture a plurality of images from an environment of a user and at least one processor. The at least one processor may be programmed to determine from at least one of the plurality of images a presence of two differing objects indicated by the user; perform a look up of the two differing objects to ascertain identities of the two differing objects; perform a look up of descriptive information about the two differing objects; compare the descriptive information about the two differing objects; and cause a display of the information about the comparing of the two differing objects in a manner permitting the user to ascertain differences between the two differing objects.

In one embodiment, a method, may comprise receiving, by a processor, a plurality of images captured by a wearable image sensor from an environment of a user; and determining from at least one of the plurality of images a presence of two differing objects indicated by the user; performing a look up of the two differing objects to ascertain identities of the two differing objects; performing a look up of descriptive information about the two differing objects; comparing the descriptive information about the two differing objects; and causing a display of the information about the comparing of the two differing objects in a manner permitting the user to ascertain differences between the two differing objects.

In one embodiment, a wearable apparatus may comprise a wearable image sensor and at least one processor. The at least one processor may be programmed to: receive, from the wearable image sensor, a facial image of an individual with whom a user of the wearable apparatus interacted in a first interaction during a time window; receive sound data captured in a vicinity of the image sensor during at least a part of the time window; process the sound data to identify at least one key word; store in memory an association between the key word and the facial image; receive, from the wearable image sensor, another facial image of the individual during a second interaction at a time other than during the time window; use image processing to determine that the individual in the first interaction is the individual in the second interaction; access the memory to locate the at least one key word from the first interaction; and during the second interaction, cause a display of at least one key word on a display visible to the user, to thereby remind the user of subject matter of the first interaction.

In one embodiment, a non-transitory computer-readable medium may be for use in a system employing a wearable image sensor pairable with a mobile communications device. The computer-readable medium may contain instructions that when executed by at least one processor cause the at least one processor to perform steps. The steps may comprise receiving from the wearable image sensor worn by a user a facial image of an individual with whom the user interacted in a first interaction during a time window; receiving sound data captured in a vicinity of the image sensor during the time window; processing the sound data to identify at least one key word in the sound data; storing in memory an association between the key word and the facial image; receiving from the wearable image sensor worn by a user another facial image of the individual during a second interaction at a time other than during the time window; using image processing to determine that the individual in the first interaction is the individual in the second interaction; accessing the memory to locate the at least one key word from the first interaction; and during the second interaction, presenting on a display visible to the user, the at least one key word, to thereby remind the user of subject matter of the first interaction.

In one embodiment, a method for retrieving and displaying key words from prior conversations may be implemented by at least one processor of a mobile communications device pairable with a wearable image sensor. The method may comprise receiving from the wearable image sensor worn by a user a facial image of an individual with whom the user interacted in a first interaction during a time window; receiving sound data captured in a vicinity of the image sensor during the time window; processing the sound data to identify at least one key word in the sound data; storing in memory an association between the key word and the facial image; receiving from the wearable image sensor worn by a user another facial image of the individual during a second interaction at a time other than during the time window; using image processing to determine that the individual in the first interaction is the individual in the second interaction; accessing the memory to locate the at least one key word from the first interaction; and during the second interaction, presenting on a display visible to the user, the at least one key word, to thereby remind the user of subject matter of the first interaction.

In one embodiment, a wearable apparatus may comprise a wearable image sensor configured to capture a plurality of images from an environment of a user of the wearable apparatus and at least one processor. The at least one processor may be programmed to receive at least one image from the wearable image sensor; perform image processing of the at least one image to identify in the at least one image an environmental condition of the user of the wearable apparatus; determine that the environmental condition is predetermined as a trigger for an action associated with a mobile communications device wirelessly paired with the wearable apparatus; and cause the mobile communications device to trigger the action in accordance with the environment condition and to thereby cause the action to occur via the mobile communications device.

In one embodiment, a non-transitory computer readable medium may contain instructions that may be executed by at least one processor. The instructions may cause the at least one processor to perform steps including: receiving at least one image from a wearable image sensor worn by a user; performing image processing of the at least one image to identify in the at least one image an environmental condition of the user of the wearable apparatus; determining that the environmental condition is predetermined as a trigger for an action associated with a mobile communications device wirelessly paired with the wearable apparatus; and causing the mobile communications device to trigger the action in accordance with the environment condition and to thereby cause the action to occur via the mobile communications device.

In one embodiment, a wearable apparatus may comprise a wearable audio input device configured to capture audio data from an environment of a user of the wearable apparatus and at least one processor. The at least one processor may be programmed to receive audio data from the wearable audio input device; perform audio processing of the audio data to identify in the audio data an environmental condition of the user of the wearable apparatus; determine that the environmental condition is predetermined as a trigger for an action associated with a mobile communications device wirelessly paired with the wearable apparatus; and cause the mobile communications device to trigger the action in accordance with the environment condition and to thereby cause the action to occur via the mobile communications device.

In an embodiment, a wearable apparatus may include a wearable audio input device configured to capture audio data from an environment of a user of the wearable apparatus, a wearable image sensor configured to capture a plurality of images from the environment of the user of the wearable apparatus, and at least one processor. The at least one processor may be programmed to receive the audio data from the wearable audio input device; receive at least one image from the wearable image sensor; perform audio processing of the audio data and image processing of the at least one image to identify an environmental condition of the user of the wearable apparatus; determine that the environmental condition is predetermined as a trigger for an action associated with a mobile communications device wirelessly paired with the wearable apparatus and having an operational state; and cause the mobile communications device to trigger the action in accordance with the environment condition and to thereby cause the action to occur via the mobile communications device.

In one embodiment, a wearable apparatus may comprise a wearable image sensor configured to capture a plurality of images; and at least one processor. The at least one processor may be programmed to receive, from a mobile communications device wirelessly paired with the wearable apparatus, a command to provide location information for the wearable apparatus; analyze, in response to the command, at least one image depicting an environment of the wearable apparatus to determine a location of the wearable apparatus; and cause information about the location of the wearable apparatus to be transmitted to the mobile communications device.

In one embodiment, a non-transitory computer readable medium may contain instructions that when executed by at least one processor cause the at least one processor to perform steps. The steps may include establishing a wireless pairing between a wearable image sensor and a mobile communications device; receiving, in a situation when the wearable image sensor is misplaced, a user input for pinging the wearable image sensor; in response to the user input, wirelessly transmitting from the mobile communications device, a ping to the wearable image sensor, wherein the ping includes an instruction for the wearable image sensor to capture at least one image of surroundings of the image sensor; analyze the at least one image to determine a location of the wearable apparatus; and cause, based on the location of the wearable apparatus, the location information to be transmitted to the mobile communications device.

In one embodiment, a method for locating a wearable apparatus may include receiving, from a mobile communications device wirelessly paired with the wearable apparatus, a command to provide location information for the wearable apparatus; analyzing, in response to the command, at least one image depicting an environment of the wearable apparatus to determine a location of the wearable apparatus; and causing information about the location of the wearable apparatus to be transmitted to the mobile communications device.

In one embodiment, a wearable apparatus may include wearable image sensor configured to capture a plurality of images and at least one processor. The at least one processor may be programmed to: analyze at least one image captured by the wearable image sensor; determine a positioning issue related to the wearable image sensor based on the analysis of the at least one image; determine, in response to the positioning issue, correction information for resolving the positioning issue; and cause the correction information to be provided to a user of the wearable apparatus.

In one embodiment, a non-transitory computer readable medium for use in a system employing a wearable image sensor pairable with a mobile communications device may contain instructions that when executed by at least one processor cause the at least one processor to perform steps. The steps may include receiving a plurality of images from the wearable image sensor; performing image processing on at least some of the images; determining based on the image processing, an impediment to quality image capture; determining, in response to the determined impediment, correction information for resolving the positioning issue; and presenting the correction information on a display of the pairable mobile communications device.

In one embodiment, a method for correcting the positioning of a wearable image sensor may include analyzing at least one image captured by the wearable image sensor; determining a positioning issue related to the wearable image sensor based on the analysis of the at least one image; determining, in response to the positioning issue, correction information for resolving the positioning issue; and causing the correction information to be provided to a user of the wearable apparatus.

In one embodiment, a wearable apparatus may include a wearable image sensor configured to capture a plurality of images and at least one processor. The at least one processor may be programmed to analyze at least one image captured by the wearable image sensor; determine a positioning issue related to the wearable image sensor based on the analysis of the at least one image; determine, in response to the positioning issue, correction information for resolving the positioning issue, wherein the correction information comprises executable instructions configured to cause the at least one processor to automatically resolve the positioning issue; and execute the correction information to automatically resolve the positioning issue.

In one embodiment, a wearable apparatus may include a wearable image sensor and at least one processor programmed to receive, from the wearable image sensor, a facial image of an individual with whom a user of the wearable apparatus is interacting; receive sound data captured during the interacting; process at least a portion of the sound data to determine a spoken name of the individual; convert the spoken name to text; store, in memory, text associated with the spoken name in a manner associating the text with the facial image; after a subsequent encounter with the individual, receive, from the wearable image sensor, a subsequent facial image of the individual; perform a look-up of an identity of the individual based on the subsequent facial image; receive, from the memory the text of the spoken name of the individual; and cause a display in text of the name of the individual on a mobile communications device paired with the wearable apparatus.

In one embodiment, a non-transitory computer-readable medium for use in a system employing a wearable image sensor pairable with a mobile communications device may contain instructions that when executed by at least one processor cause the at least one processor to perform steps. The steps may include receiving from a wearable image sensor worn by a user, a facial image of an individual with whom the user is interacting; receiving a sound file captured during the interacting; processing at least a portion of the sound file to determine a spoken name of the individual; converting the spoken name to text; storing in memory, text associated with the spoken name in a manner associating the text with the facial image; upon a subsequent encounter with the individual, receiving from the wearable image sensor a subsequent facial image of the individual; performing a look-up of an identity of the individual based on the subsequent facial image; recalling from memory the text of the spoken name of the individual; and displaying in text on the mobile communications device of the user, the name of the individual.

In one embodiment, a wearable apparatus may include a wearable image sensor configured to capture a plurality of images from an environment of a user of the wearable apparatus, a memory unit configured to store a plurality of tasks, the plurality of tasks comprises at least a first task and a second task, and at least one processing device programmed to analyze the plurality of images to obtain information related to at least some of the plurality of tasks; based on the obtained information, assign a higher priority to the first task over the second task; and provide feedback to the user based on the assigned priority.

In one embodiment, a method for capturing and processing images may comprise receiving, from a wearable image sensor, a plurality of images from an environment of a user of a wearable apparatus; analyzing the plurality of images to obtain information related to at least some of a plurality of tasks, the plurality of tasks comprising at least a first task and a second task; based on the obtained information, assigning a higher priority to the first task over the second task; and providing feedback to the user based on the assigned priority.

In one embodiment, a wearable apparatus may analyze group dynamics. The wearable apparatus may include a wearable image sensor configured to capture a plurality of images from an environment of a user of the wearable apparatus. The wearable apparatus may also include at least one processing device configured to perform a first analysis of the plurality of images to detect at least two persons, perform a second analysis of the plurality of images to determine association information related to the at least two detected persons, and update a social representation based on the determined association information.

In one embodiment, a method may analyze group dynamics. The method includes obtaining, using a wearable image sensor, a plurality of images captured from an environment of a user of a wearable apparatus, performing, using at least one processor of the wearable apparatus, a first analysis of the plurality of images to detect at least two persons, performing, using the at least one processor, a second analysis of the plurality of images to determine association information related to the at least two detected persons, and updating a social representation based on the determined association information.

Consistent with other disclosed embodiments, non-transitory computer-readable storage media may store program instructions, which are executed by at least one processor and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 3B is an exploded view of the example of the wearable apparatus shown in FIG. 3A.

FIGS. 39A and 38B are flowcharts of methods for name tagging using a wearable apparatus according to disclosed embodiments.

DETAILED DESCRIPTION

Figure 1A:
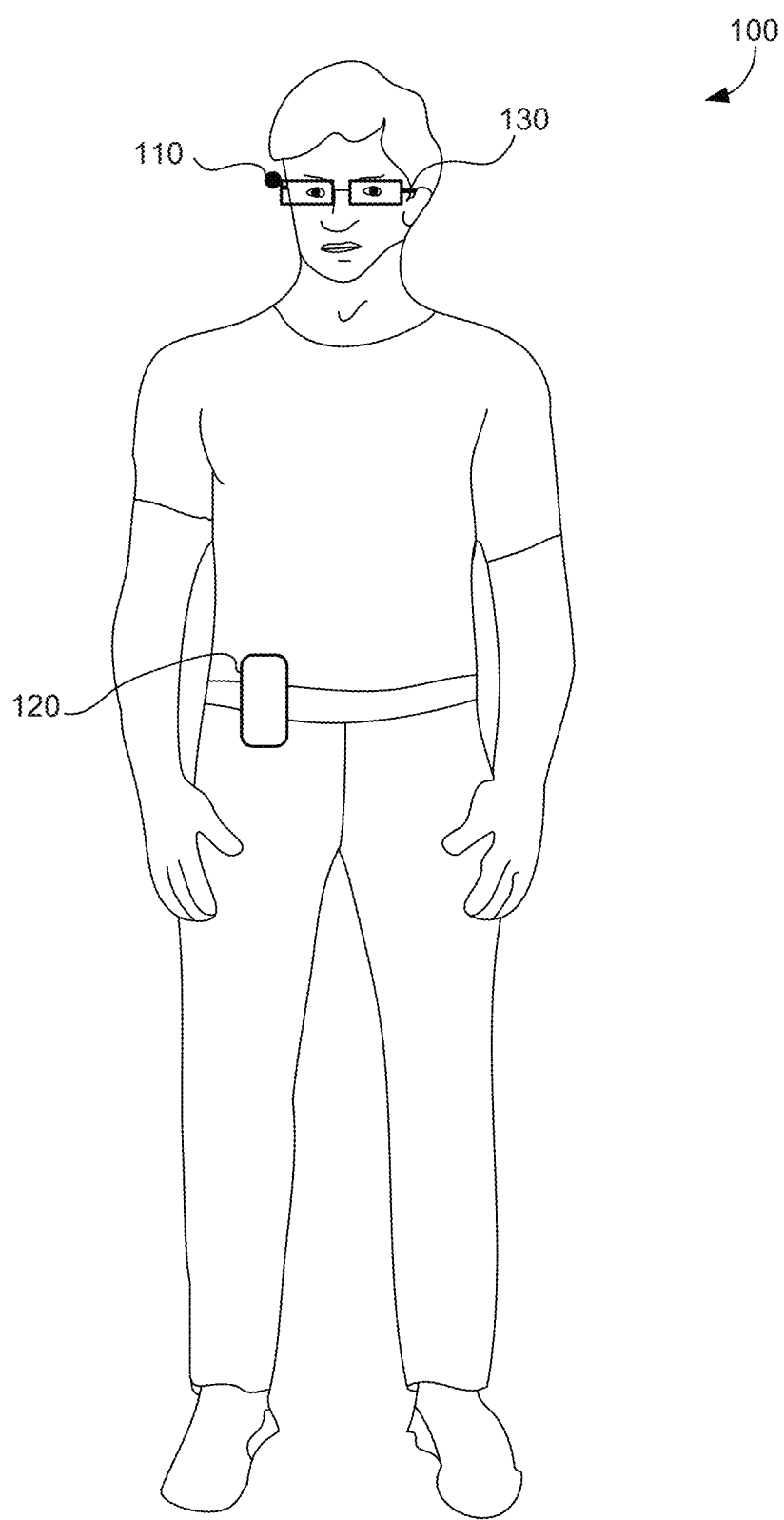
FIG. 1A is a schematic illustration of an example of a user wearing a wearable apparatus according to a disclosed embodiment.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

FIG. 1A illustrates a user 100 wearing an apparatus 110 that is physically connected (or integral) to glasses 130, consistent with the disclosed embodiments. Glasses 130 may be prescription glasses, magnifying glasses, non-prescription glasses, safety glasses, sunglasses, etc. Additionally, in some embodiments, glasses 130 may include parts of a frame and earpieces, nosepieces, etc., and one or no lenses. Thus, in some embodiments, glasses 130 may function primarily to support apparatus 110, and/or an augmented reality display device or other optical display device. In some embodiments, apparatus 110 may include an image sensor (not shown in FIG. 1A) for capturing real-time image data of the field-of-view of user 100. The term "image data" includes any form of data retrieved from optical signals in the near-infrared, infrared, visible, and ultraviolet spectrums. The image data may include video clips and/or photographs. In some embodiments, the image sensor of apparatus 110 (not shown) may have a field-of-view that is substantially similar (e.g., at least 50% overlapping, at least 70% overlapping, at least 90% overlapping, or the like) to the field-of view of user 100.

In some embodiments, a magnet or other device may be embedded within glasses 130, for example within a handle of the glasses, such that no particular device or installation is required for attaching apparatus 110 to glasses 130. The same apparatus can then be moved between different glasses of the user.

In some embodiments, apparatus 110 may communicate wirelessly or via a wire with a computing device 120. In some embodiments, computing device 120 may include, for example, a smartphone, or a tablet, or a dedicated processing unit, which may be portable (e.g., can be carried in a pocket of user 100). Although shown in FIG. 1A as an external device, in some embodiments, computing device 120 may be provided as part of wearable apparatus 110 or glasses 130, whether integral thereto or mounted thereon. In some embodiments, computing device 120 may be included in an augmented reality display device or optical head mounted display provided integrally or mounted to glasses 130. In other embodiments, for example, when computing device 120 is a smartphone, computing device 120 may include a display device which may be used as the augmented reality display device or other optical display device. In other embodiments, computing device 120 may be provided as part of another wearable or portable apparatus of user 100 including a wrist-strap, a multifunctional watch, a button, a clip-on, etc. In other embodiments, computing device 120 may be provided as part of another system, such as an on-board automobile computing or navigation system. A person skilled in the art can appreciate that different types of computing devices and arrangements of devices may implement the functionality of the disclosed embodiments. Accordingly, in other implementations, computing device 120 may include a Personal Computer (PC), laptop, an Internet server, etc.

Figure 1B:
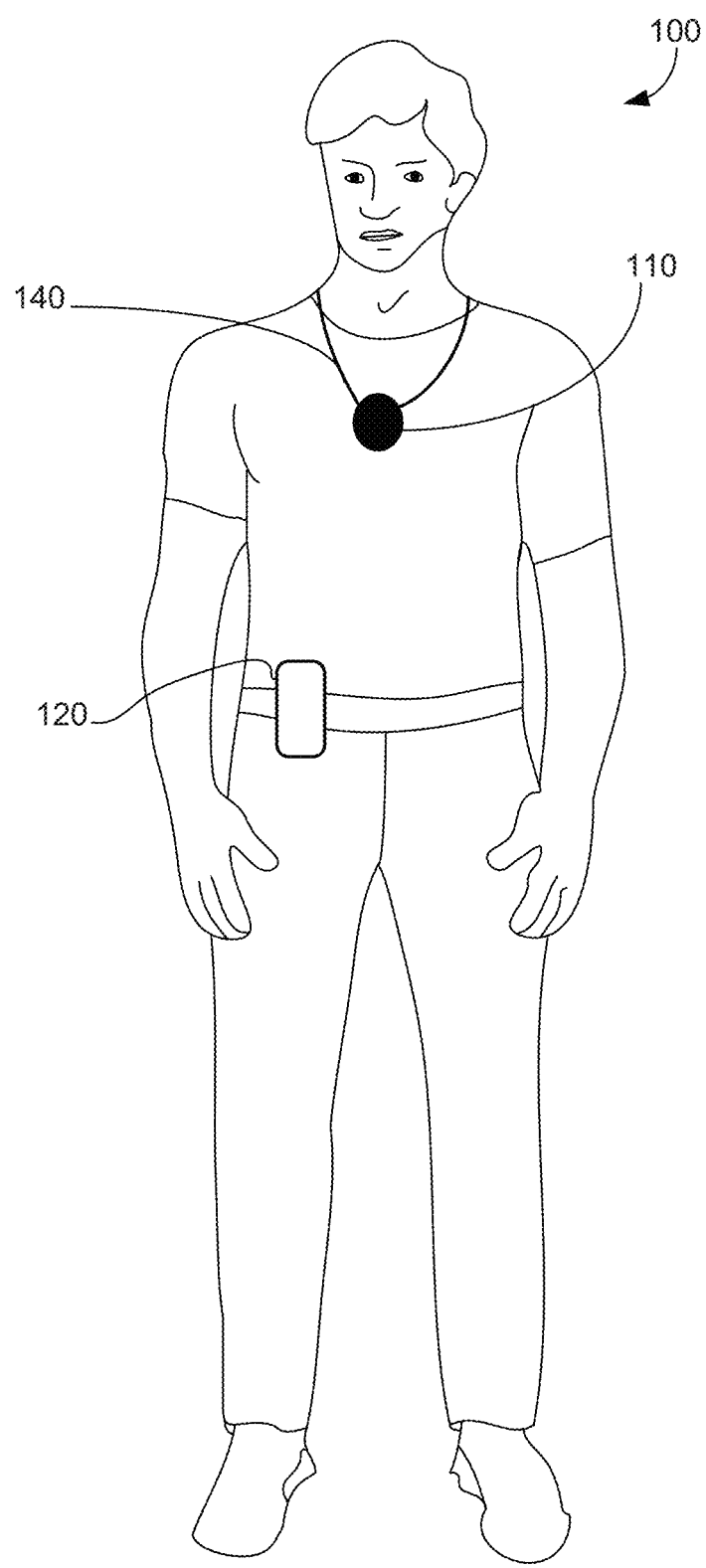
FIG. 1B is a schematic illustration of an example of the user wearing a wearable apparatus according to a disclosed embodiment.

FIG. 1B illustrates user 100 wearing apparatus 110 that is physically connected to a necklace 140, consistent with a disclosed embodiment. Such a configuration of apparatus 110 may be suitable for users that do not wear glasses some or all of the time. In this embodiment, user 100 can easily wear apparatus 110, and take it off.

Figure 1C:
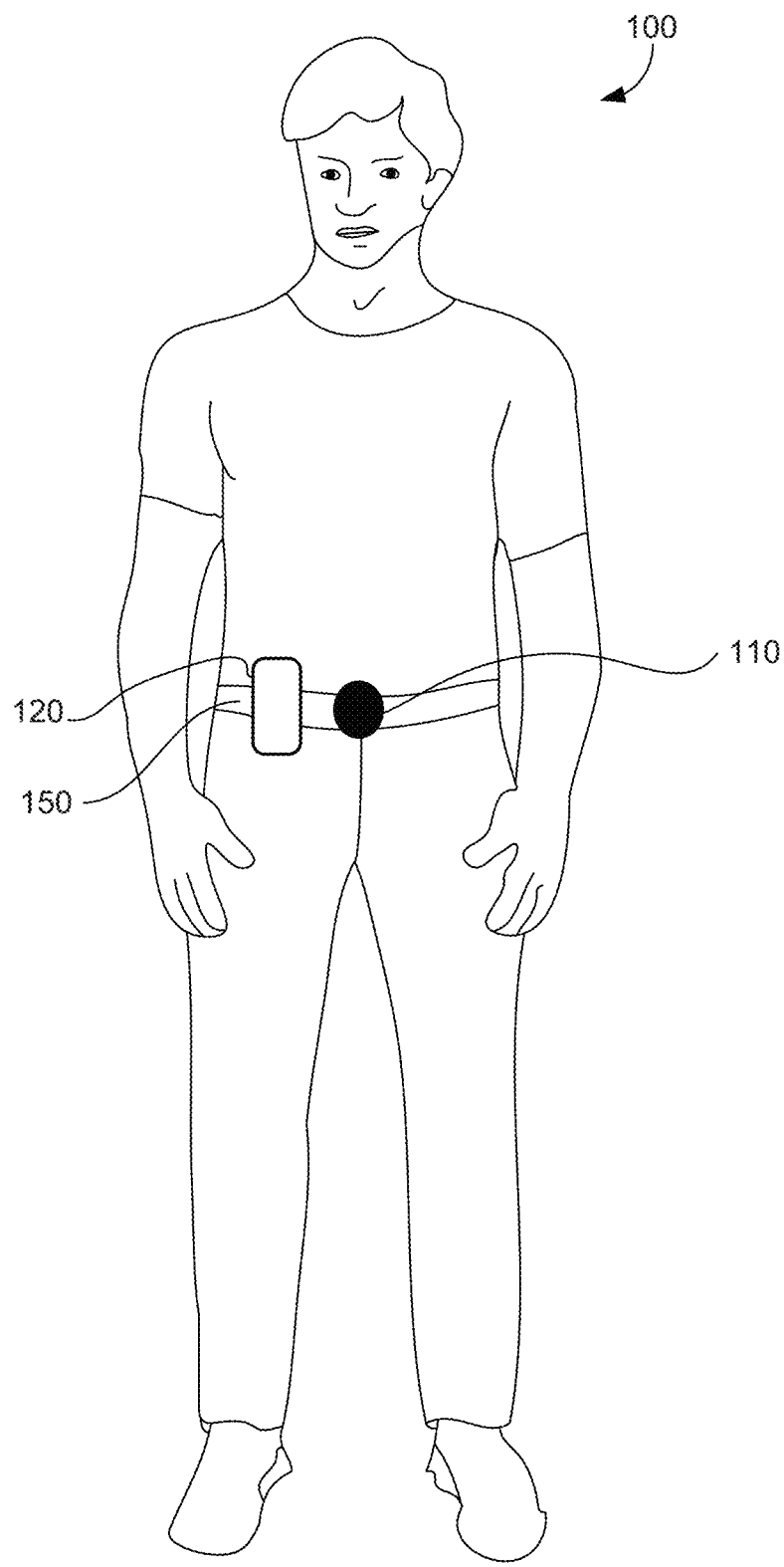
FIG. 1C is a schematic illustration of an example of the user wearing a wearable apparatus according to a disclosed embodiment.

FIG. 1C illustrates user 100 wearing apparatus 110 that is physically connected to a belt 150, consistent with a disclosed embodiment. Such a configuration of apparatus 110 may be designed as a belt buckle. Alternatively, apparatus 110 may include a clip for attaching to various clothing articles, such as belt 150, a vest, a pocket, a collar, a cap or hat or other portion of a clothing article.

Figure 1D:
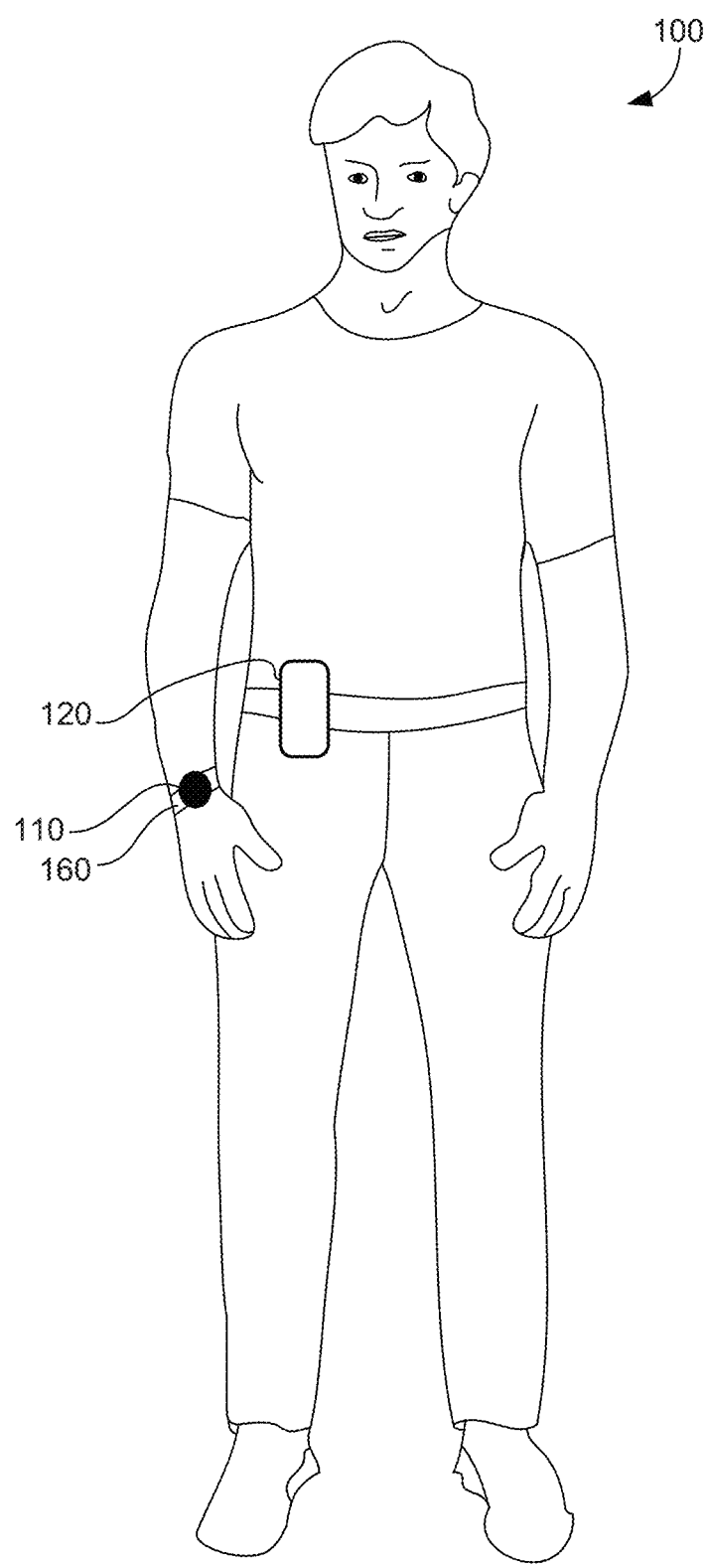
FIG. 1D is a schematic illustration of an example of the user wearing a wearable apparatus according to a disclosed embodiment.

FIG. 1D illustrates user 100 wearing apparatus 110 that is physically connected to a wrist strap 160, consistent with a disclosed embodiment. Although the aiming direction of apparatus 110, according to this embodiment, may not match the field-of-view of user 100, apparatus 110 may include the ability to identify a hand-related trigger based on the tracked eye movement of a user 100 indicating that user 100 is looking in the direction of the wrist strap 160. Wrist strap 160 may also include an accelerometer, a gyroscope, or other sensor for determining movement or orientation of a user's 100 hand for identifying a hand-related trigger.

Figure 2:
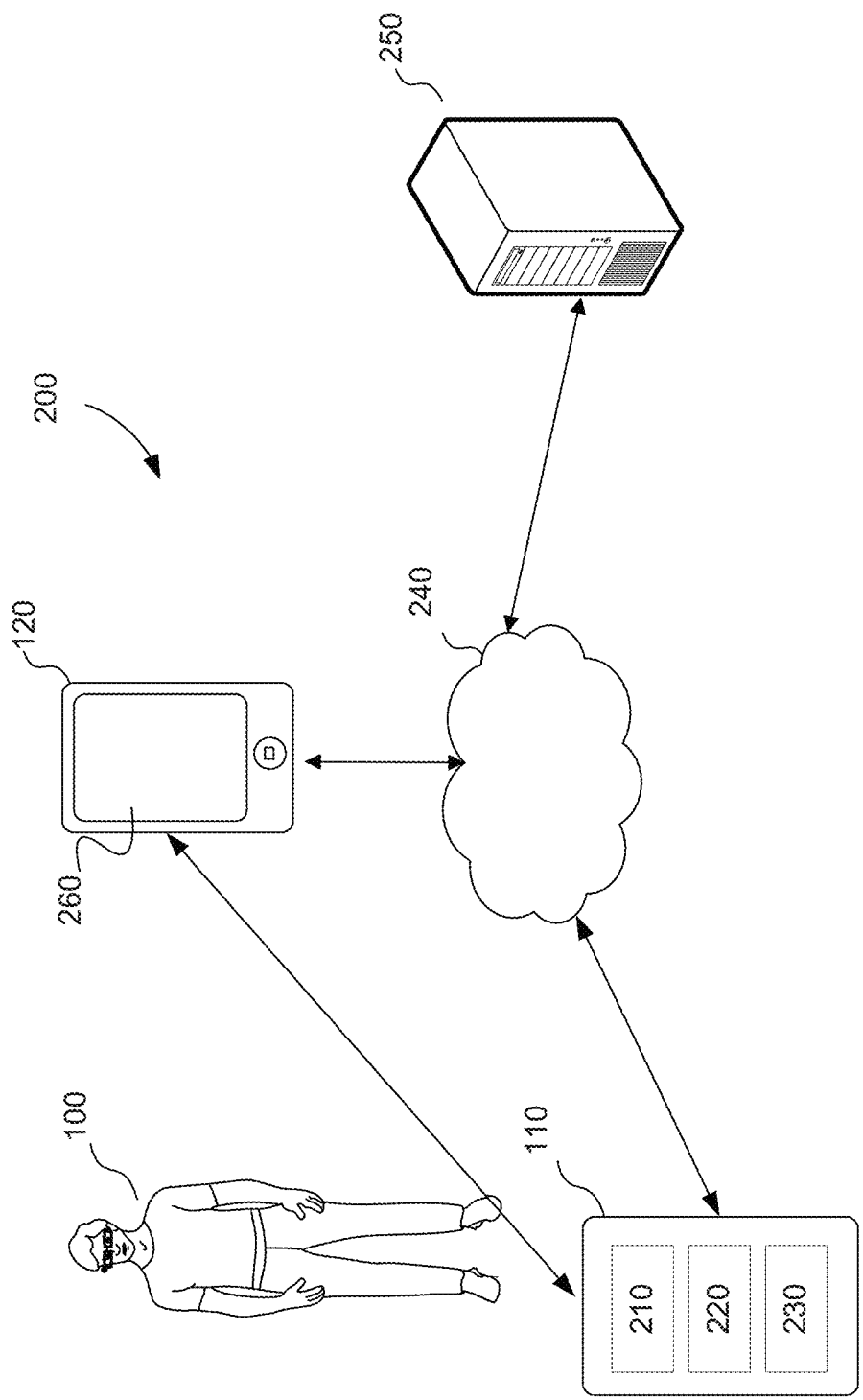
FIG. 2 is a schematic illustration of an example system consistent with the disclosed embodiments.

FIG. 2 is a schematic illustration of an exemplary system 200 including a wearable apparatus 110, worn by user 100, and an optional computing device 120 and/or a server 250 capable of communicating with apparatus 110 via a network 240, consistent with disclosed embodiments. In some embodiments, apparatus 110 may capture and analyze image data, identify a hand-related trigger present in the image data, and perform an action and/or provide feedback to a user 100, based at least in part on the identification of the hand-related trigger. In some embodiments, optional computing device 120 and/or server 250 may provide additional functionality to enhance interactions of user 100 with his or her environment, as described in greater detail below.

According to the disclosed embodiments, apparatus 110 may include an image sensor system 220 for capturing real-time image data of the field-of-view of user 100. In some embodiments, apparatus 110 may also include a processing unit 210 for controlling and performing the disclosed functionality of apparatus 110, such as to control the capture of image data, analyze the image data, and perform an action and/or output a feedback based on a hand-related trigger identified in the image data. According to the disclosed embodiments, a hand-related trigger may include a gesture performed by user 100 involving a portion of a hand of user 100. Further, consistent with some embodiments, a hand-related trigger may include a wrist-related trigger.

Additionally, in some embodiments, apparatus 110 may include a feedback outputting unit 230 for producing an output of information to user 100.

As discussed above, apparatus 110 may include an image sensor 220 for capturing image data. The term "image sensor" refers to a device capable of detecting and converting optical signals in the near-infrared, infrared, visible, and ultraviolet spectrums into electrical signals. The electrical signals may be used to form an image or a video stream (i.e. image data) based on the detected signal. The term "image data" includes any form of data retrieved from optical signals in the near-infrared, infrared, visible, and ultraviolet spectrums. Examples of image sensors may include semiconductor charge-coupled devices (CCD), active pixel sensors in complementary metal-oxide-semiconductor (CMOS), or N-type metal-oxide-semiconductor (NMOS, Live MOS). In some cases, image sensor 220 may be part of a camera included in apparatus 110.

Apparatus 110 may also include a processor 210 for controlling image sensor 220 to capture image data and for analyzing the image data according to the disclosed embodiments. As discussed in further detail below with respect to FIG. 5A, processor 210 may include a "processing device" for performing logic operations on one or more inputs of image data and other data according to stored or accessible software instructions providing desired functionality. In some embodiments, processor 210 may also control feedback outputting unit 230 to provide feedback to user 100 including information based on the analyzed image data and the stored software instructions. As the term is used herein, a "processing device" may access memory where executable instructions are stored or, in some embodiments, a "processing device" itself may include executable instructions (e.g., stored in memory included in the processing device).

In some embodiments, the information or feedback information provided to user 100 may include time information. The time information may include any information related to a current time of day and, as described further below, may be presented in any sensory perceptive manner. In some embodiments, time information may include a current time of day in a preconfigured format (e.g., 2:30 pm or 14:30). Time information may include the time in the user's current time zone (e.g., based on a determined location of user 100), as well as an indication of the time zone and/or a time of day in another desired location. In some embodiments, time information may include a number of hours or minutes relative to one or more predetermined times of day. For example, in some embodiments, time information may include an indication that three hours and fifteen minutes remain until a particular hour (e.g., until 6:00 pm), or some other predetermined time. Time information may also include a duration of time passed since the beginning of a particular activity, such as the start of a meeting or the start of a jog, or any other activity. In some embodiments, the activity may be determined based on analyzed image data. In other embodiments, time information may also include additional information related to a current time and one or more other routine, periodic, or scheduled events. For example, time information may include an indication of the number of minutes remaining until the next scheduled event, as may be determined from a calendar function or other information retrieved from computing device 120 or server 250, as discussed in further detail below.

Feedback outputting unit 230 may include one or more feedback systems for providing the output of information to user 100. In the disclosed embodiments, the audible or visual feedback may be provided via any type of connected audible or visual system or both. Feedback of information according to the disclosed embodiments may include audible feedback to user 100 (e.g., using a Bluetooth™ or other wired or wirelessly connected speaker, or a bone conduction headphone). Feedback outputting unit 230 of some embodiments may additionally or alternatively produce a visible output of information to user 100, for example, as part of an augmented reality display projected onto a lens of glasses 130 or provided via a separate heads up display in communication with apparatus 110, such as a display 260 provided as part of computing device 120, which may include an onboard automobile heads up display, an augmented reality device, a virtual reality device, a smartphone, PC, table, etc.

The term "computing device" refers to a device including a processing unit and having computing capabilities. Some examples of computing device 120 include a PC, laptop, tablet, or other computing systems such as an on-board computing system of an automobile, for example, each configured to communicate directly with apparatus 110 or server 250 over network 240. Another example of computing device 120 includes a smartphone having a display 260. In some embodiments, computing device 120 may be a computing system configured particularly for apparatus 110, and may be provided integral to apparatus 110 or tethered thereto. Apparatus 110 can also connect to computing device 120 over network 240 via any known wireless standard (e.g., Wi-Fi, Bluetooth®, etc.), as well as near-field capacitive coupling, and other short range wireless techniques, or via a wired connection. In an embodiment in which computing device 120 is a smartphone, computing device 120 may have a dedicated application installed therein. For example, user 100 may view on display 260 data (e.g., images, video clips, extracted information, feedback information, etc.) that originates from or is triggered by apparatus 110. In addition, user 100 may select part of the data for storage in server 250.

Network 240 may be a shared, public, or private network, may encompass a wide area or local area, and may be implemented through any suitable combination of wired and/or wireless communication networks. Network 240 may further comprise an intranet or the Internet. In some embodiments, network 240 may include short range or near-field wireless communication systems for enabling communication between apparatus 110 and computing device 120 provided in close proximity to each other, such as on or near a user's body, for example. Apparatus 110 may establish a connection to network 240 autonomously, for example, using a wireless module (e.g., Wi-Fi, cellular). In some embodiments, apparatus 110 may use the wireless module when being connected to an external power source, to prolong battery life. Further, communication between apparatus 110 and server 250 may be accomplished through any suitable communication channels, such as, for example, a telephone network, an extranet, an intranet, the Internet, satellite communications, off-line communications, wireless communications, transponder communications, a local area network (LAN), a wide area network (WAN), and a virtual private network (VPN).

As shown in FIG. 2, apparatus 110 may transfer or receive data to/from server 250 via network 240. In the disclosed embodiments, the data being received from server 250 and/or computing device 120 may include numerous different types of information based on the analyzed image data, including information related to a commercial product, or a person's identity, an identified landmark, and any other information capable of being stored in or accessed by server 250. In some embodiments, data may be received and transferred via computing device 120. Server 250 and/or computing device 120 may retrieve information from different data sources (e.g., a user specific database or a user's social network account or other account, the Internet, and other managed or accessible databases) and provide information to apparatus 110 related to the analyzed image data and a recognized trigger according to the disclosed embodiments. In some embodiments, calendar-related information retrieved from the different data sources may be analyzed to provide certain time information or a time-based context for providing certain information based on the analyzed image data.

Figure 3A:
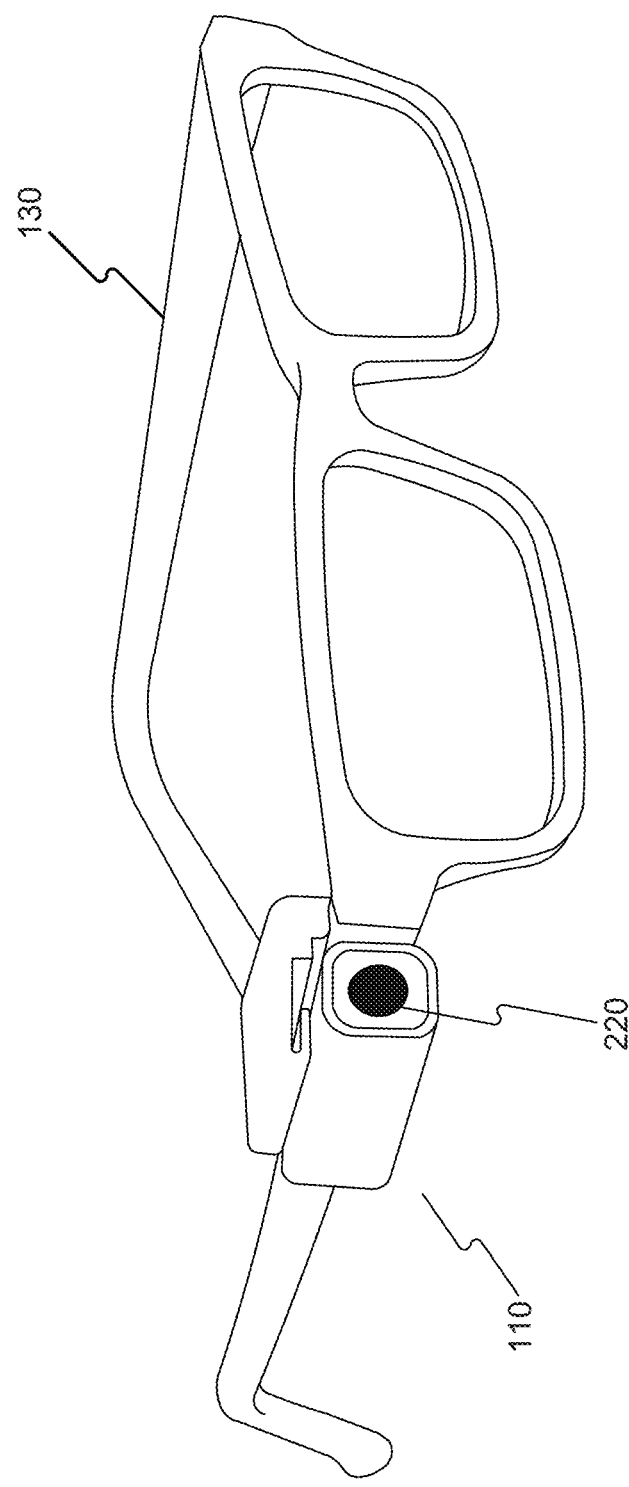
FIG. 3A is a schematic illustration of an example of the wearable apparatus shown in FIG. 1A.

An example of wearable apparatus 110 incorporated with glasses 130 according to some embodiments (as discussed in connection with FIG. 1A) is shown in greater detail in FIG. 3A. In some embodiments, apparatus 110 may be associated with a structure (not shown in FIG. 3A) that enables easy detaching and reattaching of apparatus 110 to glasses 130. In some embodiments, when apparatus 110 attaches to glasses 130, image sensor 220 acquires a set aiming direction without the need for directional calibration. The set aiming direction of image sensor 220 may substantially coincide with the field-of-view of user 100. For example, a camera associated with image sensor 220 may be installed within apparatus 110 in a predetermined angle in a position facing slightly downwards (e.g., 5-15 degrees from the horizon). Accordingly, the set aiming direction of image sensor 220 may substantially match the field-of-view of user 100.

FIG. 3B is an exploded view of the components of the embodiment discussed regarding FIG. 3A. Attaching apparatus 110 to glasses 130 may take place in the following way. Initially, a support 310 may be mounted on glasses 130 using a screw 320, in the side of support 310. Then, apparatus 110 may be clipped on support 310 such that it is aligned with the field-of-view of user 100. The term "support" includes any device or structure that enables detaching and reattaching of a device including a camera to a pair of glasses or to another object (e.g., a helmet). Support 310 may be made from plastic (e.g., polycarbonate), metal (e.g., aluminum), or a combination of plastic and metal (e.g., carbon fiber graphite). Support 310 may be mounted on any kind of glasses (e.g., eyeglasses, sunglasses, 3D glasses, safety glasses, etc.) using screws, bolts, snaps, or any fastening means used in the art.

In some embodiments, support 310 may include a quick release mechanism for disengaging and reengaging apparatus 110. For example, support 310 and apparatus 110 may include magnetic elements. As an alternative example, support 310 may include a male latch member and apparatus 110 may include a female receptacle. In other embodiments, support 310 can be an integral part of a pair of glasses, or sold separately and installed by an optometrist. For example, support 310 may be configured for mounting on the arms of glasses 130 near the frame front, but before the hinge. Alternatively, support 310 may be configured for mounting on the bridge of glasses 130. As described above with reference to FIG. 1A, in some embodiments, glasses 130 may have a magnet embedded therein, for example within a handle, such that apparatus 110 can be immediately attached or detached from glasses 130 without further structures or installations, and such that no structure is left attached to glasses 130 when apparatus 110 is detached.

In some embodiments, apparatus 110 may be provided as part of a glasses frame 130, with or without lenses. Additionally, in some embodiments, apparatus 110 may be configured to provide an augmented reality display projected onto a lens of glasses 130 (if provided), or alternatively, may include a display for projecting information, for example, according to the disclosed embodiments. Apparatus 110 may include the additional display or alternatively, may be in communication with a separately provided display system that may or may not be attached to glasses 130.

Figure 4A:
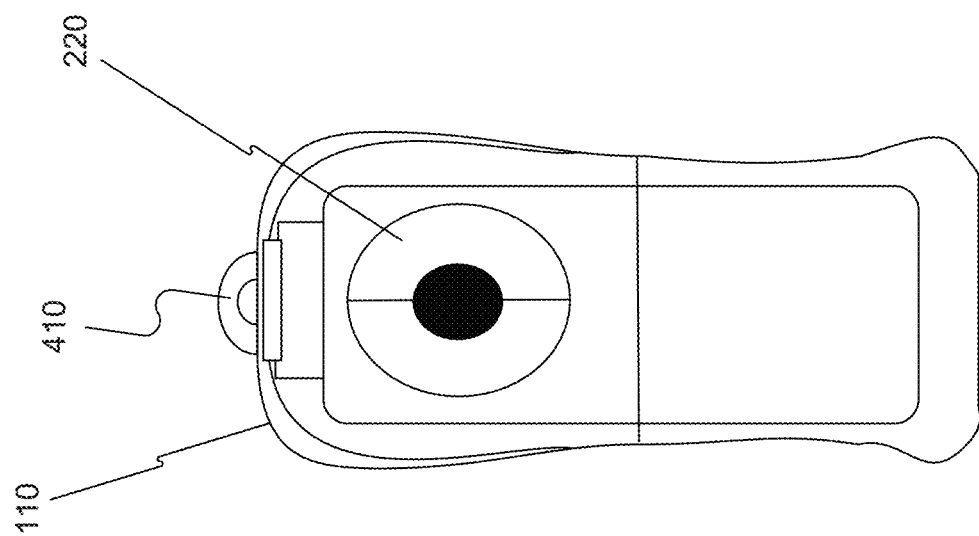
FIG. 4A is a schematic illustration of an example of the wearable apparatus shown in FIG. 1B from a first viewpoint.

In some embodiments, apparatus 110 may be implemented in a form other than wearable glasses, as described above with respect to FIGS. 1B-1D, for example. FIG. 4A is a schematic illustration of an example of an additional embodiment of apparatus 110 from a first viewpoint. The viewpoint shown in FIG. 4A is from the front of apparatus 110. Apparatus 110 includes an image sensor 220, a clip (not shown), a function button (not shown) and a hanging ring 410 for attaching apparatus 110 to, for example, necklace 140, as shown in FIG. 1B. When apparatus 110 hangs on necklace 140, the aiming direction of image sensor 220 may not fully coincide with the field-of-view of user 100, but the aiming direction would still correlate with the field-of-view of user 100.

Figure 4B:
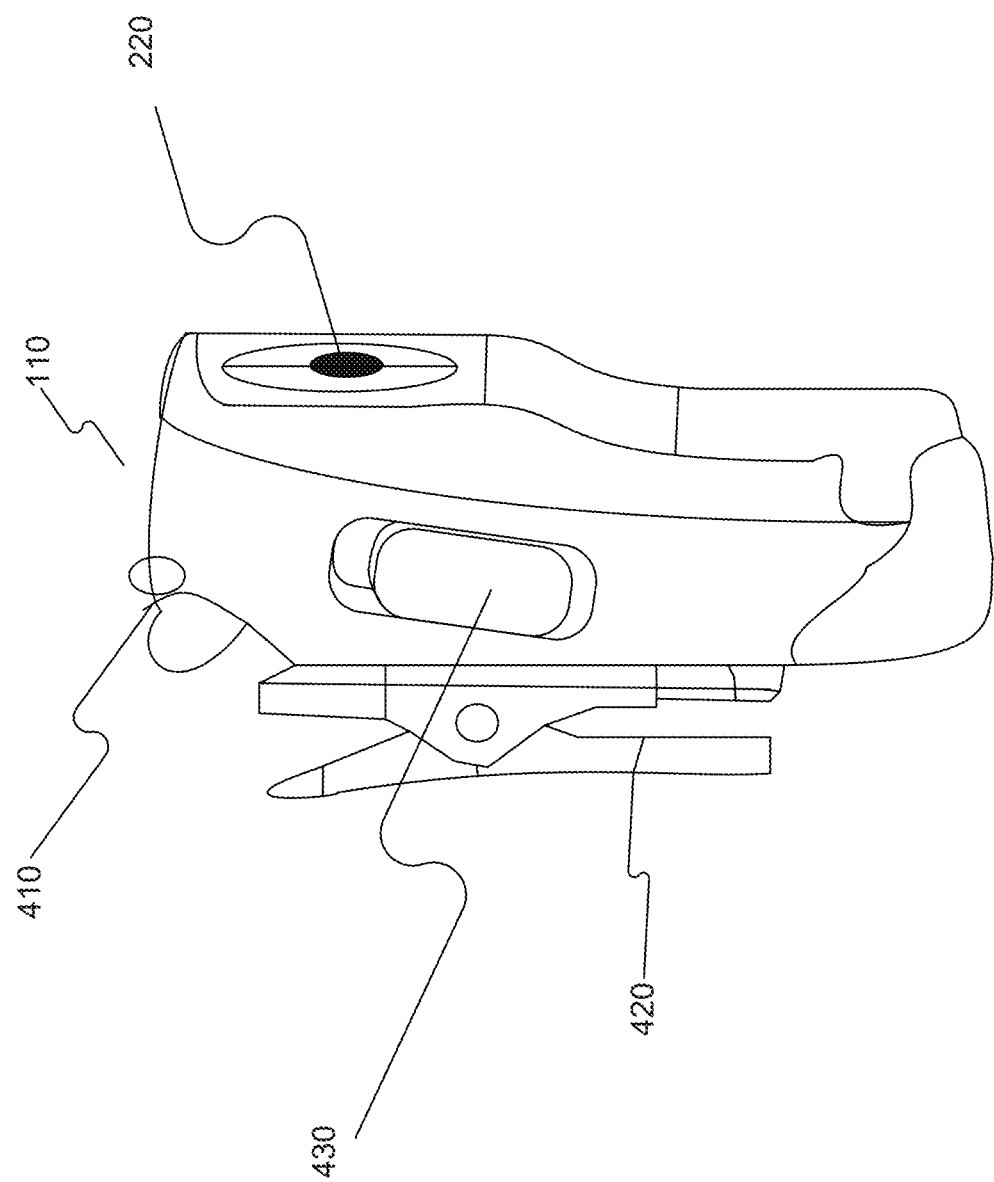
FIG. 4B is a schematic illustration of the example of the wearable apparatus shown in FIG. 1B from a second viewpoint.

FIG. 4B is a schematic illustration of the example of a second embodiment of apparatus 110, from a second viewpoint. The viewpoint shown in FIG. 4B is from a side orientation of apparatus 110. In addition to hanging ring 410, as shown in FIG. 4B, apparatus 110 may further include a clip 420. User 100 can use clip 420 to attach apparatus 110 to a shirt or belt 150, as illustrated in FIG. 1C. Clip 420 may provide an easy mechanism for disengaging and reengaging apparatus 110 from different articles of clothing. In other embodiments, apparatus 110 may include a female receptacle for connecting with a male latch of a car mount or universal stand.

In some embodiments, apparatus 110 includes a function button 430 for enabling user 100 to provide input to apparatus 110. Function button 430 may accept different types of tactile input (e.g., a tap, a click, a double-click, a long press, a right-to-left slide, a left-to-right slide). In some embodiments, each type of input may be associated with a different action. For example, a tap may be associated with the function of taking a picture, while a right-to-left slide may be associated with the function of recording a video.

The example embodiments discussed above with respect to FIGS. 3A, 3B, 4A, and 4B are not limiting. In some embodiments, apparatus 110 may be implemented in any suitable configuration for performing the disclosed methods. For example, referring back to FIG. 2, the disclosed embodiments may implement an apparatus 110 according to any configuration including an image sensor 220 and a processor unit 210 to perform image analysis and for communicating with a feedback unit 230.

Figure 5A:
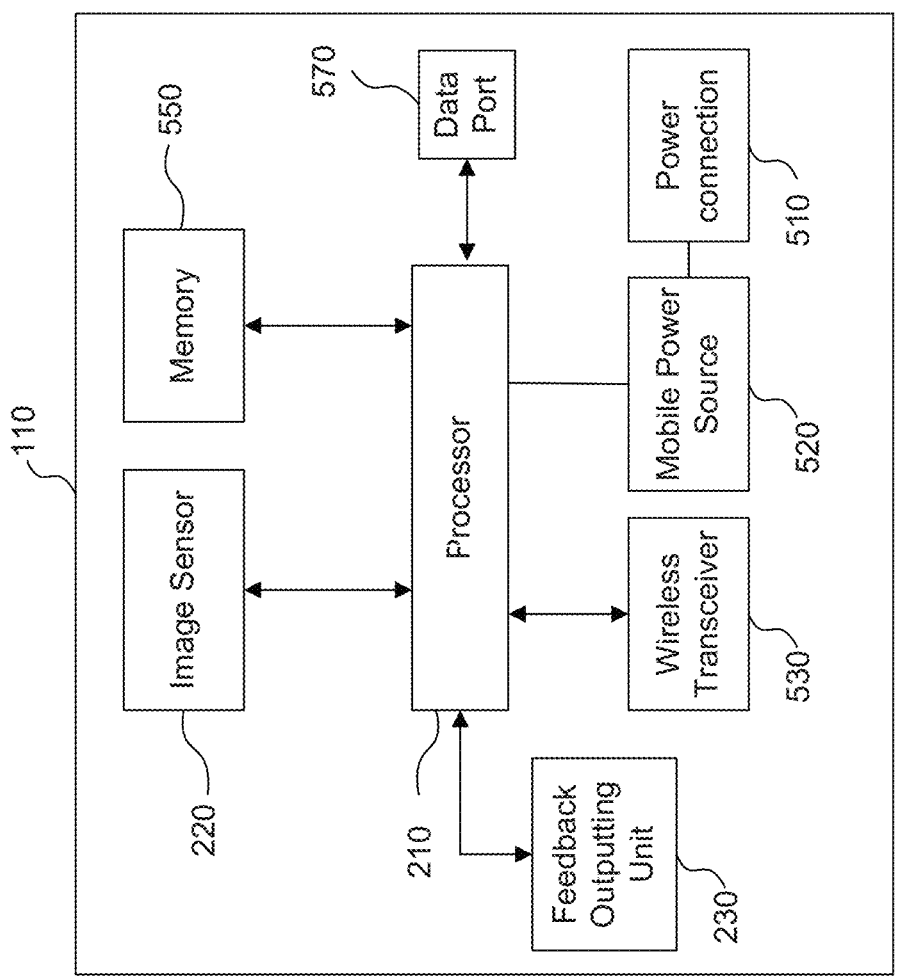
FIG. 5A is a block diagram illustrating an example of the components of a wearable apparatus according to a first embodiment.

FIG. 5A is a block diagram illustrating the components of apparatus 110 according to an example embodiment. As shown in FIG. 5A, and as similarly discussed above, apparatus 110 includes an image sensor 220, a memory 550, a processor 210, a feedback outputting unit 230, a wireless transceiver 530, and a mobile power source 520. In other embodiments, apparatus 110 may also include buttons, other sensors such as a microphone, and/or inertial measurements devices such as accelerometers, gyroscopes, magnetometers, temperature sensors, color sensors, light sensors, etc. Apparatus 110 may further include a data port 570 and a power connection 510 with suitable interfaces for connecting with an external power source or an external device (not shown).

Processor 210, depicted in FIG. 5A, may include any suitable processing device. The term "processing device" includes any physical device having an electric circuit that performs a logic operation on input or inputs. For example, processing device may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by the processing device may, for example, be pre-loaded into a memory integrated with or embedded into the processing device or may be stored in a separate memory (e.g., memory 550). Memory 550 may comprise a Random Access Memory (RAM), a Read-Only Memory (ROM), a hard disk, an optical disk, a magnetic medium, a flash memory, other permanent, fixed, or volatile memory, or any other mechanism capable of storing instructions.

Although, in the embodiment illustrated in FIG. 5A, apparatus 110 includes one processing device (e.g., processor 210), apparatus 110 may include more than one processing device. Each processing device may have a similar construction, or the processing devices may be of differing constructions that are electrically connected or disconnected from each other. For example, the processing devices may be separate circuits or integrated in a single circuit. When more than one processing device is used, the processing devices may be configured to operate independently or collaboratively. The processing devices may be coupled electrically, magnetically, optically, acoustically, mechanically or by other means that permit them to interact.

In some embodiments, processor 210 may process a plurality of images captured from the environment of user 100 to determine different parameters related to capturing subsequent images. For example, processor 210 can determine, based on information derived from captured image data, a value for at least one of the following: an image resolution, a compression ratio, a cropping parameter, frame rate, a focus point, an exposure time, an aperture size, and a light sensitivity. Additionally or alternatively, one or more of the values may be received from image sensor 220. The determined or received value may be used in capturing at least one subsequent image. Additionally, processor 210 can detect images including at least one hand-related trigger in the environment of the user and perform an action and/or provide an output of information to a user via feedback outputting unit 230.

In another embodiment, processor 210 can change the aiming direction of image sensor 220. For example, when apparatus 110 is attached with clip 420, the aiming direction of image sensor 220 may not coincide with the field-of-view of user 100. Processor 210 may recognize certain situations from the analyzed image data and adjust the aiming direction of image sensor 220 to capture relevant image data. For example, in one embodiment, processor 210 may detect an interaction with another individual and sense that the individual is not fully in view, because image sensor 220 is tilted down. Responsive thereto, processor 210 may adjust the aiming direction of image sensor 220 to capture image data of the individual. Other scenarios are also contemplated where processor 210 may recognize the need to adjust an aiming direction of image sensor 220.

In some embodiments, processor 210 may communicate data to feedback-outputting unit 230, which may include any device configured to provide information to a user 100. Feedback outputting unit 230 may be provided as part of apparatus 110 (as shown) or may be provided external to apparatus 110 and communicatively coupled thereto. Feedback-outputting unit 230 may be configured to output visual or nonvisual feedback based on signals received from processor 210, such as when processor 210 recognizes a hand-related trigger in the analyzed image data.

The term "feedback" refers to any output or information provided in response to processing at least one image in an environment. In some embodiments, as similarly described above, feedback may include an audible or visible indication of time information, detected text or numerals, the value of currency, a branded product, a type of food or drink, a person's identity, the identity of a landmark or other environmental situation or condition including the street names at an intersection or the color of a traffic light, etc., a machine or device, as well as other information associated with each of these. For example, in some embodiments, feedback may include additional information regarding the amount of currency still needed to complete a transaction, information regarding the identified person, historical information or times and prices of admission etc. of a detected landmark etc. In some embodiments, feedback may include an audible tone, a tactile response, and/or information previously recorded by user 100. Feedback-outputting unit 230 may comprise appropriate components for outputting acoustical and tactile feedback. For example, feedback-outputting unit 230 may comprise audio headphones, a hearing aid type device, a speaker, a bone conduction headphone, interfaces that provide tactile cues, vibrotactile stimulators, etc. In some embodiments, processor 210 may communicate signals with an external feedback outputting unit 230 via a wireless transceiver 530, a wired connection, or some other communication interface. In some embodiments, feedback outputting unit 230 may also include any suitable display device for visually displaying information to user 100.

As shown in FIG. 5A, apparatus 110 includes memory 550. Memory 550 may store one or more sets of instructions accessible to processor 210 to perform the disclosed methods, including instructions for recognizing a hand-related trigger in the image data. In some embodiments memory 550 may store image data (e.g., images, videos) captured from the environment of user 100. In addition, memory 550 may store information specific to user 100, such as image representations of known individuals, favorite products, personal items, and calendar or appointment information, etc. In some embodiments, processor 210 may determine, for example, which type of image data to store based on available storage space in memory 550. In another embodiment, processor 210 may extract information from the image data stored in memory 550.

As further shown in FIG. 5A, apparatus 110 includes mobile power source 520. The term "mobile power source" includes any device capable of providing electrical power, which can be easily carried by hand (e.g., mobile power source 520 may weigh less than a pound). The mobility of the power source enables user 100 to use apparatus 110 in a variety of situations. In some embodiments, mobile power source 520 may include one or more batteries (e.g., nickel-cadmium batteries, nickel-metal hydride batteries, and lithium-ion batteries) or any other type of electrical power supply. In other embodiments, mobile power source 520 may be rechargeable and contained within a casing that holds apparatus 110. In yet other embodiments, mobile power source 520 may include one or more energy harvesting devices for converting ambient energy into electrical energy (e.g., portable solar power units, human vibration units, etc.).

Mobile power source 520 may power one or more wireless transceivers (e.g., wireless transceiver 530 in FIG. 5A). The term "wireless transceiver" refers to any device configured to exchange transmissions over an air interface by use of radio frequency, infrared frequency, magnetic field, or electric field. Wireless transceiver 530 may use any known standard to transmit and/or receive data (e.g., Wi-Fi, Bluetooth®, Bluetooth Smart, 802.15.4, or ZigBee). In some embodiments, wireless transceiver 530 may transmit data (e.g., raw image data, processed image data, extracted information) from apparatus 110 to computing device 120 and/or server 250. Wireless transceiver 530 may also receive data from computing device 120 and/or server 250. In other embodiments, wireless transceiver 530 may transmit data and instructions to an external feedback outputting unit 230.

Figure 5B:
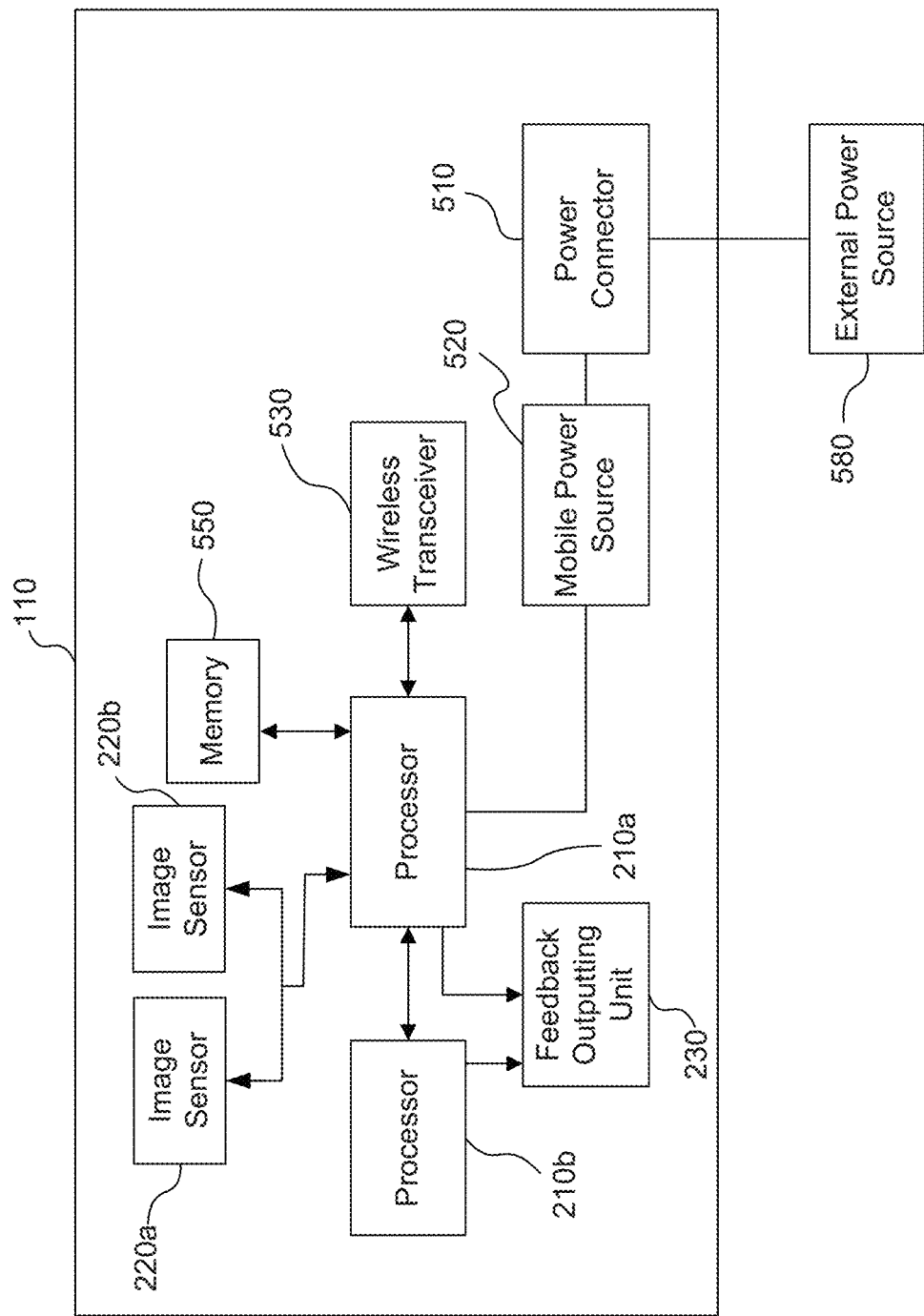
FIG. 5B is a block diagram illustrating an example of the components of a wearable apparatus according to a second embodiment.

FIG. 5B is a block diagram illustrating the components of apparatus 110 according to another example embodiment. In some embodiments, apparatus 110 includes a first image sensor 220a, a second image sensor 220b, a memory 550, a first processor 210a, a second processor 210b, a feedback outputting unit 230, a wireless transceiver 530, a mobile power source 520, and a power connector 510. In the arrangement shown in FIG. 5B, each of the image sensors may provide images in different parameters such as image resolution, or face a different direction. Alternatively, each image sensor may be associated with a different type of camera (e.g., a wide angle camera, a narrow angle camera, an IR camera, etc.). In some embodiments, apparatus 110 can select which image sensor to use based on various factors. For example, processor 210a may determine, based on available storage space in memory 550, to capture subsequent images in a certain resolution.

Apparatus 110 may operate in a first processing-mode and in a second processing-mode, such that the first processing-mode may consume less power than the second processing-mode. For example, in the first processing-mode, apparatus 110 may capture images and process the captured images to make real-time decisions based on an identified hand-related trigger, for example. In the second processing-mode, apparatus 110 may extract information from stored images in memory 550 and delete images from memory 550. In some embodiments, mobile power source 520 may provide more than fifteen hours of processing in the first processing-mode and about three hours of processing in the second processing-mode. Accordingly, different processing-modes may allow mobile power source 520 to produce sufficient power for powering apparatus 110 for various time periods (e.g., more than two hours, more than four hours, more than ten hours, etc.).

In some embodiments, apparatus 110 may use first processor 210a in the first processing-mode when powered by mobile power source 520, and second processor 210b in the second processing-mode when powered by external power source 580 that is connectable via power connector 510. In other embodiments, apparatus 110 may determine, based on predefined conditions, which processors or which processing modes to use. Apparatus 110 may operate in the second processing-mode even when apparatus 110 is not powered by external power source 580. For example, apparatus 110 may determine that it should operate in the second processing-mode when apparatus 110 is not powered by external power source 580, if the available storage space in memory 550 for storing new image data is lower than a predefined threshold. Accordingly, apparatus 110 may extract information from stored images in memory 550 and delete images from memory 550 even if apparatus 110 is not powered by external power source 580 when memory 550 has free space not exceeding the predefined threshold.

Although one wireless transceiver is depicted in FIG. 5B, apparatus 110 may include more than one wireless transceiver (e.g., two wireless transceivers). In an arrangement with more than one wireless transceiver, each of the wireless transceivers may use a different standard to transmit and/or receive data. In some embodiments, a first wireless transceiver may communicate with server 250 or computing device 120 using a cellular standard (e.g., LTE or GSM), and a second wireless transceiver may communicate with server 250 or computing device 120 using a short-range standard (e.g., Wi-Fi or Bluetooth®). In some embodiments, apparatus 110 may use the first wireless transceiver when the wearable apparatus is powered by a mobile power source included in the wearable apparatus, and use the second wireless transceiver when the wearable apparatus is powered by an external power source.

Figure 5C:
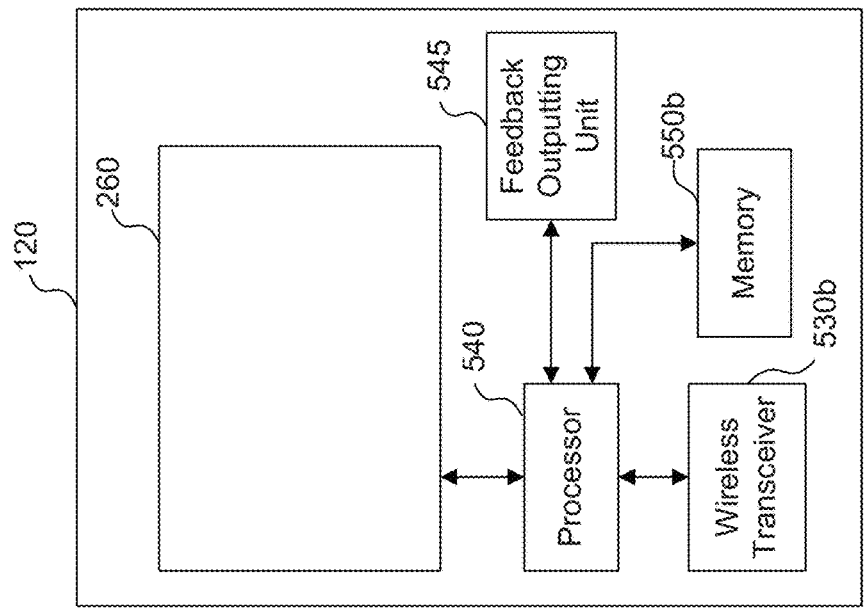
FIG. 5C is a block diagram illustrating an example of the components of a wearable apparatus according to a third embodiment.
Figure 5C:
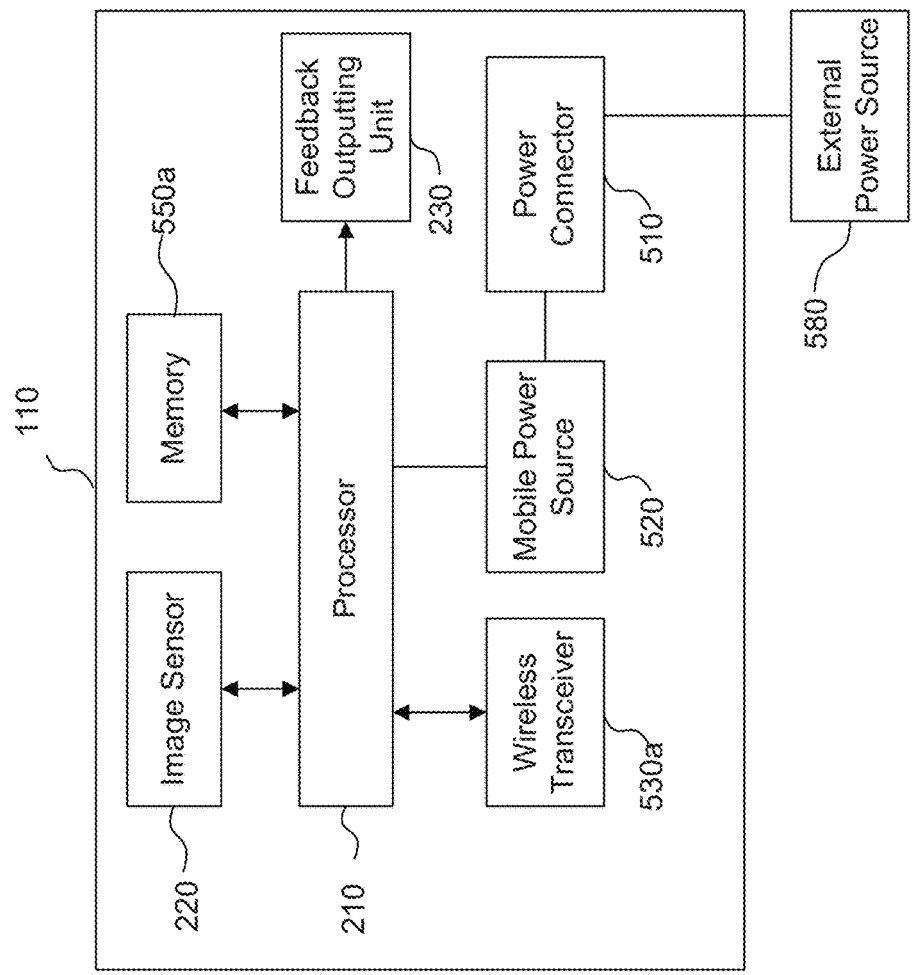

FIG. 5C is a block diagram illustrating the components of apparatus 110 according to another example embodiment including computing device 120. In this embodiment, apparatus 110 includes an image sensor 220, a memory 550a, a first processor 210, a feedback-outputting unit 230, a wireless transceiver 530a, a mobile power source 520, and a power connector 510. As further shown in FIG. 5C, computing device 120 includes a processor 540, a feedback-outputting unit 545, a memory 550b, a wireless transceiver 530b, and a display 260. One example of computing device 120 is a smartphone or tablet having a dedicated application installed therein. In other embodiments, computing device 120 may include any configuration such as an on-board automobile computing system, a PC, a laptop, and any other system consistent with the disclosed embodiments. In this example, user 100 may view feedback output in response to identification of a hand-related trigger on display 260. Additionally, user 100 may view other data (e.g., images, video clips, object information, schedule information, extracted information, etc.) on display 260. In addition, user 100 may communicate with server 250 via computing device 120.

In some embodiments, processor 210 and processor 540 are configured to extract information from captured image data. The term "extracting information" includes any process by which information associated with objects, individuals, locations, events, etc., is identified in the captured image data by any means known to those of ordinary skill in the art. In some embodiments, apparatus 110 may use the extracted information to send feedback or other real-time indications to feedback outputting unit 230 or to computing device 120. In some embodiments, processor 210 may identify in the image data the individual standing in front of user 100, and send computing device 120 the name of the individual and the last time user 100 met the individual. In another embodiment, processor 210 may identify in the image data, one or more visible triggers, including a hand-related trigger, and determine whether the trigger is associated with a person other than the user of the wearable apparatus, to selectively determine whether to perform an action associated with the trigger. One such action may be to provide a feedback to user 100 via feedback-outputting unit 230 provided as part of (or in communication with) apparatus 110 or via a feedback unit 545 provided as part of computing device 120. For example, feedback-outputting unit 545 may be in communication with display 260 to cause the display 260 to visibly output information. In some embodiments, processor 210 may identify in the image data a hand-related trigger and send computing device 120 an indication of the trigger. Processor 540 may then process the received trigger information and provide an output via feedback outputting unit 545 or display 260 based on the hand-related trigger. In other embodiments, processor 540 may determine a hand-related trigger and provide suitable feedback similar to the above, based on image data received from apparatus 110. In some embodiments, processor 540 may provide instructions or other information, such as environmental information to apparatus 110 based on an identified hand-related trigger.

In some embodiments, processor 210 may identify other environmental information in the analyzed images, such as an individual standing in front user 100, and send computing device 120 information related to the analyzed information such as the name of the individual and the last time user 100 met the individual. In a different embodiment, processor 540 may extract statistical information from captured image data and forward the statistical information to server 250. For example, certain information regarding the types of items a user purchases, or the frequency a user patronizes a particular merchant, etc. may be determined by processor 540. Based on this information, server 250 may send computing device 120 coupons and discounts associated with the user's preferences.

When apparatus 110 is connected or wirelessly connected to computing device 120, apparatus 110 may transmit at least part of the image data stored in memory 550a for storage in memory 550b. In some embodiments, after computing device 120 confirms that transferring the part of image data was successful, processor 210 may delete the part of the image data. The term "delete" means that the image is marked as 'deleted' and other image data may be stored instead of it, but does not necessarily mean that the image data was physically removed from the memory.

As will be appreciated by a person skilled in the art having the benefit of this disclosure, numerous variations and/or modifications may be made to the disclosed embodiments. Not all components are essential for the operation of apparatus 110. Any component may be located in any appropriate apparatus and the components may be rearranged into a variety of configurations while providing the functionality of the disclosed embodiments. For example, in some embodiments, apparatus 110 may include a camera, a processor, and a wireless transceiver for sending data to another device. Therefore, the foregoing configurations are examples and, regardless of the configurations discussed above, apparatus 110 can capture, store, and/or process images.

Further, the foregoing and following description refers to storing and/or processing images or image data. In the embodiments disclosed herein, the stored and/or processed images or image data may comprise a representation of one or more images captured by image sensor 220. As the term is used herein, a "representation" of an image (or image data) may include an entire image or a portion of an image. A representation of an image (or image data) may have the same resolution or a lower resolution as the image (or image data), and/or a representation of an image (or image data) may be altered in some respect (e.g., be compressed, have a lower resolution, have one or more colors that are altered, etc.).

For example, apparatus 110 may capture an image and store a representation of the image that is compressed, for example, as a .JPG file. As another example, apparatus 110 may capture an image in color, but store a black-and-white representation of the color image. As yet another example, apparatus 110 may capture an image and store a different representation of the image (e.g., a portion of the image). For example, apparatus 110 may store a portion of an image that includes a face of a person who appears in the image, but that does not substantially include the environment surrounding the person. Similarly, apparatus 110 may, for example, store a portion of an image that includes a product that appears in the image, but does not substantially include the environment surrounding the product. As yet another example, apparatus 110 may store a representation of an image at a reduced resolution (i.e., at a resolution that is of a lower value than that of the captured image). Storing representations of images may allow apparatus 110 to save storage space in memory 550. Furthermore, processing representations of images may allow apparatus 110 to improve processing efficiency and/or help to preserve battery life.

In addition to the above, in some embodiments, any one of apparatus 110 or computing device 120, via processor 210 or 540, may further process the captured image data to provide additional functionality to recognize objects and/or gestures and/or other information in the captured image data. In some embodiments, actions may be taken based on the identified objects, gestures, or other information. In some embodiments, processor 210 or 540 may identify in the image data, one or more visible triggers, including a hand-related trigger, and determine whether the trigger is associated with a person other than the user to determine whether to perform an action associated with the trigger.

Some embodiments of the present disclosure may include an apparatus securable to an article of clothing of a user. Such an apparatus may include two portions, connectable by a connector. A capturing unit may be designed to be worn on the outside of a user's clothing, and may include an image sensor for capturing images of a user's environment. The capturing unit may be connected to or connectable to a power unit, which may be configured to house a power source and a processing device. The capturing unit may be a small device including a camera or other device for capturing images. The capturing unit may be designed to be inconspicuous and unobtrusive, and may be configured to communicate with a power unit concealed by a user's clothing. The power unit may include bulkier aspects of the system, such as transceiver antennas, at least one battery, a processing device, etc. In some embodiments, communication between the capturing unit and the power unit may be provided by a data cable included in the connector, while in other embodiments, communication may be wirelessly achieved between the capturing unit and the power unit. Some embodiments may permit alteration of the orientation of an image sensor of the capture unit, for example to better capture images of interest.

Figure 6:
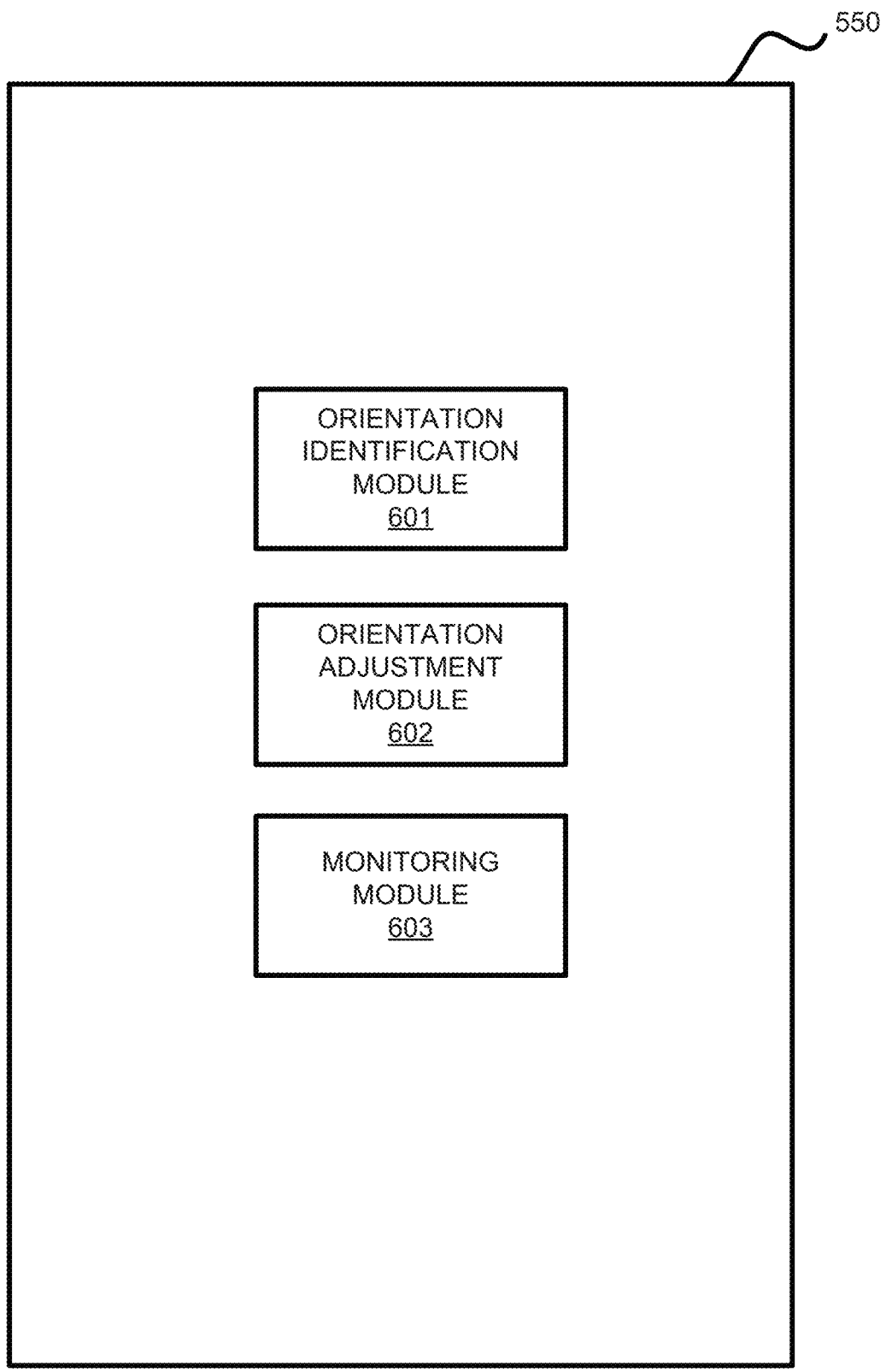
FIG. 6 illustrates an exemplary embodiment of a memory containing software modules consistent with the present disclosure.

FIG. 6 illustrates an exemplary embodiment of a memory containing software modules consistent with the present disclosure. Included in memory 550 are orientation identification module 601, orientation adjustment module 602, and monitoring module 603. Modules 601, 602, 603 may contain software instructions for execution by at least one processing device, e.g., processor 210, included with a wearable apparatus. Orientation identification module 601, orientation adjustment module 602, and monitoring module 603 may cooperate to provide orientation adjustment for a capturing unit incorporated into wireless apparatus 110.

Figure 7:
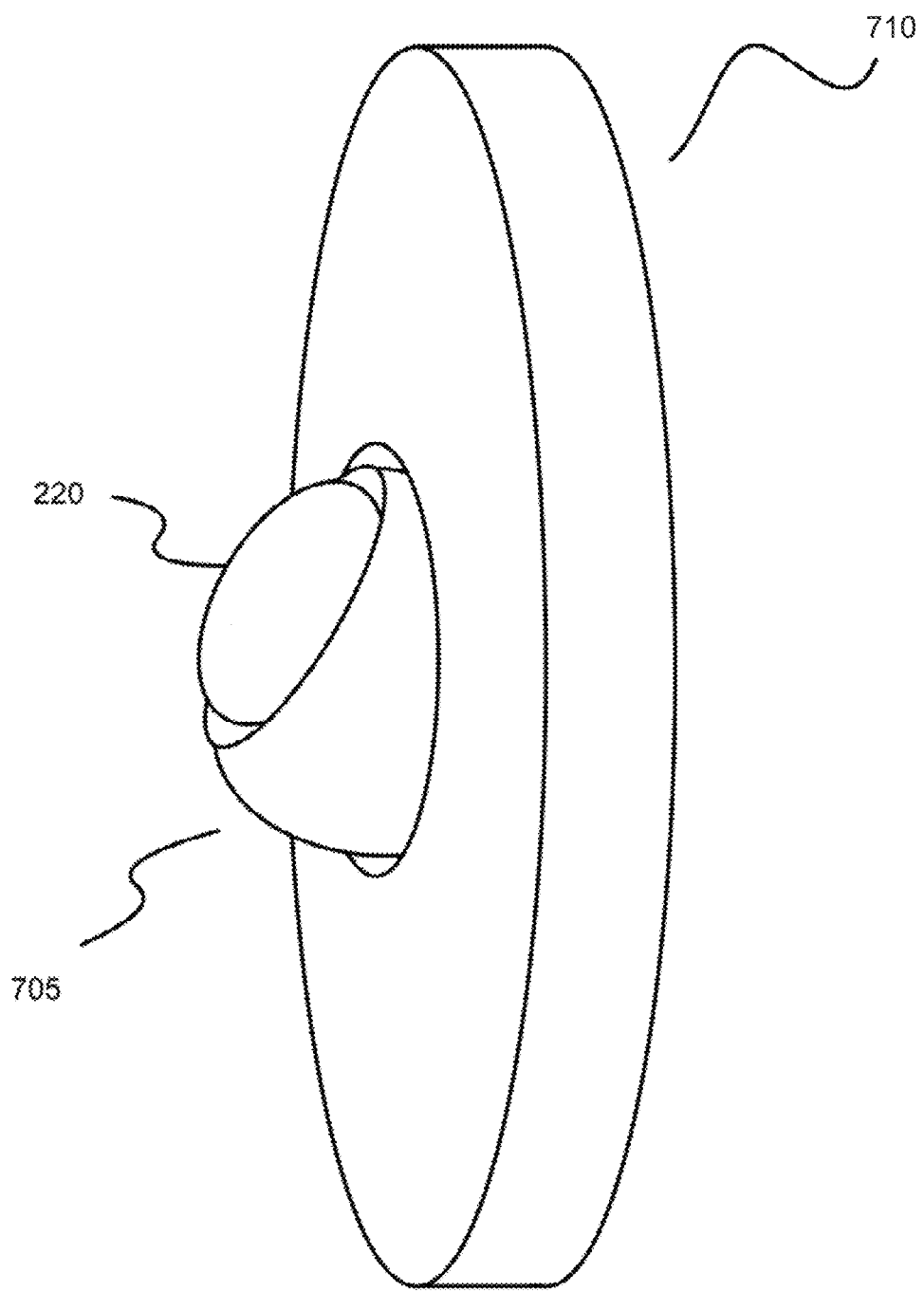
FIG. 7 is a schematic illustration of an embodiment of a wearable apparatus including an orientable image capture unit.

FIG. 7 illustrates an exemplary capturing unit 710 including an orientation adjustment unit 705. Orientation adjustment unit 705 may be configured to permit the adjustment of image sensor 220. As illustrated in FIG. 7, orientation adjustment unit 705 may include an eye-ball type adjustment mechanism. In alternative embodiments, orientation adjustment unit 705 may include gimbals, adjustable stalks, pivotable mounts, and any other suitable unit for adjusting an orientation of image sensor 220.

Image sensor 220 may be configured to be movable with the head of user 100 in such a manner that an aiming direction of image sensor 220 substantially coincides with a field of view of user 100. For example, as described above, a camera associated with image sensor 220 may be installed within capturing unit 710 at a predetermined angle in a position facing slightly upwards or downwards, depending on an intended location of capturing unit 710. Accordingly, the set aiming direction of image sensor 220 may match the field-of-view of user 100. In some embodiments, processor 210 may change the orientation of image sensor 220 using image data provided from image sensor 220. For example, processor 210 may recognize that a user is reading a book and determine that the aiming direction of image sensor 220 is offset from the text. That is, because the words in the beginning of each line of text are not fully in view, processor 210 may determine that image sensor 220 is tilted in the wrong direction. Responsive thereto, processor 210 may adjust the aiming direction of image sensor 220.

Orientation identification module 601 may be configured to identify an orientation of an image sensor 220 of capturing unit 710. An orientation of an image sensor 220 may be identified, for example, by analysis of images captured by image sensor 220 of capturing unit 710, by tilt or attitude sensing devices within capturing unit 710, and by measuring a relative direction of orientation adjustment unit 705 with respect to the remainder of capturing unit 710.

Orientation adjustment module 602 may be configured to adjust an orientation of image sensor 220 of capturing unit 710. As discussed above, image sensor 220 may be mounted on an orientation adjustment unit 705 configured for movement. Orientation adjustment unit 705 may be configured for rotational and/or lateral movement in response to commands from orientation adjustment module 602. In some embodiments orientation adjustment unit 705 may be adjust an orientation of image sensor 220 via motors, electromagnets, permanent magnets, and/or any suitable combination thereof.

In some embodiments, monitoring module 603 may be provided for continuous monitoring. Such continuous monitoring may include tracking a movement of at least a portion of an object included in one or more images captured by the image sensor. For example, in one embodiment, apparatus 110 may track an object as long as the object remains substantially within the field-of-view of image sensor 220. In additional embodiments, monitoring module 603 may engage orientation adjustment module 602 to instruct orientation adjustment unit 705 to continually orient image sensor 220 towards an object of interest. For example, in one embodiment, monitoring module 603 may cause image sensor 220 to adjust an orientation to ensure that a certain designated object, for example, the face of a particular person, remains within the field-of view of image sensor 220, even as that designated object moves about. In another embodiment, monitoring module 603 may continuously monitor an area of interest included in one or more images captured by the image sensor. For example, a user may be occupied by a certain task, for example, typing on a laptop, while image sensor 220 remains oriented in a particular direction and continuously monitors a portion of each image from a series of images to detect a trigger or other event. For example, image sensor 210 may be oriented towards a piece of laboratory equipment and monitoring module 603 may be configured to monitor a status light on the laboratory equipment for a change in status, while the user's attention is otherwise occupied.

In some embodiments consistent with the present disclosure, capturing unit 710 may include a plurality of image sensors 220. The plurality of image sensors 220 may each be configured to capture different image data. For example, when a plurality of image sensors 220 are provided, the image sensors 220 may capture images having different resolutions, may capture wider or narrower fields of view, and may have different levels of magnification. Image sensors 220 may be provided with varying lenses to permit these different configurations. In some embodiments, a plurality of image sensors 220 may include image sensors 220 having different orientations. Thus, each of the plurality of image sensors 220 may be pointed in a different direction to capture different images. The fields of view of image sensors 220 may be overlapping in some embodiments. The plurality of image sensors 220 may each be configured for orientation adjustment, for example, by being paired with an image adjustment unit 705. In some embodiments, monitoring module 603, or another module associated with memory 550, may be configured to individually adjust the orientations of the plurality of image sensors 220 as well as to turn each of the plurality of image sensors 220 on or off as may be required. In some embodiments, monitoring an object or person captured by an image sensor 220 may include tracking movement of the object across the fields of view of the plurality of image sensors 220.

Embodiments consistent with the present disclosure may include connectors configured to connect a capturing unit and a power unit of a wearable apparatus. Capturing units consistent with the present disclosure may include at least one image sensor configured to capture images of an environment of a user. Power units consistent with the present disclosure may be configured to house a power source and/or at least one processing device. Connectors consistent with the present disclosure may be configured to connect the capturing unit and the power unit, and may be configured to secure the apparatus to an article of clothing such that the capturing unit is positioned over an outer surface of the article of clothing and the power unit is positioned under an inner surface of the article of clothing. Exemplary embodiments of capturing units, connectors, and power units consistent with the disclosure are discussed in further detail with respect to FIGS. 8-14.

Figure 8:
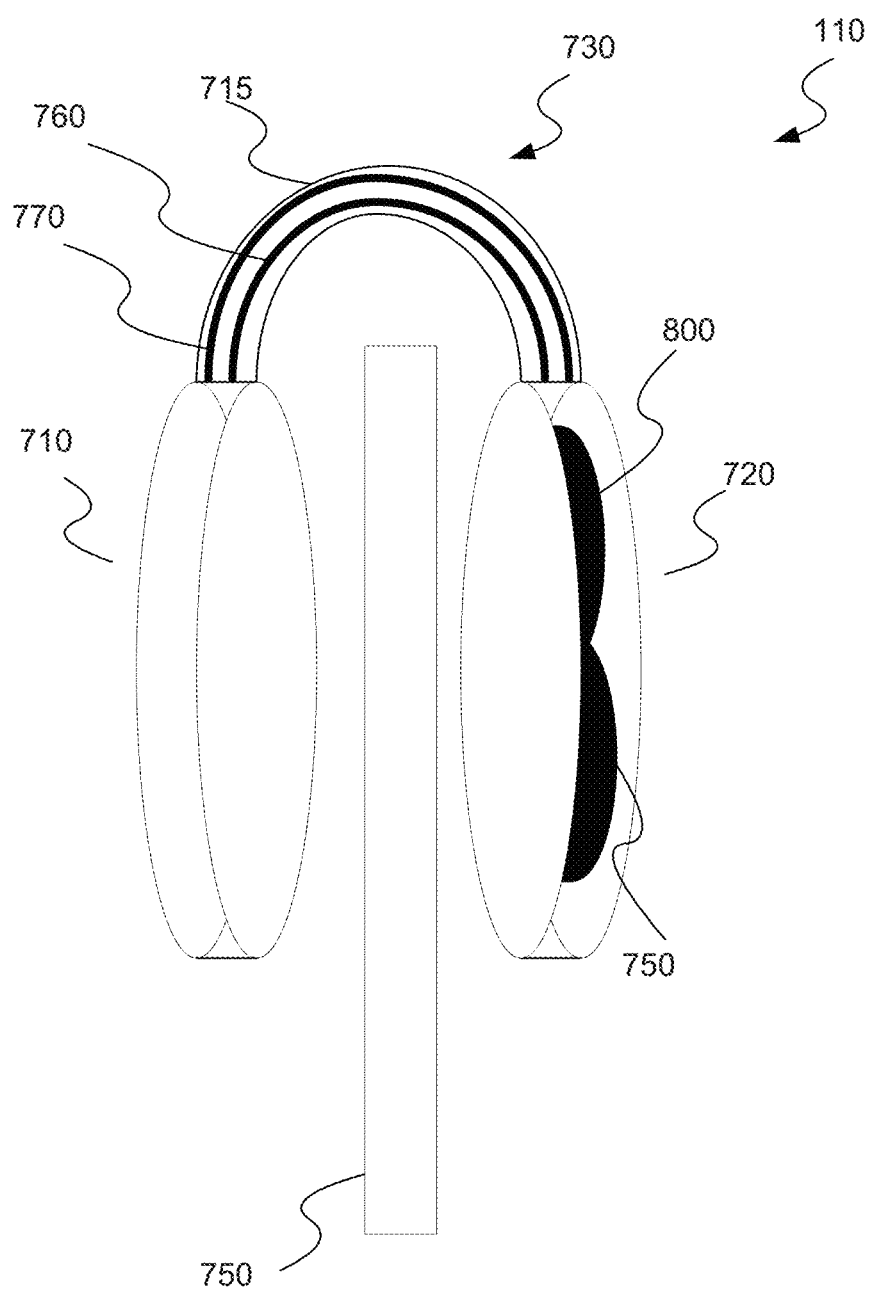
FIG. 8 is a schematic illustration of an embodiment of a wearable apparatus securable to an article of clothing consistent with the present disclosure.

FIG. 8 is a schematic illustration of an embodiment of wearable apparatus 110 securable to an article of clothing consistent with the present disclosure. As illustrated in FIG. 8, capturing unit 710 and power unit 720 may be connected by a connector 730 such that capturing unit 710 is positioned on one side of an article of clothing 750 and power unit 720 is positioned on the opposite side of the clothing 750. In some embodiments, capturing unit 710 may be positioned over an outer surface of the article of clothing 750 and power unit 720 may be located under an inner surface of the article of clothing 750. The power unit 720 may be configured to be placed against the skin of a user.

Capturing unit 710 may include an image sensor 220 and an orientation adjustment unit 705 (as illustrated in FIG. 7). Power unit 720 may include mobile power source 520 and processor 210. Power unit 720 may further include any combination of elements previously discussed that may be a part of wearable apparatus 110, including, but not limited to, wireless transceiver 530, feedback outputting unit 230, memory 550, and data port 570.

Connector 730 may include a clip 715 or other mechanical connection designed to clip or attach capturing unit 710 and power unit 720 to an article of clothing 750 as illustrated in FIG. 8. As illustrated, clip 715 may connect to each of capturing unit 710 and power unit 720 at a perimeter thereof, and may wrap around an edge of the article of clothing 750 to affix the capturing unit 710 and power unit 720 in place. Connector 730 may further include a power cable 760 and a data cable 770. Power cable 760 may be capable of conveying power from mobile power source 520 to image sensor 220 of capturing unit 710. Power cable 760 may also be configured to provide power to any other elements of capturing unit 710, e.g., orientation adjustment unit 705. Data cable 770 may be capable of conveying captured image data from image sensor 220 in capturing unit 710 to processor 800 in the power unit 720. Data cable 770 may be further capable of conveying additional data between capturing unit 710 and processor 800, e.g., control instructions for orientation adjustment unit 705.

Figure 9:
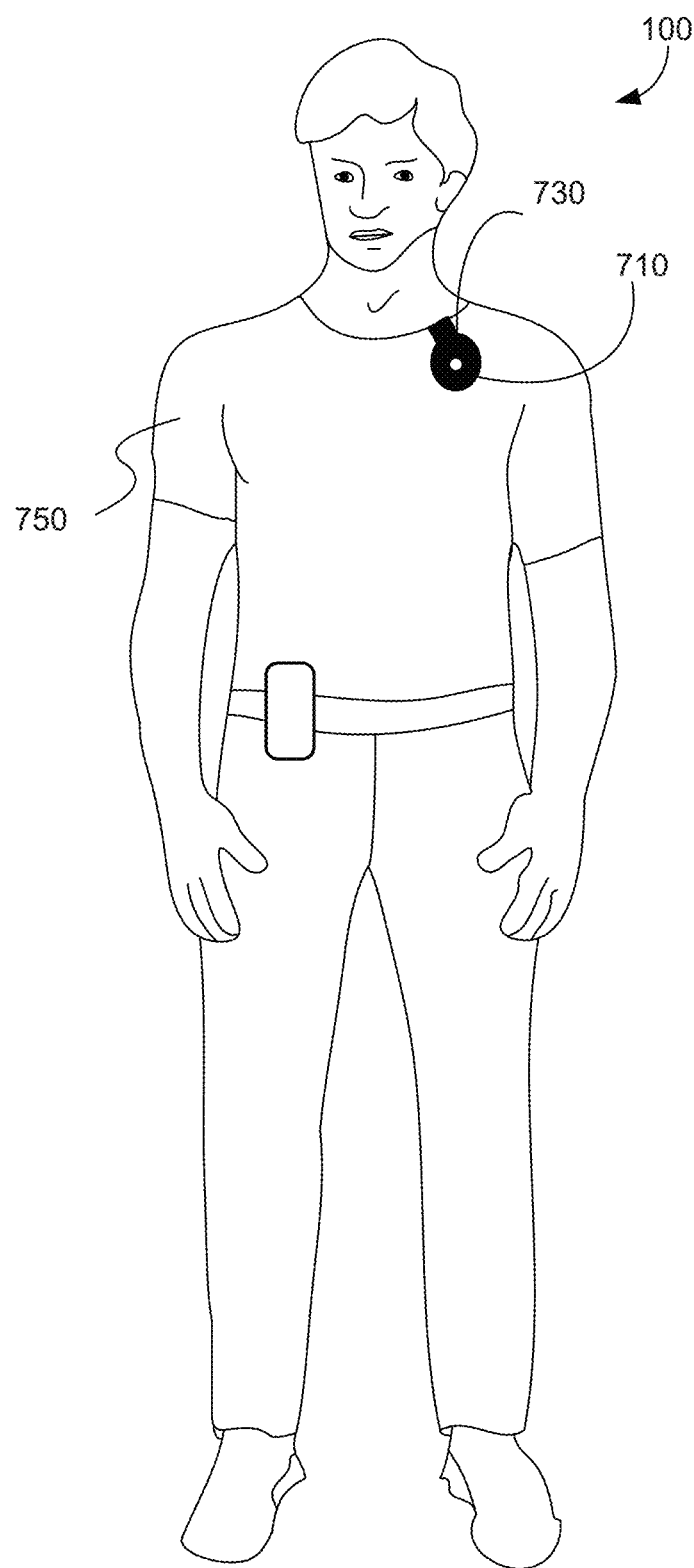
FIG. 9 is a schematic illustration of a user wearing a wearable apparatus consistent with an embodiment of the present disclosure.

FIG. 9 is a schematic illustration of a user 100 wearing a wearable apparatus 110 consistent with an embodiment of the present disclosure. As illustrated in FIG. 9, capturing unit 710 is located on an exterior surface of the clothing 750 of user 100. Capturing unit 710 is connected to power unit 720 (not seen in this illustration) via connector 730, which wraps around an edge of clothing 750.

Figure 10:
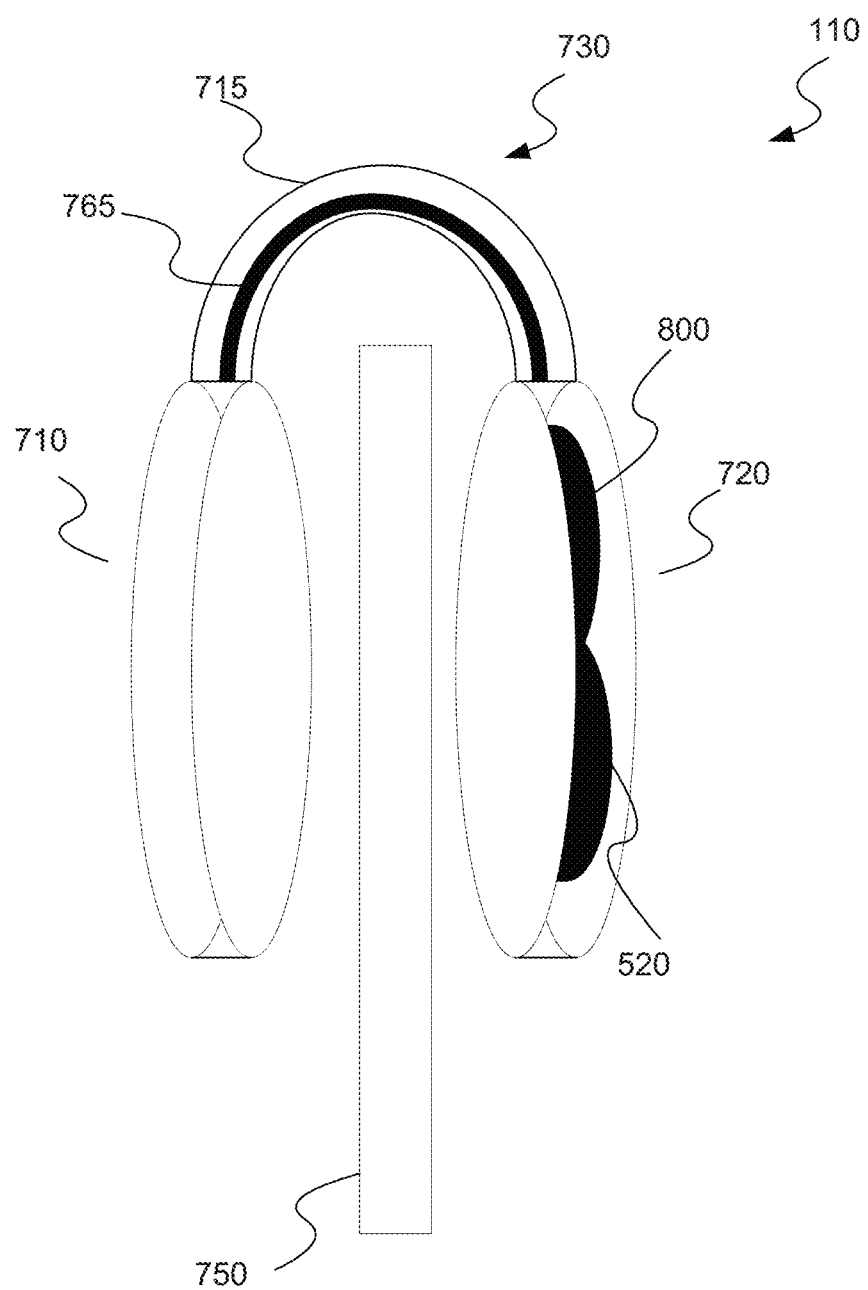
FIG. 10 is a schematic illustration of an embodiment of a wearable apparatus securable to an article of clothing consistent with the present disclosure.

In some embodiments, connector 730 may include a flexible printed circuit board (PCB). FIG. 10 illustrates an exemplary embodiment wherein connector 730 includes a flexible printed circuit board 765. Flexible printed circuit board 765 may include data connections and power connections between capturing unit 710 and power unit 720. Thus, in some embodiments, flexible printed circuit board 765 may serve to replace power cable 760 and data cable 770. In alternative embodiments, flexible printed circuit board 765 may be included in addition to at least one of power cable 760 and data cable 770. In various embodiments discussed herein, flexible printed circuit board 765 may be substituted for, or included in addition to, power cable 760 and data cable 770.

Figure 11:
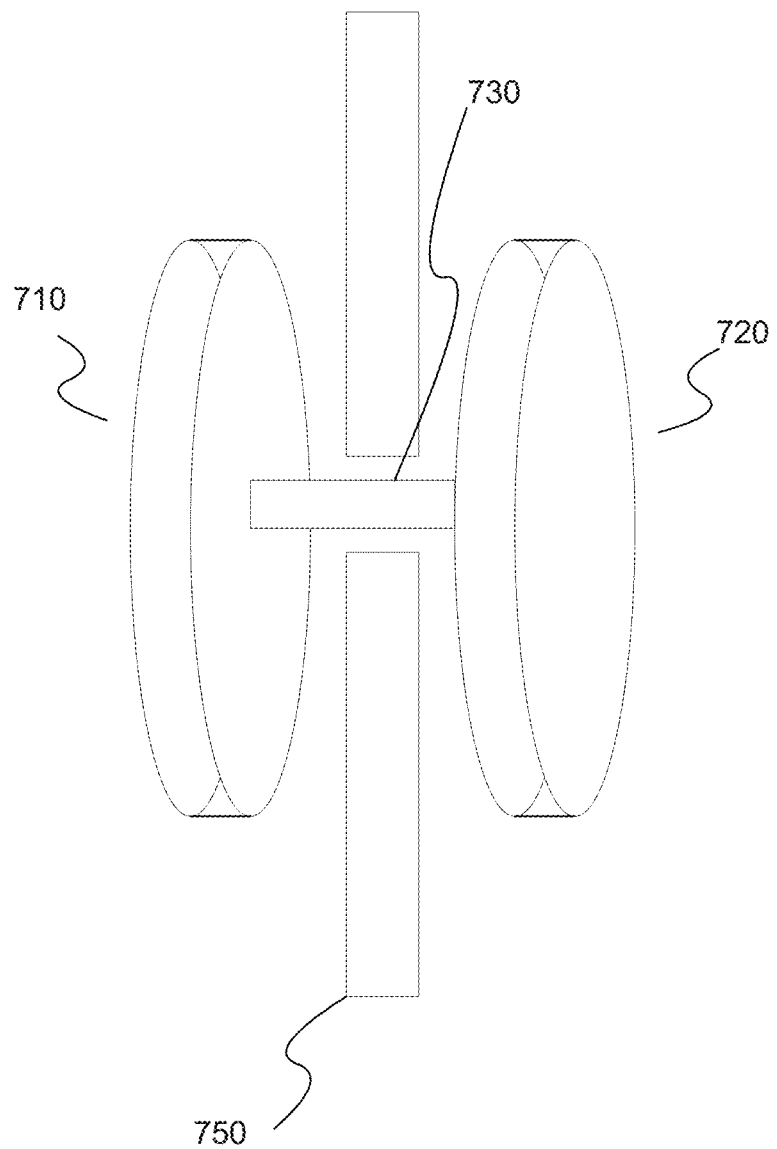
FIG. 11 is a schematic illustration of an embodiment of a wearable apparatus securable to an article of clothing consistent with the present disclosure.

FIG. 11 is a schematic illustration of another embodiment of a wearable apparatus securable to an article of clothing consistent with the present disclosure. As illustrated in FIG. 11, connector 730 may be centrally located with respect to capturing unit 710 and power unit 720. Central location of connector 730 may facilitate affixing apparatus 110 to clothing 750 through a hole in clothing 750 such as, for example, a button-hole in an existing article of clothing 750 or a specialty hole in an article of clothing 750 designed to accommodate wearable apparatus 110.

Figure 12:
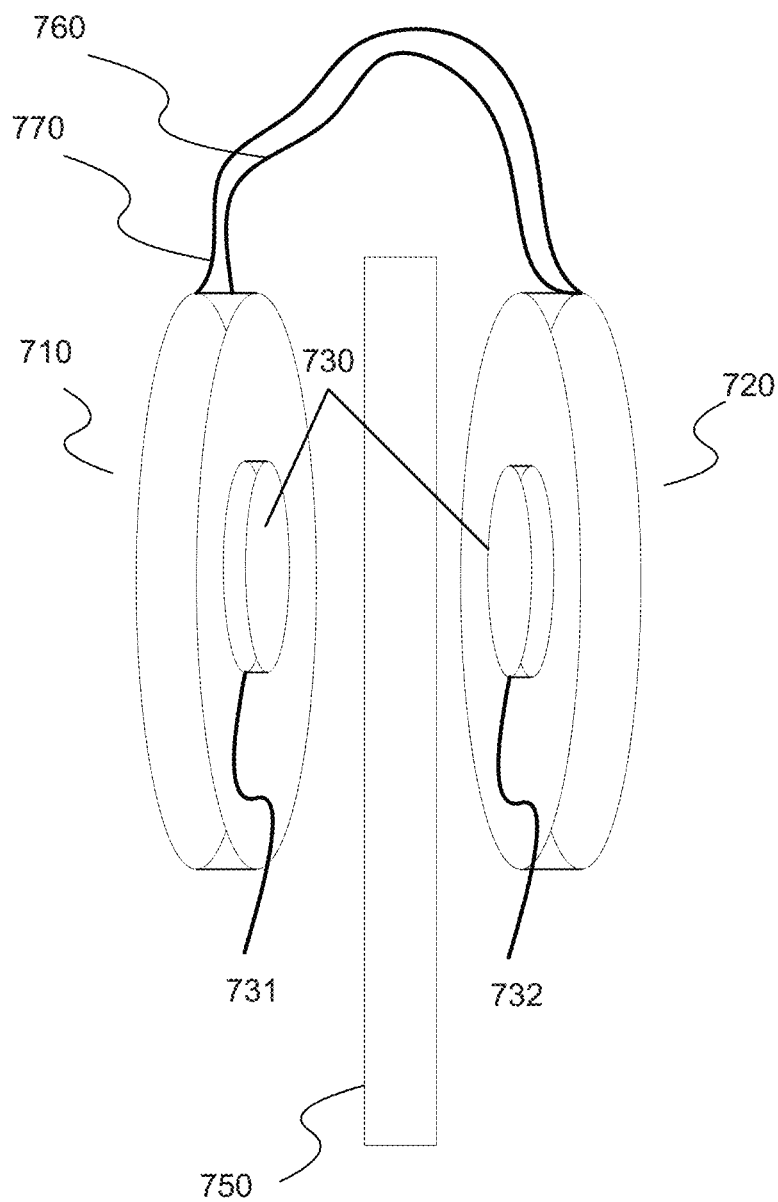
FIG. 12 is a schematic illustration of an embodiment of a wearable apparatus securable to an article of clothing consistent with the present disclosure.

FIG. 12 is a schematic illustration of still another embodiment of wearable apparatus 110 securable to an article of clothing. As illustrated in FIG. 12, connector 730 may include a first magnet 731 and a second magnet 732. First magnet 731 and second magnet 732 may secure capturing unit 710 to power unit 720 with the article of clothing positioned between first magnet 731 and second magnet 732. In embodiments including first magnet 731 and second magnet 732, power cable 760 and data cable 770 may also be included. In these embodiments, power cable 760 and data cable 770 may be of any length, and may provide a flexible power and data connection between capturing unit 710 and power unit 720. Embodiments including first magnet 731 and second magnet 732 may further include a flexible PCB 765 connection in addition to or instead of power cable 760 and/or data cable 770. In some embodiments, first magnet 731 or second magnet 732 may be replaced by an object comprising a metal material.

Figure 13:
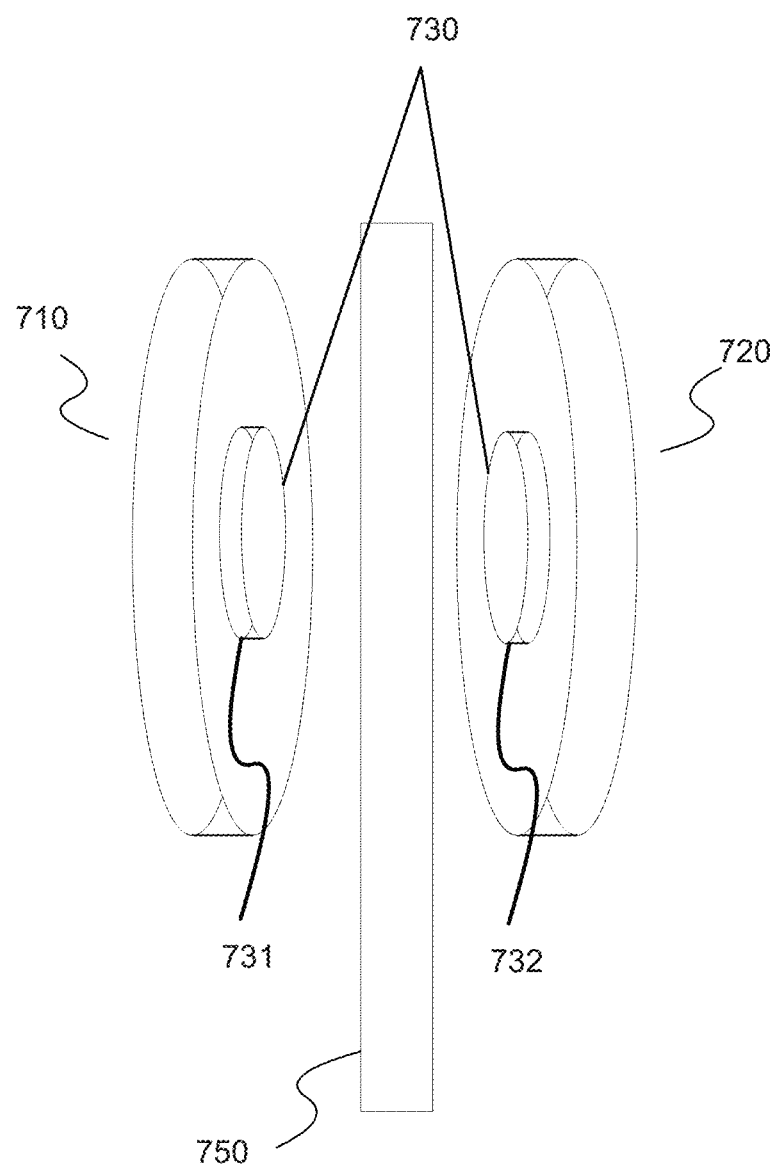
FIG. 13 is a schematic illustration of an embodiment of a wearable apparatus securable to an article of clothing consistent with the present disclosure.

FIG. 13 is a schematic illustration of yet another embodiment of a wearable apparatus 110 securable to an article of clothing. FIG. 13 illustrates an embodiment wherein power and data may be wirelessly transferred between capturing unit 710 and power unit 720. As illustrated in FIG. 13, first magnet 731 and second magnet 732 may be provided as connector 730 to secure capturing unit 710 and power unit 720 to an article of clothing 750. Power and/or data may be transferred between capturing unit 710 and power unit 720 via any suitable wireless technology, for example, magnetic and/or capacitive coupling, near field communication technologies, radiofrequency transfer, and any other wireless technology suitable for transferring data and/or power across short distances.

Figure 14:
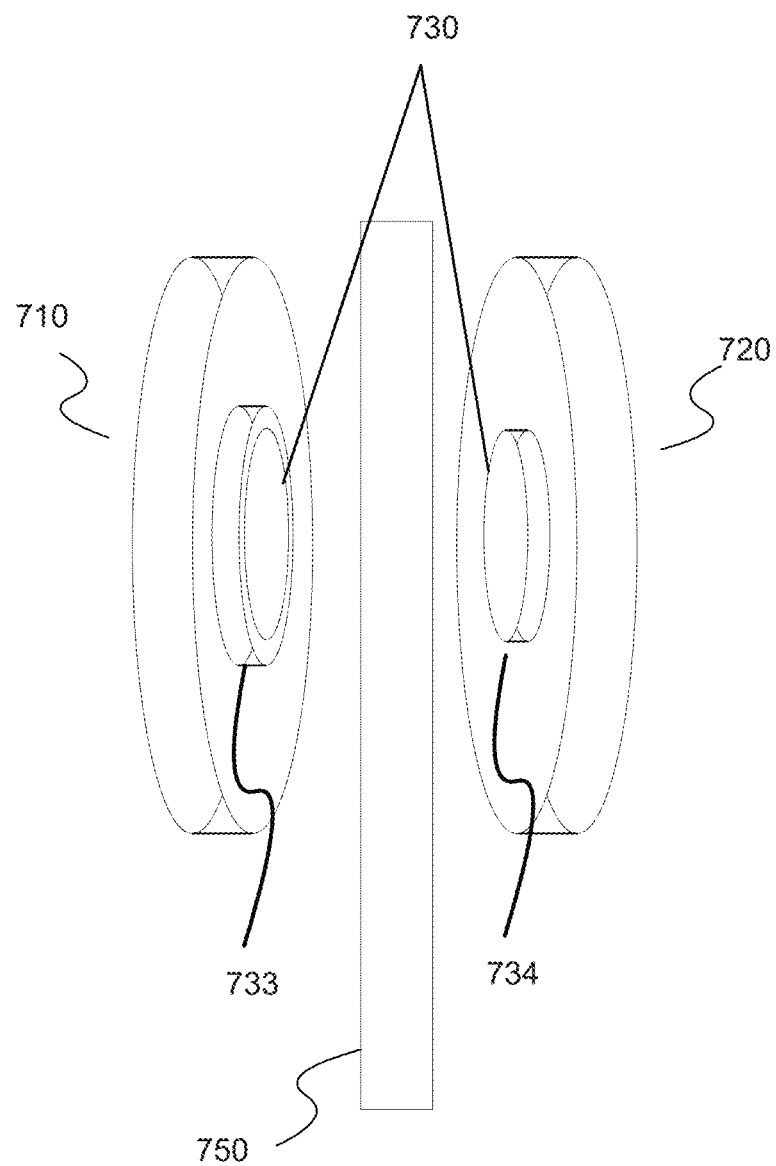
FIG. 14 is a schematic illustration of an embodiment of a wearable apparatus securable to an article of clothing consistent with the present disclosure.

FIG. 14 illustrates still another embodiment of wearable apparatus 110 securable to an article of clothing 750 of a user. As illustrated in FIG. 14, connector 730 may include features designed for a contact fit. For example, capturing unit 710 may include a ring 733 with a hollow center having a diameter slightly larger than a disk-shaped protrusion 734 located on power unit 720. When pressed together with fabric of an article of clothing 750 between them, disk-shaped protrusion 734 may fit tightly inside ring 733, securing capturing unit 710 to power unit 720. FIG. 14 illustrates an embodiment that does not include any cabling or other physical connection between capturing unit 710 and power unit 720. In this embodiment, capturing unit 710 and power unit 720 may transfer power and data wirelessly. In alternative embodiments, capturing unit 710 and power unit 720 may transfer power and data via at least one of cable 760, data cable 770, and flexible printed circuit board 765.

Figure 15:
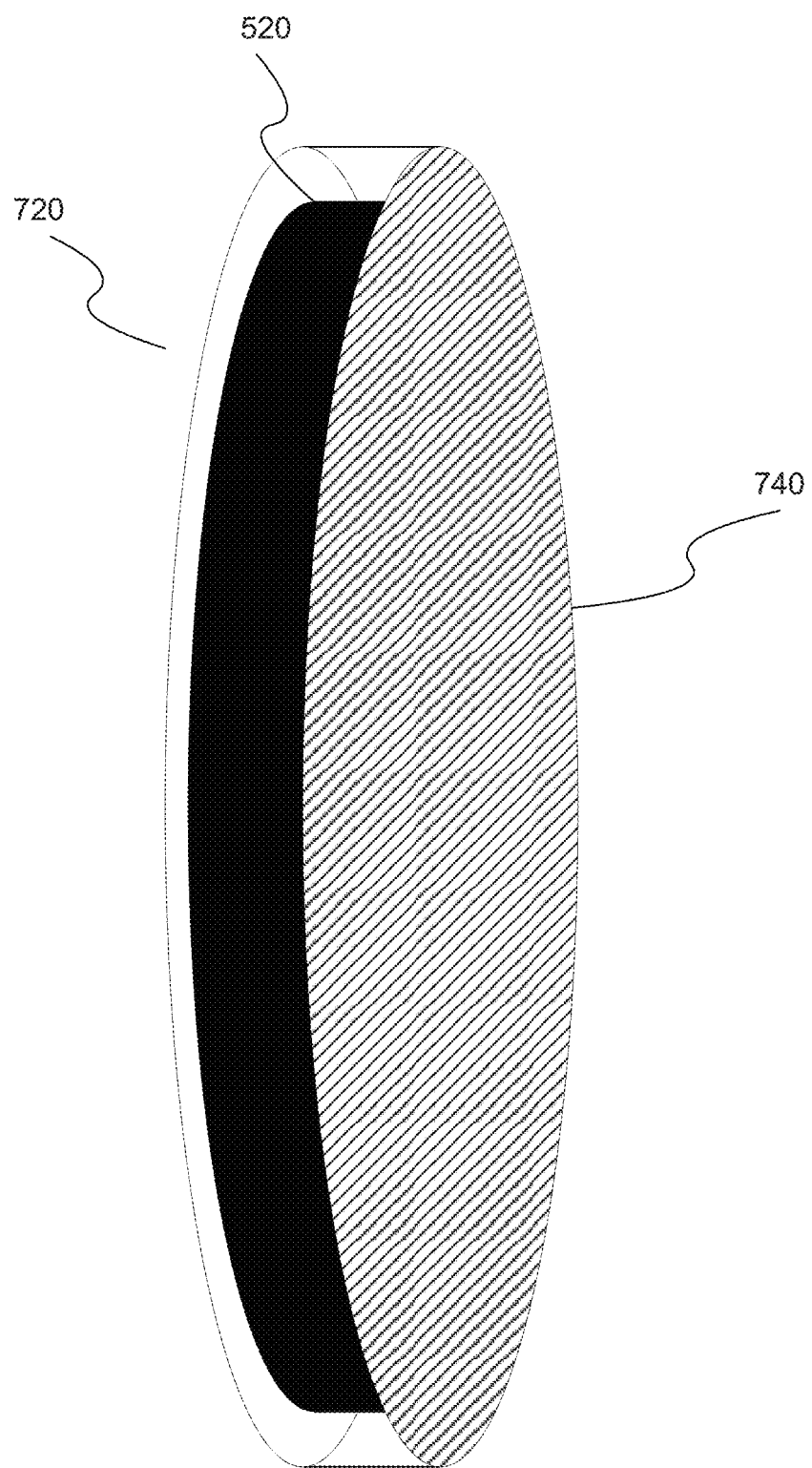
FIG. 15 is a schematic illustration of an embodiment of a wearable apparatus power unit including a power source.

FIG. 15 illustrates another aspect of power unit 720 consistent with embodiments described herein. Power unit 720 may be configured to be positioned directly against the user's skin. To facilitate such positioning, power unit 720 may further include at least one surface coated with a biocompatible material 740. Biocompatible materials 740 may include materials that will not negatively react with the skin of the user when worn against the skin for extended periods of time. Such materials may include, for example, silicone, PTFE, kapton, polyimide, titanium, nitinol, platinum, and others. Also as illustrated in FIG. 15, power unit 720 may be sized such that an inner volume of the power unit is substantially filled by mobile power source 520. That is, in some embodiments, the inner volume of power unit 720 may be such that the volume does not accommodate any additional components except for mobile power source 520. In some embodiments, mobile power source 520 may take advantage of its close proximity to the skin of user's skin. For example, mobile power source 520 may use the Peltier effect to produce power and/or charge the power source.

Figure 16:
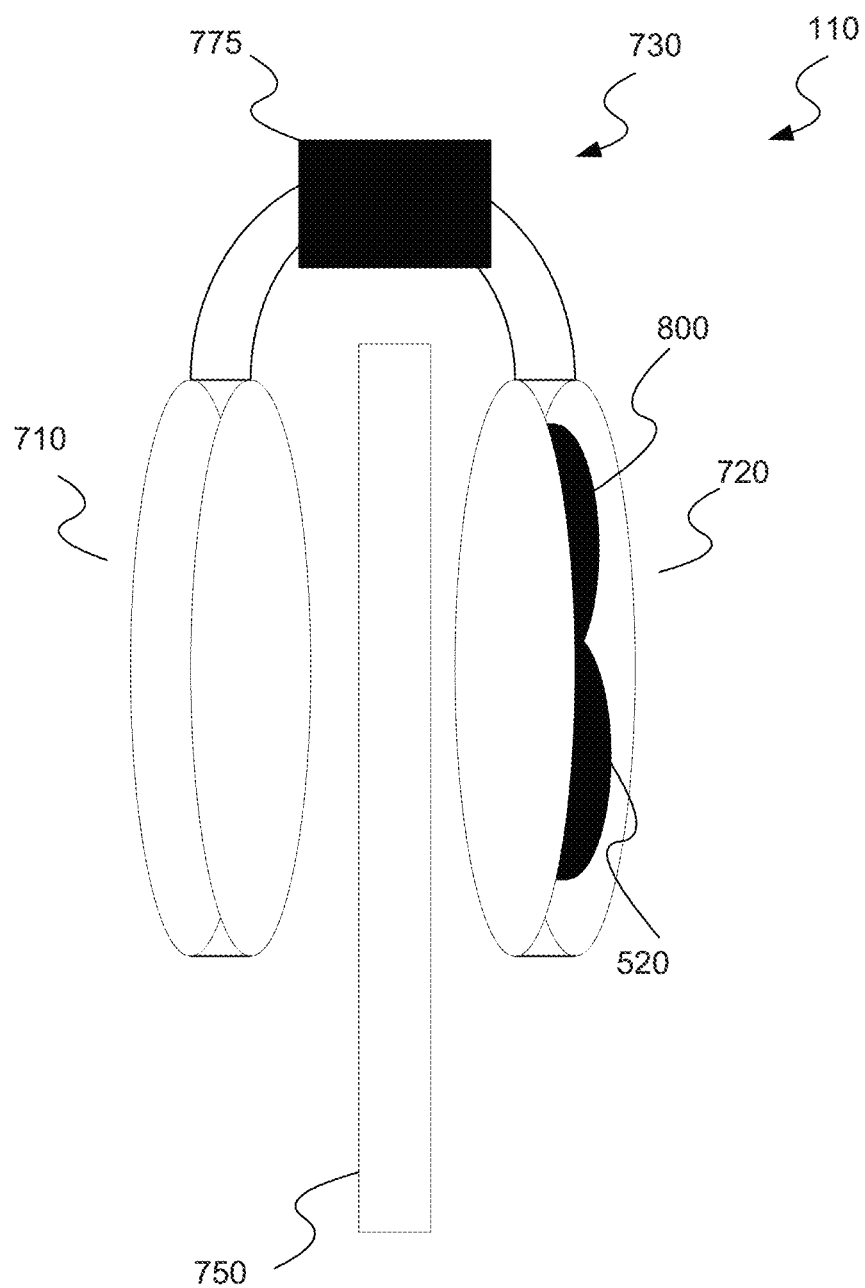
FIG. 16 is a schematic illustration of an exemplary embodiment of a wearable apparatus including protective circuitry.

In further embodiments, an apparatus securable to an article of clothing may further include protective circuitry associated with power source 520 housed in power unit 720. FIG. 16 illustrates an exemplary embodiment including protective circuitry 775. As illustrated in FIG. 16, protective circuitry 775 may be located remotely with respect to power unit 720. In alternative embodiments, protective circuitry 775 may also be located in capturing unit 710, on flexible printed circuit board 765, or in power unit 720.

Protective circuitry 775 may be configured to protect image sensor 220 and/or other elements of capturing unit 710 from potentially dangerous currents and/or voltages produced by mobile power source 520. Protective circuitry 775 may include passive components such as capacitors, resistors, diodes, inductors, etc., to provide protection to elements of capturing unit 710. In some embodiments, protective circuitry 775 may also include active components, such as transistors, to provide protection to elements of capturing unit 710. For example, in some embodiments, protective circuitry 775 may comprise one or more resistors serving as fuses. Each fuse may comprise a wire or strip that melts (thereby braking a connection between circuitry of image capturing unit 710 and circuitry of power unit 720) when current flowing through the fuse exceeds a predetermined limit (e.g., 500 milliamps, 900 milliamps, 1 amp, 1.1 amps, 2 amp, 2.1 amps, 3 amps, etc.) Any or all of the previously described embodiments may incorporate protective circuitry 775.

In some embodiments, the wearable apparatus may transmit data to a computing device (e.g., a smartphone, tablet, watch, computer, etc.) over one or more networks via any known wireless standard (e.g., cellular, Wi-Fi, Bluetooth®, etc.), or via near-filed capacitive coupling, other short range wireless techniques, or via a wired connection. Similarly, the wearable apparatus may receive data from the computing device over one or more networks via any known wireless standard (e.g., cellular, Wi-Fi, Bluetooth®, etc.), or via near-field capacitive coupling, other short range wireless techniques, or via a wired connection. The data transmitted to the wearable apparatus and/or received by the wireless apparatus may include images, portions of images, identifiers related to information appearing in analyzed images or associated with analyzed audio, or any other data representing image and/or audio data. For example, an image may be analyzed and an identifier related to an activity occurring in the image may be transmitted to the computing device (e.g., the "paired device"). In the embodiments described herein, the wearable apparatus may process images and/or audio locally (on board the wearable apparatus) and/or remotely (via a computing device). Further, in the embodiments described herein, the wearable apparatus may transmit data related to the analysis of images and/or audio to a computing device for further analysis, display, and/or transmission to another device (e.g., a paired device). Further, a paired device may execute one or more applications (apps) to process, display, and/or analyze data (e.g., identifiers, text, images, audio, etc.) received from the wearable apparatus.

Some of the disclosed embodiments may involve systems, devices, methods, and software products for determining at least one keyword. For example, at least one keyword may be determined based on data collected by apparatus 110. At least one search query may be determined based on the at least one keyword. The at least one search query may be transmitted to a search engine.

In some embodiments, at least one keyword may be determined based on at least one or more images captured by image sensor 220. In some cases, the at least one keyword may be selected from a keywords pool stored in memory. In some cases, optical character recognition (OCR) may be performed on at least one image captured by image sensor 220, and the at least one keyword may be determined based on the OCR result. In some cases, at least one image captured by image sensor 220 may be analyzed to recognize: a person, an object, a location, a scene, and so forth. Further, the at least one keyword may be determined based on the recognized person, object, location, scene, etc. For example, the at least one keyword may comprise: a person's name, an object's name, a place's name, a date, a sport team's name, a movie's name, a book's name, and so forth.

In some embodiments, at least one keyword may be determined based on the user's behavior. The user's behavior may be determined based on an analysis of the one or more images captured by image sensor 220. In some embodiments, at least one keyword may be determined based on activities of a user and/or other person. The one or more images captured by image sensor 220 may be analyzed to identify the activities of the user and/or the other person who appears in one or more images captured by image sensor 220. In some embodiments, at least one keyword may be determined based on at least one or more audio segments captured by apparatus 110. In some embodiments, at least one keyword may be determined based on at least GPS information associated with the user. In some embodiments, at least one keyword may be determined based on at least the current time and/or date.

In some embodiments, at least one search query may be determined based on at least one keyword. In some cases, the at least one search query may comprise the at least one keyword. In some cases, the at least one search query may comprise the at least one keyword and additional keywords provided by the user. In some cases, the at least one search query may comprise the at least one keyword and one or more images, such as images captured by image sensor 220. In some cases, the at least one search query may comprise the at least one keyword and one or more audio segments, such as audio segments captured by apparatus 110.

In some embodiments, the at least one search query may be transmitted to a search engine. In some embodiments, search results provided by the search engine in response to the at least one search query may be provided to the user. In some embodiments, the at least one search query may be used to access a database.

For example, in one embodiment, the keywords may include a name of a type of food, such as quinoa, or a brand name of a food product; and the search will output information related to desirable quantities of consumption, facts about the nutritional profile, and so forth. In another example, in one embodiment, the keywords may include a name of a restaurant, and the search will output information related to the restaurant, such as a menu, opening hours, reviews, and so forth. The name of the restaurant may be obtained using OCR on an image of signage, using GPS information, and so forth. In another example, in one embodiment, the keywords may include a name of a person, and the search will provide information from a social network profile of the person. The name of the person may be obtained using OCR on an image of a name tag attached to the person's shirt, using face recognition algorithms, and so forth. In another example, in one embodiment, the keywords may include a name of a book, and the search will output information related to the book, such as reviews, sales statistics, information regarding the author of the book, and so forth. In another example, in one embodiment, the keywords may include a name of a movie, and the search will output information related to the movie, such as reviews, box office statistics, information regarding the cast of the movie, show times, and so forth. In another example, in one embodiment, the keywords may include a name of a sport team, and the search will output information related to the sport team, such as statistics, latest results, future schedule, information regarding the players of the sport team, and so forth. For example, the name of the sport team may be obtained using audio recognition algorithms.

Generating and Displaying Face Clouds

As used herein, a "face cloud" refers to any arrangement of a plurality of visual representations of people's faces, where the arrangement is determined, at least in part, by one or more parameters and not randomly. For example, as explained below, linking attributes may be used to arrange the plurality of visual representations in a face cloud.

In some embodiments, a wearable apparatus of the present disclosure may generate a customized user interface comprising a face cloud. The face cloud may be displayed over a display device comprised in or associated with the wearable apparatus. The face cloud may improve the user experience by providing a visual interface that summarizes a user's interactions. Accordingly, embodiments of the present disclosure provide for improved display interfaces, particularly for wearable devices.

Some embodiments of the present disclosure, rather than using conventional user interface methods to display a generic list of people, instead use a specific manner of displaying a limited set of information to the user in a visual and easily perceptible manner. Extant interfaces for summarizing a user's interactions are heavily text-based and difficult to manipulate. Accordingly, embodiments of the present disclosure provide for improved display interfaces that are organized visually and allow for easy manipulation by the user.

Figure 17:
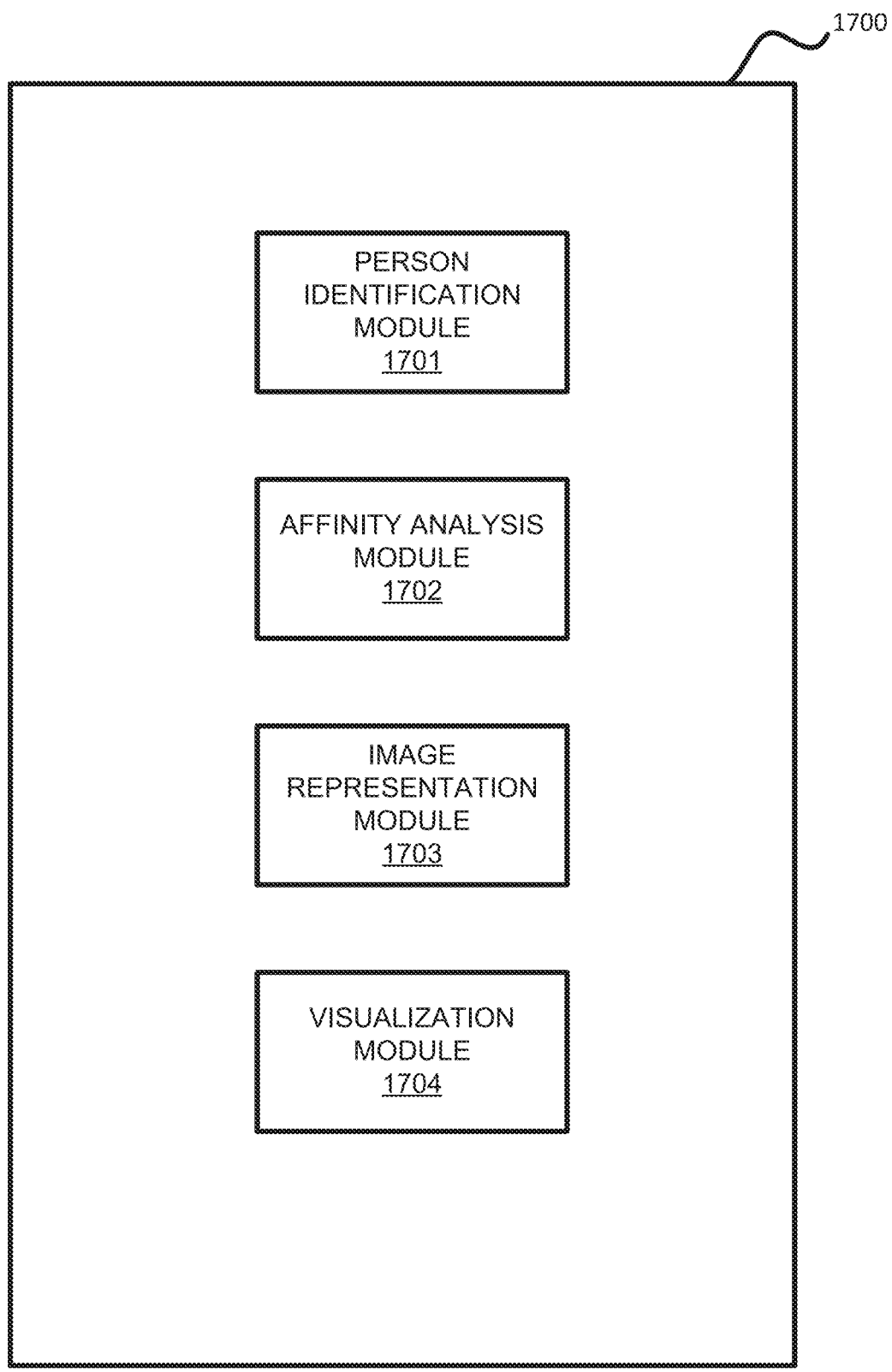
FIG. 17 illustrates an exemplary embodiment of a memory containing software modules for generating a face cloud consistent with the present disclosure.

FIG. 17 illustrates an exemplary embodiment of a memory containing software modules consistent with the present disclosure. Included in memory 1700 are person identification module 1701, affinity analysis module 1702, image representation module 1703, and visualization module 1704. Modules 1701, 1702, 1703, and 1704 may contain software instructions for execution by at least one processing device, e.g., processor 210, included with a wearable apparatus. In some embodiments, memory 1700 may comprise a non-transitory computer readable medium that resides on a mobile communications device (e.g., a smart phone) configured to be wirelessly paired with wearable image sensor 220 of capturing unit 710.

Person identification module 1701, affinity analysis module 1702, image representation module 1703, and visualization module 1704 may cooperate to generate and present face clouds to a user of wireless apparatus 110, as well as cooperating to allow interaction therewith. Memory 1700 may be separate from and/or integrated with memory 550 of FIG. 6, described above. Similarly, orientation identification module 601, orientation adjustment module 602, and monitoring module 603 of FIG. 6 may operate in tandem or concurrently with person identification module 1701, affinity analysis module 1702, image representation module 1703, and visualization module 1704 of FIG. 17.

Person identification module 1701 may be configured to receive a plurality of images from an environment of a user of wearable apparatus 110 captured by image sensor 220 of capturing unit 710 and analyze the plurality of images to identify a plurality of people. As discussed herein, received images or facial images may vary in size, shape, and content. For example, in some embodiments, an image including a wider scene (e.g., a plurality of individuals, or an individual and his or her surrounding environment) may be cropped or otherwise truncated to a face, a portion of a face, a headshot of a person (e.g., head and shoulders), or a portion of a person's body including the person's face. In other embodiments, received images may include such wider scenes (e.g., a plurality of individuals, or an individual and his or her surrounding environment). In still other embodiments, received images may include a face, a portion of a face, a headshot of a person (e.g., head and shoulders), or a portion of a person's body including the person's face.

Person identification module 1701 may identify persons in received images using any known techniques. For example, person identification module 1701 may perform image processing on a currently received facial image and determine that the received facial image corresponds to a face of a recognized individual whose facial image has been previously stored in memory. Thus, person identification module 1701 may perform pixel-by-pixel matching. In other embodiments, person identification module 1701 may perform more sophisticated techniques. For example, person identification module 1701 may use one or more classifiers (or cascading classifiers) to derive an identity of a person included in the plurality of images. Additionally or alternatively, person identification module 1701 may use a neural network to identify one or more likely identifications of a person included in the plurality of images. Alternatively, person identification module 1701 may use a neural network to derive a plurality of features (e.g., a feature set) from one or more of the images and then map the derived features (or feature set) onto one or more likely identifications. The mapping may be performed using simple correlation or using more sophisticated techniques, such as another neural network.

In any of the embodiments above, likely matches may have associated probabilities, e.g., output from the neural network; calculated based on percentage of matching pixels, features, etc.; or the like. Accordingly, person identification module 1701 may select an identification of a person from a plurality of likely matches by selecting the highest probability match.

In any of the embodiments above, one or more of the plurality of images may include more than one person or no persons. Person identification module 1701 may therefore use a bounding box architecture, such as You Only Look Once (YOLO) or Single-Shot Detector (SSD), to identify bounding boxes including a person therein. For example, if person identification module 1701 uses a bounding box architecture and receives no bounding boxes classified as persons or receives bounding boxes all having person classifications below a threshold (e.g., less than 50%, less than 40%, less than 25%, less than 10%, less than 5%, or the like), person identification module 1701 may discard the image out of the plurality of images as including no persons. Similarly, if person identification module 1701 uses a bounding box architecture and receives a plurality of bounding boxes classified as persons or receives a plurality of bounding boxes having person classifications above a threshold (e.g., more than 50%, more than 40%, more than 25%, more than 10%, more than 5%, or the like), person identification module 1701 may perform identification on portions of the image defined by the plurality of bounding boxes.

In any of the embodiments above, person identification module 1701 may replace for use in a face cloud or other visualization (e.g., generated by visualization module 1704), a previously stored facial image with a currently received facial image. Accordingly, person identification module 1701 may ensure that stored facial images are up-to-date. In such embodiments, person identification module 1701 may update the stored facial image only if the one or more quality measures of the currently received facial image exceed one or more quality measures of the previously stored facial image. For example, in some embodiments, person identification module 1701 may update the stored facial image only if a resolution, a sharpness, a peak signal to noise ratio (PSNR), a structural similarity (SSIM), a visual information fidelity (VIF), or the like of the currently received facial image are higher than the same (or a similar) measure for the previously stored facial image. In another example, person identification module 1701 may update the stored facial image only if a noise or the like of the currently received facial image are lower than the same (or a similar) measure for the previously stored facial image.

In any of the embodiments above, person identification module 1701 may receive a plurality of facial images including a plurality of facial images of a same individual. In such embodiments, person identification module 1701 may perform image processing on the plurality of images of the same individual to determine an existence of a plurality of images of the same individual, and select a single image of the individual for use (e.g., for presentation in a face cloud determined by visualization module 1704).

Affinity analysis module 1702 may be configured to analyze the plurality of images to determine an affinity level between the user and each of the plurality of people. For example, affinity analysis module 1702 may analyze the plurality of images received by person identification module 1701. Affinity analysis module 1702 may calculate the affinity level based on a relationship between the user of wearable apparatus 110 and individuals identified by person identification module 1701. For example, affinity analysis module 1702 may determine whether the user and the identified person are family (e.g., siblings, parents, grandparents, cousins, or the like), friends, coworkers, or the like. In such embodiments, affinity analysis module 1702 may use information from one or more social media accounts of the user (e.g., Facebook, Instagram, Twitter, or the like) to assist with determining the relationship.

Additionally or alternatively, affinity analysis module 1702 may determine the affinity level in accordance with a time or frequency at which the facial image was captured. Thus, affinity analysis module 1702 may determine the affinity level based on a number of interactions between the user and the identified person. For example, affinity analysis module 1702 may determine how many times the user had an interaction with the identified person during the last day, the last week, the last month, or the like. Accordingly, affinity analysis module 1702 may use historical information about the user (e.g., previous images, videos, audio, or the like) to determine the number of interactions. Additionally or alternatively, affinity analysis module 1702 may use a time of capture and/or a place of capture of images in which the identified person appears to determine an affinity level. For example, a person appearing in an image captured at home may be determined to have a higher affinity level than a person appearing in an image captured at a bar or a club. In another example, a person appearing in an image captured during dinner may be determined to have a higher affinity level than a person appearing in an image captured during a work day. Additionally or alternatively, the user may indicate levels of affinity with identified persons, e.g., by grouping known persons into clusters such as "friends," "acquaintances," or the like.

In some embodiments, affinity analysis module 1702 may operate without person identification module 1701. For example, affinity analysis module 1702 may receive, from wearable image sensor 220 of capturing unit 710, a plurality of facial images of individuals with whom a user of wearable apparatus 110 interacted and may store, in association with each of the plurality of facial images, at least one linking attribute. In such an example, the at least one linking attribute may include at least one of an environmental characteristic, a geographical location, an associated word, a social interconnection, or a temporal indicator.

The environmental characteristic may include at least one of a background characteristic and an object in a vicinity of a facial image. For example, the environmental characteristic may include a brightness of the background such that the linking attribute may include 'inside' or 'outside.' In another example, the environmental characteristic may include an object such as a coffee cup such that the linking attribute includes 'coffee.' An example of the latter is depicted in FIG. 18F, described below.

The geographical location may include at least one of an event, a physical space, and a GPS coordinate. For example, the geographical location may include a 'work retreat' or 'concert.' In another example, the geographical location may include a 'coffee shop' or a 'neighbor's house.' An example of this is depicted in FIG. 18E, described below.

An associated word may include at least one of a word derived from a sound file associated with a facial image and a word previously associated with an individual of the facial image. A microphone of wearable apparatus 110 may capture the sound file and time stamp of the sound file such that it may be synchronized with time stamps of images received from wearable apparatus 110. In one example, affinity analysis module 1702 may receive a list of words parsed from a sound file captured during a time period associated with detection of a presence of the plurality of individuals in a vicinity of the wearer and associate in memory, the list of parsed words with a corresponding individual. The words may be parsed using any audio analysis technique, such as limited vocabulary recognition, large vocabulary recognition, with or without speaker separation, recognition, verification, or the like. In some embodiments, the voice analysis operations may be enhanced in accordance with training one or more engines upon the user's voice and optionally the voices of people close to the user, such as the user's spouse. Accordingly, affinity analysis module 1702 may transcribe the sound file in order to parse words therefrom and then store the parsed words in association with corresponding facial images.

Additionally or alternatively, affinity analysis module 1702 may associate in memory a frequency of use indication associated with each parsed word. For example, the frequency of use indication may include a histogram associated with each word in a word list. Accordingly, the word list may include key words extracted from a conversation. In such embodiments, affinity analysis module 1702 may eliminate common words such as articles ('the,' 'a,' 'an,' or the like), prepositions ('of,' 'from,' 'to,' or the like), or the like from the histogram (or before determining the histogram).

The social interconnection may include at least one of an individual detected proximate a field of view of a facial image and otherwise recognized individuals. For example, an individual detected proximate to other recognized individuals (e.g., matching one or more known individuals in memory) may be determined as having a social interconnection with the other recognized individuals. Additionally or alternatively, as explained above, affinity analysis module 1702 may use social media information to determine social interconnections. For example, individuals may be determined to have social interconnections based on the level of connection between a recognized individual and the user.

The temporal indicator may include at least one of a date and a time stamp associated with a facial image. For example, facial images having time stamps and/or date stamps that are the same (or are in proximity, e.g., within 15 minutes, within an hour, within a day, within a week, or the like) may be linked together.

These embodiments may be combined with corresponding identifications from person identification module 1701. For example, affinity analysis module 1702 may store, in association with each of the plurality of facial images identified by person identification module 1701, the at least one linking attribute. Affinity analysis module 1702 may also store the corresponding identification from person identification module 1701 in association with each of the plurality of facial images.

In any of the embodiments above, linking attributes may be associated with each individual in a histographic manner. For example, each individual (e.g., identified by person identification module 1701) may have an associated histogram including one or more linking attributes. The histogram may indicate the level of connection between the individual and the user (and/or other individuals) based on each linking attribute. Additionally or alternatively, affinity analysis module 1702 may use the histogram to determine the level of connection between the individual and the user (and/or other individuals) based on each linking attribute in the histogram. For example, affinity analysis module 1702 may use one or more word frequencies included in the histogram to link individuals having histograms with the same words (or similar words, such as synonyms) having the same or similar (e.g., within 1 word per day, within 5 words per day, or the like) frequencies.

Image representation module 1703 may be configured to obtain an image representation of each of the plurality of people. For example, image representation module 1703 may obtain image representations from a memory storing a plurality of image representations indexed by identification. Accordingly, image representation module 1703 may obtain images based on identifications from person identification module 1701.

In embodiments where affinity analysis module 1702 calculates or obtains a list of words parsed from a sound file, image representation module 1703 may select a specific parsed word and choose the subset of facial images for display based on the selection. For example, image representation module 1703 may select the specific parsed word, obtain a list of individuals based on stored associations between individuals and parsed words, and obtain image representations of the list of individuals. In embodiments where each individual has an associated histogram, image representation module 1703 may select the specific parsed word, obtain a list of individuals based on stored histograms associated with individuals, and obtain image representations of the list of individuals.

In some embodiments, the selecting may occur as a result of input from the user, based on context in a current environment of the user, based on words used in a current conversation, or based on an object in a recent field of view of the wearable image sensor. For example, the user may input the selected word that image representation module 1703 uses, to obtain a list of individuals and corresponding image representations. In another example, a context in an environment of the user of wearable apparatus 110 may include a location (such as work, a store, a coffee shop, or the like), one or more recognized individuals, one or more words (e.g., printed on a sign in the environment), or the like. Accordingly, a description of the location, a relationship between the recognized individual(s) and the user, a word in the environment, or the like, may be selected as the selected word. In yet another example, a word used in a current conversation (e.g., recorded by a microphone of wearable apparatus 110) may be selected as the selected word. Image representation module 1703 may be configured to select a word most frequently used in a current conversation but may also eliminate common words such as articles, prepositions, or the like and/or proper names. In another example, an object identified by wearable apparatus 110, such as a 'coffee,' 'cake,' a 'file,' or the like, may be selected as the selected word.

Visualization module 1704 may be configured to generate, based on the affinity levels (e.g., determined by affinity analysis module 1702), a visualization comprising the image representations (e.g., obtained by image representation module 1703). Additionally or alternatively, visualization module 1704 may cause a visual representation to be displayed, the visual representation including the plurality of facial images, and the plurality of facial images being arranged based on the at least one linking attribute. In some embodiments, the visual representation may comprise a face cloud such that visualization module 1704 is configured to display, in a face cloud, the plurality of facial images, the plurality of facial images being arranged based on the at least one linking attribute.

In embodiments where linking attributes are associated with each individual in a histographic manner, during display, the facial images may be arranged based on histographic strength. For example, facial images with stronger historgraphic strength may be arranged in proximity to each other, closer to a focal point, or the like. Additionally or alternatively, during display, facial images of individuals with greater histographic strength may be displayed larger, more prominently, and/or with a different shape than facial images of individuals with lesser histographic strength.

Additionally or alternatively, a prominence level in the visualization of at least one of the image representations of a person from among the plurality of people may depend on the affinity level associated with the person. For example, the prominence level may be indicated in the visualization by at least one of size, shape, and color.

Additionally or alternatively, sizes, shapes, and/or colors of facial images may be indicative of time spent with an individual and/or indicative of histographic strength to a linking attribute that is a focal point of the face cloud. For example, visualization module 1704 may increase a size of a facial image if an individual associated with the facial image appears in more images captured by wearable apparatus 110, has more interactions with a user of wearable apparatus 110, or otherwise has spent more time with the user of wearable apparatus 110 than another individual associated with another facial image. Similarly, visualization module 1704 may select a different color or shape of one facial image if an individual associated with the facial image appears in more images captured by wearable apparatus 110, has more interactions with a user of wearable apparatus 110, or otherwise has spent more time with the user of wearable apparatus 110 than another individual associated with another facial image. In another example, example, visualization module 1704 may increase a size of a facial image if a histogram of an individual associated with the facial image has a higher frequency or other measure of a linking attribute than another histogram of another individual associated with another facial image. Similarly, visualization module 1704 may select a different color or shape of one facial image if a histogram of an individual associated with the facial image has a higher frequency or other measure of a linking attribute than another histogram of another individual associated with another facial image.

For example, the linking attributes of each of the facial images may include an importance level. Accordingly, in embodiments where size is adjusted, the facial images may be displayed in different sizes according to the importance levels. For example, people the user meets more often and/or for longer periods of time may be determined to be more important and thus be displayed as larger.

Additionally or alternatively, the linking attribute may include unrecognized individuals. For example, facial images may be adjusted based on a level of connection between associated individuals and one or more unrecognized individuals. The level of connection may be determined using a plurality of measures, e.g., based on a proximity between the associated individuals and the one or more unrecognized individuals in the received images, based on being participants in one or more of the same conversations, based on connections determined using social media information, or any combination thereof.

Additionally or alternatively, the linking attribute may be generated through image analysis to determine context. For example, as explained above, a location (such as work, a coffee shop, or the like), one or more recognized individuals, one or more words (e.g., printed on a sign in the environment), or the like such that the linking attribute comprises the location, a relationship between recognized individuals and the user, the one or more words in the environment, or the like.

Additionally or alternatively, the linking attribute may be determined at least on part, through reference to a calendar of the user. For example, visualization module 1704 may select a location, one or more recognized individuals, one or more words, or the like by mapping time stamps of the received images to one or more events stored in the calendar.

Additionally or alternatively, the linking attribute may be user defined. For example, as explained above, the user may select an environmental characteristic, a geographical location, an associated word, a social interconnection, a temporal indicator, or any other linking attribute.

In any of the embodiments using a linking attribute, visualization module 1704 may, for a given face cloud, display an indication of at least one linking attribute serving as a basis for organization of the face cloud. An example of such an indication is depicted in FIGS. 18C and 18D, described below. In such embodiments, greater commonality to a linking attribute may be indicated on the display through proximity to a focal location of the face cloud.

In any of the embodiments using a word list, as described above with respect to affinity analysis module 1703, visualization module 1704 may present, on a screen of a display (e.g., of wearable apparatus 110 or of a mobile communications device wirelessly paired with wearable apparatus 110), a subset of the plurality of facial images of individuals whose word lists contain overlapping common words.

Additionally or alternatively, the set of the plurality of facial images may be displayed based on a stored set of rules. For example, the stored set of rules may include at least one of most recent (such that only the most recent plurality of facial images are displayed in the face cloud), most often (such that only facial images appearing in a highest number of images captured by wearable device 110 are displayed in the face cloud), and longest duration (such that only facial images being in images captured by wearable device 110 for a longest length of time are displayed in the face cloud).

In any of the embodiments including a face cloud, displaying of the face cloud may include displaying only a portion of the face cloud existing in a focal region. For example, visualization module 1704 may generate a face cloud by organizing and/or arranging facial images according to one or more linking attributes and then select the portion of the face cloud for display based on the focal point and a range extending from the focal point. The range, for example, may comprise a circle, an ellipse, a square, a rhombus, a rectangle, a parallelogram, or any other shape, whether regular or irregular.

In such embodiment, the focal region may be dynamically selected based on a detected variable. For example, the detected variable may include the presence of the mobile communication device in a particular geographical area such that the focal region includes images of individuals previously associated with the particular geographical area. Additionally or alternatively, the detected variable may include the presence of the mobile communication device in a vicinity of a known individual such that the focal region includes images of individuals previously associated with the known individual. Additionally or alternatively, the detected variable may include at least one word derived from a sound file (e.g., recorded by a microphone of wearable apparatus 110) such that the focal region includes images of individuals previously associated with the at least one word.

In any of the embodiments above, causing the visual representation to be displayed may include transmitting information for generating the visualization to a mobile communication device wirelessly paired with the wearable apparatus. For example, visualization module 1704 may transmit the face cloud or any other generated visualization via a computer network, such as Bluetooth®, a WiFi network, a cellular network (such as 3G, 4G, LTE, or the like), or any other radio frequency or other wireless network.

In any of the embodiments above, the face cloud may be displayed in two dimensions or displayed as a virtual 3D representation. For example, the 3D representation may comprise a 3D image displayed on a two-dimensional screen (e.g., of wearable apparatus 110 or of a mobile communications device wirelessly paired with wearable apparatus 110) or may comprise a holographic projection, e.g., formed using one or more lasers.

In some embodiments, the form of the face cloud may include a series of homogeneously sized and shaped facial images arranged in a cluster formation. Additionally or alternatively, the form of the face cloud may include an arrangement of the plurality of facial images in a cluster such that at least one of the facial images has either a size, shape, or color indicator that differs from other facial images in the cluster, as explained above. For example, the form of the face cloud may include an arrangement of the plurality of facial images in a cluster, a prominence level of a facial image from among the plurality of facial images depending on an affinity level between the user and a person depicted in the facial image. Additionally or alternatively, displaying the face cloud may include arranging the facial images in the face cloud such that facial images sharing at least one common linking attribute are displayed or oriented adjacent to each other.

Visualization module 1704 may also be configured to enable interaction with a generated face cloud or other visualization. For example, visualization module 1704 may be configured to enable a user to select a particular facial image to be a focal point of the face cloud. In such an example, visualization module 1704 may allow a user to click, tap, or otherwise select the particular facial image. In such embodiments, visualization module 1704 may receive a designation of a focal point individual such that the input causes a rearrangement of the face cloud while maintaining the focal point individual.

Additionally or alternatively, visualization module 1704 may be configured such that, upon touching a facial image displayed on a touch screen, additional information appears. For example, the additional information may include at least one of name, contact information, and linking attribute information for the selected facial image. In some embodiments, a scope of information presented may depend on duration of pressing and/or a level of pressure applied. For example, visualization module 1704 may display a name associated with the touched facial image if the press is short (e.g., less than 0.5 second) and/or light (e.g., less than 50 pascals) but may display a name, contact information, and the linking attribute if the press is long (e.g., more than 0.5 second) and/or hard (e.g., more than 50 pascals).

Additionally or alternatively, visualization module 1704 may enable a user to select at least one linking attribute, the arrangement of faces in the cloud occurring based on the selected at least one linking attribute. For example, visualization module 1704 may generate a separate interface with a list of linking attributes such that the user may click, tap, or otherwise select a desired linking attribute. In another example, visualization module 1704 may generate a list of linking attributes adjacent to a generated face cloud or other visualization such that the user may click, tap, or otherwise select a desired linking attribute.

Accordingly, input may occur through selection of an attribute from a pick list. Alternatively, input may occur through sound processing on a voice capture, e.g., captured via a microphone of wearable apparatus 110.

In any of the embodiments above, the face cloud may be initially arranged based on at least a first common attribute, and in response to the input, the face cloud may be rearranged based on a second common attribute. An example of such rearrangement is depicted in FIG. 18H, described below.

In any of the embodiments above, the face cloud may be displayed in motion. For example, the face cloud may be displayed as a flow and may move or change as images come and go, such as on a street where people move in various directions. Additionally or alternatively, the face cloud may dynamically change based on a location of the user of wearable device 110 and/or people visible in a field of view of image sensor 220 of capturing unit 710.

In embodiments where modules 1701, 1702, 1703, and 1704 run on a mobile communications device, visualization module 1704 may be configured to rearrange the face cloud in response to an input received via the mobile communications device. For example, visualization module 1704 may receive input including a signal received from an accelerometer in the mobile communications device that is reflective of a shaking of the mobile communications device and rearrange the face cloud accordingly.

Figure 18A:
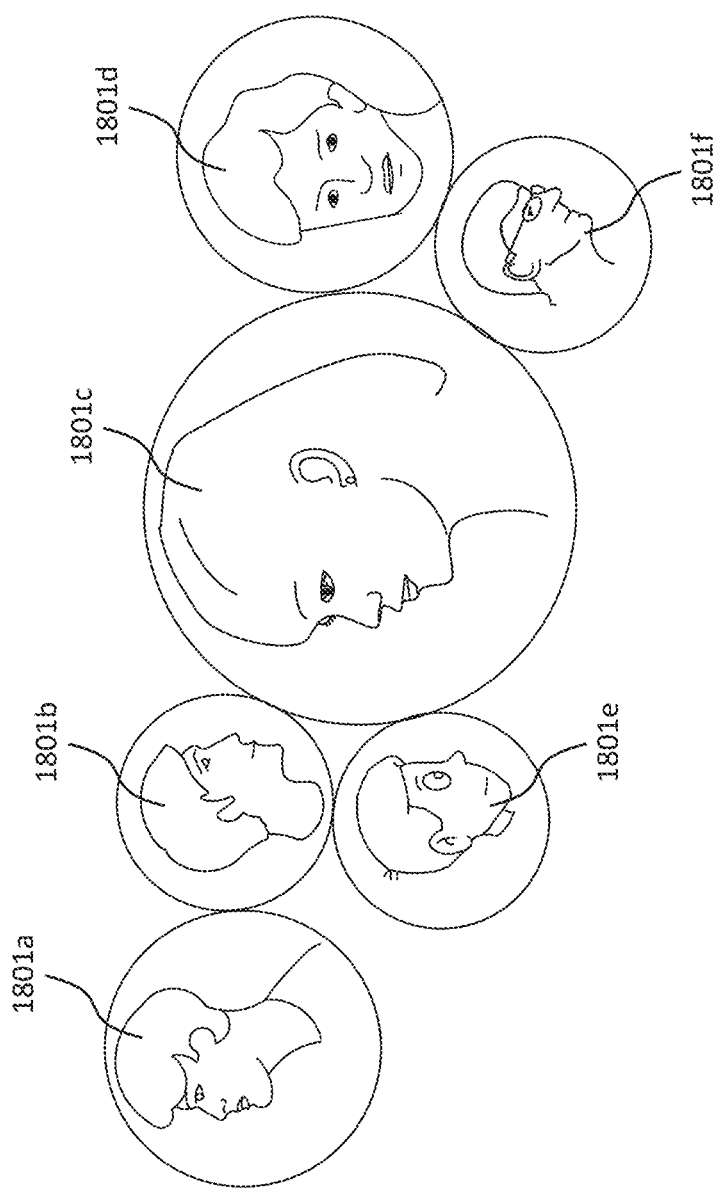
FIG. 18A illustrates an example of a face cloud having prominence levels indicated by size consistent with the present disclosure.

FIG. 18A illustrates an example of a face cloud having prominence levels indicated by size consistent with the present disclosure. For example, as depicted in FIG. 18A, a plurality of facial images (e.g., images 1801a, 1801b, 1801c, 1801d, 1801e, and 1801f) are displayed in a cluster. Although depicted as within shapes (circles in the example of FIG. 18A), the facial images may be displayed without shapes.

In the example of FIG. 18A, the sizes of the facial images (and the shapes enclosing the facial images) vary. For example, the sizes may vary based on prominence levels (e.g., based on affinity levels), importance levels, histographic strength of a linking attribute, or the like, as described above with respect to visualization module 1704 of memory 1700. Although not depicted in FIG. 18A, distances between the facial images and a focal point of the face cloud or between facial images and/or thickness of connecting lines (not pictured) may vary based on prominence levels (e.g., based on affinity levels), importance levels, histographic strength to a linking attribute, or the like, as described above with respect to visualization module 1704 of memory 1700.

Figure 18B:
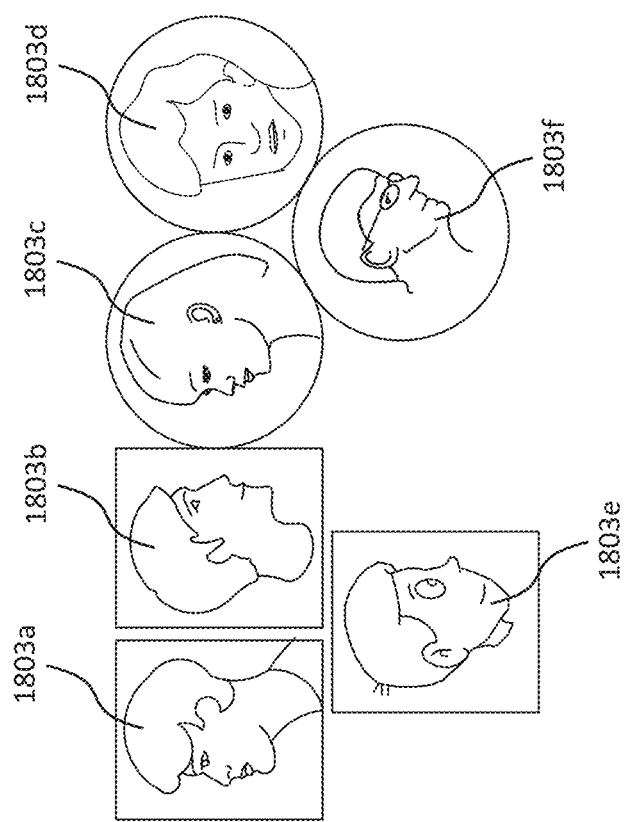
FIG. 18B illustrates an example of a face cloud having prominence levels indicated by shape consistent with the present disclosure.
Figure 18C:
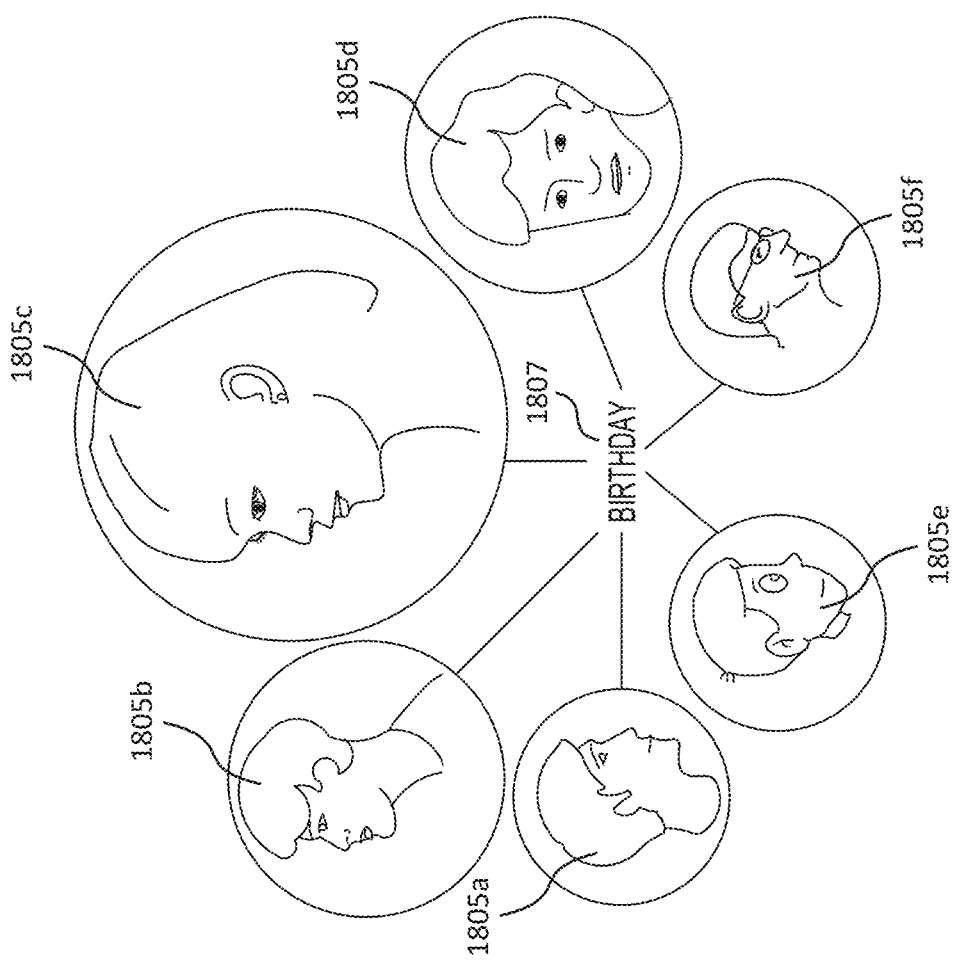
FIG. 18C illustrates an example of a face cloud including a linking word consistent with the present disclosure.
Figure 18D:
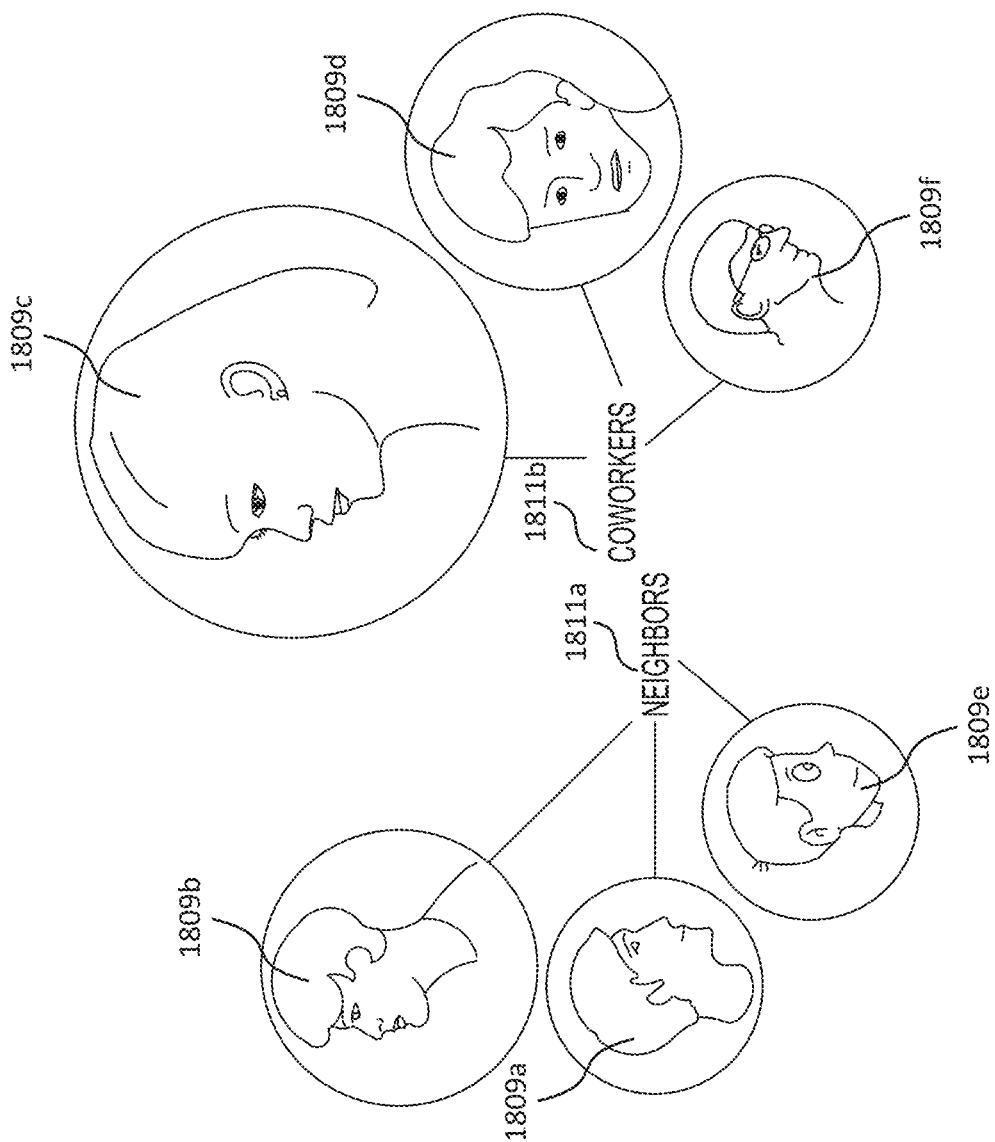
FIG. 18D illustrates an example of a face cloud including a plurality of linking words consistent with the present disclosure.
Figure 18E:
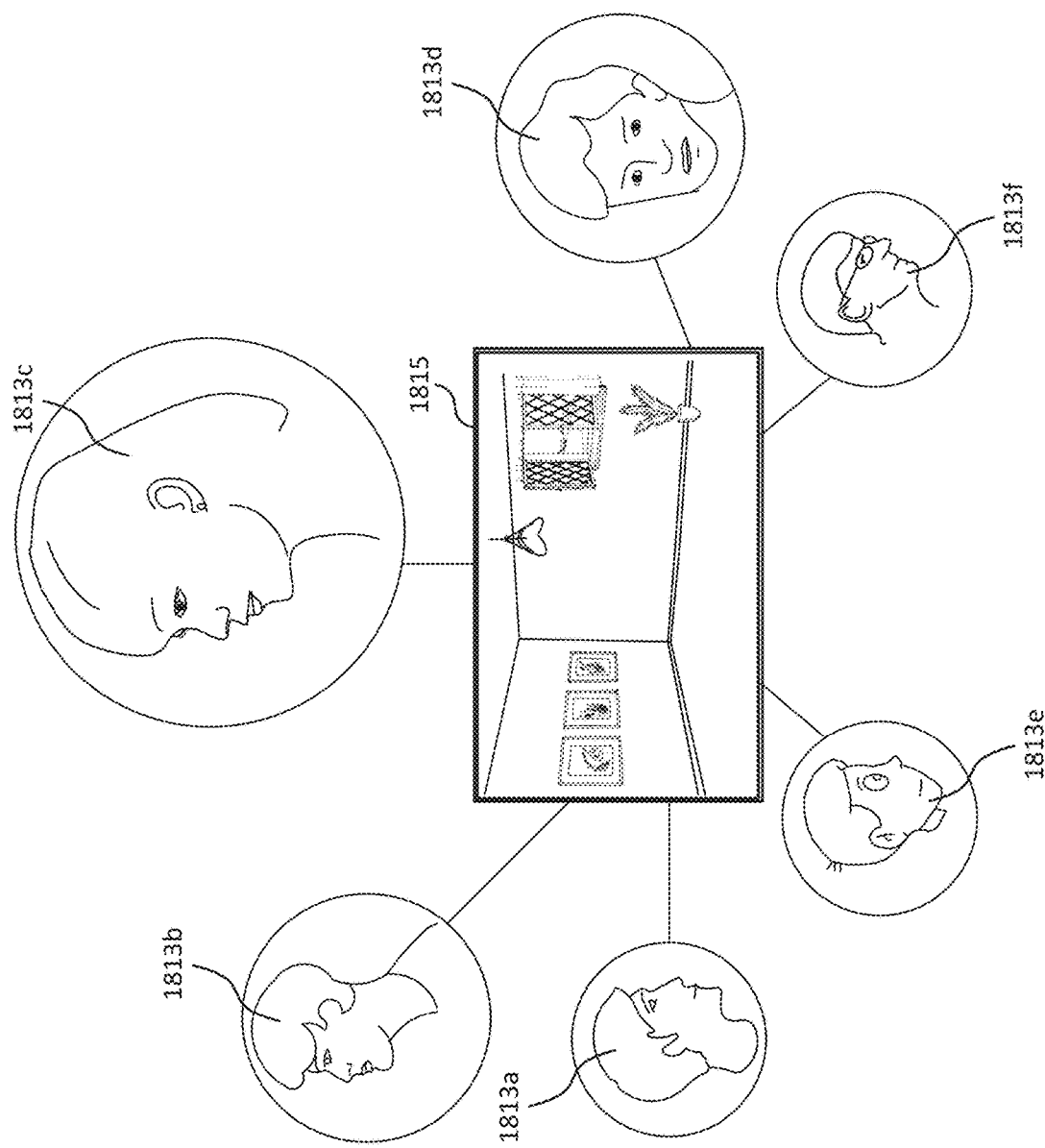
FIG. 18E illustrates an example of a face cloud including a linking geographic location consistent with the present disclosure.
Figure 18F:
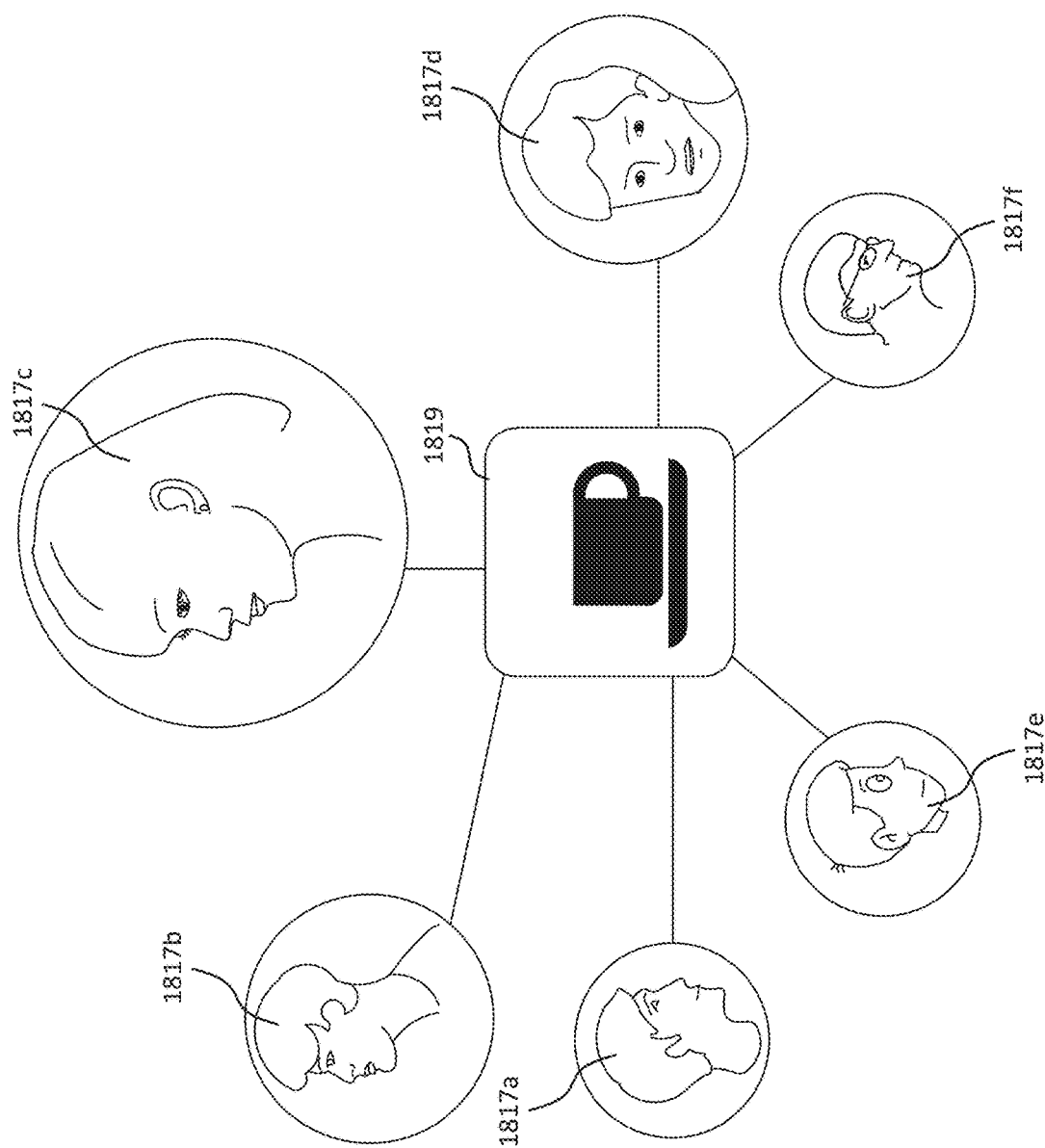
FIG. 18F illustrates an example of a face cloud including a linking environmental characteristic consistent with the present disclosure.

FIG. 18B illustrates an example of a face cloud having prominence levels indicated by shape consistent with the present disclosure. For example, as depicted in FIG. 18B, a plurality of facial images (e.g., images 1803a, 1803b, 1803c, 1803d, 1803e, and 1803f) are displayed in a cluster. Moreover, in the example of FIG. 18B, the shapes enclosing of the facial images vary. For example, the shapes may vary based on prominence levels (e.g., based on affinity levels), importance levels, histographic strength to a linking attribute, or the like, as described above with respect to visualization module 1704 of memory 1700. Although not depicted in FIG. 18B, distances between the facial images and a focal point of the face cloud or between facial images and/or thickness of connecting lines (not pictured) may vary based on prominence levels (e.g., based on affinity levels), importance levels, histographic strength to a linking attribute, or the like, as described above with respect to visualization module 1704 of memory 1700.

FIG. 18C illustrates an example of a face cloud including a linking word consistent with the present disclosure. For example, as depicted in FIG. 18C, a plurality of facial images (e.g., images 1805a, 1805b, 1805c, 1805d, 1805e, and 1805f) are clustered around an indication 1807 of a linking word (e.g., "Birthday"). Although depicted as within shapes (circles in the example of FIG. 18C), the facial images may be displayed without shapes.

In the example of FIG. 18C, the sizes of the facial images (and the shapes enclosing the facial images) vary. For example, the sizes may vary based on histographic strength to a linking attribute, or the like, as described above with respect to visualization module 1704 of memory 1700. As further depicted in FIG. 18C, distances between the facial images and the indication 1807 (or between facial images and/or thickness of connecting lines), vary based on histographic strength to a linking attribute, as described above with respect to visualization module 1704 of memory 1700.

FIG. 18D illustrates an example of a face cloud including a plurality of linking words (e.g., "Neighbors" and "Coworkers") consistent with the present disclosure. For example, as depicted in FIG. 18D, a plurality of facial images (e.g., images 1809a, 1809b, 1809c, 1809d, 1809e, and 1809f) are clustered around indications 1811a and 1811b of linking words. Although depicted as within shapes (circles in the example of FIG. 18D), the facial images may be displayed without shapes.

In the example of FIG. 18D, the sizes of the facial images (and the shapes enclosing the facial images) vary. For example, the sizes may vary based on histographic strength to a linking attribute, or the like, as described above with respect to visualization module 1704 of memory 1700. As further depicted in FIG. 18D, distances between the facial images and the indications 1811a and 1811b (or between facial images and/or thickness of connecting lines) vary based on histographic strength to the corresponding linking attribute, as described above with respect to visualization module 1704 of memory 1700.

FIG. 18E illustrates an example of a face cloud including a linking geographic location consistent with the present disclosure. For example, as depicted in FIG. 18E, a plurality of facial images (e.g., images 1813a, 1813b, 1813c, 1813d, 1813e, and 1813f) are clustered around a geographical location 1815 (e.g., a room, a particular person's home, etc.). Although depicted as within shapes (circles in the example of FIG. 18E), the facial images may be displayed without shapes.

In the example of FIG. 18E, the sizes of the facial images (and the shapes enclosing the facial images) vary. For example, the sizes may vary based on histographic strength to a linking attribute, or the like, as described above with respect to visualization module 1704 of memory 1700. As further depicted in FIG. 18E, distances between the facial images and the geographical location 1815 (or between facial images and/or thickness of connecting lines) vary based on histographic strength to the corresponding linking attribute, as described above with respect to visualization module 1704 of memory 1700.

FIG. 18F illustrates an example of a face cloud including a linking concept or environmental characteristic consistent with the present disclosure. For example, as depicted in FIG. 18F, a plurality of facial images (e.g., images 1817a, 1817b, 1817c, 1817d, 1817e, and 1817f) are clustered around an object 1819 (e.g., a coffee cup). Although depicted as within shapes (circles in the example of FIG. 18F), the facial images may be displayed without shapes.

In the example of FIG. 18F, the sizes of the facial images (and the shapes enclosing the facial images) vary. For example, the sizes may vary based on histographic strength to a linking attribute, or the like, as described above with respect to visualization module 1704 of memory 1700. As further depicted in FIG. 18F, distances between the facial images and the object 1819 (or between facial images and/or thickness of connecting lines) vary based on histographic strength to the corresponding linking attribute, as described above with respect to visualization module 1704 of memory 1700.

Figure 18G:
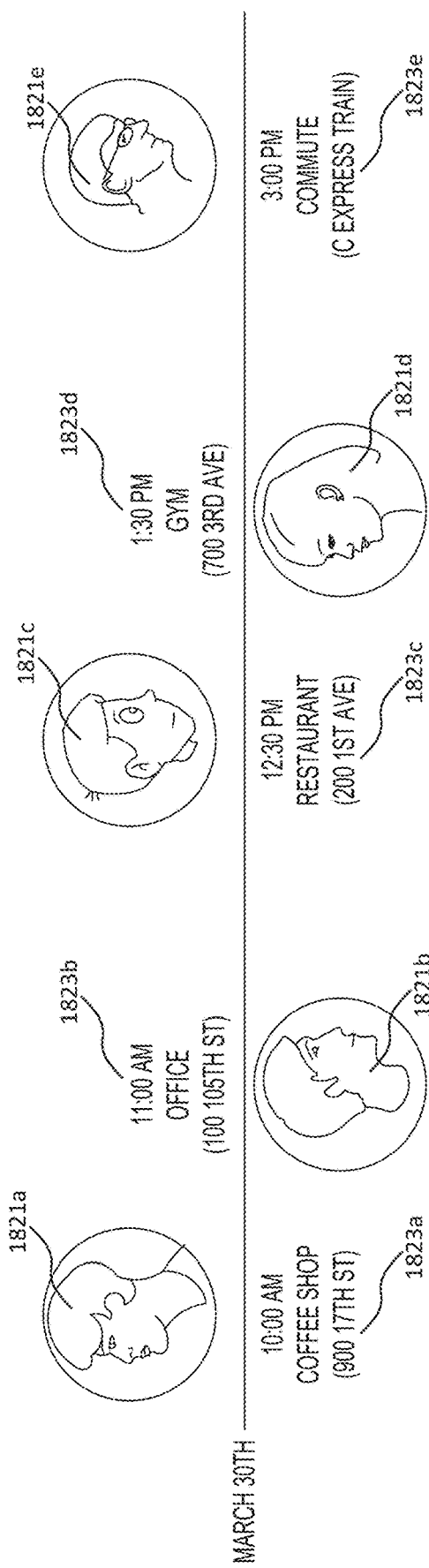
FIG. 18G illustrates an example of a face cloud organized using a temporal indicator consistent with the present disclosure.
Figure 18H:
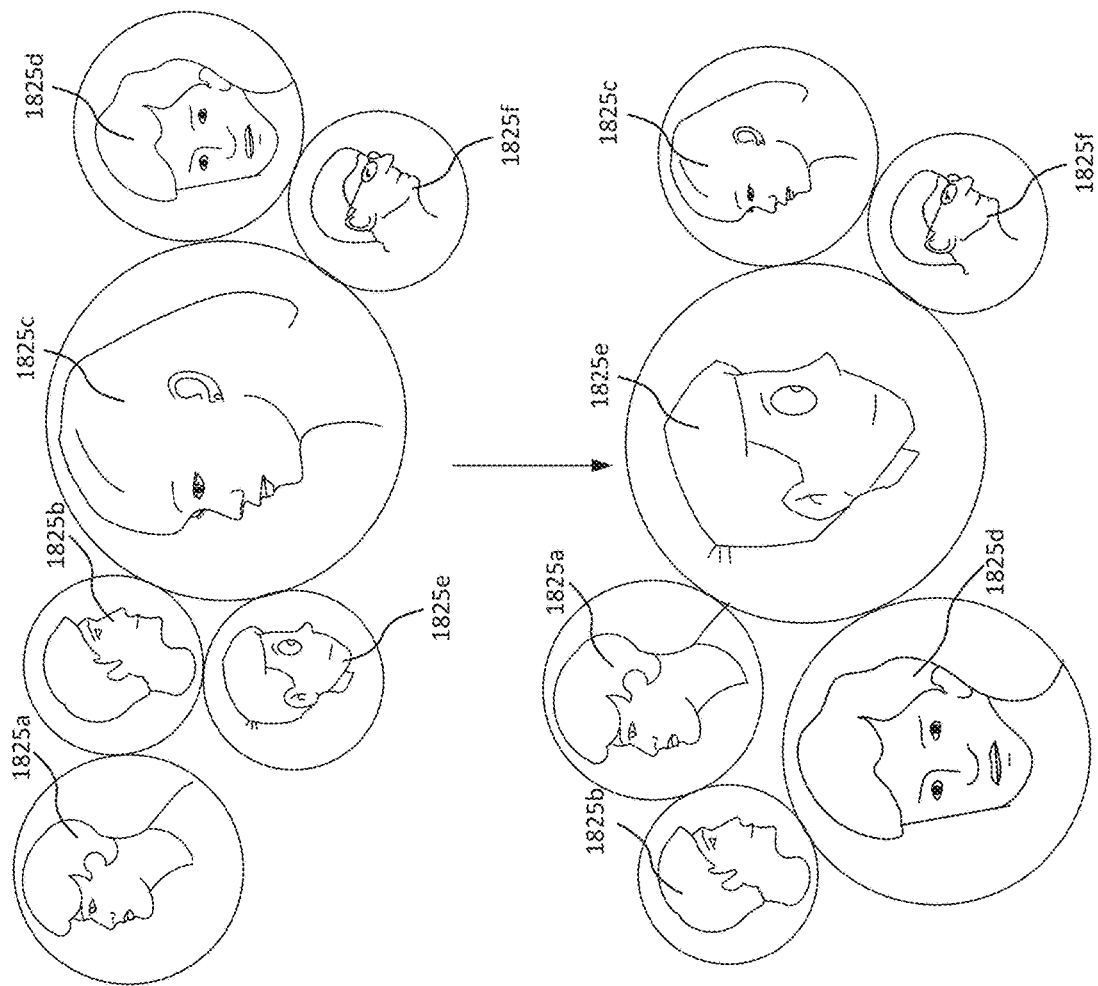
FIG. 18H illustrates an example of designation of a focal point individual that causes a rearrangement of the face cloud consistent with the present disclosure.

FIG. 18G illustrates an example of a face cloud organized using a temporal indicator consistent with the present disclosure. For example, as depicted in FIG. 18G, a plurality of facial images (e.g., images 1821a, 1821b, 1821c, 1821d, and 1821e) are ordered with temporal (and context) indicators 1823a, 1823b, 1823c, 1823d, and 1823e. Although depicted as within shapes (circles in the example of FIG. 18G), the facial images may be displayed without shapes.

Although depicted in FIG. 18G as having uniform sizes, the sizes of the facial images (and the shapes enclosing the facial images) may vary in some embodiments. For example, the sizes may vary based on prominence levels (e.g., based on affinity levels), importance levels, histographic strength to a linking attribute, or the like, as described above with respect to visualization module 1704 of memory 1700. Moreover, although not depicted in FIG. 18G, distances between the facial images and a timeline of the face cloud may vary based on prominence levels (e.g., based on affinity levels), importance levels, histographic strength to a linking attribute, or the like, as described above with respect to visualization module 1704 of memory 1700.

FIG. 18H illustrates an example of designation of a focal point individual that causes a rearrangement of the face cloud consistent with the present disclosure. As depicted in the example of FIG. 18H, a plurality of facial images (e.g., images 1825a, 1825b, 1825c, 1825d, 1825e, and 1825f) are displayed in a cluster. Although depicted as within shapes (circles in the example of FIG. 18H), the facial images may be displayed without shapes.

In the example of FIG. 18H, the sizes of the facial images (and the shapes enclosing the facial images) vary. For example, the sizes may vary based on prominence levels (e.g., based on affinity levels), importance levels, histographic strength to a linking attribute, or the like, as described above with respect to visualization module 1704 of memory 1700. Although not depicted in FIG. 18A, distances between the facial images and a focal point of the face cloud may vary based on prominence levels (e.g., based on affinity levels), importance levels, histographic strength to a linking attribute, or the like, as described above with respect to visualization module 1704 of memory 1700.

As further depicted in FIG. 18H, facial image 1825c may serve as a default or initial focal individual in the face cloud. Accordingly, the sizes of other facial images and/or distances to facial image 1825c may depend on a level of interconnection between the individual associated with facial image 1825*c* and other individuals associated with other facial images. Based on input from a user (e.g., via a click, a tap, or the like), facial image 1825*e* may be selected as the focal individual. Accordingly, the face cloud may be rearranged while maintaining the focal point individual associated with facial image 1825*e*. In the example of FIG. 18H, sizes, placement, and distances of other facial images may shift in accordance with the selected focal individual, e.g., to show a level of interconnection between the individual associated with facial image 1825*e* and other individuals associated with other facial images. Although not depicted in FIG. 18H, the selection may also result in the removal of one or more facial images from the previous face cloud or the addition of one or more facial images to the new face cloud. Any of these changes may be animated such that the transformation depicted in FIG. 18H is fluid rather than sudden.

Indeed, in any of the embodiments above, the generated face cloud may be animated such that it comprises a movie or a video. For example, the face cloud may comprise a video such that at least one of the plurality of facial images present in a first frame is not present in a second, later frame. Additionally or alternatively, the face cloud may comprise a video such that at least one facial image not present in a first frame is present in a second, later frame. In one implementation, the face cloud may comprise a plurality of facial images of individuals present in a location of the user and may comprise a video such that the plurality of facial images move within the face cloud as the user moves around in the location. Additionally or alternatively, the facial images may change as individuals exit the location and enter the location or as the user moves such that individuals are beyond a threshold distance of the user and that other individuals are within the threshold distance.

Figure 19A:
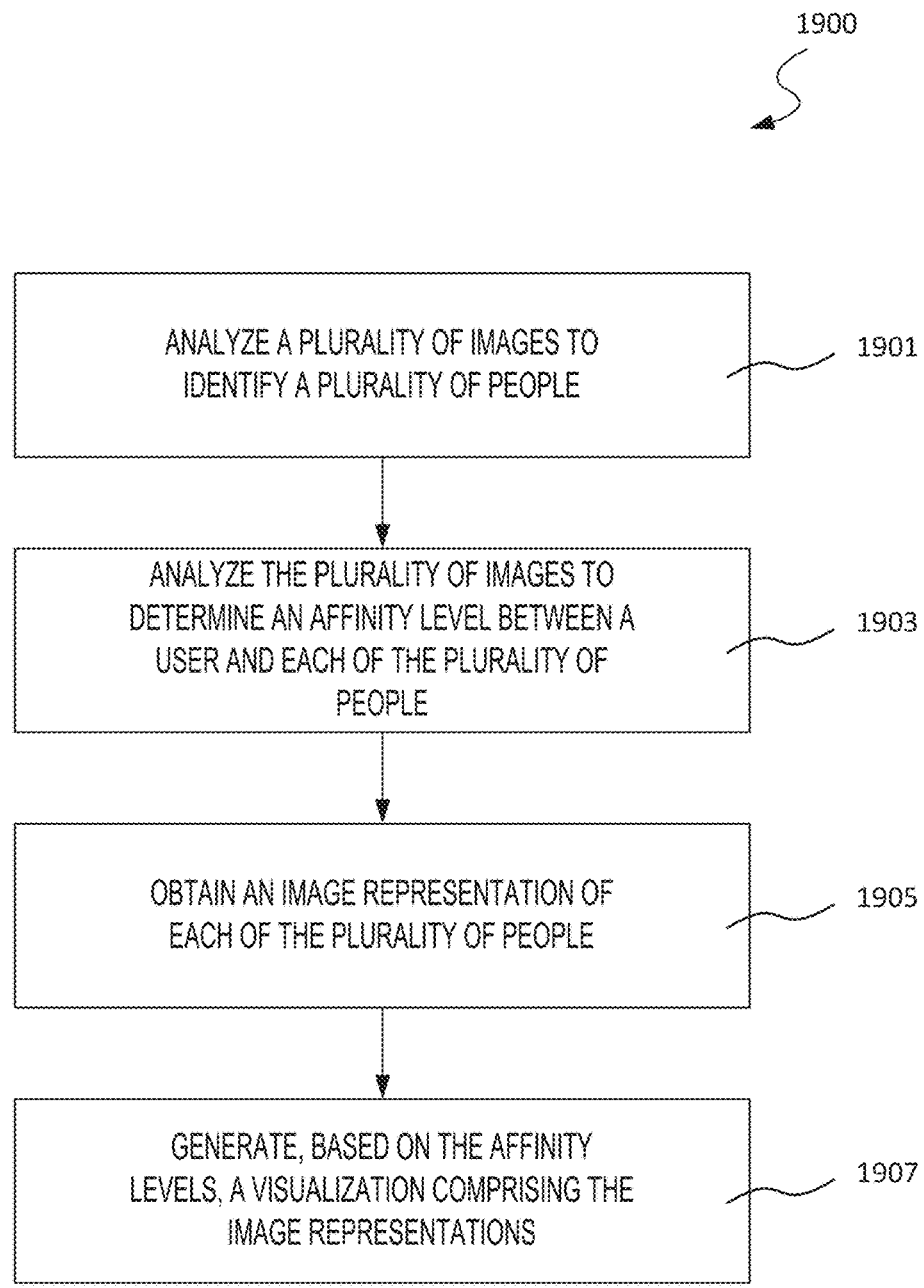
FIG. 19A is a flowchart of an exemplary embodiment of a method for generating a visualization of image representations of a plurality of people consistent with the present disclosure.

FIG. 19A is a flowchart of a method 1900 for generating a visualization of image representations of a plurality of people. Method 1900 may be implemented by a general-purpose computer or a special-purpose computer built according to embodiments of the present disclosure. For example, method 1900 may be executed by at least one of processors 210, 210*a*, 210*b*, and 540. In some embodiments, the steps of method 1900 may be performed by wearable apparatus 110. In other embodiments, the steps of method 1900 may be performed by wearable apparatus 110 and one or more external devices (e.g., a processor included in an external server that receives data from wearable apparatus 110 over a network and/or a processor included in an external device such as a laptop, smartwatch, smartphone, tablet, ear phones, etc.).

At step 1901, the processor may analyze the plurality of images to identify a plurality of people. For example, the processor may use any of the analysis techniques described above with respect to person identification module 1701 of FIG. 17.

At step 1903, the processor may analyze the plurality of images to determine an affinity level between the user and each of the plurality of people. For example, the processor may calculate the affinity level as described above with respect to affinity analysis module 1702 of FIG. 17.

At step 1905, the processor may obtain an image representation of each of the plurality of people. For example, the processor may obtain the image representations from a database, as explained above with respect to image representation module 1703 of FIG. 17.

At step 1907, the processor may generate, based on the affinity levels, a visualization comprising the image representations. For example, the processor may generate a face cloud, as explained above with respect to visualization module 1704 of FIG. 17. Examples of generated face clouds are also depicted in FIGS. 18A-18H, described above.

In some embodiments, method 1900 may include additional steps. For example, method 1900 may include transmitting the visualization comprising the image representations to a mobile communications device wirelessly paired with the wearable apparatus. As explained above with respect to visualization module 1704 of FIG. 17, the processor may transmit the visualization via one or more computer networks and/or radio frequencies.

Moreover, any of the interactions described above with respect to visualization module 1704 of FIG. 17 may be implemented in method 1900. For example, the generated visualization may be updated and/or animated in response to input from the user.

Figure 19B:
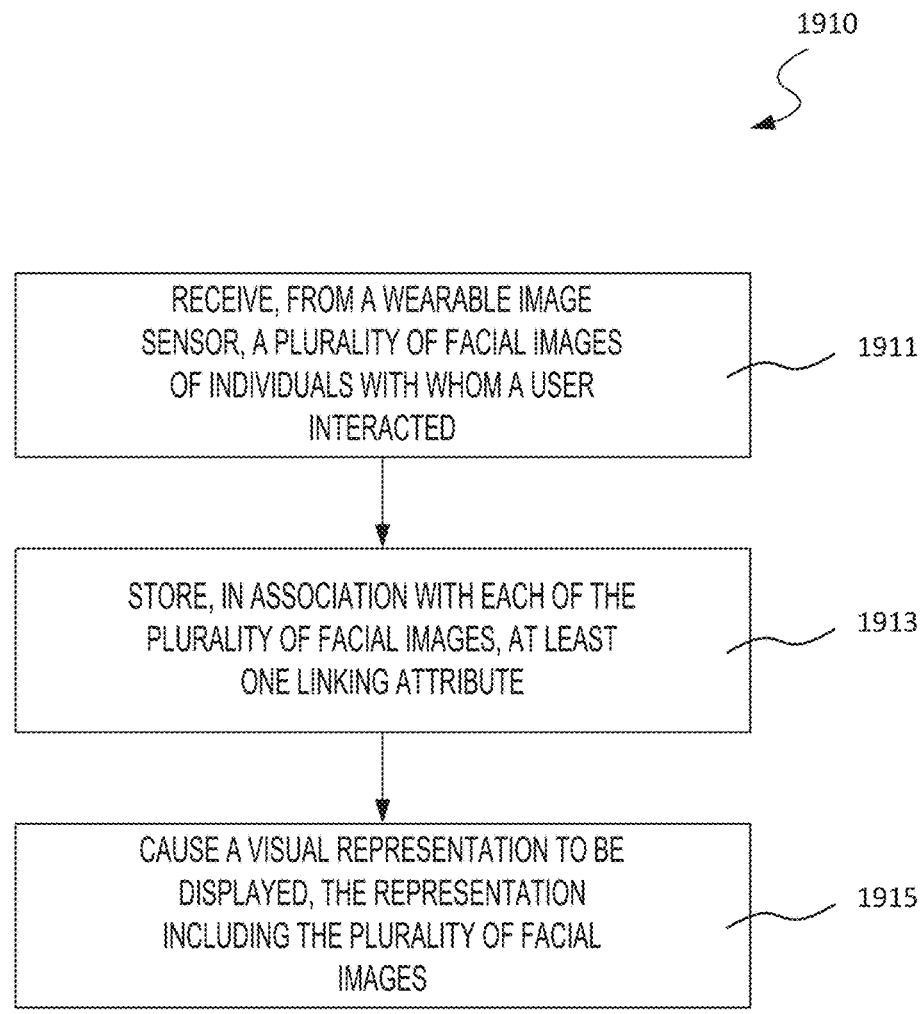
FIG. 19B is a flowchart of an exemplary embodiment of a method for generating a visual representation including a plurality of facial images arranged based on at least one linking attribute consistent with the present disclosure.

FIG. 19B is a flowchart of a method 1910 for generating a visual representation including a plurality of facial images arranged based on at least one linking attribute. Method 1910 of FIG. 19B may represent an alternative to method 1900 for generating a face cloud. Method 1910 may be implemented by a general-purpose computer or a special-purpose computer built according to embodiments of the present disclosure. For example, method 1910 may be executed by at least one of processors 210, 210*a*, 210*b*, and 540. In some embodiments, the steps of method 1910 may be performed by wearable apparatus 110. In other embodiments, the steps of method 1910 may be performed by wearable apparatus 110 and one or more external devices (e.g., a processor included in an external server that receives data from wearable apparatus 110 over a network and/or a processor included in an external device such as a laptop, smartwatch, smartphone, tablet, or ear phones, etc.).

At step 1911, the processor may receive from the wearable image sensor a plurality of facial images of individuals with whom the user interacted. For example, the processor may receive images from image sensor 220 of capturing unit 710.

In some embodiments, receiving a plurality of facial images may include receiving a plurality of facial images of a same individual. In such embodiments, the processor may further perform image processing on the plurality of images of the same individual, determine an existence of a plurality of images of the same individual, and select a single image of the individual for presentation in the face cloud of step 1915. For example, the processor may use any of the analysis techniques described above with respect to person identification module 1701 of FIG. 17.

In some embodiments, the processor may perform image processing on a currently received facial image, and determine that the received facial image corresponds to a face of a recognized individual with a facial image previously stored in memory. In such embodiments, the processor may replace, for use in the face cloud of step 1915, the previously stored facial image with the currently received facial image. For example, the processor may perform the replacement as described above with respect to person identification module 1701 of FIG. 17.

At step 1913, the processor may store, in association with each of the plurality of facial images, at least one linking attribute. The at least one linking attribute may include at least one of an environmental characteristic, a geographical location, an associated word, a social interconnection, or a temporal indicator. The at least one linking attribute may be determined as described above with respect to affinity analysis module 1702 of FIG. 17.

At step 1915, the processor may cause a visual representation to be displayed, the visual representation including the plurality of facial images and/or may display, in a face cloud, the plurality of facial images. The plurality of facial images may be arranged based on the at least one linking attribute. For example, the processor may generate the face cloud as explained above with respect to visualization module 1704 of FIG. 17. Examples of generated face clouds are also depicted in FIGS. 18A-18H, described above.

In some embodiments, causing the visual representation to be displayed may include transmitting information for generating the visualization to a mobile communications device wirelessly paired with the wearable apparatus. For example, as explained above with respect to visualization module 1704 of FIG. 17, the processor may transmit the visualization via one or more computer networks and/or radio frequencies.

In some embodiments, displaying may include arranging the facial images in the face cloud such that facial images sharing at least one common linking attribute are oriented or located adjacent to each other. For example, FIG. 18D is an example of facial images organized adjacent to other facial images sharing a common linking word.

In some embodiments, method 1910 may include additional steps. For example, method 1910 may include enabling a user to select a particular facial image to be a focal point of the face cloud. Additionally or alternatively, method 1910 may include enabling a user to select at least one linking attribute such that the arrangement of the face cloud occurs based on the selected at least one linking attribute. Accordingly, any of the interactions described above with respect to visualization module 1704 of FIG. 17 may be implemented in method 1910.

In some embodiments, method 1910 may be executed by a mobile communications device. In such embodiments, the processor may rearrange the face cloud in response to an input received via the mobile communications device. Additionally or alternatively, the face cloud may be initially arranged based on at least a first common attribute, and in response to the input, the face cloud may be rearranged based on a second common attribute.

Figure 19C:
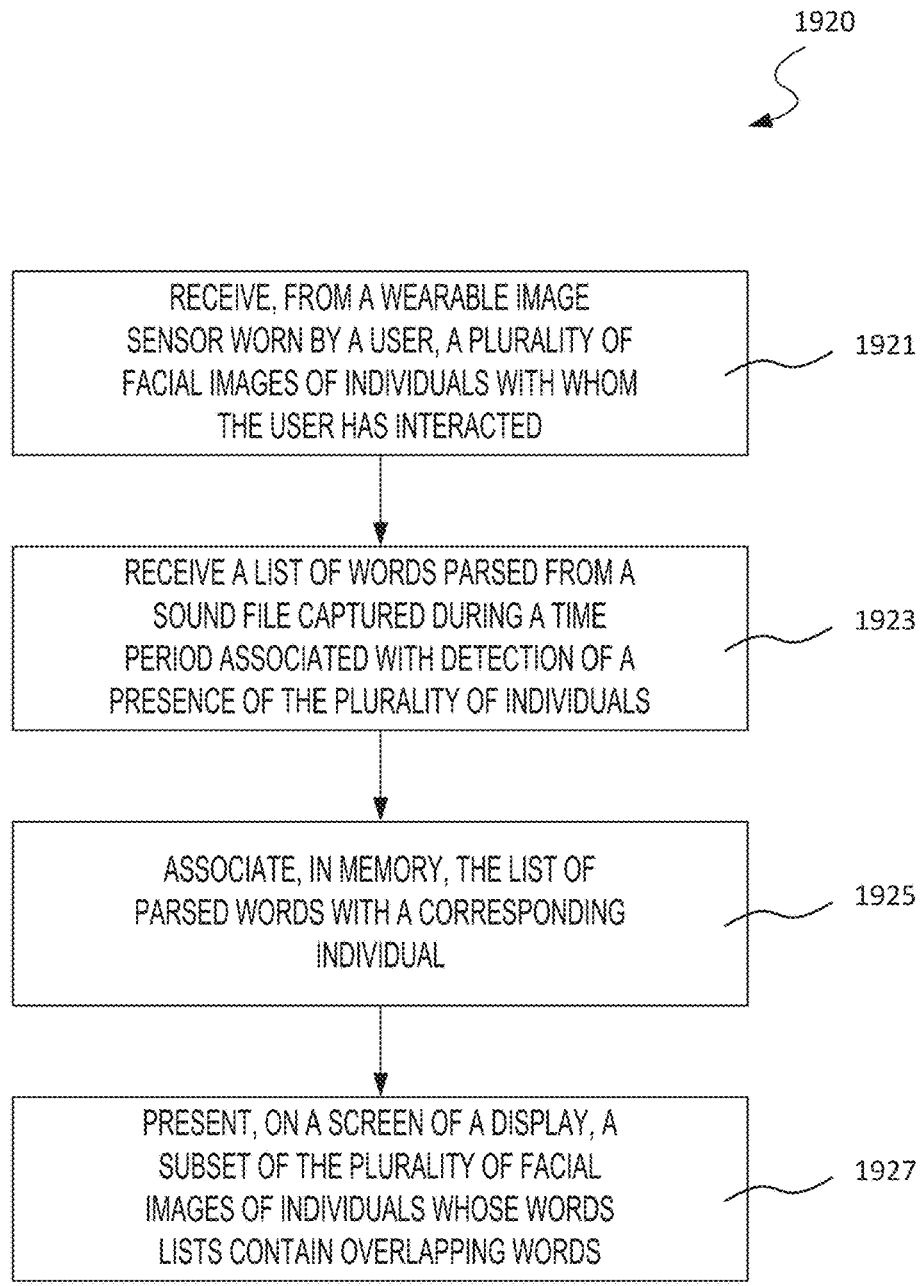
FIG. 19C is a flowchart of exemplary embodiment of a method for generating a subset of a plurality of facial images of individuals having word lists with overlapping common words consistent with the present disclosure.

FIG. 19C is a flowchart of a method 1920 for generating a subset of a plurality of facial images of individuals having word lists with overlapping common words. Method 1920 of FIG. 19C may represent an alternative to method 1900 or method 1910 for generating a face cloud. Method 1920 may be implemented by a general-purpose computer or a special-purpose computer built according to embodiments of the present disclosure. For example, method 1920 may be executed by at least one of processors 210, 210*a*, 210*b*, and 540. In some embodiments, the steps of method 1920 may be performed by wearable apparatus 110. In other embodiments, the steps of method 1920 may be performed by wearable apparatus 110 and one or more external devices (e.g., a processor included in an external server that receives data from wearable apparatus 110 over a network and/or a processor included in an external device such as a laptop, smartwatch, smartphone, tablet, ear phones, etc.).

At step 1921, the processor may receive from a wearable image sensor worn by a user a plurality of facial images of individuals with whom the user has interacted. For example, the processor may receive images from image sensor 220 of capturing unit 710.

At step 1923, the processor may receive a list of words parsed from a sound file captured during a time period associated with detection of a presence of the plurality of individuals in a vicinity of the wearer. For example, the processor may use any of the analysis techniques described above with respect to affinity analysis module 1702 of FIG. 17.

At step 1925, the processor may associate in memory the list of parsed words with a corresponding individual. In some embodiments, the processor may further associate in memory a frequency of use indication associated with each parsed word. The parsed words may be determined as described above with respect to affinity analysis module 1702 of FIG. 17.

At step 1927, the processor may present on a screen of a display a subset of the plurality of facial images of individuals whose word lists contain overlapping common words. For example, the processor may generate a face cloud, as explained above with respect to visualization module 1704 of FIG. 17. Examples of generated face clouds are also depicted in FIGS. 18A-18H, described above.

In some embodiments, method 1920 may include additional steps. For example, method 1920 may include selecting a specific parsed word and choosing the subset of facial images for display based on the selection. In such embodiments, the selecting may occur as a result of input from the user, based on context in a current environment of the user, based on words used in a current conversation, or based on an object in a recent field of view of the wearable image sensor. Accordingly, any of the interactions described above with respect to visualization module 1704 of FIG. 17 may be implemented in method 1920.

Moreover, any of the generated visualizations or face clouds may be animated. For example, selected facial images may appear to move closer toward a screen on which the visualization is shown as the identified person moves closer to the user or the user moves closer to the person. In such an example, the facial image may disappear and/or appear to move off the screen as the identified person moves away from the user or passes them while walking, or the user moves away or passes the person. Accordingly, the generated visualizations or face clouds may represent a dynamic or real-time visualization of identified persons around the user.

Indexing and Searching Persons and Objects

In some embodiments, a wearable apparatus of the present disclosure may index images of persons and objects in particular ways to assist with searching. The database may associate facial images captured by a wearable apparatus with key words from sound files, calendar dates, and/or contextual information from images captured by the wearable apparatus. Accordingly, by constructing and indexing the database according to the particular rules of the present disclosure, facial images may be searched with greater speed and accuracy than in conventional systems.

In addition, rather than using conventional user interface methods to display search results, embodiments of the present disclosure instead may use a specific manner of displaying a limited set of information to the user in a visual and easily perceptible manner. Conventional interfaces for displaying search results are heavily text-based and difficult to manipulate. Accordingly, embodiments of the present disclosure provide for improved display interfaces that are organized visually and allow for easy manipulation by the user.

Figure 20:
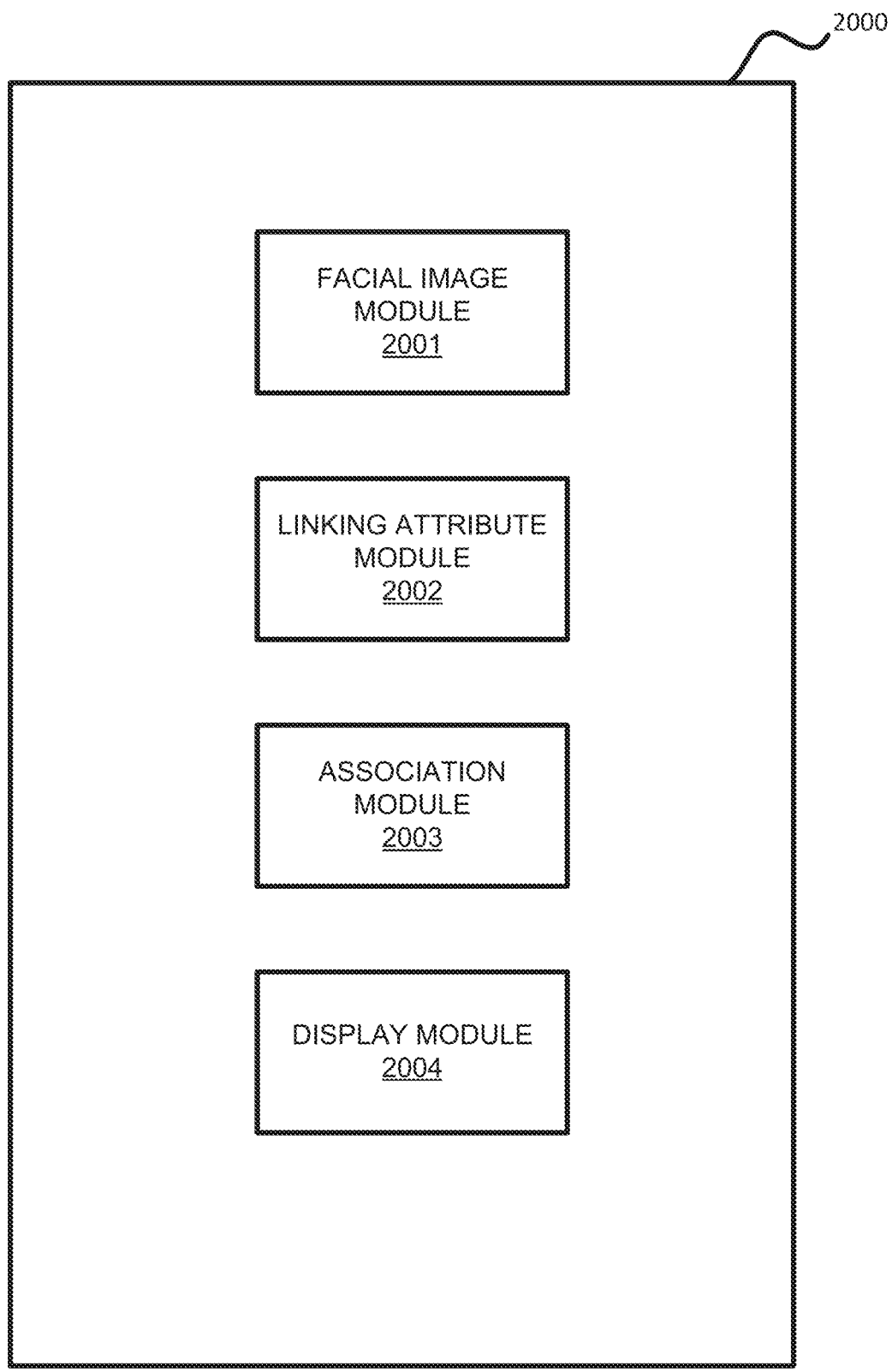
FIG. 20 illustrates an exemplary embodiment of a memory containing software modules for indexing and searching people and objects consistent with the present disclosure.

FIG. 20 illustrates an exemplary embodiment of a memory 2000 containing software modules consistent with the present disclosure. Included in memory 2000 are facial image module 2001, linking attribute module 2002, association module 2003, and display module 2004. Modules 2001, 2002, 2003, and 2004 may contain software instructions for execution by at least one processing device, e.g., processor 210, included with a wearable apparatus. In some embodiments, memory 2000 may comprise a non-transitory computer readable medium that resides on a mobile communications device (e.g., a smart phone) configured to be wirelessly paired with wearable image sensor 220 of capturing unit 710.

Facial image module 2001, linking attribute module 2002, association module 2003, and display module 2004 may cooperate to generate a database with indexed images and/or sounds from wireless apparatus 110, as well as cooperating to allow searches of the database and particular displays of results therefrom. Memory 2000 may be separate from and/or integrated with memory 550 of FIG. 6, described above. Similarly, orientation identification module 601, orientation adjustment module 602, and monitoring module 603 of FIG. 6 may operate in tandem or concurrently with facial image module 2001, linking attribute module 2002, association module 2003, and display module 2004 of FIG. 20.

Facial image module 2001 may be configured to receive images captured by image sensor 220 of capturing unit 710. For example, the images may be from an environment of a user of a wearable apparatus.

In some embodiments, the images may include an object image. The object image may include a facial image or be a facial image.

Additionally or alternatively, facial image module 2001 may receive facial images of a plurality of individuals with whom a user of a wearable apparatus interacted. For example, facial image module 2001 may discard images captured by image sensor 220 that do not include at least a portion of at least one person in the image and/or do not include at least a portion of at least one face in the image while retaining images that include at least a portion of at least one person and/or at least a portion of at least one face. For example, facial image module 2001 may apply image analysis to determine whether a person, a face, and/or a portion thereof are present in the image.

Facial image module 2001 may detect persons and/or faces in received images using any known techniques. For example, facial image module 2001 may perform image processing on a currently received image and determine that the received image corresponds to an image of a person or a face that has been previously stored in memory. Thus, facial image module 2001 may perform pixel-by-pixel matching. In other embodiments, facial image module 2001 may perform more sophisticated techniques. For example, facial image module 2001 may use one or more classifiers (or cascading classifiers) to detect a person or a face included in the image. Additionally or alternatively, facial image module 2001 may use a neural network to detect a person or a face included in the image. Alternatively, facial image module 2001 may use a neural network to derive a plurality of features (e.g., a feature set) from the image and then map the derived features (or feature set) onto features associated with detection of a person or a face. The mapping may be performed using simple correlation or using more sophisticated techniques, such as another neural network.

In any of the embodiments above, detections may have associated probabilities or confidence levels, e.g., output from the neural network; calculated based on percentage of matching pixels, features, etc.; or the like. Accordingly, in some embodiments, facial image module 2001 may finalize a detection of a person or a face only if the detection has an associated probability above a threshold. Alternatively, facial image module 2001 may apply further detection techniques if the detection is indeterminate, e.g., above a first threshold but below a second, higher threshold. In such an embodiment, facial image module 2001 may apply a classifier and may, if the classifier produces a detection with an indeterminate probability, then apply one or more additional classifiers and/or a neural network to produce one or more additional detection probabilities. Based on the additional detection probabilities, e.g., if they exceed the second threshold, facial image module 2001 may finalize the detection. Any detection not finalized may be discarded.

In any of the embodiments above, the image may include more than one person and/or more than one face or may include no persons and/or no faces. Facial image module 2001 may therefore use a bounding box architecture, such as You Only Look Once (YOLO) or Single-Shot Detector (SSD), to identify bounding boxes including a person therein. For example, if person identification module 2001 uses a bounding box architecture and receives no bounding boxes classified as persons and/or faces or receives bounding boxes all having person and/or facial classifications below a threshold (e.g., less than 50%, less than 40%, less than 25%, less than 10%, less than 5%, or the like), facial image module 2001 may discard the image as including no persons and/or no faces. Similarly, if facial image module 2001 uses a bounding box architecture and receives a plurality of bounding boxes classified as persons and/or faces or receives a plurality of bounding boxes having person and/or facial classifications above a threshold (e.g., more than 50%, more than 40%, more than 25%, more than 10%, more than 5%, or the like), facial image module 2001 may detect portions of the image defined by the plurality of bounding boxes as including persons and/or faces.

In some embodiments, the images may comprise a first plurality of facial images of individuals with whom the user interacted on a first calendar date and a second plurality of facial images of individuals with whom the user interacted on a second calendar date. For example, image sensor 220 may time-stamp the generate image such that facial image module 2001 receives an associated calendar date with each received image. Alternatively, facial image module 2001 may generate and attach the associated calendar date to each image upon receipt.

Additionally or alternatively, facial image module 2001 may receive, from an image sensor of the wearable apparatus, at least one image captured in a time window. For example, as explained above, image sensor 220 or facial image module 2001 may stamp an image with an associated date. Accordingly, the time window may comprise one or more days between one calendar date and another calendar date, whether counting inclusively of the one calendar date and/or the other calendar date or exclusively of both.

Additionally, image sensor 220 or facial image module 2001 may stamp the image with an associated time. Accordingly, the time window may comprise a period of time between a start time and an end time. The start time and end time may comprise times on the same calendar date or may comprise times on different calendar dates.

In addition to receiving images during a time window, facial image module 2001 may also receive a file of sound captured during the time window. The file of sound may also have been captured in a vicinity (e.g., within 5 meters, within 10 meters, within 20 meters, or the like) of image sensor 220 of capturing unit 710. In some embodiments, the sound file may be received from a mobile communications device other than the wearable image sensor. For example, a mobile communications device associated with the same user as the user of the wearable apparatus may record the sound file in a vicinity of image sensor 220 of capturing unit 710.

Additionally or alternatively, facial image module 2001 may receive sound data associated with the facial images. For example, the sound data may be retrieved from a memory where it is stored in association with the facial images. Additionally or alternatively, the sound data may be recorded in a vicinity (e.g., within 5 meters, within 10 meters, within 20 meters, or the like) of image sensor 220 of capturing unit 710 and/or in a vicinity (e.g., 5 seconds, 10 seconds, 30 seconds, 1 minute, 5 minute, or the like) of the facial images being captured.

In any of the embodiments discussed above, received images or facial images may vary in size, shape, and content. For example, in some embodiments, an image including a wider scene (e.g., a plurality of individuals, or an individual and his or her surrounding environment) may be cropped or otherwise truncated to a face, a portion of a face, a headshot of a person (e.g., head and shoulders), or a portion of a person's body including the person's face. In other embodiments, received images may include such wider scenes (e.g., a plurality of individuals, or an individual and his or her surrounding environment). In still other embodiments, received images may include a face, a portion of a face, a headshot of a person (e.g., head and shoulders), or a portion of a person's body including the person's face.

Linking attribute module 2002 may be configured to receiving at least one linking attribute for each of the plurality of facial images. For example, linking attribute module 2002 may analyze at least one image received by facial image module 2001 to determine the at least one linking attribute.

The at least one linking attribute may include an identity of a person appearing in one or more images. In another example, the at least one linking attribute may include a location. The location may include at least one of an event, a physical space, and a GPS coordinate. For example, the location may include a 'work retreat' or 'concert.' In another example, the geographical location may include a 'coffee shop' or a 'neighbor's house.' In any of the embodiments above, linking attribute module 2002 may use image analysis, e.g., as described above with respect to facial image module 2001, to identify the location.

In another example, the at least one linking attribute may include an occupation. For example, the location may include 'contractor, 'teacher,' or the like. Linking attribute module 2002 may use image analysis, e.g., as described above with respect to facial image module 2001, to identify the occupation. For example, linking attribute module 2002 may identify the occupation by classifying a uniform, a location, one or more tools associated with the occupation, or the like within the images.

In another example, the at least one linking attribute may include a workplace. For example, the workplace may include 'university, '123 A Street,' or the like. Linking attribute module 2002 may use image analysis, e.g., as described above with respect to facial image module 2001, to identify the workplace. For example, linking attribute module 2002 may identify the workplace by classifying a building, a location, one or more items associated with the workplace, or the like within the images.

In another example, the at least one linking attribute may include a family relationship. For example, the family relationship may include 'immediate,' 'extended,' 'first generation,' 'second generation,' 'parents,' 'siblings,' or the like. In yet another example, the at least one linking attribute may include a social relationship. For example, the social relationship may include 'close friends,' 'friends,' 'acquaintances,' or the like.

Linking attribute module 2002 may use image analysis, e.g., as described above with respect to facial image module 2001, to identify the family relationship or social relationship. For example, linking attribute module 2002 may identify the family relationship or social relationship by identifying one or more people within the images. The identity of the user may also be used to determine the family relationship or social relationship.

Additionally or alternatively, the at least one linking attribute may be based on user input. For example, a user may input one or more words comprising the at least one linking attribute. In some embodiments, linking attribute module 2002 may present a user with a pick list of linking attributes.

In embodiments where facial image module 2001 also receives a file of sound, linking attribute module 2002 may process the sound file to identify at least one word in the sound file. For example, the at least one word may be parsed using any audio analysis technique, such as limited vocabulary recognition, large vocabulary recognition, with or without speaker separation, recognition, verification, or the like. In some embodiments, linking attribute module 2002 may transcribe the sound file in order to parse the at least one word therefrom.

Additionally or alternatively, linking module 2002 may extract the at least one word based on a frequency of use associated with each word in the sound file. For example, linking attribute module 2002 may eliminate stop words or other common words such as articles ('the,' 'a,' 'an,' or the like), prepositions ('of,' 'from,' 'to,' or the like), or the like from the parsed at least one word.

Additionally with or alternatively to receiving at least one linking attribute, linking attribute 2002 may analyze the plurality of images to identify contextual information associated with the detected person (e.g., detected by facial image module 2001). For example, the contextual information may be based, at least in part, on a second person appearing in the plurality of images in conjunction with the detected person. Accordingly, linking attribute module 2002 may use image analysis, e.g., as described above with respect to facial image module 2001, to identify the second person.

Additionally or alternatively, the contextual information may be based, at least in part, on a uniform the detected person is wearing. Accordingly, linking attribute module 2002 may use image analysis, e.g., as described above with respect to facial image module 2001, to identify the uniform.

Additionally or alternatively, the contextual information may be based, at least in part, on a room the detected person appears in. Accordingly, linking attribute module 2002 may use image analysis, e.g., as described above with respect to facial image module 2001, to identify the room.

Additionally with or alternatively to receiving at least one linking attribute, linking attribute 2002 may analyze the plurality of images to identify a visual context indicator. Accordingly, linking attribute module 2002 may use image analysis, e.g., as described above with respect to facial image module 2001, to identify the visual context indicator.

Association module 2003 may be configured to associate in memory each of the plurality of facial images with the at least one linking attribute received for a corresponding one of the plurality of facial images. The at least one linking attribute may be determined using image analysis and/or user input, as explained above with respect to linking attribute module 2002.

In some embodiments, association module 2003 may store a measure of occurrences of linking attributes associated with each individual's facial image. For example, the measure of occurrences may comprise a number of times the linking attributes appear in images. The number of times may be averaged over a number of images and/or over a period of time in order to obtain the measure of occurrences. Additionally or alternatively, the measure of occurrences may comprise a measure of strength of the linking attributes, e.g., based on sizes within images, prominence within images, or the like.

In embodiments where linking attribute module 2002 processes the sound file to identify at least one word in the sound file, association module 2003 may store in memory an association between the word and the object image. Similarly, in embodiments where linking attribute module 2002 processes sound data associated with the facial images to extract key words, association module 2003 may store the key words in memory associated with a date of recording.

In embodiments where facial image module 2001 receives a first plurality of facial images of individuals with whom the user interacted on a first calendar date and a second plurality of facial images with whom the user interacted on a second calendar date, association module 2003 may store an indicator of the first calendar date in association with each of the first plurality of individuals and store an indicator of the second calendar date in association with each of the second plurality of individuals. For example, the indicators may be stored such that they are retrievable when an individual in the first plurality of individuals or the second plurality of individuals, respectively, are searched for. Additionally or alternatively, the indicators may be indexed such that the first plurality of facial images of individuals or the second plurality of facial images of individuals are retrievable when the first calendar date or the second calendar date, respectively, are searched for.

In embodiments where the linking attribute module 2002 identifies contextual information associated with the detected person, association module 2003 may select at least one record associated with the detected person and update the at least one record based on the contextual information. For example, the identified contextual information may be stored in the record such that it is retrievable when the detected person is searched for. Additionally or alternatively, the identified contextual information may be indexed such that the detected person is retrievable when the contextual information is searched for.

In embodiments where the linking attribute module 2002 identifies a visual context indicator, association module 2003 may determine contextual category based on the detected person and associate the visual context indicator with the determined contextual category. For example, the contextual category may be a work related category, a social category, or a family category. Additionally or alternatively, association module 2003 may determine a context of a room or a location based on one or more persons identified in the room.

Attribute module 2002 may store the visual context indicator with the determined contextual category such that the indicator is retrievable when the contextual category is searched for. Additionally or alternatively, the visual context indicator may be indexed such that the contextual category is retrievable when the visual context indicator is searched for.

Display module 2004 may be configured to, for a selected linking attribute, present on a screen of a display a set of the plurality of facial images that share the selected linking attribute. For example, the set of the plurality of facial images may be arranged in any way described above with respect to visualization module 1704. Accordingly, the set of the plurality of facial images may be displayed as a face cloud In some embodiments, during presenting, facial images with a higher number of occurrences of a common linking attribute may be displayed with a prominence greater than facial images of individuals with a lower number of occurrences of a common linking attribute. For example, greater prominence may be reflected in a presented size of facial images, as depicted above with respect to FIG. 18A. Additionally or alternatively, greater prominence may be reflected in a proximity to a focal location on the display, as depicted above with respect to FIGS. 18C-18F.

In embodiments where linking attribute module 2002 presents a user with a pick list of linking attributes, display module 2004 may alter a presentation of facial images on the display in response to a selection from the pick list. For example, display module 2004 may add facial images to the display and/or remove facial images from the display. In embodiments where facial images with a higher number of occurrences of a common linking attribute are displayed with a greater prominence, display module 2004 may modify prominences of the facial images based on the selection.

In embodiments where linking attribute module 2002 processes a sound file to identify at least one word in the sound file, display module 2004 may receive, at a time remote from the time window, a search input of the at least one key word. For example, display module 2004 may generate a text box to receive the search input. Additionally or alternatively, display module 2004 may generate a list of keywords and display the list of keywords to the user such that the user may input the search by selecting one or more keywords from the list.

In such embodiments, display module 2004 may access the memory to locate the association between the at least one key word and the at least one object image and cause a display of the object image on a mobile communications device of the user, separate from the wearable image sensor. Accordingly, display module 2004 may allow for rapid and efficient searches of images obtained from a wearable apparatus. In addition, display module 2004 may allow for display of the results on a mobile communications device separate from the wearable image sensor, which comprises a non-generic and non-conventional combination of components for providing search results. The efficient search and unique combination of components may improve the user's experience.

In such embodiments, causing the display may include displaying a plurality of facial images each associated with the keyword. For example, as explained above, the set of the plurality of facial images may be arranged in any way described above with respect to visualization module 1704. Accordingly, the set of the plurality of facial images may be displayed as a face cloud.

In embodiments where facial image module 2001 receives a first plurality of facial images of individuals with whom the user interacted on a first calendar date and a second plurality of facial images of individuals with whom the user interacted on a second calendar date, display module 2004 may receive a first input request by the user for recall of interactions on the first calendar date. For example, display module 2004 may display a calendar to the user, and the first input may be a result of a user's respective touch interactions with screen regions corresponding to the first calendar date. In response to the first input, display module 2004 may display to the user images of at least some of the first plurality of individuals.

Additionally or alternatively, display module 2004 may receive a second input request by the user for recall of interactions on the second calendar date. Similar to the first input, display module 2004 may display a calendar to the user, and the second input may be a result of a user's respective touch interactions with screen regions corresponding to the second calendar date. In response to the second input, display module 2004 may display to the user images of at least some of the second plurality of individuals.

The display of images of at least some of the first plurality of individuals and/or images of at least some of the second plurality of individuals may be arranged in any way described above with respect to visualization module 1704. Accordingly, the set of the plurality of facial images may be displayed as a face cloud.

In any of the embodiments above, display module 2004 may additionally or alternatively present to the user the key words associated with interactions on the first calendar date and the second calendar date. For example, the key words may have been extracted from a sound file (or sound data associated with the facial images) by linking attribute module 2002. In addition, the key words may have been associated with the first calendar date and the second calendar date based on a calendar date at which the sound from which the key word was extracted was recorded.

Additionally or alternatively, display module 2004 may receive a search input by the user, the search input including at least one of the key words. For example, as explained above, display module 2004 may generate a text box to receive the search input. Additionally or alternatively, display module 2004 may generate a list of keywords and display the list of keywords to the user such that the user may input the search by selecting one or more keywords from the list. In such embodiments, the at least some of the first plurality of individuals and the at least some of the second plurality of individuals may be associated with the at least one of the key words.

In any of the embodiments above, display may occur on a mobile communications device wirelessly paired to the wearable image sensor. For example, display module 2004 may generate any of the user interfaces described above and transmit the generated interfaces to the mobile communications device.

Display module 2004 may also be configured to enable interaction with any of the displays above. For example, display module 2004 may be configured to enable a user to select a particular facial image to be a focal point of the face cloud. In such an example, display module 2004 may allow a user to click, tap, or otherwise select the particular facial image. In such embodiments, display module 2004 may receive a designation of a focal point individual such that the input causes a rearrangement of the face cloud while maintaining the focal point individual.

Figure 21A:
FIG. 21A illustrates an example of a database for indexing facial images to linking attributes consistent with the present disclosure.

FIG. 21A illustrates an example of a database 2100 for indexing facial images to linking attributes consistent with the present disclosure. As depicted in FIG. 21A, a plurality of facial images (e.g., images 2101a, 2101b, 2101c, and 2101d) are stored in the database.

The facial images are indexed to one or more linking attributes for fast retrieval. In the example of FIG. 21A, facial images 2101a, 2101b, 2101c, and 2101d are indexed by first linking attributes 2103a, 2103b, 2103c, and 2103d, respectively, along with second linking attributes 2107a, 2107b, 2107c, and 2107d. Although the first linking attributes are depicted as locations and the second linking attributes are depicted as social relationships, the linking attributes may additionally or alternatively comprise an occupation, a workplace, a family relationship, or another linking attribute.

As further depicted in the example of FIG. 21A, first linking attributes 2103a, 2103b, 2103c, and 2103d may be indexed to corresponding occurrences 2105a, 2105b, 2105c, and 2105d, and second linking attributes 2107a, 2107b, 2107c, and 2107d may be indexed to corresponding occurrences 2109a, 2109b, 2109c, and 2109d. For example, occurrences 2105a, 2105b, 2105c, and 2105d may comprise a number of times a person depicted in corresponding facial images 2101a, 2101b, 2101c, and 2101d, respectively, was captured in an image by a wearable apparatus while at corresponding locations 2103a, 2103b, 2103c, and 2103d, respectively. The occurrences may comprise a total number of images in which the person was captured or a total number of interactions with a user of the wearable apparatus during which one or more images were captured. Therefore, in FIG. 21A, the person associated with facial image 2101a was either captured in one image while at the coffee shop or was captured in images during one interaction with the user at the coffee shop; the person associated with facial image 2101b was either captured in two images or was captured in images during two interactions with the user at the coffee shop; the person associated with facial image 2101c was either captured in four images or was captured in images during four interactions with the user at the gym; and the person associated with facial image 2101d was either captured in one image or was captured in images during one interaction with the user at the park.

In another example, occurrences 2109a, 2109b, 2109c, and 2109d may comprise a number of times a person depicted in corresponding facial images 2101a, 2101b, 2101c, and 2101d, respectively, was captured in an image by a wearable apparatus during a particular time period. The occurrences may comprise a total number of images in which the person was captured or a total number of interactions with a user of the wearable apparatus during which one or more images were captured. Therefore, in FIG. 21A, the person associated with facial image 2101a was either captured in two images this week or was captured in images during two interactions with the user this week; the person associated with facial image 2101b was either captured in three images this week or was captured in images during three interactions with the user this week; the person associated with facial image 2101c was either captured in five images this week or was captured in images during five interactions with the user this week; and the person associated with facial image 2101d was either captured in one image this week or was captured in images during one interaction with the user this week. Although one week is used as the time period, other time periods such as one day, two weeks, one month, six months, one year, or the like may be used.

Figure 21B:
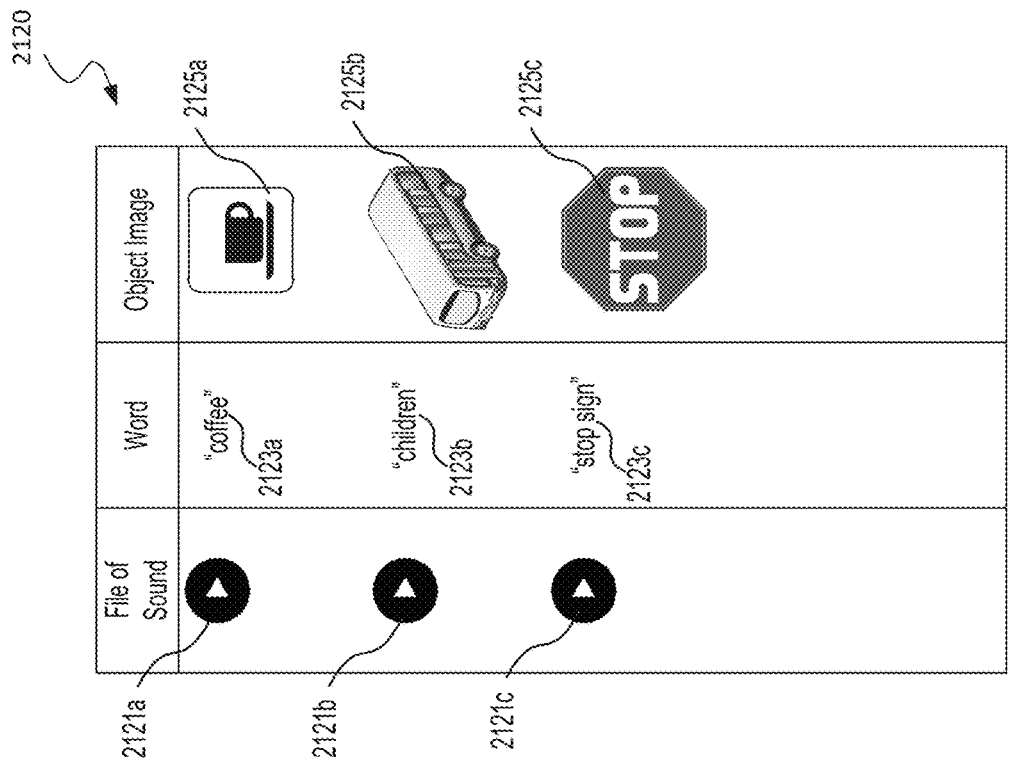
FIG. 21B illustrates an example of a database for indexing sound files to extracted words and object images consistent with the present disclosure.

FIG. 21B illustrates an example of a database 2120 for indexing sound files to extracted words and object images consistent with the present disclosure. As depicted in FIG. 21B, a plurality of sound files (e.g., files 2121a, 2121b, and 2121c) are stored in the database. The sound files may have been captured in a vicinity of a wearable image sensor during a time window. The sounds files may have been captured by a microphone of the wearable apparatus or by a mobile communications device other than the wearable image sensor. Additionally or alternatively, one or more words (e.g., words 2123a, 2123b, and 2123c) may be stored in the database. The one or more words may be extracted from the plurality of sound files, as explained above with respect to linking attribute module 2002.

As further depicted in FIG. 21B, the database may store a plurality of object images (e.g., images 2125a, 2125b, and 2125c). The object images may have been captured by the wearable image sensor during the time window. Although depicted as images of inanimate objects in FIG. 21B, the database may include an object image that includes a facial image or is a facial image. Words 2123a, 2123b, and 2123c may be used to index images 2125a, 2125b, and 2125c, respectively, for fast retrieval.

Figure 21C:
FIG. 21C illustrates an example of a database for indexing facial images to calendar dates consistent with the present disclosure.

FIG. 21C illustrates an example of a database 2140 for indexing facial images to calendar dates consistent with the present disclosure. As depicted in FIG. 21C, a plurality of calendar dates (e.g., dates 2141a and 2141b) are stored in the database and used to index a plurality of facial images (e.g., images 2145a, 2145b, 2145c, 2145d, and 2145e), for fast retrieval.

Although not depicted in FIG. 21C, database 2140 may further store key words from sound data associated with the facial images. The stored key words may be indexed by the stored dates and/or may be used to index the stored facial images.

It will be appreciated that wherever images or sound files are depicted in FIGS. 21A-21C, they may refer to a pointer to an image or a sound file or another storage unit, or to metadata describing the image or sound file.

Figure 22A:
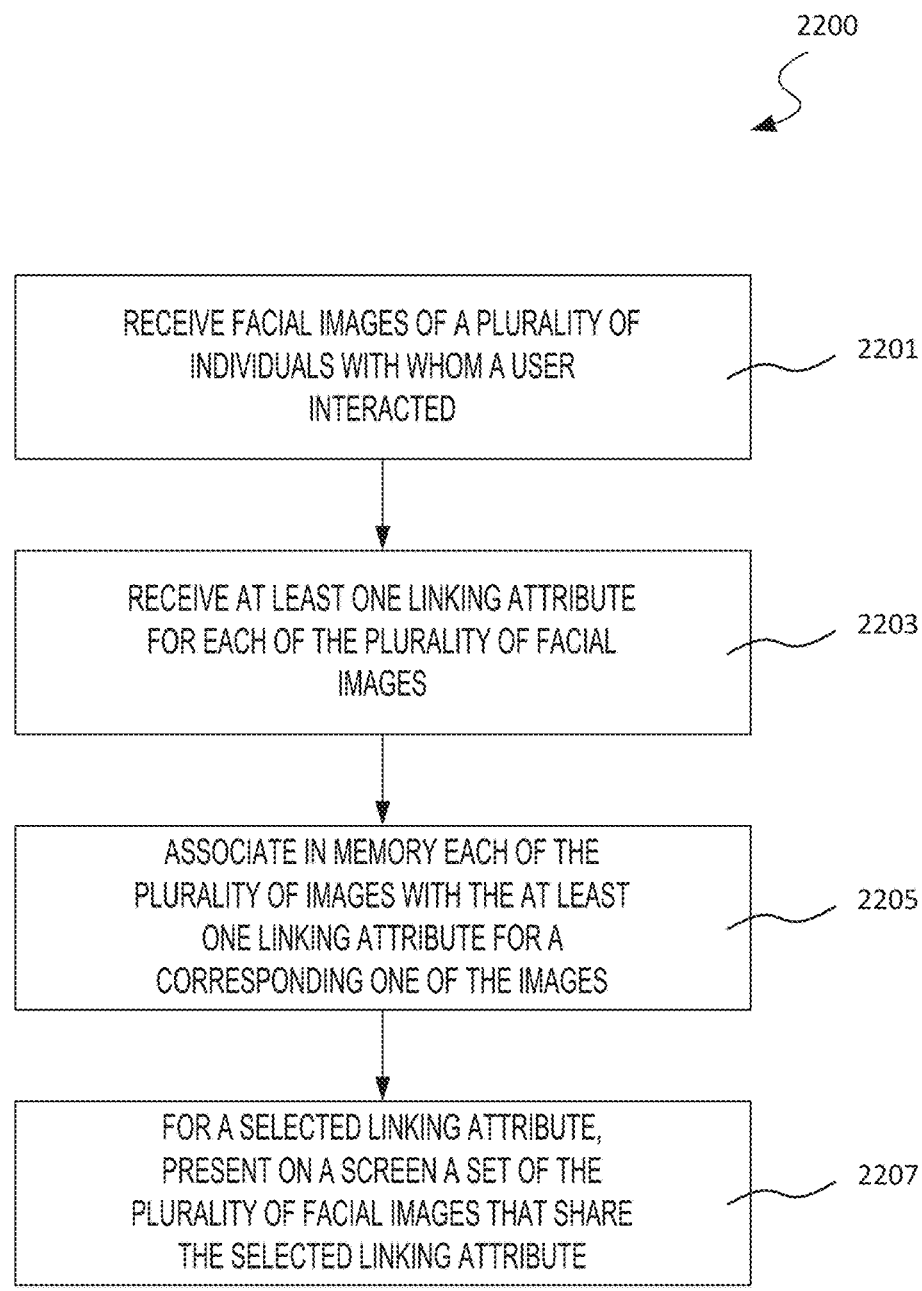
FIG. 22A is a flowchart of an exemplary embodiment of a method for indexing facial images to linking attributes consistent with the present disclosure.

FIG. 22A is a flowchart of a method 2200 for indexing facial images to linking attributes. Method 2200 may be implemented by a general-purpose computer or a special-purpose computer built according to embodiments of the present disclosure. For example, method 2200 may be executed by at least one of processors 210, 210a, 210b, and 540. In some embodiments, the steps of method 2200 may be performed by wearable apparatus 110. In other embodiments, the steps of method 2200 may be performed by wearable apparatus 110 and one or more external devices (e.g., a processor included in an external server that receives data from wearable apparatus 110 over a network and/or a processor included in an external device such as a laptop, smartwatch, smartphone, tablet, ear phones, etc.).

At step 2201, the processor may receive facial images of a plurality of individuals with whom a user interacted. For example, the processor may receive the facial images from an image sensor worn by a user (e.g., image sensor 220 of capturing unit 710).

At step 2203, the processor may determine or receive at least one linking attribute for each of the plurality of facial images. For example, the processor may determine the at least one linking attribute using image analysis and/or receive the at least one linking attribute as input from a user, as described above with respect to linking attribute module 2002 of FIG. 20. The at least one linking attribute may include at least one of a location, an occupation, a workplace, a family relationship, and a social relationship.

At step 2205, the processor may associate in memory each of the plurality of facial images with the at least one linking attribute received for a corresponding one of the plurality of facial images. For example, the processor may store the facial images indexed by the at least one linking attribute, as depicted in the example of FIG. 21A.

In some embodiments, the processor may further store a measure of occurrences of linking attributes associated with each individual's facial image. For example, the processor may store the facial images and/or the at least one linking attribute indexed by the occurrences, as depicted in the example of FIG. 21A.

At step 2207, the processor may, for a selected linking attribute, present on a screen of a display a set of the plurality of facial images that share the selected linking attribute. For example, the processor may generate a face cloud, as explained above with respect to visualization module 1704 of FIG. 17. Examples of generated face clouds are also depicted in FIGS. 18A-18H described above.

In embodiments where occurrences are also stored, during presenting, facial images with a higher number of occurrences of a common linking attribute may be displayed with a prominence greater than facial images of individuals with a lower number of occurrences of a common linking attribute. For example, greater prominence may be reflected in a presented size of facial images, as depicted above with respect to FIG. 18A. Additionally or alternatively, greater prominence may be reflected in a proximity to a focal location on the display, as depicted above with respect to FIGS. 18C-18F.

In some embodiments, method 2200 may include additional steps. For example, method 2200 may include presenting a user with a pick list of linking attributes and altering a presentation of facial images on the display in response to a selection from the pick list, as explained above with respect to display module 2004 of FIG. 20.

Moreover, any of the interactions described above with respect to visualization module 1704 of FIG. 17 may be implemented in method 2200. For example, the set of the plurality of facial images may be updated and/or animated in response to input from the user.

Figure 22B:
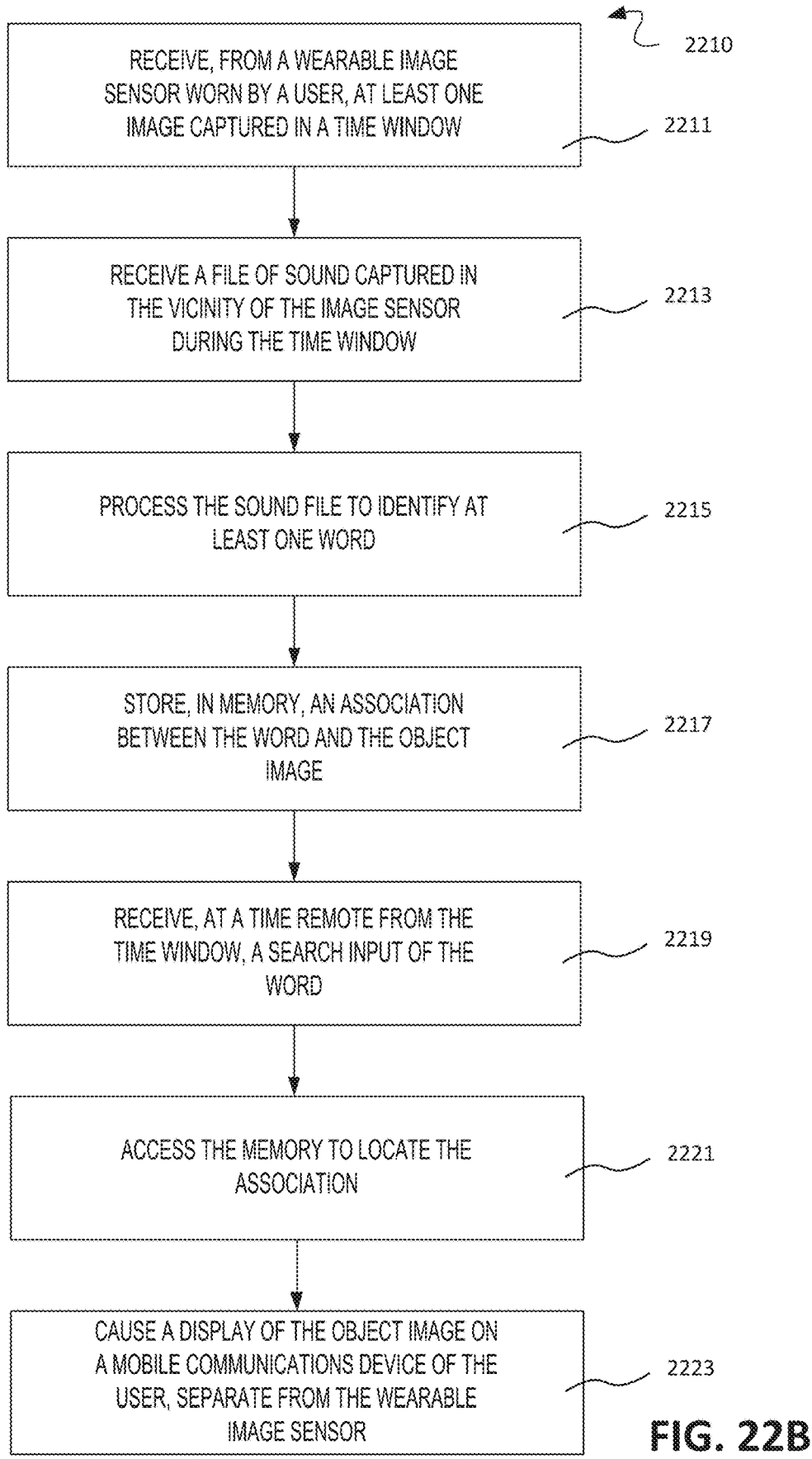
FIG. 22B is a flowchart of an exemplary embodiment of a method for indexing words in sound files to object images consistent with the present disclosure.

FIG. 22B is a flowchart of a method 2210 for indexing words in sound files to object images. Method 2210 may be implemented by a general-purpose computer or a special-purpose computer built according to embodiments of the present disclosure. For example, method 2210 may be executed by at least one of processors 210, 210a, 210b, and 540. In some embodiments, the steps of method 2210 may be performed by wearable apparatus 110. In other embodiments, the steps of method 2210 may be performed by wearable apparatus 110 and one or more external devices (e.g., a processor included in an external server that receives data from wearable apparatus 110 over a network and/or a processor included in an external device such as a laptop, smartwatch, smartphone, tablet, or ear phones, etc.).

At step 2211, the processor may receive from a wearable image sensor worn by a user at least one image captured in a time window. For example, the processor may receive images from image sensor 220 of capturing unit 710. The image may comprise an object image. In some embodiments, the object image may include a facial image or be a facial image.

At step 2213, the processor may receive a file of sound captured in a vicinity of the image sensor during the time window. For example, a microphone of a wearable apparatus including the wearable image sensor may capture the file of sound. Additionally or alternatively, a mobile communications device other than the wearable image sensor may capture the file of sound and send the file to the processor.

At step 2215, the processor may process the sound file to identify at least one word in the sound file. For example, the processor may process the file as described above with respect to linking attribute module 2002.

At step 2217, the processor may store in memory an association between the word and the object image. For example, the processor may store the object image indexed by the at least one word, as depicted in the example of FIG. 21B.

At step 2219, the processor may receive at a time remote from the time window a search input of the at least one key word. As used herein, "remote" may refer to any time at least a threshold amount of time later than the time window, such as at least 1 minute, 5 minutes, 15 minutes, 1 hour, 1 day, 1 week, or the like. As explained above with respect to display module 2004, the processor may generate a text box (e.g., for display on the wearable apparatus or on the mobile communications device) to receive the search input and/or may generate a list of keywords and display the list of keywords to the user (e.g., via the wearable apparatus or on the mobile communications device) such that the user may input the search by selecting one or more keywords from the list.

At step 2221, the processor may access the memory to locate the association between the at least one key word and the at least one object image. For example, the processor may search indexed keywords to obtain at least one object image stored in a database and indexed to the at least one key word.

At step 2223, the processor may cause a display of the object image on a mobile communications device of the user, separate from the wearable image sensor. For example, the processor may transmit the object image to the mobile communications device for display.

In some embodiments, the display may occur on a mobile communications device wirelessly paired to the wearable image sensor. For example, the mobile communications device may be paired to the wearable sensor via a radio frequency, such as Bluetooth®, or via a computer network, such as the Internet.

In some embodiments, causing the display may include displaying a plurality of facial images each associated with the keyword. For example, the processor may generate a face cloud, as explained above with respect to visualization module 1704 of FIG. 17. Examples of generated face clouds are also depicted in FIGS. 18A-18H, described above.

Moreover, any of the interactions described above with respect to visualization module 1704 of FIG. 17 may be implemented in method 2220. For example, the object image (or the plurality of facial images) may be updated and/or animated in response to input from the user.

Figure 22C:
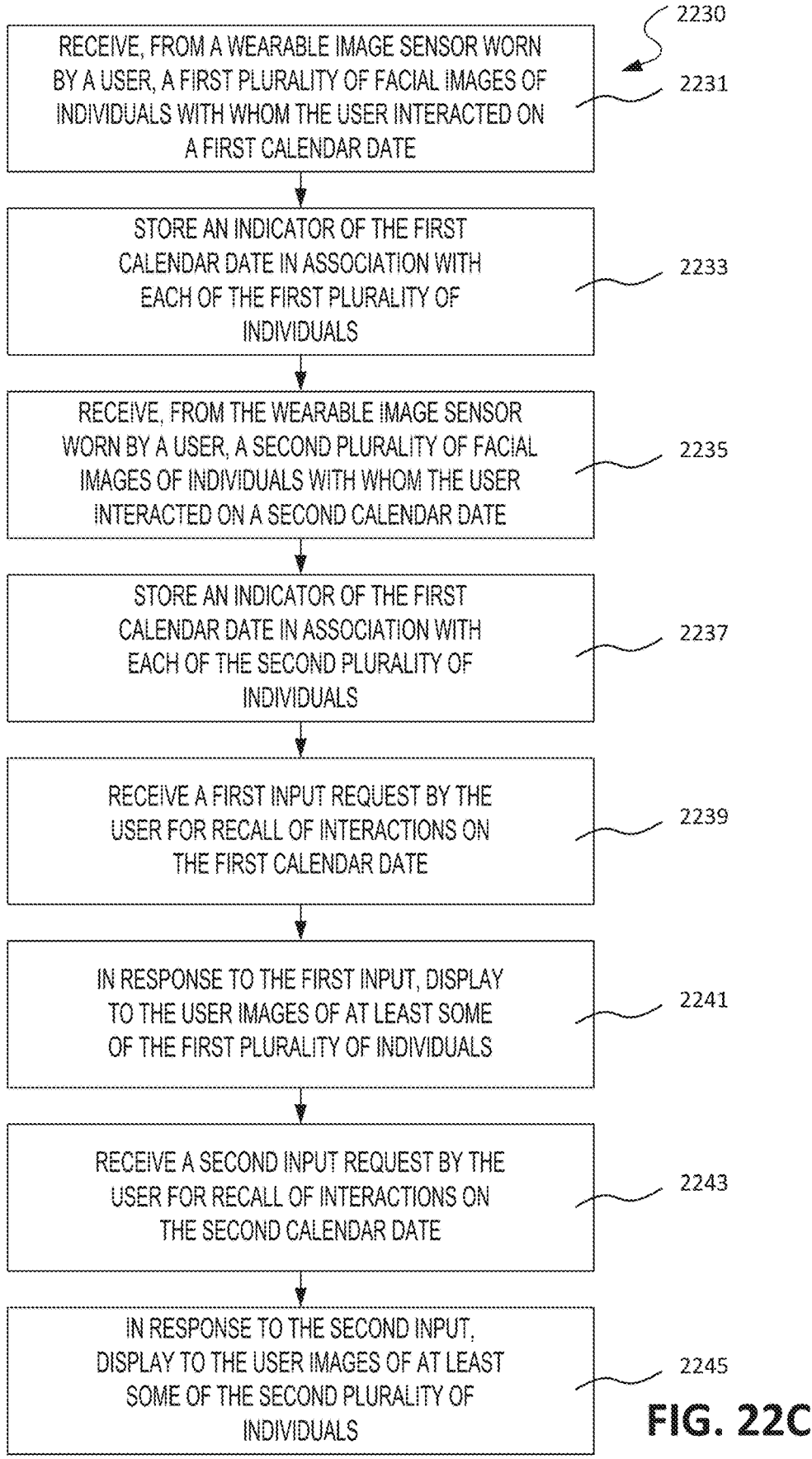
FIG. 22C is a flowchart of an exemplary embodiment of a method for indexing facial images to calendar dates consistent with the present disclosure.

FIG. 22C is a flowchart of a method 2230 for indexing facial images to calendar dates. Method 2230 may be implemented by a general-purpose computer or a special-purpose computer built according to embodiments of the present disclosure. For example, method 2230 may be executed by at least one of processors 210, 210a, 210b, and 540. In some embodiments, the steps of method 2230 may be performed by wearable apparatus 110. In other embodiments, the steps of method 2230 may be performed by wearable apparatus 110 and one or more external devices (e.g., a processor included in an external server that receives data from wearable apparatus 110 over a network and/or a processor included in an external device such as a laptop, smartwatch, smartphone, tablet, ear phones, etc.).

At step 2231, the processor may receive from a wearable image sensor worn by a user a first plurality of facial images of individuals with whom the user interacted on a first calendar date. For example, the processor may receive the first plurality of facial images from image sensor 220 of capturing unit 710.

At step 2233, the processor may store an indicator of the first calendar date in association with each of the first plurality of individuals. For example, as explained above with respect to FIG. 20, image sensor 220 or facial image module 2001 may stamp the plurality of images with the first calendar date.

At step 2235, the processor may receive from the wearable image sensor worn by the user a second plurality of facial images of individuals with whom the user interacted on a second calendar date. For example, the processor may receive the second plurality of facial images from image sensor 220 of capturing unit 710.

At step 2237, the processor may store an indicator of the second calendar date in association with each of the second plurality of individuals. For example, as explained above with respect to FIG. 20, image sensor 220 or facial image module 2001 may stamp the plurality of images with the second calendar date. It will be appreciated that a date may include a day, a month, and a year, or a subset thereof, for example a month and a year, or just a year, a day of week, or the like.

In some embodiments, the processor may further receive sound data associated with the facial images. For example, a microphone of a wearable apparatus including the wearable image sensor may capture the sound data. Additionally or alternatively, a mobile communications device other than the wearable image sensor may capture the sound data and send the data to the processor.

In embodiments where the processor receives sound data, the processor may further extract key words from the sound data. For example, the processor may process the file as described above with respect to linking attribute module 2002.

In embodiments where the processor extracts key words, the processor may further store the key words in memory associated with a date of recording. For example, as explained above with respect to FIG. 20, facial image module 2001 may stamp the sound data with the date of recording, which may be the first calendar date or the second calendar date.

At step 2239, the processor may receive a first input request by the user for recall of interactions on the first calendar date. For example, the processor may generate a text box (e.g., for display on the wearable apparatus or on a mobile communications device other than the wearable image sensor) to receive the input and/or may display a calendar to the user (e.g., via the wearable apparatus or on the mobile communications device) such that the first input is a result of a user's respective touch interactions with screen regions corresponding to the first calendar date.

At step 2241, the processor may, in response to the first input, display to the user images of at least some of the second plurality of individuals. For example, the processor may generate a face cloud, as explained above with respect to visualization module 1704 of FIG. 17. Examples of generated face clouds are also depicted in FIGS. 18A-18H, described above.

In embodiments where the processor stores key words, the processor may further present to the user the key words associated with interactions on the first calendar date. For example, the processor may present the key words in a list or in a graphic, such as a word cloud.

At step 2243, the processor may receive a second input request by the user for recall of interactions on the second calendar date. For example, the processor may generate a text box (e.g., for display on the wearable apparatus or on a mobile communications device other than the wearable image sensor) to receive the input and/or may display a calendar to the user (e.g., via the wearable apparatus or on the mobile communications device) such that the second input is a result of a user's respective touch interactions with screen regions corresponding to the second calendar date.

At step 2245, the processor may, in response to the second input, display to the user images of at least some of the first plurality of individuals. For example, the processor may generate a face cloud, as explained above with respect to visualization module 1704 of FIG. 17. Examples of generated face clouds are also depicted in FIGS. 18A-18H, described above.

In embodiments where the processor stores key words, the processor may further present to the user the key words associated with interactions on the second calendar date. For example, the processor may present the key words in a list or in a graphic, such as a word cloud.

Moreover, any of the interactions described above with respect to visualization module 1704 of FIG. 17 may be implemented in method 2230. For example, the object image (or the plurality of facial images) may be updated and/or animated in response to input from the user.

In some embodiments, method 2230 may include additional steps. For example, in embodiments where the processor stores key words, method 2230 may include receiving a search input by the user, the search input including at least one of the key words. As explained above, the processor may generate a text box (e.g., for display on the wearable apparatus or on the mobile communications device) to receive the search input and/or may generate a list of keywords and display the list of keywords to the user (e.g., via the wearable apparatus or on the mobile communications device) such that the user may input the search by selecting one or more keywords from the list. In such embodiments, the at least some of the first plurality of individuals displayed in step 2241 and/or the at least some of the second plurality of individuals displayed in step 2245 may be associated with the at least one of the key words.

Figure 22D:
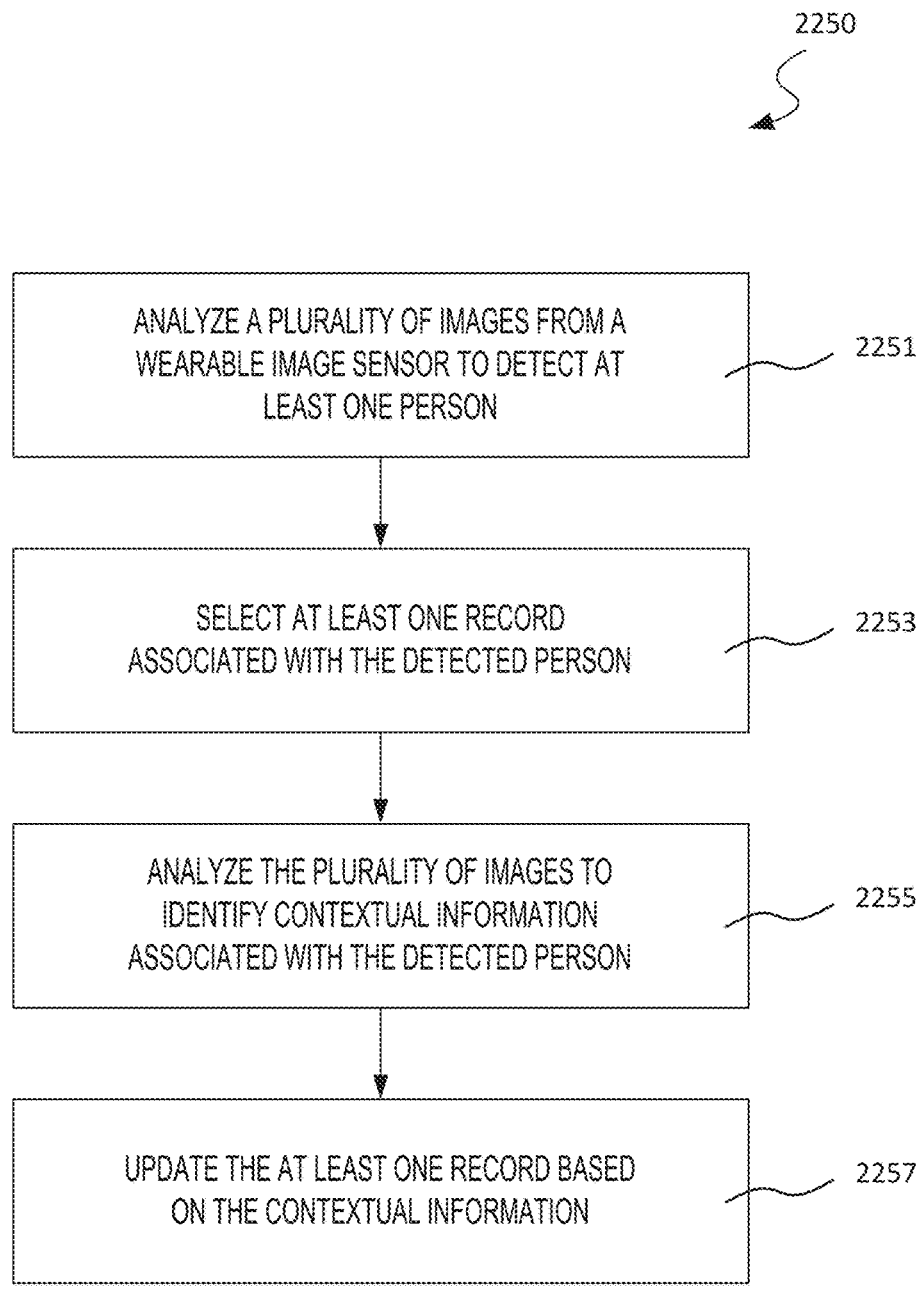
FIG. 22D is a flowchart of an exemplary embodiment of a method for indexing facial images to contextual information extracted from images consistent with the present disclosure.

FIG. 22D is a flowchart of a method 2250 for indexing facial images to contextual information extracted from images. Method 2250 may be implemented by a general-purpose computer or a special-purpose computer built according to embodiments of the present disclosure. For example, method 2250 may be executed by at least one of processors 210, 210*a*, 210*b*, and 540. In some embodiments, the steps of method 2250 may be performed by wearable apparatus 110. In other embodiments, the steps of method 2250 may be performed by wearable apparatus 110 and one or more external devices (e.g., a processor included in an external server that receives data from wearable apparatus 110 over a network and/or a processor included in an external device such as a laptop, smartwatch, smartphone, tablet, ear phones, etc.).

At step 2251, the processor may analyze a plurality of images to detect at least one person. For example, the processor may receive the plurality of images from a wearable image sensor configured to capture a plurality of images from an environment of a user of the wearable apparatus (e.g., image sensor 220 of capturing unit 710). The processor may detect the at least one person using image analysis, e.g., as described above with respect to facial image module 2001.

At step 2253, the processor may select at least one record associated with the detected person. For example, the processor may identify the detected at least one person using image analysis, e.g., as described above with respect to person identification module 1701. The at least one record may be selected based on the identification.

At step 2255, the processor may analyze the plurality of images to identify contextual information associated with the detected person. The processor may identify the contextual information using image analysis, e.g., as described above with respect to linking attribute module 2002.

Contextual information may be based, at least in part, on a second person appearing in the plurality of images in conjunction with the detected person. For example, the processor may identify the second person using image analysis, e.g., as described above with respect to person identification module 1701. The contextual information may comprise a relationship determined between the detected person and the second person, such as 'family,' 'friend,' 'father-son,' or the like. Additionally or alternatively, the contextual information may comprise a determined mood of the detected person toward the second person and/or a determined mood of the second person toward the detected person. As an example, the contextual information may comprise 'exasperated' if the detected person rolls her eyes at the second person, may comprise 'angry' if the second person has furrowed brows and/or is yelling at the detected person, or the like.

Additionally or alternatively, contextual information may be based, at least in part, on a uniform the detected person is wearing. For example, if the detected person is wearing a police uniform, the contextual information may comprise 'police,' 'police officer,' or the like. In another example, if the detected person is wearing a pilot uniform, the contextual information may comprise 'pilot' or the like.

Additionally or alternatively, contextual information may be based, at least in part, on a room the detected person appears in. For example, if the detected person is in a gym, the contextual information may comprise 'gym,' 'workout,' or the like. In another example, if the detected person is in an office, the contextual information may comprise 'office,' 'coworker,' or the like.

Any of the examples above may be combined. For example, if the room the detected person appears in is a conference room and the second person is identified as a boss, the contextual information may comprise 'conference meeting,' 'important meeting,' or the like. In another example, if the room the detected person appears in is a police station and the uniform is a police uniform, the contextual information may comprise 'crime report' or the like. In yet another example, if the uniform is a business suit, and the second person is identified as a CEO, the contextual information may comprise 'business meeting,' 'client meeting,' 'board meeting,' or the like.

At step 2257, the processor may update the at least one record based on the contextual information. For example, the processor may store the contextual information in association with the at least one record and/or may index the at least one record by the contextual information.

Figure 22E:
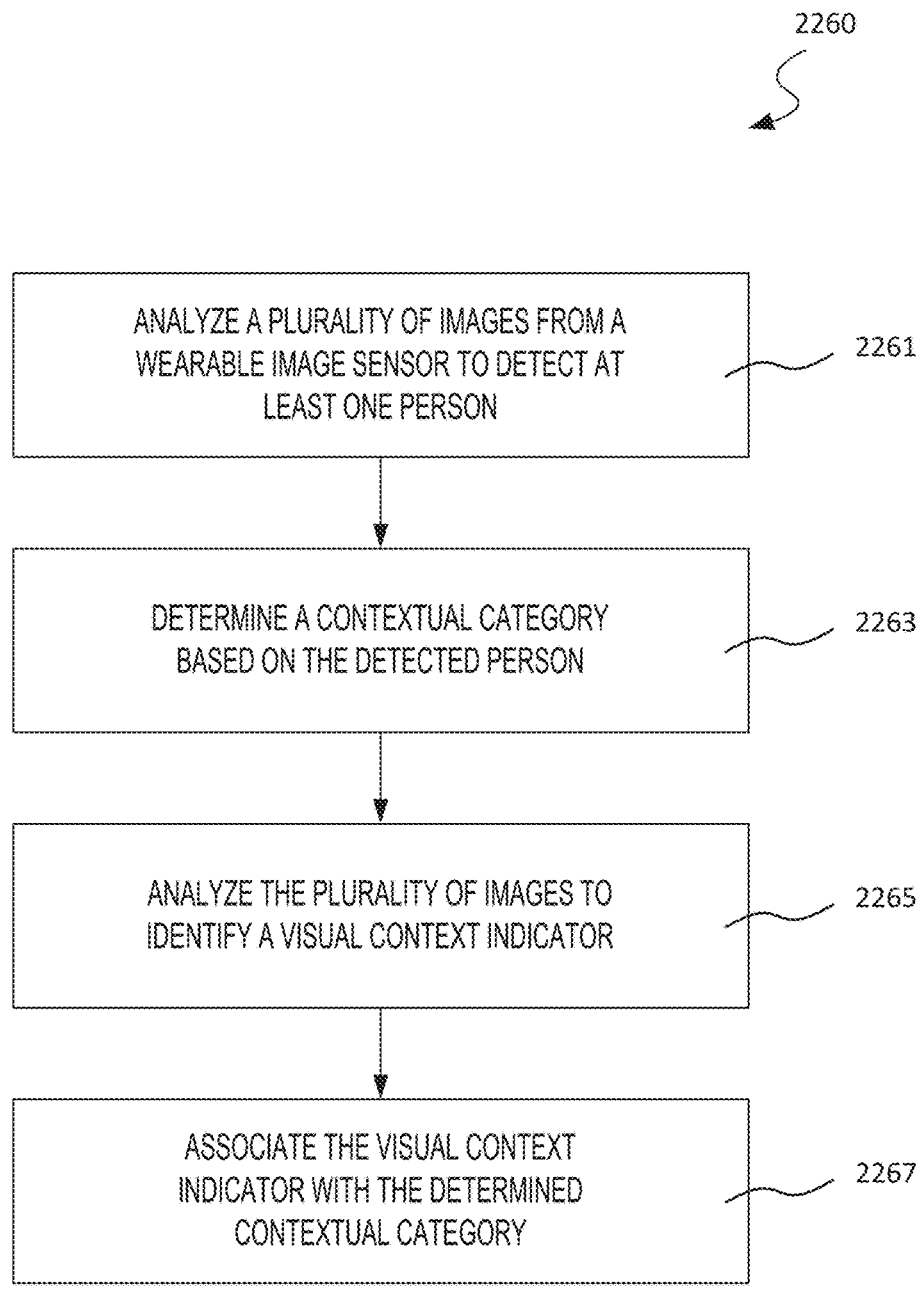
FIG. 22E is a flowchart of an exemplary embodiment of a method for indexing visual context indicators extracted from images to contextual categories associated with persons consistent with the present disclosure.

FIG. 22E is a flowchart of a method 2260 for indexing visual context indicators extracted from images to contextual categories associated with persons. Method 2260 may be implemented by a general-purpose computer or a special-purpose computer built according to embodiments of the present disclosure. For example, method 2260 may be executed by at least one of processors 210, 210*a*, 210*b*, and 540. In some embodiments, the steps of method 2260 may be performed by wearable apparatus 110. In other embodiments, the steps of method 2260 may be performed by wearable apparatus 110 and one or more external devices (e.g., a processor included in an external server that receives data from wearable apparatus 110 over a network and/or a processor included in an external device such as a laptop, smartwatch, smartphone, tablet, ear phones, etc.).

At step 2261, the processor may analyze a plurality of images to detect at least one person. For example, the processor may receive the plurality of images from a wearable image sensor configured to capture a plurality of images from an environment of a user of the wearable apparatus (e.g., image sensor 220 of capturing unit 710). The processor may detect the at least one person using image analysis, e.g., as described above with respect to facial image module 2001.

At step 2263, the processor may determine a contextual category based on the detected person. For example, the processor may identify the detected at least one person using image analysis, e.g., as described above with respect to person identification module 1701. The contextual category may be selected based on the identification.

The contextual category may be work related. For example, the contextual category may comprise an event, such as 'meeting,' 'conference,' or the like; a person, such as 'coworker, 'boss,' or the like; a location, such as 'office,' 'breakroom,' or the like; etc.

Additionally or alternatively, the contextual category may be a social category. For example, the contextual category may comprise an event, such as 'coffee,' 'lunch,' or the like; a person, such as 'close friend, 'acquaintance,' or the like; a location, such as 'coffee shop,' 'subway,' or the like; etc.

Additionally or alternatively, the contextual category may be a family category. For example, the contextual category may comprise an event, such as 'dinner,' 'family vacation,' or the like; a person, such as 'parent, 'sibling,' or the like; a location, such as 'home,' 'grandma's house,' or the like; etc.

Additionally or alternatively, the contextual category may be based on a context of a room or a location based on one or more persons identified in the room. For example, the room may be identified as the bedroom such that a family category is selected, the location may be identified as an office building such that a work related category is selected, or the like.

At step 2265, the processor may analyze the plurality of images to identify a visual context indicator. The processor may identify the visual context indicator using image analysis, e.g., as described above with respect to facial image module 2001.

The visual context indicator may comprise an object, a person, or a gesture associated with the contextual category. For example, a stapler, a boss, or typing may all be associated with a work related contextual category. In another example, tickets to a sporting game or event, a friend, or laughing may all be associated with a social category. In yet another example, a toy, a sibling, or hugging may all be associated with a family category.

At step 2267, the processor may associate the visual context indicator with the determined contextual category. For example, the processor may store the visual context indicator in association with the determined contextual category. Additionally or alternatively, the processor may index the visual context indicator by the determined contextual category and/or may index the determined contextual category by the visual context indicator.

Automatic Object Comparison

In some embodiments, a wearable apparatus of the present disclosure may provide for automatic object comparison. For example, the apparatus may automatically identify two objects, look-up information related to the identities of the two objects, and display the comparison such that the user may ascertain differences between the two objects. By performing the look-up, the wearable apparatus may provide for a faster and more accurate comparison as compared with manual, subjective forms of comparison.

In addition, rather than using conventional user interfaces, embodiments of the present disclosure instead use specific triggers to automatically perform the comparison. Conventional interfaces are generally text-based rather than trigger-based and therefore difficult to use for fast and automatic comparison. Accordingly, embodiments of the present disclosure provide for improved user experiences with the wearable apparatus by providing for easier manipulation by the user.

Figure 23:
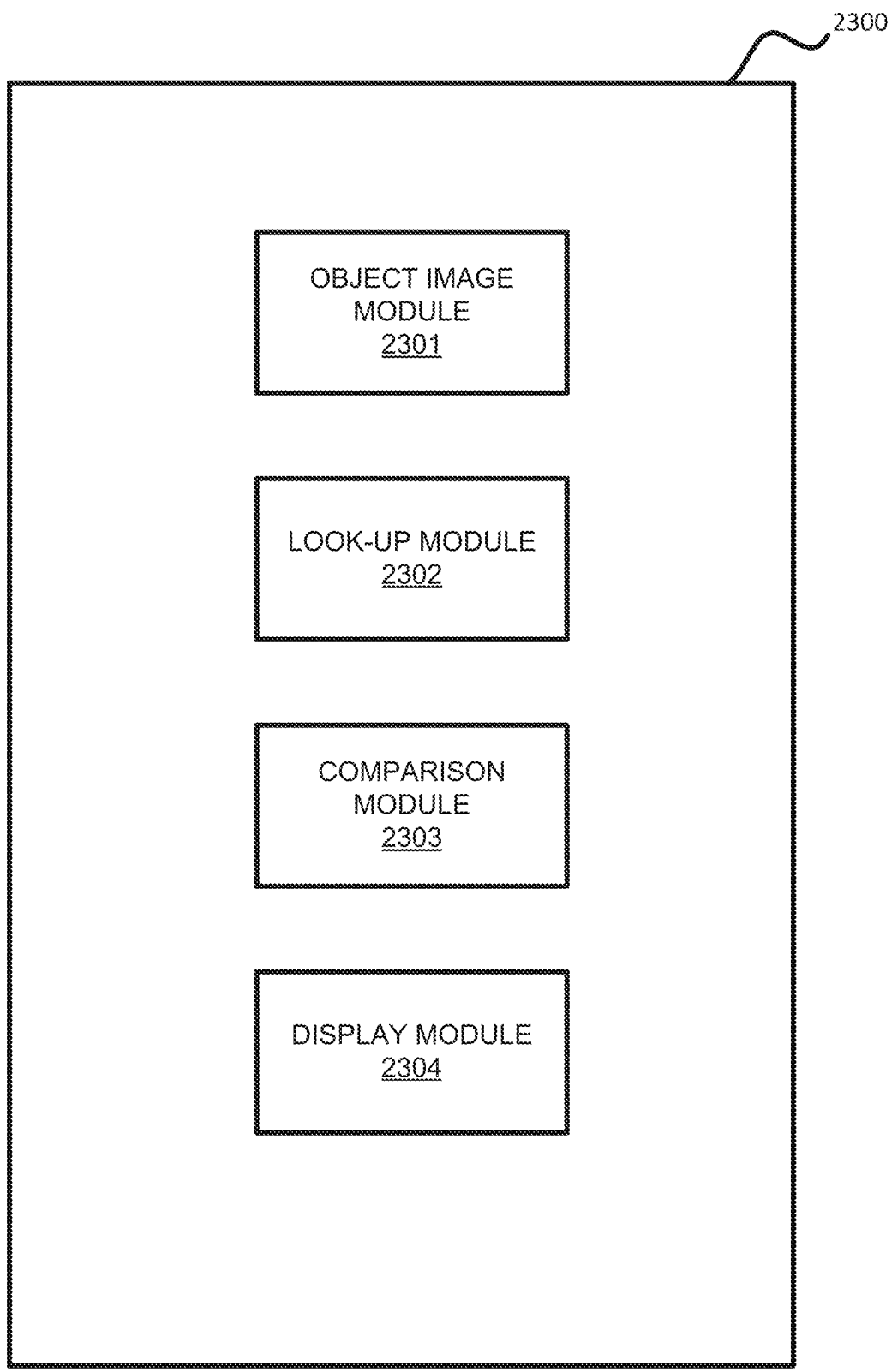
FIG. 23 illustrates an exemplary embodiment of a memory containing software modules for automatic object comparison consistent with the present disclosure.

FIG. 23 illustrates an exemplary embodiment of a memory 2300 containing software modules consistent with the present disclosure. Included in memory 2300 are object image module 2301, look-up module 2302, comparison module 2303, and display module 2304. Modules 2301, 2302, 2303, and 2304 may contain software instructions for execution by at least one processing device, e.g., processor 210, included with a wearable apparatus. In some embodiments, memory 2300 may comprise a non-transitory computer readable medium that resides on a mobile communications device (e.g., a smart phone) configured to be wirelessly paired with wearable image sensor 220 of capturing unit 710.

Object image module 2301, look-up module 2302, comparison module 2303, and display module 2304 may cooperate to perform automatic object comparison, as well as cooperating to allow particular displays of such comparisons. Memory 2300 may be separate from and/or integrated with memory 550 of FIG. 6, described above. Similarly, orientation identification module 601, orientation adjustment module 602, and monitoring module 603 of FIG. 6 may operate in tandem or concurrently with object image module 2301, look-up module 2302, comparison module 2303, and display module 2304 of FIG. 23.

Object image module 2301 may be configured to determine from at least one of a plurality of images a presence of two differing objects indicated by a user. For example, the images may be from a wearable image sensor configured to capture the images from an environment of the user (e.g., image sensor 220 of capturing unit 710).

In some embodiments, object image module 2301 may discard images captured by image sensor 220 that do not include at least two differing objects while retaining images that include at least two differing objects. For example, object image module 2301 may apply image analysis to determine objects present in the image.

Object image module 2301 may detect objects in received images using any known techniques. For example, object image module 2301 may perform image processing on a currently received image and determine that the received image corresponds to an image of an object that has been previously stored in memory. Thus, object image module 2301 may perform pixel-by-pixel matching. In other embodiments, object image module 2301 may perform more sophisticated techniques. For example, object image module 2301 may use one or more classifiers (or cascading classifiers) to detect an object included in the image. Additionally or alternatively, object image module 2301 may use a neural network to detect an object included in the image. Alternatively, object image module 2301 may use a neural network to derive a plurality of features (e.g., a feature set) from the image and then map the derived features (or feature set) onto features associated with detection of an object. The mapping may be performed using simple correlation or using more sophisticated techniques, such as another neural network.

In any of the embodiments, detections may have associated probabilities, e.g., output from the neural network; calculated based on percentage of matching pixels, features, etc.; or the like. Accordingly, object image module 2301 may finalize a detection of an object only if the detection has an associated probability above a threshold. Alternatively, object image module 2301 may apply further detection techniques if the detection is indeterminate, e.g., above a first threshold but below a second, higher threshold. In such an embodiment, object image module 2301 may apply a classifier and may, if the classifier produces a detection with an indeterminate probability, then apply one or more additional classifiers and/or a neural network to produce one or more additional detection probabilities. Based on the additional detection probabilities, e.g., if they exceed the second threshold, object image module 2301 may finalize the detection. Any detection not finalized may be discarded.

In any of the embodiments, the image may include at least two differing objects. Object image module 2301 may therefore use a bounding box architecture, such as You Only Look Once (YOLO) or Single-Shot Detector (SSD), to identify bounding boxes including objects. For example, if object image module 2301 uses a bounding box architecture and receives no bounding boxes classified as objects or receives bounding boxes all having object classifications below a threshold (e.g., less than 50%, less than 40%, less than 25%, less than 10%, less than 5%, or the like), object image module 2301 may discard the image as including no objects. Similarly, if object image module 2301 uses a bounding box architecture and receives a plurality of bounding boxes such that only a single object is present in the image or that all objects in the image are classified as the same object, object image module 2301 may discard the image as failing to include at least two differing objects. On the other hand, if object image module 2301 uses a bounding box architecture and receives a plurality of bounding boxes classified as objects but not all the same object or receives a plurality of bounding boxes having object classifications above a threshold (e.g., more than 50%, more than 40%, more than 25%, more than 10%, more than 5%, or the like) but not all the same object, object image module 2301 may detect portions of the image defined by the plurality of bounding boxes as including differing objects.

In any of the embodiments discussed, received images may vary in size, shape, and content. For example, in some embodiments, an image including a wider scene (e.g., a plurality of individuals, or an individual and his or her surrounding environment) may be cropped or otherwise truncated to a face, a portion of a face, a headshot of a person (e.g., head and shoulders), or a portion of a person's body including the person's face. In other embodiments, received images may include such wider scenes (e.g., a plurality of individuals, or an individual and his or her surrounding environment). In still other embodiments, received images may include a face, a portion of a face, a headshot of a person (e.g., head and shoulders), or a portion of a person's body including the person's face. An image may also be truncated to include a portion containing an inanimate object, such as a product.

Look-up module 2302 may be configured to perform a look up of the two differing objects to ascertain identities of the two differing objects. For example, look-up module 2302 may perform an image search using the image including each object or one or more portion of the image including the objects, e.g., portions remaining after cropping the image to only include a bounding box associated with each object. The cropped portion may include a buffer between the bounding box and the cropping.

Additionally or alternatively, an identification produced by classifiers, neural networks, or any other technique or a combination thereof from object image module 2301 may be used to perform the look-up. For example, look-up module 2302 may use one or more strings of text identifying the objects to perform the look-up in addition to or in lieu of using the image (or a portion thereof) including the objects.

Look-up module 2302 may perform the look-up separately for each of the two differing objects. Alternatively, look-up module 2302 may perform the look-up in parallel for each of the two differing objects. As used herein, "in parallel" refers to multithreading, parallel computing, or any other known technique for performing tasks in parallel even if the underlying architecture (such as a conventional processor) still requires switching between threads during execution.

Figure 24A:
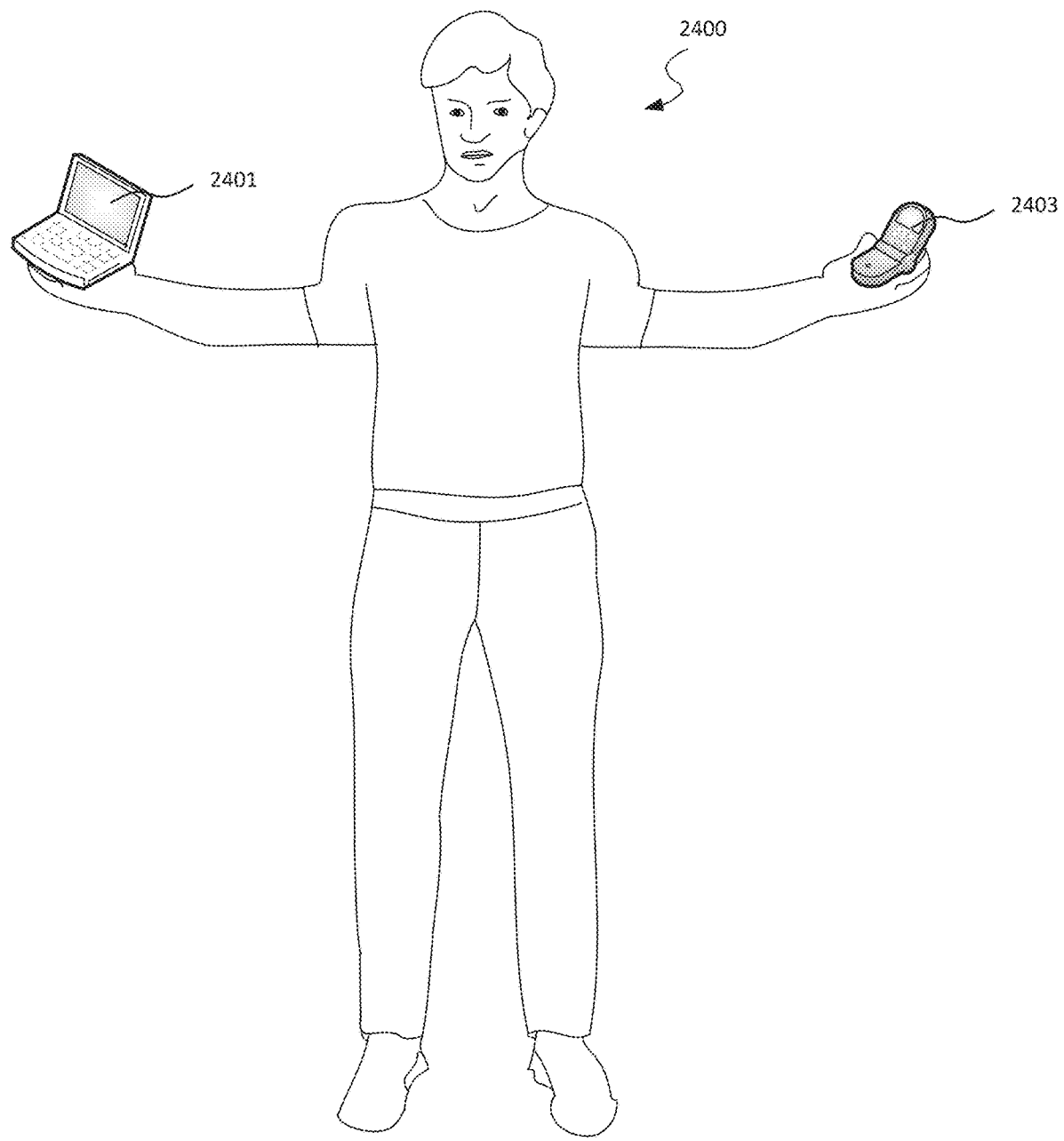
FIG. 24A illustrates an example of a trigger for performing a look up of two differing objects consistent with the present disclosure.
Figure 24B:
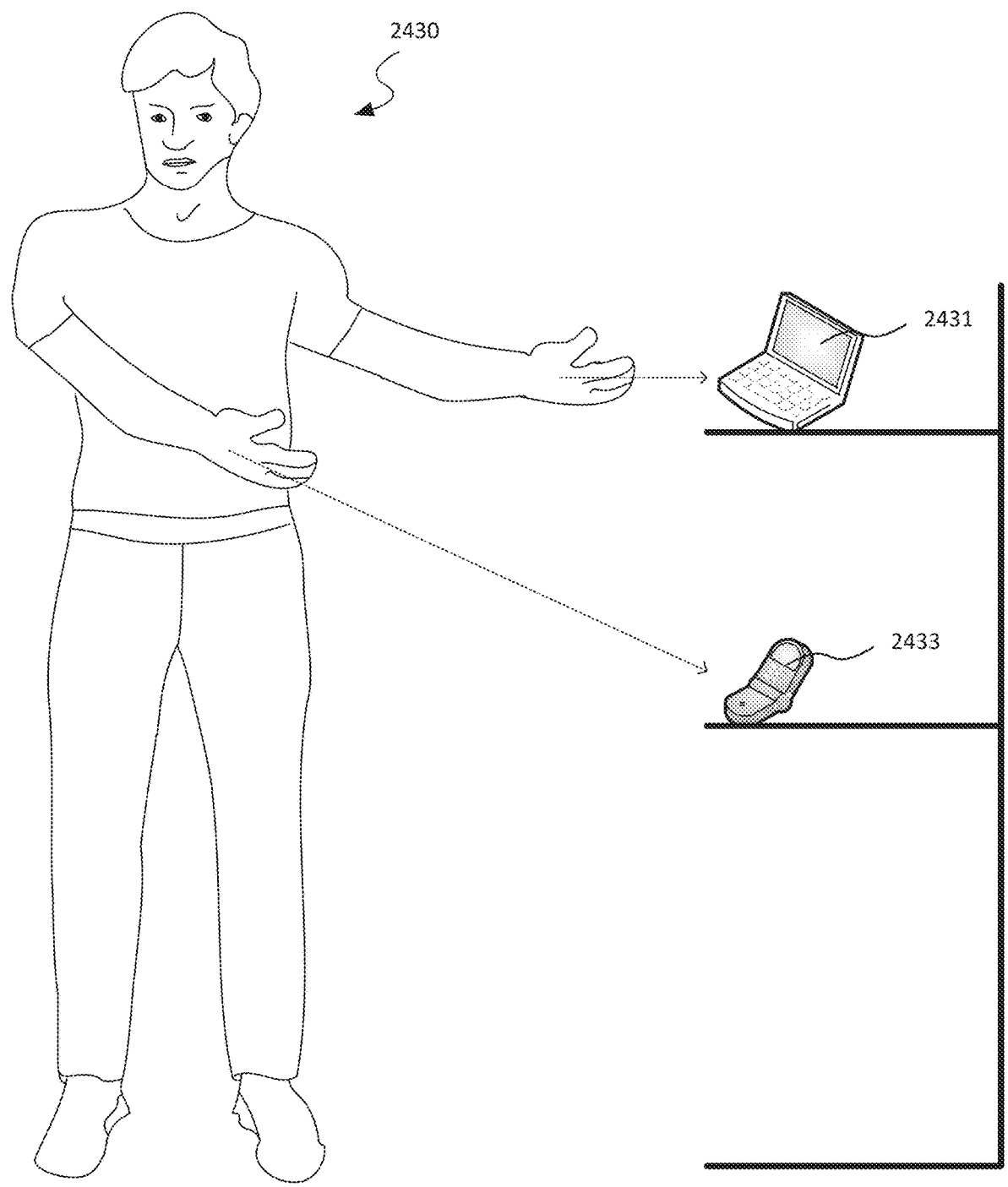
FIG. 24B illustrates another example of a trigger for performing a look up of two differing objects consistent with the present disclosure.

In some embodiments, the two differing objects may be held in at least one hand of the user. Accordingly, the look up of the two differing objects to ascertain identities of the two differing objects may be triggered based on a presence of the two differing objects in the hands of the user, as depicted in FIG. 24A, described below. Additionally or alternatively, performing the look up of the two differing objects to ascertain identities of the two differing objects may be triggered based on the two differing objects being pointed at by the user, as depicted in FIG. 24B, described below.

In any of the embodiments described above with triggers, look-up module 2302 and/or image module 2301 may use image analysis to detect the trigger. Accordingly, one or more classifiers and/or neural networks may be used to identify the user's hands (or other body parts) and determine a gesture therefrom. For example, the image analysis may generate a trigger when the user's hands are identified and classified as holding two differing objects, when the user's hands (or fingers) are identified and classified as pointing at two differing objects, or the like.

Additionally with or alternatively to a gesture-based trigger, performing the look up of the two differing objects to ascertain identities of the two differing objects may be triggered based on receiving an input from the user. For example, the input from the user may include a gesture, a voice command and/or a depressed button. The input may be received from the wearable apparatus and/or from a mobile communications device associated with the user. In embodiments where input is combined with a gesture-based trigger, the input may function to confirm that the user desires an automatic object comparison to be performed. For example, look-up module 2302 and/or image module 2301 may detect the trigger and then send a command (to the wearable apparatus and/or a mobile communications device associated with the user) to prompt the user for confirmation.

In some embodiments, performing the look up of the two differing objects to ascertain the identities of the two differing objects may include undertaking Internet searches on at least one image of each of the differing objects. For example, as explained above, look-up module 2302 may perform an Internet image search and/or an Internet text search.

Look-up module 2302 may be further configured to perform a look up of descriptive information about the two differing objects. For example, look-up module 2302 may perform an image search using the image including each object or one or more portion of the image including the objects, e.g., portions remaining after cropping the image to only include a bounding box associated with each object. The cropped portion may include a buffer between the bounding box and the cropping.

Additionally or alternatively, the identities produced from the first look-up described above may be used to perform the look-up for descriptive information. For example, look-up module 2302 may use one or more strings of text comprising the identities to perform the look-up for descriptive information in addition to or in lieu of using the image (or a portion thereof) including the objects.

Look-up module 2302 may perform the look-up for identities and the look-up for descriptive information separately, as described above. Alternatively, look-up module 2302 may perform the look-ups simultaneously. For example, an image search and/or use of classifiers, neural networks, or any combination thereof from object image module 2301 may produce both identities of the two differing objects as well as descriptive information thereabout. Additionally or alternatively, one or more strings of text identifying the objects may be used to perform the look-ups for identities of the two differing objects as well as descriptive information thereabout.

In some embodiments, performing the look up of the descriptive information about the two differing objects may include undertaking an Internet search of product reviews. For example, as explained above, look-up module 2302 may perform a text search of one or more Internet-based sources identified as indexing or otherwise including product reviews using the identities of the differing objects. Internet-based sources identified as indexing or otherwise including product reviews may include online stores (such as Amazon®, Wal-Mart®, or the like), social networks (such as Facebook®, Twitter®, or the like), review aggregators (such as Consumer Reports™, CNET®, or the like), or the like.

Additionally or alternatively, performing the look up of the descriptive information about the two differing objects may include undertaking an Internet search in one or more social networks. For example, as explained above, look-up module 2302 may perform a text search of one or more social networks using the identities of the differing objects.

Additionally or alternatively, performing the look up of the descriptive information about the two differing objects may include undertaking an Internet search of text identified on at least one of the two differing objects. For example, look-up module 2302 may perform a text search of one or more Internet-based sources using text identified (e.g., using optical character recognition) on the objects. The text on the objects may have been identified during classification by image module 2301 and/or during the look-up for identities described above.

Additionally or alternatively, performing the look up of the descriptive information about the two differing objects may include undertaking an Internet search of dietary information identified on at least one of the two differing objects. For example, look-up module 2302 may perform a text search of one or more Internet-based sources using dietary information identified (e.g., using optical character recognition) on the objects and/or dietary information obtained during the look-up for identities described above.

Additionally or alternatively, performing the look up of the descriptive information about the two differing objects may include undertaking an Internet search to determine a price of at least one of the two differing objects. For example, as explained above, look-up module 2302 may perform a text search of one or more Internet-based sources identified as stores or otherwise including prices using the identities of the differing objects. Internet-based sources identified as stores may include Amazon®, Wal-Mart®, or the like, and Internet-based sources identified as otherwise including prices may include Google® Shopping, Price.com, or the like.

Comparison attribute 2303 may be configured to compare the descriptive information about the two differing objects. Any of the descriptive information obtained by look-up module 2302, such as product ratings and/or reviews, social network mentions, search engine results, dietary information, prices, or the like, may be used for the comparison. In some embodiments, comparing the descriptive information about the two differing objects includes isolating common attributes and collecting information about at least one common attribute of each of the two differing objects.

Display module 2304 may be configured to cause a display of the information about the comparison of the two differing objects in a manner permitting the user to ascertain differences between the two differing objects. For example, the user interface may include non-overlapping images of each object on a screen, e.g., on opposite sides of the screen. The user interface may further include the looked-up identities and/or looked-up descriptive information in spatial proximity to the corresponding object. The looked-up identities and/or looked-up descriptive information may be depicted visually and/or textually.

In any of the embodiments above, causing the display of the information about the comparison of the two differing objects may include transmitting the information about the comparison of the two differing objects to a mobile communications device. For example, the mobile communications device may be paired to the wearable sensor via a radio frequency, such as Bluetooth®, or via a computer network, such as the Internet.

FIG. 24A illustrates an example of a trigger for performing a look up of two differing objects consistent with the present disclosure. As depicted in FIG. 24A, a user 2400 may hold a first object 2401 in one hand and a second object 2403 in another hand in order to trigger automatic object comparison. Although depicted as using separate hands, user 2400 may hold the two differing objects (e.g., object 2401 and object 2403) in the same hand.

FIG. 24B illustrates another example of a trigger for performing a look up of two differing objects consistent with the present disclosure. As depicted in FIG. 24B, a user 2430 may point to a first object 2431 and to a second object 2433 in order to trigger automatic object comparison. Although depicted as pointing with her hands, user 2400 may point with any portion of her hands (such as one or more fingers, including a thumb). Moreover, although depicted as pointing with separate hands, user 2400 may point with the same hand, e.g., first pointing at object 2431 and then at object 2433 within a threshold period of time (such as 1 second, 5 seconds, 10 seconds, or the like).

Figure 24C:
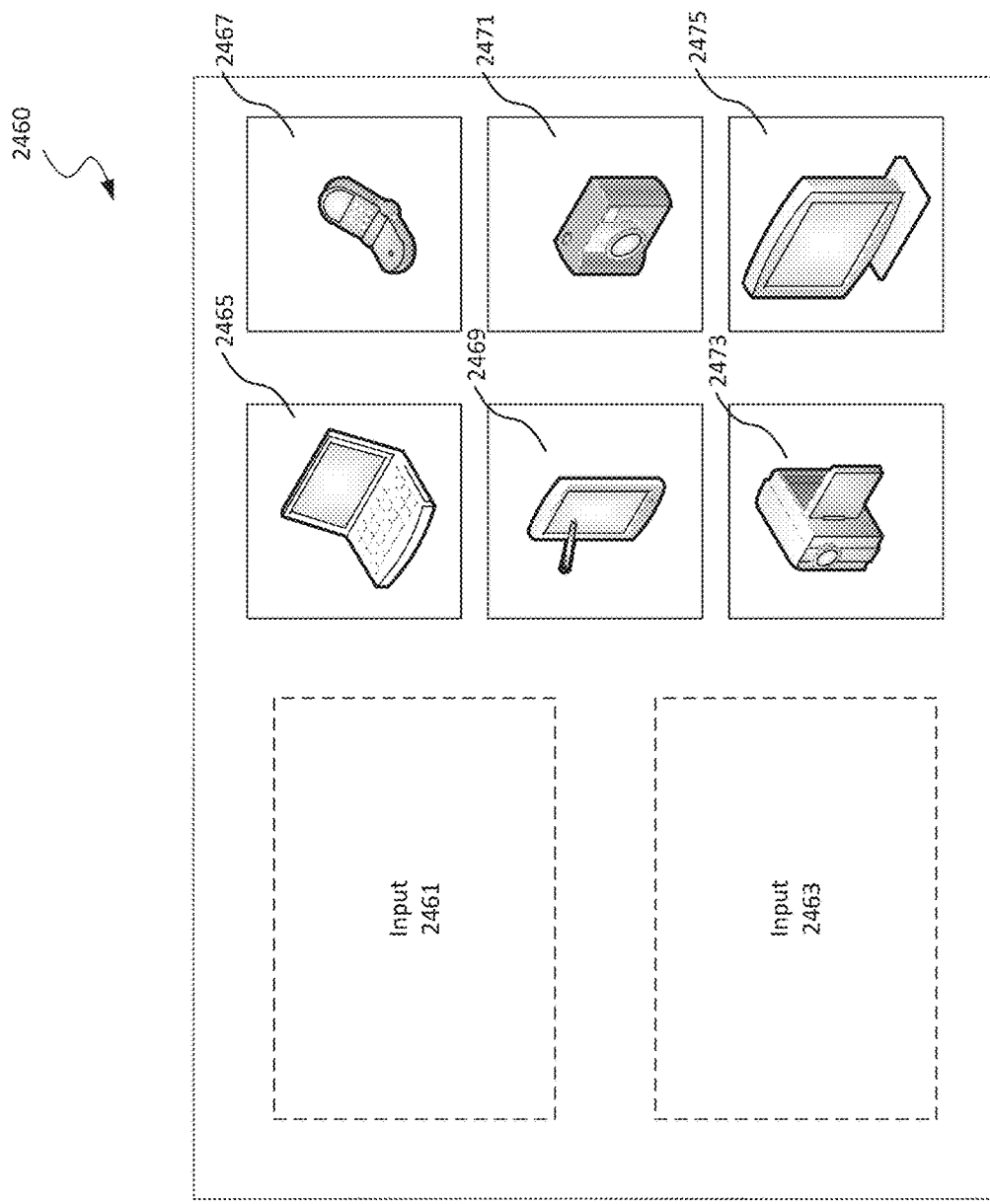
FIG. 24C illustrates an example of a user interface for performing a look up of two differing objects consistent with the present disclosure.

FIG. 24C illustrates an example of a user interface 2460 for performing a look up of two differing objects consistent with the present disclosure. Interface 2460 may be displayed on the wearable apparatus and/or on a mobile communications device associated with the user. In the example of FIG. 24C, a user of interface 2460 may drag-and-drop (e.g., with a mouse, a finger, or the like) any of stored images of objects, such as images 2465, 2467, 2469, 2471, 2473, and 2475, onto input 2461 to identify the dragged image as the first object. In addition, a user of interface 2460 may drag-and-drop (e.g., with a mouse, a finger, or the like) any of stored images of objects, such as images 2465, 2467, 2469, 2471, 2473, and 2475, onto input 2463 to identify the dragged image as the second object. The automatic object comparison may then proceed based on the dragged images. Although depicted as a standalone process, an input from a user obtained using a user interface (e.g., interface 2460 depicted in FIG. 24C) may be used instead to confirm a user's desire to perform automatic object comparison based on a detected trigger (e.g., as depicted in FIGS. 24A and 24B).

In any of the examples depicted in FIG. 24A-24C, the status of a gesture as a trigger and/or use of input may depend on settings selected by a user. For example, a user may select one or more triggers as triggers for automatic object comparison such that other triggers do not function. In such an example, a user may select an option such that pointing at objects triggers comparison while holding objects does not or vice versa.

Additionally or alternatively, a user may set an option to require confirmation before performing automatic object comparison based on one or more triggers. For example, a user may require confirmation before performing automatic object comparison based on pointing at objects and/or based on holding objects. In another example, a user may require confirmation before performing automatic object comparison based on pointing at objects but not before performing automatic object comparison based on holding objects or vice versa.

Figure 25:
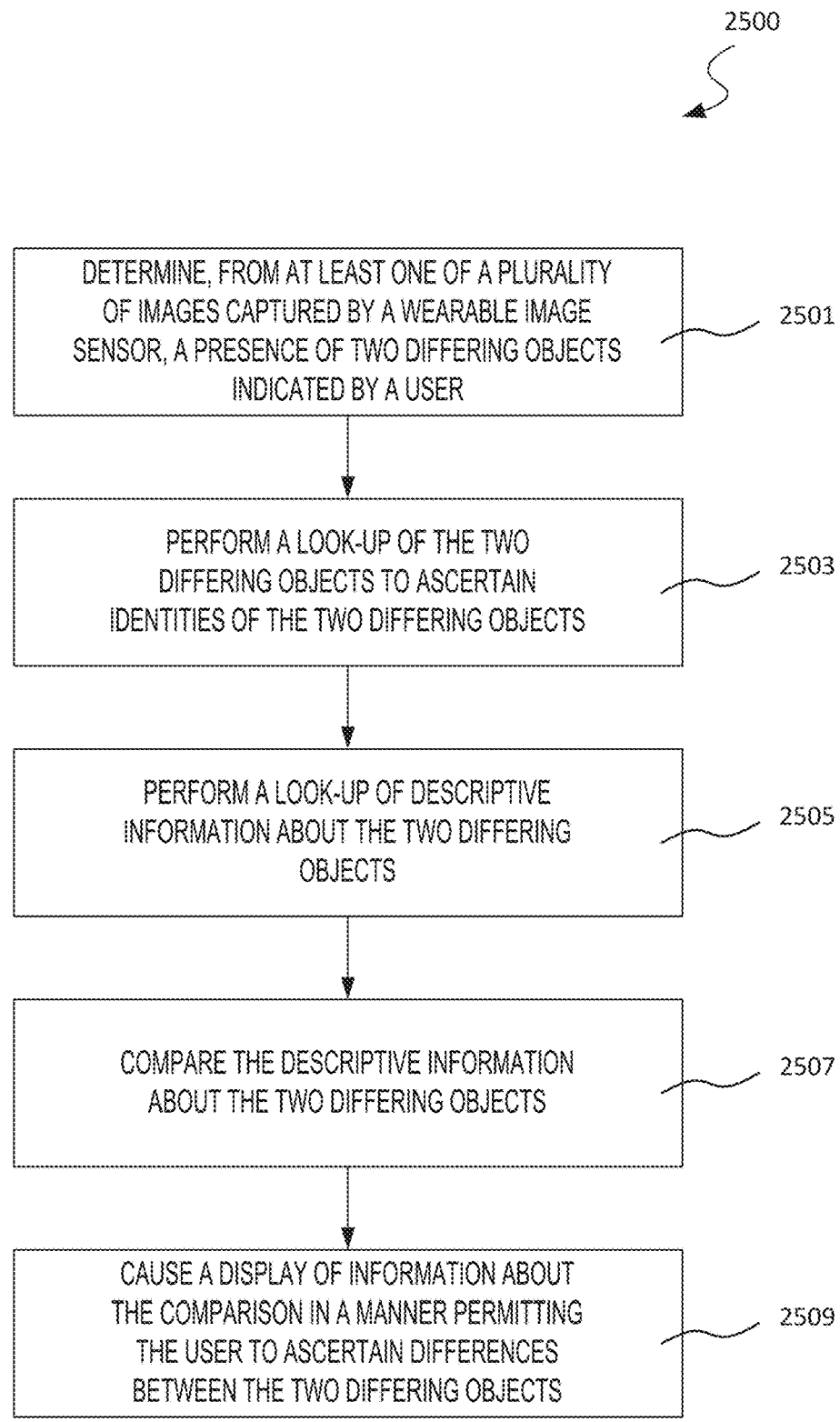
FIG. 25 is a flowchart of an exemplary embodiment of a method for automatic object comparison consistent with the present disclosure.

FIG. 25 is a flowchart of a method 2500 for automatic object comparison. Method 2500 may be implemented by a general-purpose computer or a special-purpose computer built according to embodiments of the present disclosure. For example, method 2500 may be executed by at least one of processors 210, 210*a*, 210*b*, and 540. In some embodiments, the steps of method 2500 may be performed by wearable apparatus 110. In other embodiments, the steps of method 2500 may be performed by wearable apparatus 110 and one or more external devices (e.g., a processor included in an external server that receives data from wearable apparatus 110 over a network and/or a processor included in an external device such as a laptop, smartwatch, smartphone, tablet, ear phones, etc.).

At step 2501, the processor may determine from at least one of a plurality of images a presence of two differing objects indicated by a user. For example, the images may be received by the processor from a wearable image sensor configured to capture the images from an environment of the user (e.g., image sensor 220 of capturing unit 710). The processor may determine the presence of the two differing objects using image analysis, as described above with respect to object image module 2301 of FIG. 23.

At step 2503, the processor may perform a look up of the two differing objects to ascertain identities of the two differing objects. For example, the processor may perform the look-up in response to one or more triggers and/or user input, as described above with respect to look-up module 2302 of FIG. 23.

At step 2505, the processor may perform a look up of descriptive information about the two differing objects. For example, the processor may undertake one or more Internet searches, as described above with respect to look-up module 2302 of FIG. 23. Accordingly, the descriptive information may comprise product reviews associated with the two differing objects, social network activity associated with the two differing objects, text identified on at least one of the two differing objects, dietary information identified on at least one of the two differing objects, a price of at least one of the two differing objects, or any combination thereof.

In some embodiments, steps 2503 and 2505 may be performed together as one search for each product. In other embodiments steps 2503 and 2505 may be performed concurrently, sequentially or in any other manner.

At step 2507, the processor may compare the descriptive information about the two differing objects. For example, the processor may isolate common attributes and collect information about at least one common attribute of each of the two differing objects. In one example, a brand of the two differing objects may be isolated as a common attribute while prices of the two differing objects may be identified as different. In another example, calorie counts or other portions of dietary information on the two differing may be isolated as a common attribute while other portions of dietary information on the two differing objects may be identified as different. In another example, product reviews associated with the two differing objects may be isolated as a common attribute while prices of the two differing objects and/or text identified on at least one of the two differing objects may be identified as different. In another example, product reviews associated with the two differing objects may be isolated as a common attribute while prices of and/or social network activity associated with the two differing objects may be identified as different. None of the examples given above is mutually exclusive.

At step 2509, the processor may cause a display of the information about the comparing of the two differing objects in a manner permitting the user to ascertain differences between the two differing objects. For example, as explained above with respect to display module 2304 of FIG. 23, the user interface may include non-overlapping images of each object on a screen, e.g., on opposite sides of the screen, and may include the looked-up identities and/or looked-up descriptive information, depicted visually and/or textually, in spatial proximity to the corresponding object.

In one example, a logo of a brand and/or text of a name of the brand of each object may be displayed near the corresponding object if different and displayed near the center if the same. In another example, calorie counts or other portions of dietary information of each object may be displayed near the corresponding object if different and displayed near the center if the same. The dietary information may be shown textually and/or visually (e.g., as a graph such as a bar graph or a pie chart). In another example, product reviews of each object may be displayed near the corresponding object if different and displayed near the center if the same. The product reviews may be shown textually (e.g., with ratings and/or excerpts) and/or visually (e.g., a number of stars, a bar graph, or the like). The product reviews may be collated into an overall rating and/or review and/or a representative rating and/or review may be selected. In another example, social network activity of each object may be displayed near the corresponding object if different and displayed near the center if the same. The social network activity may be displayed textually (e.g., as excerpts from posts and/or as numbers regarding likes, retweets, etc.) and/or visually (e.g., a bar graph of likes, retweets, etc.). None of the examples given above is mutually exclusive. In the discussion above, the term "the same" may refer to absolute identity, or to a degree of similarity, for example a different of up to 5%, 10%, 20% or the like in numeric values.

Retrieving and Displaying Key Words from Prior Conversations

In some embodiments, a wearable apparatus of the present disclosure may provide for retrieval and display of key words from prior conversations by a user of the wearable apparatus. For example, the apparatus may automatically extract key words from audio recorded within a time window and index the key words to facial images captured within the time window. Accordingly, by constructing and indexing the database according to the particular rules of the present disclosure, key words related to interactions between users and known individuals may be retrieved with greater speed and accuracy than in conventional systems and may be retrieved automatically with rules rather than manually with subjective judgment.

Figure 26:
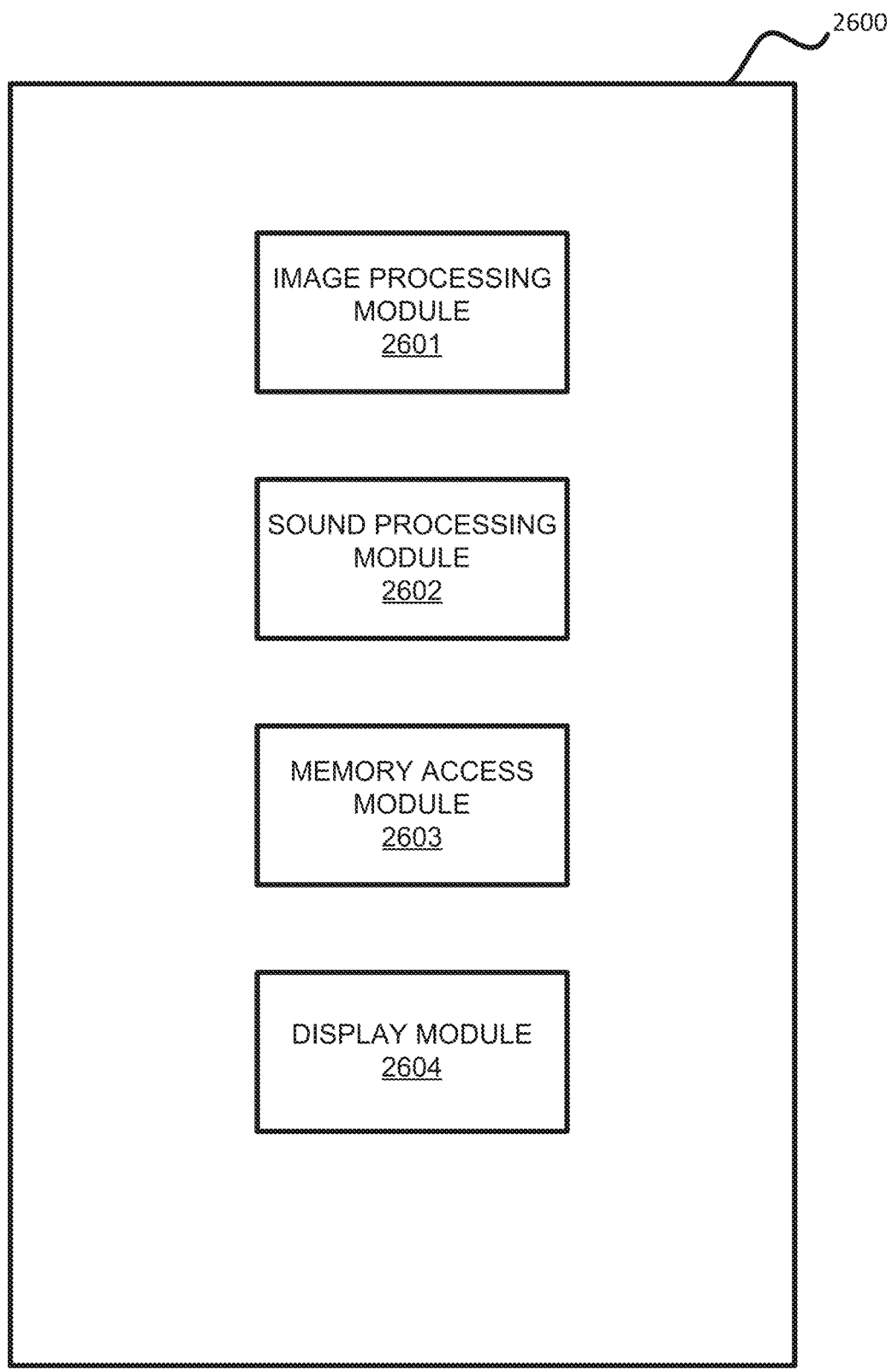
FIG. 26 illustrates an exemplary embodiment of a memory containing software modules for retrieving and displaying key words from prior conversations, consistent with the present disclosure.

FIG. 26 illustrates an exemplary embodiment of a memory 2600 containing software modules consistent with the present disclosure. Included in memory 2600 are image processing module 2601, sound processing module 2602, memory access module 2603, and display module 2604. Modules 2601, 2602, 2603, and 2604 may contain software instructions for execution by at least one processing device, e.g., processor 210, included with a wearable apparatus. In some embodiments, memory 2600 may comprise a non-transitory computer readable medium that resides on a mobile communications device (e.g., a smart phone) configured to be wirelessly paired with wearable image sensor 220 of capturing unit 710.

Image processing module 2601, sound processing module 2602, memory access module 2603, and display module 2604 may cooperate for retrieval and display of key words from prior conversations. Memory 2600 may be separate from and/or integrated with memory 550 of FIG. 6, described above. Similarly, orientation identification module 601, orientation adjustment module 602, and monitoring module 603 of FIG. 6 may operate in tandem or concurrently with image processing module 2601, sound processing module 2602, memory access module 2603, and display module 2604 of FIG. 26.

Image processing module 2601 may be configured to receive, from the wearable image sensor, a facial image of an individual with whom a user of the wearable apparatus interacted in a first interaction during a time window. For example, image processing module 2601 may receive images from wearable apparatus 110 captured by image sensor 220 of capturing unit 710. As discussed herein, received images or facial images may vary in size, shape, and content. For example, in some embodiments, an image including a wider scene (e.g., a plurality of individuals, or an individual and his or her surrounding environment) may be cropped or otherwise truncated to a face, a portion of a face, a headshot of a person (e.g., head and shoulders), or a portion of a person's body including the person's face. In other embodiments, received images may include such wider scenes (e.g., a plurality of individuals, or an individual and his or her surrounding environment). In still other embodiments, received images may include a face, a portion of a face, a headshot of a person (e.g., head and shoulders), or a portion of a person's body including the person's face.

Image processing module 2601 may further receive, from the wearable image sensor, another facial image of the individual during a second interaction at a time other than during the time window. Image processing module 2601 may use image processing to determine that the individual in the second interaction is the individual in the first interaction. For example, person identification module 1701 may perform image processing on the other received facial image and determine that the other received facial image corresponds to a face of the individual in the facial image received from the first interaction. Thus, image processing module 2601 may perform pixel-by-pixel matching. In other embodiments, image processing module 2601 may perform more sophisticated techniques. For example, image processing module 2601 may use one or more classifiers (or cascading classifiers) to derive an identity of a person included in the received facial images. Additionally or alternatively, image processing module 2601 may use a neural network to identify one or more likely identifications of a person included in the received facial images. Alternatively, image processing module 2601 may use a neural network to derive a plurality of features (e.g., a feature set) from the received facial images and then map the derived features (or feature set) onto one or more likely identifications. The mapping may be performed using simple correlation or using more sophisticated techniques, such as another neural network. It will be appreciated that the term "identification" does not necessarily relate to a true identity of a person, and may also relate to associating a captured image of a person with a person previously captured by the apparatus. Furthermore, the identification of a particular individual may include, for example, a formal name, a nickname, etc.

In any of the embodiments above, likely matches may have associated probabilities, e.g., output from the neural network; calculated based on percentage of matching pixels, features, etc.; or the like. Accordingly, image processing module 2601 may select an identification of a person from a plurality of likely matches by selecting the highest probability match.

In any of the embodiments above, one or more of the received facial images may include more than one person. Image processing module 2601 may therefore use a bounding box architecture, such as You Only Look Once (YOLO) or Single-Shot Detector (SSD), to identify bounding boxes including a person (or a portion thereof) therein. For example, if image processing module 2601 uses a bounding box architecture and receives a plurality of bounding boxes classified as persons, or receives a plurality of bounding boxes having person classifications above a threshold (e.g., more than 50%, more than 40%, more than 25%, more than 10%, more than 5%, or the like), image processing module 2601 may perform identification on portions of the image defined by the plurality of bounding boxes.

Sound processing module 2602 may be configured to receive sound data captured in a vicinity of the image sensor during at least a part of the time window. For example, the sound data may have been captured in a vicinity (e.g., within 5 meters, within 10 meters, within 20 meters, or the like) of image sensor 220 of capturing unit 710 and/or in a vicinity (e.g., 5 seconds, 10 seconds, 30 seconds, 1 minute, 5 minute, or the like) of when the facial image was captured.

Sound processing module 2602 may be further configured to process the sound data to identify at least one key word. For example, the at least one key word may be parsed using any audio analysis technique, such as limited vocabulary recognition, large vocabulary recognition, with or without speaker separation, recognition, verification, or the like. In some embodiments, sound processing module 2602 may transcribe the sound data in order to parse the at least one key word therefrom.

Additionally or alternatively, sound processing module 2602 may extract the at least one key word based on a frequency of use associated with each word in the sound data. For example, sound processing module 2602 may eliminate common or stop words such as articles ('the,' 'a,' 'an,' or the like), prepositions ('of,' 'from,' 'to,' or the like), or the like from the parsed at least one key word.

In some embodiments, processing the sound data to identify at least one key word may include accessing a remote server. For example, sound processing module 2602 may access the remote server to obtain a list of common words, uniqueness rankings for words included in the sound data, or any combination thereof to assist with extraction of the at least one key word. Alternatively, sound processing module 2602 may transmit the sound data to the remote server for extraction of the at least one key word and may thus receive the at least one key word from the remote server.

Memory access module 2603 may be configured to store in memory an association between the key word and the facial image. For example, memory access module 2603 may store the key word with the facial image (and/or an identity of an individual included in the facial image) such that the key word is retrievable when the facial image (or the identity of the individual) is searched for. In some embodiments, memory access module 2603 may store the association in a database. The database may be a relational database, in which the identities serve as an index. Additionally or alternatively, the facial image (and/or an identity of an individual included in the facial image) may be indexed such that it is retrievable when the key word is searched for.

In some embodiments, storing in the memory the association between the key word and the facial image may include storing the association in a remote server. For example, the memory may be included in a remote server accessible over one or more networks.

Memory access module 2603 may be further configured to access the memory to locate the at least one key word from the first interaction. For example, memory access module 2602 may search by an identity of an individual in the first interaction to retrieve the at least one key word. Accordingly, memory access module 2602 may generate a query including the identity to run against an index of identities to retrieve the corresponding at least one key word.

In some embodiments, memory access module 2603 may further be configured to search stored keywords according to a relationship between the user and the individual, keyword, location, synonym, or subject. For example, a plurality of key words may be associated with the same identity (or facial image) in the memory. To select a key word for display, memory access module 2603 may use a relationship between the user and the individual, a keyword included in the plurality of key words, a location of the first interaction or the second interaction, a synonym of one or more key words in the plurality of keywords, or a subject of the first interaction or the second interaction.

Display module 2604 may be configured to, during the second interaction, cause a display of at least one key word on a display visible to the user, to thereby remind the user of subject matter of the first interaction. The display may be included on the wearable apparatus. Alternatively, the display may be included in a mobile communications device paired with the wearable apparatus. For example, the mobile communications device may be paired to the wearable sensor via a radio frequency, such as Bluetooth®, or via a computer network, such as the Internet.

Figure 27A:
FIG. 27A illustrates an example of a database for indexing key words to interaction frequencies, consistent with the present disclosure.

FIG. 27A illustrates an example of a database 2700 for indexing key words to interaction frequencies consistent with the present disclosure. As depicted in FIG. 27A, a plurality of key words (e.g., words 2701a, 2701b, and 2701c) are stored in the database. In some embodiments, the database may pertain to a particular user. In other embodiments, the database may store data for a plurality of users.

Although not depicted in FIG. 27A, the words may be indexed to facial images and/or identities of individuals extracted from facial images for fast retrieval. As further depicted in FIG. 27A, the words 2701a, 2701b, and 2701c are further indexed by interaction frequency levels 2703a, 2703b, and 2703c, respectively. The interaction frequency level may comprise a number of interactions between the user and a corresponding individual. In some embodiments, the interaction frequency may be per time unit, or normalized across time, e.g., averaged over a day, a week, a month, or the like.

As depicted in FIG. 27A, the number of key words stored for each individual may be proportional (whether linearly, quadratically, or the like) with an interaction frequency level. For example, more keywords (or even a full conversation) may be stored if the interaction between the user and the individual is identified as frequent. Alternatively, the number of key words may be reduced in accordance with an interaction frequency level. For example, fewer may be stored for someone with whom the user meets daily. A reduction in the number of key words may result in stricter parsing of sound data. For example, sound processing module 2602 may require greater uniqueness (e.g., a higher threshold that a uniqueness ranking must exceed) of a word before storing it and/or greater frequency of the word (e.g., a number of times the word appears in the sound data) before storing it.

Figure 27B:
FIG. 27B illustrates another example of a database for indexing key words to importance levels of individuals, consistent with the present disclosure.

FIG. 27B illustrates an example of a database 2750 for indexing key words to importance levels within the context of the individuals consistent with the present disclosure. As depicted in FIG. 27B, a plurality of key words (e.g., words 2751a, 2751b, and 2751c) are stored in the database.

Although not depicted in FIG. 27B, the words may be indexed to facial images and/or identities of individuals extracted from facial images for fast retrieval. As further depicted in FIG. 27A, the words 2751a, 2751b, and 2751c are further indexed by importance levels 2753a, 2753b, and 2753c, respectively. The importance level may comprise a numerical representation of an importance within the context of the corresponding individual based on job title, professional relationship with the user, social relationship with the user, number of mentions and/or followers on one or more social networks, or any combination thereof.

As depicted in FIG. 27B, the number of key words stored for each individual may be proportional (whether linearly, quadratically, or the like) with an importance level. For example, more keywords (or even, as depicted in FIG. 27B, a full conversation) may be stored if the corresponding individual is particularly important, e.g., a family member, a CEO, a celebrity, or the like. An increase in the number of key words may result in looser parsing of sound data. For example, sound processing module 2602 may require lesser uniqueness (e.g., a lower threshold that a uniqueness ranking must exceed) of a word before storing it and/or lesser frequency of the word (e.g., a number of times the word appears in the sound data) before storing it.

Figure 28:
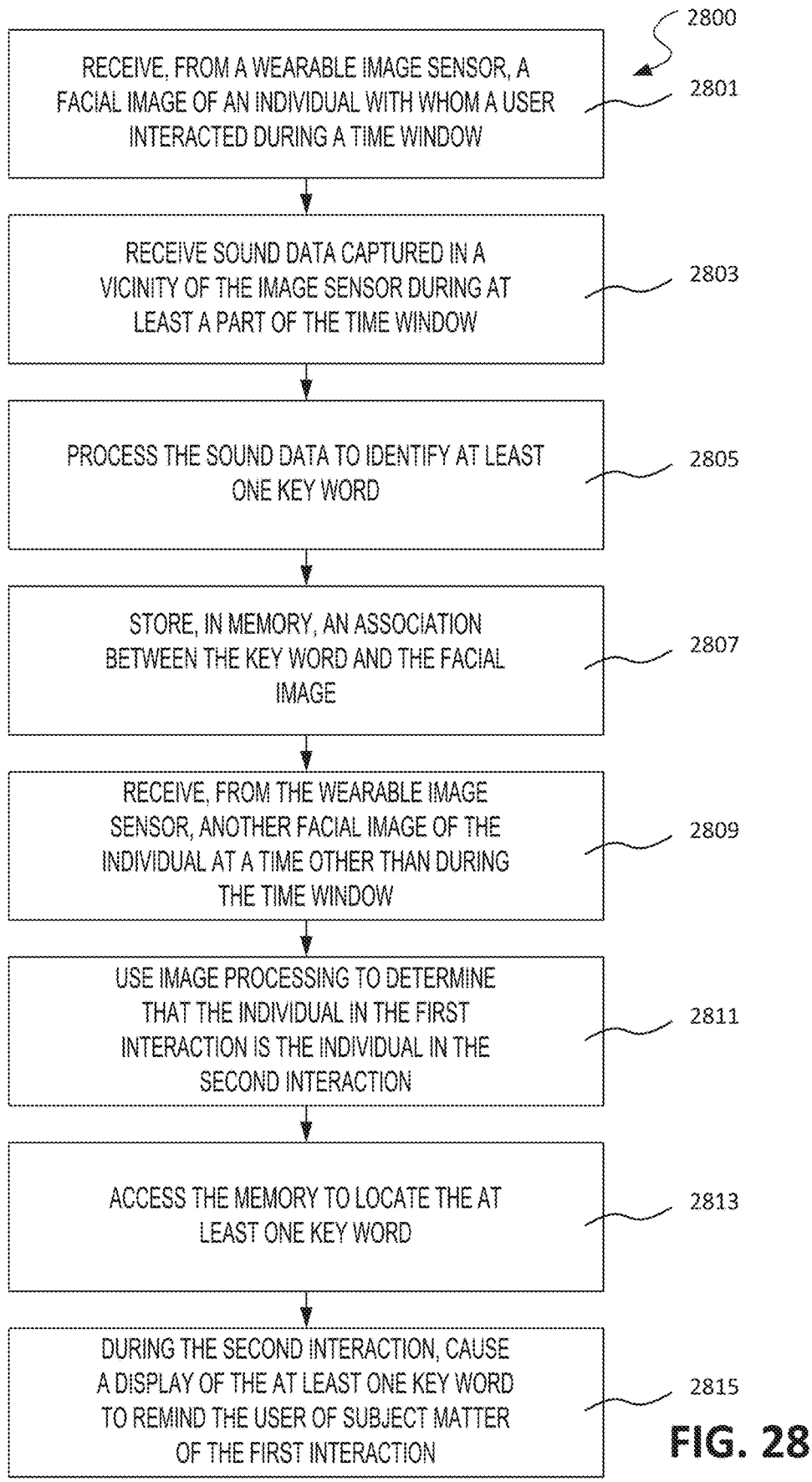
FIG. 28 is a flowchart of an exemplary embodiment of a method for retrieving and displaying key words from prior conversations, consistent with the present disclosure.

FIG. 28 is a flowchart of a method 2800 for retrieving and displaying key words from prior conversations. Method 2800 may be implemented by a general-purpose computer or a special-purpose computer built according to embodiments of the present disclosure. For example, method 2800 may be executed by at least one of processors 210, 210a, 210b, and 540. In some embodiments, the steps of method 2800 may be performed by wearable apparatus 110. In other embodiments, the steps of method 2800 may be performed by wearable apparatus 110 and one or more external devices (e.g., a processor included in an external server that receives data from wearable apparatus 110 over a network and/or a processor included in an external device such as a laptop, smartwatch, smartphone, tablet, ear phones, etc.).

At step 2801, the processor may receive, from the wearable image sensor, a facial image of an individual with whom a user of the wearable apparatus interacted in a first interaction during a time window. For example, the image may be from image sensor 220 of capturing unit 710. The processor may determine an identity of the individual using image analysis, as described above with respect to image processing module 2601 of FIG. 26.

At step 2803, the processor may receive sound data captured in a vicinity of the image sensor during at least a part of the time window. For example, a microphone of a wearable apparatus including the wearable image sensor may have captured the sound data. In such an example, the sound data may be obtained from a sound sensor within a housing that includes the wearable image sensor. Additionally or alternatively, a mobile communications device other than the wearable image sensor may have captured the sound data.

At step 2805, the processor may process the sound data to identify at least one key word. For example, the processor may use sound processing techniques as described above with respect to sound processing module 2602 of FIG. 26.

At step 2807, the processor may store in memory an association between the key word and the facial image. For example, the processor may index the key word by the facial image or an identity of an individual included in the facial image, as described above with respect to memory access module 2603 of FIG. 26.

In some embodiments, at least a portion of the sound data may be stored, the portion determined in accordance with an interaction frequency level. For example, as explained above with respect to the example of FIG. 27A, the portion may be stored if the interaction frequency level is below a particular threshold (e.g., only for interactions that are uncommon for the user). Alternatively, the portion may be stored if the interaction frequency level is above a particular threshold (e.g., only for frequent interactions for the user).

In some embodiments, at least a portion of the sound data is stored, the portion determined in accordance with an importance level of the individual. For example, as explained above with respect to the example of FIG. 27B, the portion may be stored if the importance level is above a particular threshold (e.g., only for individuals identified as particularly important).

In some embodiments, further information may be stored, such as importance level, frequency, or the like.

At step 2809, the processor may receive, from the wearable image sensor, another facial image of the individual during a second interaction at a time other than during the time window. At step 2811, the processor may use image processing to determine that the individual in the first interaction is the individual in the second interaction. For example, the image may be from image sensor 220 of capturing unit 710. The image analysis used may be as described above with respect to image processing module 2601 of FIG. 26.

At step 2813, the processor may access the memory to locate the at least one key word from the first interaction. For example, the processor may run a query including an identity of the individual against an index of identities to retrieve the at least one key word, as described above with respect to memory access module 2603 of FIG. 26.

At step 2815, the processor may, during the second interaction, cause a display of at least one key word on a display visible to the user, to thereby remind the user of subject matter of the first interaction. As explained with respect to display module 2604 of FIG. 26, the display may be included on the wearable apparatus or in a mobile communications device paired with the wearable apparatus.

Method 2800 may further include additional steps. For example, method 2800 may include searching stored keywords according to a relationship between the user and the individual, keyword, location, synonym, or subject, as explained above with respect to memory access module 2603. For example, a plurality of key words may be associated with the same identity (or facial image) in the memory such that the processor may use at least one of a relationship between the user and the individual, keyword, location, synonym, or subject to select a key word for display.

In one example, the processor may select at least one of the plurality of key words, in accordance with the frequency, such that the words having the highest frequency are selected. In another example, the processor may select at least one of the plurality of key words associated with laughter (such as a key word from a joke) if the relationship between the user and the individual is social but may select at least one of the plurality of key words associated with a job task (such as a key word from a meeting or from an assignment) if the relationship between the user and the individual is professional. In another example, the processor may select at least one of the plurality of key words associated with a keyword input by the user, spoken by the user, or spoken by the individual (e.g., during the second interaction). Accordingly, the processor may select which of the plurality of key words to display based on currently spoken words by the user and/or the individual. In another example, the processor may select at least one of the plurality of key words associated with a location of the first interaction and/or the second interaction. Accordingly, the processor may select which of the plurality of key words to display based on a locational context of the current interaction. In another example, the processor may select at least one of the plurality of key words by eliminating key words that are determined to be synonyms. Additionally or alternatively, the processor may select at least one of the plurality of key words that is a synonym with a keyword input by the user, spoken by the user, or spoken by the individual (e.g., during the second interaction). In another example, the processor may select at least one of the plurality of key words that is associated with a subject of the second interaction. The processor may determine the subject based on words spoken during the second interaction, facial expressions and/or gestures of the user and/or the individual during the second interaction, a context of the second interaction (such as a location of the second interaction), or the like. None of the examples given above is mutually exclusive with any other example.

Wearable Apparatus Controlled by Environmental Condition

In some embodiments, wearable apparatus 110 may collect information related to the environment of the user of the wearable apparatus 110. The user may configure certain characteristics of his environment to trigger the wearable apparatus 110 to communicate with a mobile communications device associated with the user to execute an action. Thus, the wearable apparatus 110 may be able to execute an action for the user, without prompting. For example, if the user enters a meeting room, the apparatus 110 may silence the user's mobile device based on collected image and/or audio data indicating that the user is in a meeting room, thereby eliminating the need for the user to manually set his mobile device to silent. In another embodiment, apparatus 110 may include a learning mechanism such that, if the user typically silences a mobile communications device upon entering a meeting room, the apparatus 110 may initiate the action of silencing the mobile communications device without the user programming entering a meeting room as a trigger for silencing the mobile communications device.

Currently, wearable devices or apparatuses may allow a user to control one or more mobile devices. However, current technology does not execute one or more actions without a user prompt. Specifically, current technology is not capable of analyzing image data for direct and indirect cues indicating one or more environmental conditions of a user and based on those conditions, initiating an action.

As described above, in some embodiments, any one of apparatus 110 or computing device 120, via processor 210 or 540, may further process at least the captured image data to provide additional functionality to recognize environmental conditions and/or other information in the captured image data. In some embodiments, apparatus 110 may process audio data received via a microphone to recognize environmental conditions. In some embodiments, actions may be taken based on the environmental condition, such as controlling a device. For example, if the apparatus recognizes that the wearer is in a meeting, then the apparatus might permit the phone paired with the camera to switch to vibrate mode, so that phone calls during the meeting do not cause an interruption. Other triggers and actions based on environmental conditions are possible.

An environmental condition, as used herein, may refer to any physical characteristic of the environment of the user. For example, an environmental condition may be any one or more of: an object present in the environment, a classification of an environment based on the types of objects present, or an activity that the user is engaged in. An environmental condition may be, for example, that another person in the environment is speaking or that the user is viewing a video presentation that may or may not include audio. In some embodiments, the environmental condition includes an ambient condition. An ambient condition may be, for example, lighting level or temperature. An exemplary environmental condition may include the user of the wearable apparatus entering a meeting room. In another embodiment, an environmental condition may include the user of the wearable apparatus exiting a meeting room.

In some embodiments, wearable apparatus 110 may collect information about one or more environmental conditions by processing images captured by image sensor 220. Image sensor 220 may collect direct information, for example, that the user is in a room containing a desk and a chair, and may collect indirect information. Indirect information may be, for example, that the user is in a cold room, which is inferred by analyzing images containing one or more people, to determine whether the one or more people are giving visual clues about the temperature in the room, e.g., shivering.

In some embodiments, a user of the wearable apparatus 110 may configure an environmental condition as a trigger associated with an action. Thus, when apparatus 110 detects one or more environmental conditions that are triggers, apparatus 110 may communicate with a mobile communications device associated with the user to execute the action associated with the trigger. In some embodiments, the user may receive a text or another notification on his mobile communications device indicating that the apparatus 110 executed the action associated with the trigger. In some embodiments, the user may execute an action, not stored in association with a trigger, every time a certain environmental condition is detected by image sensor 220. If the user executes this same action a threshold number of times, apparatus 110 may automatically execute the action upon detection of the environmental condition and execute instructions causing the mobile communications device to prompt the user to store the environmental condition and action such that the apparatus 110 executes the action each time the environmental condition is detected.

Figure 29:
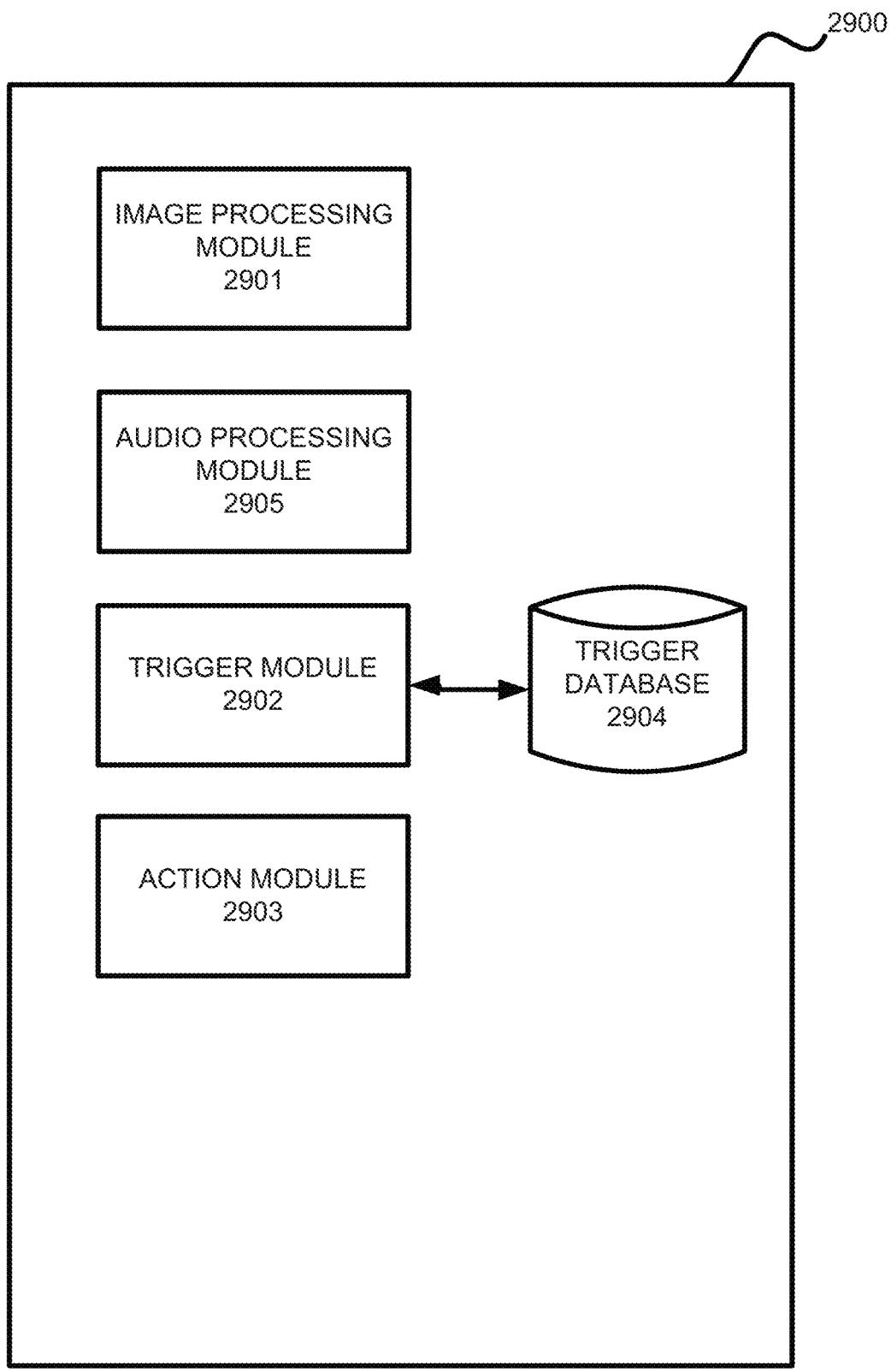
FIG. 29 illustrates an exemplary embodiment of a memory containing software modules consistent with the present disclosure.

FIG. 29 illustrates an exemplary embodiment of a memory 2900 containing software modules consistent with the present disclosure. Included in memory 2900 are an image processing module 2901, an audio processing module 2905, a trigger module 2902, an action module 2903, and an action database 2904. Modules 2901, 2902, 2903, 2905 may contain software instructions for execution by at least one processing device, e.g., processor 210, included with a wearable apparatus. Image processing module 2901, audio processing module 2905, trigger module 2902, and action module 2903 may cooperate to process an image from an image sensor, e.g., image sensor 220, identify one or more triggers present in the environment of the user, and execute an action based on the one or more triggers. Memory 2900 may be separate from and/or integrated with memory 550 of FIG. 6, described above. Similarly, orientation identification module 601, orientation adjustment module 602, and motion tracking module 603 of FIG. 6 may operate in tandem or concurrently with image analysis module 2901, audio processing module 2905, trigger module 2902, and action module 2903 of FIG. 29.

Image processing module 2901 may be configured to identify at least one environmental condition from one or more images. In some embodiments, the at least one environmental condition may be identified through the application of one or more image classification techniques. For example, at least one image classification technique may be used to classify at least one feature of an image. In some embodiments, an image classification technique may include one or more of image enhancement, edge detection, image analysis, and data extraction. Specific examples of the methods for identifying at least one environmental condition are exemplary only, and a person of ordinary skill in the art will recognize other methods for identifying the at least one environmental condition that remains consistent with the present disclosure. In some examples, at least one environmental condition may be detected using an object detection algorithm, using a neural network trained to detect objects and/or objects in images, using a machine learning system, using a pattern recognition system, and so forth.

In some examples, at least one person may be identified in the environment of the user using a facial recognition algorithm, using a neural network trained to detect faces and/or persons in images, and so forth. In other embodiments, the wearable apparatus 110 may capture thermal images, either alone or in combination with visual images, for processing by the thermal signature algorithm. Thermal recognition of at least one person or object may be desirable in implementations in which the wearable apparatus 110 is operating in reduced lighting situations.

An environmental condition may be identified, for example, by analyzing one or more images. An environmental condition may be any physical characteristic of the environment of the user. Environmental conditions may include, for example, furniture such as a conference table indicating a conference room, a clock displaying a time, one or more people, etc. In some embodiments, an environmental condition may be identified by identifying text in an image and analyzing the text. For example, identifying the text of a sign hanged outside a room and reading "Meeting Room," and comparing it to predefined texts may provide for identifying an environmental condition being a meeting. In some embodiments, environmental conditions may include ambient conditions, such as light level and temperature. For example, the image processor may identify a person appearing to be cold, thus indicating a low temperature as an ambient condition. Image processing module 2901 may additionally identify other objects in the environment of the user, for example, a book, a newspaper, a computer screen, etc. and associate the object with a certain task such as reading or viewing a presentation. Image processing module 2901 may also have a machine analysis algorithm incorporated such that a library of known environmental conditions may be updated each time image processing module 2901 may be used.

In some embodiments, audio processing module 2905 may be configured to identify at least one environmental condition from audio input received via a microphone of the apparatus 110. In some embodiments, the at least one environmental condition may be identified through the application of one or more audio classification techniques. For example, at least one audio classification technique may be used to classify speech by the wearer of apparatus 110 or by a person other than the wearer of apparatus 110. In some embodiments, an audio classification technique may include one or more of audio enhancement, natural language processing, speech recognition, and data extraction. For example, recognizing specific words related to the situation, e.g., a meeting, may be useful in identifying an environmental condition and taking associated actions. Specific examples of the methods for identifying at least one environmental condition are exemplary only, and a person of ordinary skill in the art will recognize other methods for identifying the at least one environmental condition that remains consistent with the present disclosure. Audio processing module 2905 may also have a machine analysis algorithm incorporated such that a library of known environmental conditions may be updated each time audio processing module 2905 may be used.

Further, in some embodiments, apparatus 110 may identify at least one environment condition based on analysis of one or more images in combination with audio data. For example, in such embodiments, image processing module 2901 and/or audio processing module 2905 may work in conjunction to identify the at least one environmental condition. As an example, image processing module 2901 may identify a conference table and one or more people in the environment of the user. Additionally, audio processing module 2905, may detect audio data indicative of a person speaking in the vicinity of the user. In this example, an environmental condition may be that the user is in a meeting, based on analysis of audio and image data.

Trigger module 2902 may be configured to identify one or more environmental conditions in an image, as identified by image processing module 2901, as being associated with a particular action to be executed by the processor 210. In some embodiments, in addition to image data, trigger module 2902 may be configured to identify one or more environmental conditions in audio data, as identified by audio processing module 2905, as being associated with a particular action to be executed by processor 210. Triggers may be preconfigured and/or defined by the user and stored in a trigger database 2904. For example, a user may configure triggers via a mobile application on a mobile communications device. Trigger module 2902 may also comprise learning capabilities, such that learned behaviors are adopted as triggers. For example, if a user is always silencing his phone at a particular location, the location will be adopted as a trigger for silencing the phone for the user. In some embodiments, if, for example, when image processing module 2901 identifies one or more objects in the field of view, and each time that set of one or more objects is detected, the user executes an action, processor 210 may store the one or more objects and action as a trigger-action in trigger database 2904. In some embodiments, the number of times a trigger-action is executed before it is stored in trigger database 2904 is a preconfigured numerical value. In other embodiments, the user may modify the value.

Trigger database 2904 may store associations between triggers and actions. In some embodiments, a trigger may be a single environmental condition. For example, image processing module 2901 may identify, using facial recognition or an image processing technique described above, a person who is sweating in the environment of the user. The presence of a person sweating may be a trigger associated with the action of lowering the temperature, via a thermostat, in the room occupied by the person and the user. In another example, image processing module 2901 may identify an illuminated screen with moving pictures, i.e., a television, in the environment of the user. A broadcasting television may be a trigger for the processor 210 to execute a command to dim or turn off one or more ambient light sources.

In some embodiments, a trigger may be a combination of environmental conditions. For example, image processing module may identify several objects in a room such as chairs, a conference table, and one or more people. The existence of these objects in the environment, or for example a sign in the entrance to a space containing text indicating a meeting room, may indicate that the user is in a meeting room, which triggers the processor 210 to silence the user's mobile communication device. In another example, the combination of image data indicating that the user is in a meeting room and audio data indicating that another person is speaking may trigger the processor 210 to silence the user's mobile communication device. In another example, a trigger may be that the ambient lighting in the environment of the user is below a predefined threshold and that a book is present in front of the user, indicating that the user is engaged in reading a book in low light. The combination of the low ambient light and the activity of reading text may be a trigger for the processor 210 to increase the ambient lighting level.

Action module 2903 may receive the action associated with the identified trigger and communicate with one or more devices and/or components to execute the action. For example, processor 210 may determine that an environmental condition is predetermined as a trigger for an action associated with a mobile communications device wirelessly paired with the wearable apparatus and cause the mobile communications device to trigger the action in accordance with the environment condition and to thereby cause the action to occur via the mobile communications device. In other embodiments, the action may be associated with one or more devices, such as a smart home system and/or components thereof, a security system, and one or more personal computing devices of the user (e.g., laptop computer, desktop computer, tablet, additional mobile communications device, other wearable device, etc.). For example, action module 2903 may communicate directly with a smart home system or smart security system, or may communicate with a smart device associated with the user through which the system may alter one or more environmental conditions.

As described above, a trigger may be associated with one or more actions, such that when trigger module 2902 identifies one or more triggers in an environment, apparatus 110 executes one or more predefined actions. The trigger-action associations may be preconfigured on the apparatus 110 or may be customizable by the user, for example via a mobile application. The apparatus 110 may execute the one or more actions by communicating with a device, via any known wireless standard (e.g., wifi, Bluetooth®, etc.), as well as near-field capacitive coupling, and other short range wireless techniques, or via a wired connection.

In one example, a trigger may be associated with the action of silencing the user's mobile communications device. In this case, action module 2903 may send instructions, wirelessly, to the mobile communications device to change the sound settings to silent. In another example, a trigger may be associated with dimming or strengthening a light near the user of the apparatus 110. The processor 210 may send instructions to a mobile device to communicate with the light and/or lighting system to changing the light level. In another embodiment, the processor 210 may send instructions, wirelessly, directly to the light and/or lighting system to change the light level.

In some embodiments, the user may configure the parameters of an action via a mobile application on a mobile communications device. In another embodiment, the action parameters may be preconfigured on the apparatus 110. For example, parameters may include a level of brightness of ambient light, a specific volume (e.g., decibel level) of the mobile device, a brightness of a screen, lighting level, or a temperature. In one example, a user may configure a trigger such that if the image processing module 2901 detects a screen in front of the user at a high level of brightness, the processor 210 communicates instructions to the mobile communications device of the user to dim the screen to the user's preferred level of brightness. In another embodiment, the same trigger and action may be preconfigured such that the screen brightness is adjusted to a level that decreases eye strain.

Additionally, in some embodiments, the processor may be programmed to override the action associated with the mobile communications device. In some embodiments, the action associated with the mobile communications device may be overridden according to a context. The context level may include an importance level of an individual. Other exemplary contexts may be whether an email or other communications indicates an "Urgent" status, local emergency alerts pushed to the mobile communications device, and/or calendar events marked as important. In one example, a user may set up an emergency/important contact list on his mobile communications device such that when an incoming communication is received from one of those contacts, the communications device rings even though the environmental condition of the user's presence in a meeting room triggered the processor 210 to silence the user's mobile communications device. In another example, a user may configure an overriding context to be the type of a received communication, e.g., a telephone call, email, SMS message, video call, notification, etc. The user may configure telephonic calls to override a certain trigger/action, but other communications, such as text message and email to abide by the configured action.

In some embodiments, the processor may be programmed to restore the mobile communications device settings when the user leaves an environment associated with a trigger. For example, a user having a mobile communications device set to ring at a certain volume may enter a meeting room, which may trigger the processor to silence the user's mobile communications device. When the user leaves the meeting room, the processor may communicate with the user's mobile communications device to set the device to ring at the certain volume, consistent with the device's settings before entering the meeting room.

Modules 2901-2903 and 2905 may be implemented in software, hardware, firmware, a mix of any of those, or the like. For example, if the modules are implemented in software, they may be stored, for example, in memory 550. However, in some embodiments, any one or more of modules 2901-2903 and 2905 may, for example, be stored in processor 540 and/or located on server 250, which may include one or more processing devices. Processing devices of server 250 may be configured to execute the instructions of modules 2901-2903. In some embodiments, aspects of modules 2901-2903 and 2905 may include software, hardware, or firmware instructions (or a combination thereof) executable by one or more processors, alone or in various combinations with each other. For example, modules 2901-2903 and 2905 may be configured to interact with each other and/or other modules of server 250 and/or a wearable camera system to perform functions consistent with disclosed embodiments. In some embodiments, any of the disclosed modules may each include dedicated sensors (e.g., IR, image sensors, etc.) and/or dedicated application processing devices to perform the functionality associated with each module.

Figure 30A:
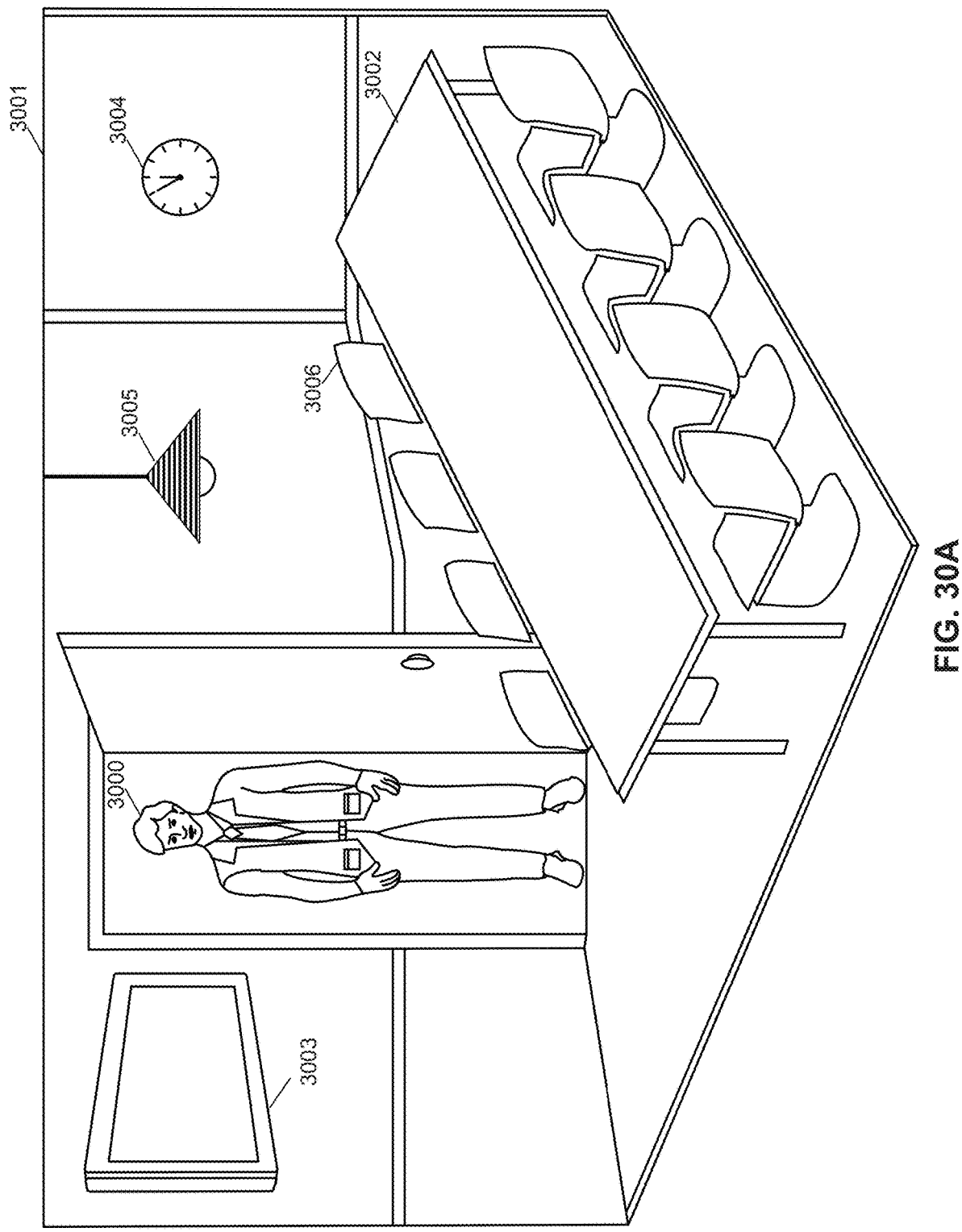
FIGS. 30A and 30B are illustrations of exemplary environments detected by a wearable apparatus consistent with the present disclosure.

FIG. 30A is an exemplary scenario in which the system may identify an environmental condition such as the user 3000 entering a meeting room 3001. The user 3000 may enter a meeting room 3001 wearing an apparatus, e.g., wearable apparatus 110. One or more objects in the meeting room 3001, such as conference table 3002, screen 3003, clock 3004, and lamp 3005 may be identifiable by image processing module 2901. Additionally, image processing module 2901 may identify one or more ambient conditions in meeting room 3001 such as the lighting level. Each of these objects and/or ambient conditions may be an environmental condition classified as a trigger for an action associated with the mobile communications device of the user.

For example, an environmental condition may be that the room the user entered is identified as a meeting room because of the presence of a conference table 3002 and chairs 3006. The identification of a meeting room as an environmental condition may be a trigger for the processor 210 to send instructions to the mobile communications device of the user to execute an action associated with the mobile communications device. For example, the action associated with the mobile communications device may include enabling a vibrate mode. In another example, the action associated with the mobile communications device may include at least one of deactivating sounds and reducing a sound level of the mobile communications device. In an additional example, the action associated with the mobile communications device may be to send an automated response by text message or email to contacts from whom calls or emails were received by the mobile communications device.

In another example, a trigger may be based on both audio and image data. For example, processor 210 may cause the mobile communications device to be set to a vibrate mode when the user enters a conference room. If audio processing module 2905 additionally receives audio data indicative of a single person speaking in the conference room, e.g., giving a presentation, processor 210 may further cause the mobile phone to be set to a silent mode.

Similarly, in another example, when the user exits the meeting room 3001, the image processing module 2901 may analyze one or more images to determine that the conference table 3002 and presentation screen 3003 are no longer present in the user environment, therefore the environmental condition is no longer valid. Thus, the processor 210 may communicate instructions to the mobile communications device to execute one or more actions associated with the mobile communications device that are triggered when the user exits a meeting room. For example, the action associated with the mobile communications device may include discontinuing a vibrate mode or retrieving a mode employed prior to the user entering the meeting. In another example, the action associated with the mobile communications device may include at least one of activating sounds and increasing a sound level of the mobile communications device. In another example, if the user's device was set to silent before entering a meeting room and the trigger of entering a meeting room initiated the device to set the volume to silent, upon exiting the meeting room the device may remain silent, consistent with the settings of the device before entering the meeting room.

In another embodiment, the apparatus 110 may detect a presentation being shared on screen 3003 and communicate with a device or smart lighting system to dim the lamp 3005 in the conference room or to dim the lights nearest the screen 3003. Additionally, when the presentation is over and the screen 3003 dims, the apparatus 110 may communicate with a device and/or smart lighting system to increase the lighting level in the meeting room 3001 to a default ambient level. In another example, the action of dimming the lights and/or silencing the user's device may be triggered upon identification, by audio processing module 2905, of sound coming from one or more speakers alone or in combination with the detected light emitted from screen 3003. In another example, a combination of low ambient lighting detected by image sensor 220 and audio data indicating a person speaking may trigger the processor 210 to reduce the volume level of the mobile communications device or silence the mobile communications device.

Figure 30B:
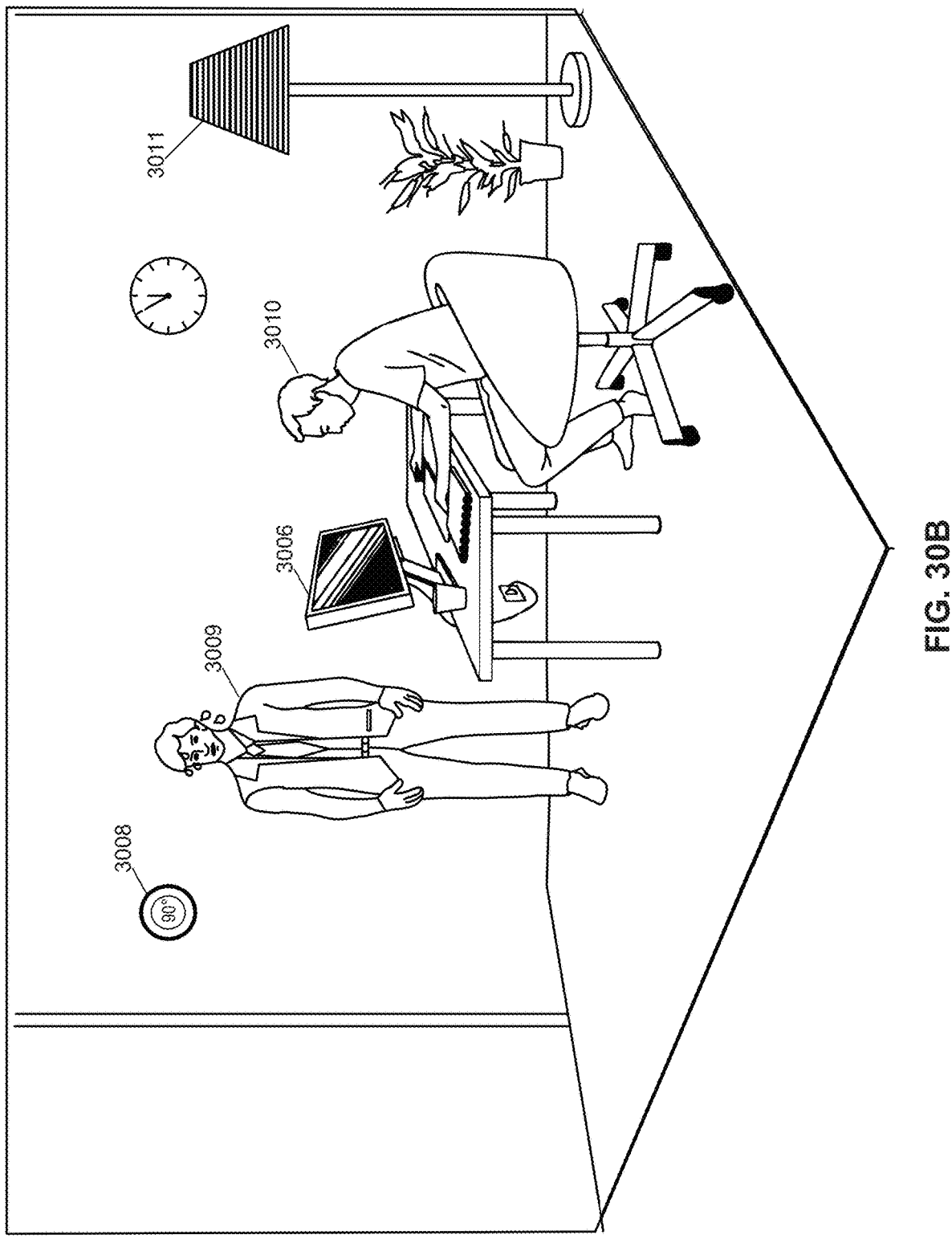

FIG. 30B is another exemplary scenario in which the image processing module 2901 may identify one or more environmental conditions such as a computer 3007, a thermostat 3008, and another person 3009 in at least one image received by image sensor 220. The processor 210 may be programmed to identify in the at least one image that a human depicted in the image is overheated, and the trigger causes the mobile communications device to send a signal to a thermostat to decrease temperature. For example, image processing module 2901 may detect, via facial recognition software or other methods previously described, that person 3009 is sweating and therefore is too hot. An environmental condition of a person sweating may be a trigger for the processor 210 to send instructions to a mobile communications device to communicate with the thermostat 3008 to decrease the temperature in the environment of the apparatus wearer 3010 and person 3009. Other image features may indicate the person 3009 is too hot, for example, if person 3009 is fanning himself or if he removes his blazer. The temperature to which thermostat 3008 is set may be preconfigured or may be manually set up by the user via a mobile application.

Similarly, the system may also detect that person 3009 is too cold in at least one image. The processor 210 may be programmed to identify in the at least one image that a human depicted in the image is cold, and the trigger causes the mobile communications device to send a signal to a thermostat to increase temperature. For example, person 3009 may be shivering or may be wearing a scarf, jacket, and/or gloves, prompting the processor 210 to communicate with the mobile communications device of the user to raise the temperature of the environment via thermostat 3008. Additionally or alternatively, audio analysis may indicate that person 3009 sneezes a number of times exceeding a threshold, for example two or more times, thus indicating that person 3009 is cold. The temperature to which the apparatus adjusts the thermostat 3008 may be preconfigured or may be pre-set by the wearer 3010 via a mobile application. In another embodiment, processor 210 may communicate directly with thermostat 3008 via a wireless network.

In another example, audio data from audio processing module 2905 may indicate that the person 3009 is speaking. The environmental condition of another person speaking may be a trigger to the apparatus 110 to silence the mobile communications device. When the person 3009 is finished speaking, apparatus 110 may restore the mobile communications device to its previous settings from before the trigger was detected. In another example, apparatus 110 may analyze both audio and image data to determine that, for example, another person is present and that a conversation or meeting is taking place, and therefore apparatus 110 may silence the mobile communications device. In another example, a sign in or in the vicinity of a room may indicate that it is a meeting room or a conference room, and apparatus 110 may use optical character recognition to determine the text. The text may be used alone or in connection with other visual and/or audio cues to determine that a meeting is taking place.

In another example, the processor may be programmed to identify that the user is engaged in an activity where a higher or lower light level is desirable, and the trigger causes the mobile communications device to send a signal to a lighting system to increase or decrease an amount of light. Image processing module 2901 may detect, as environmental conditions, the level of ambient lighting and the brightness of the computer screen 3007 that the apparatus wearer 3010 is looking at. This combination of environmental conditions may trigger the action of sending instructions to the mobile communications device to increase or decrease either one or both of the ambient lighting level, e.g., lamp 3011, or the screen to an optimal brightness to reduce eye strain. Other activities where a lower light level is desirable may be when the user is watching television or a movie, or certain laboratory activities in which a user may handle photosensitive material. In some embodiments, processor 210 may identify the light source nearest to a light emitting object, such as a television screen, and send instructions to the mobile communications device to increase or decrease the light level of only that light source. The number of light sources and level of light adjusted as a result of the presence of a trigger may be configured by the user or may be preconfigured.

In yet another example, the processor may be programmed to identify that reading is occurring and ambient light is insufficient, and the trigger causes the mobile communications device to send a signal to a lighting system to increase an amount of light. Image processing module 2901 may identify an un-illuminated book or text in front of the user as an environmental condition. This environmental condition may trigger the processor 210 to send instructions to the mobile communications device to increase the light level. In some embodiments, the processor 210 may directly execute instructions to modify the light level via a smart home or smart lighting system.

Figure 31A:
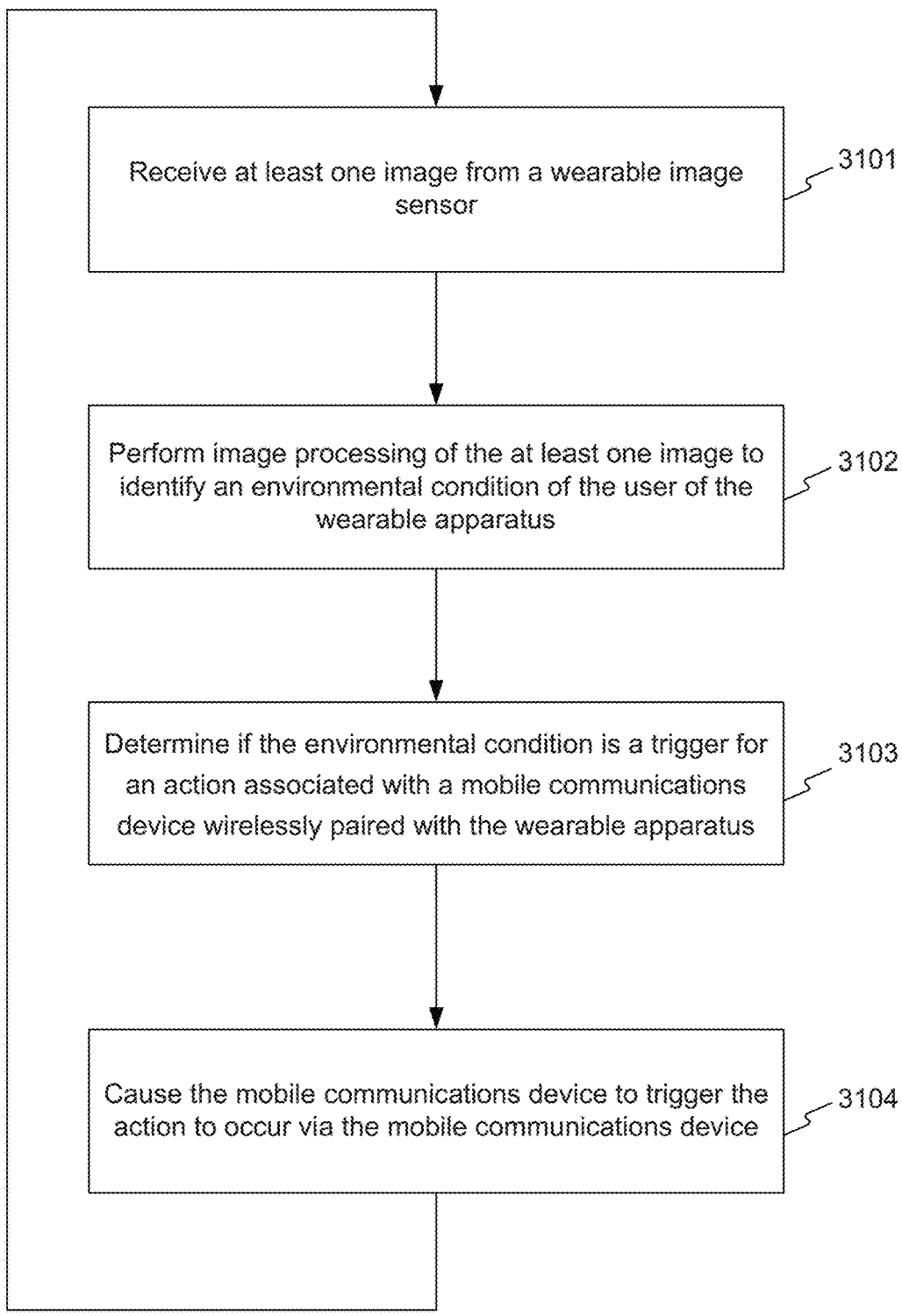
FIG. 31A is a flowchart of a method for detecting a trigger in the environment of a user of the wearable apparatus according to a disclosed embodiment.

FIG. 31A is a flowchart of a method 3100 for identifying triggers in at least one image received by image sensor 220 and executing an action associated with a mobile communications device of the user according to a disclosed embodiment. Method 3100 may be implemented by a general-purpose computer or a special-purpose computer built according to embodiments of the present disclosure. For example, method 3100 may be executed by at least one of processors 210, 210a, 210b, and 540. In some embodiments, the steps of method 3100 may be performed by wearable apparatus 110. In other embodiments, the steps of method 3100 may be performed by wearable apparatus 110 and one or more external devices (e.g., a processor included in an external server that receives data from wearable apparatus 110 over a network and/or a processor included in an external device such as a laptop, smartwatch, smartphone, tablet, or ear phones, etc.).

At step 3101, the processor may receive at least one image from a wearable image sensor, e.g., sensor 220.

At step 3102, the processor may perform image processing of the at least one image to identify an environmental condition of the user of the wearable apparatus. For example, image processing module 2901 may receive image data from image sensor 220 and identify one or more environmental conditions such as objects, people, and/or ambient conditions in the at least one image as described with reference to FIG. 29. As previously described, processor 210 may use image classification techniques to identify the one or more environmental conditions present in the at least one image. In some embodiments, an environmental condition may be determined based on the difference between one or more subsequently captured images. For example, one image may capture a conference table and chairs (objects associated with the environmental condition of a meeting room) and a subsequent image may not contain those objects, indicating the environmental condition of the user is exiting a meeting room.

At step 3103, the processor may determine if the environmental condition is a trigger for an action associated with a mobile communications device wirelessly paired with the wearable apparatus. As previously described with reference to FIG. 29, trigger database 2904 may store one or more environmental conditions that are triggers, the associated actions, and the parameters of the associated actions. Trigger module 2902 may access trigger database 2904 to retrieve trigger data associated with the environmental conditions identified by image processing module 2901 at step 3102.

At step 3104, the processor may cause the mobile communications device to trigger the action to occur via the mobile communications device. As previously described, action module 2903 may cause the processor to send instructions, via a wired or wireless connection, to the mobile communications device associated with the user. The instructions may cause the mobile communications device to execute an action on itself or may cause the mobile communications device to further send instructions to another device and/or system to execute the action. For example, a mobile communications device may store one or more applications configured to control other devices and/or systems. In another example, the processor 210 may be configured to communicate directly with another device or system without first sending instructions to the mobile communications device. For example, the processor 210 may communicate wirelessly with one or more of a smart home system, security system, or personal computing device.

Figure 31B:
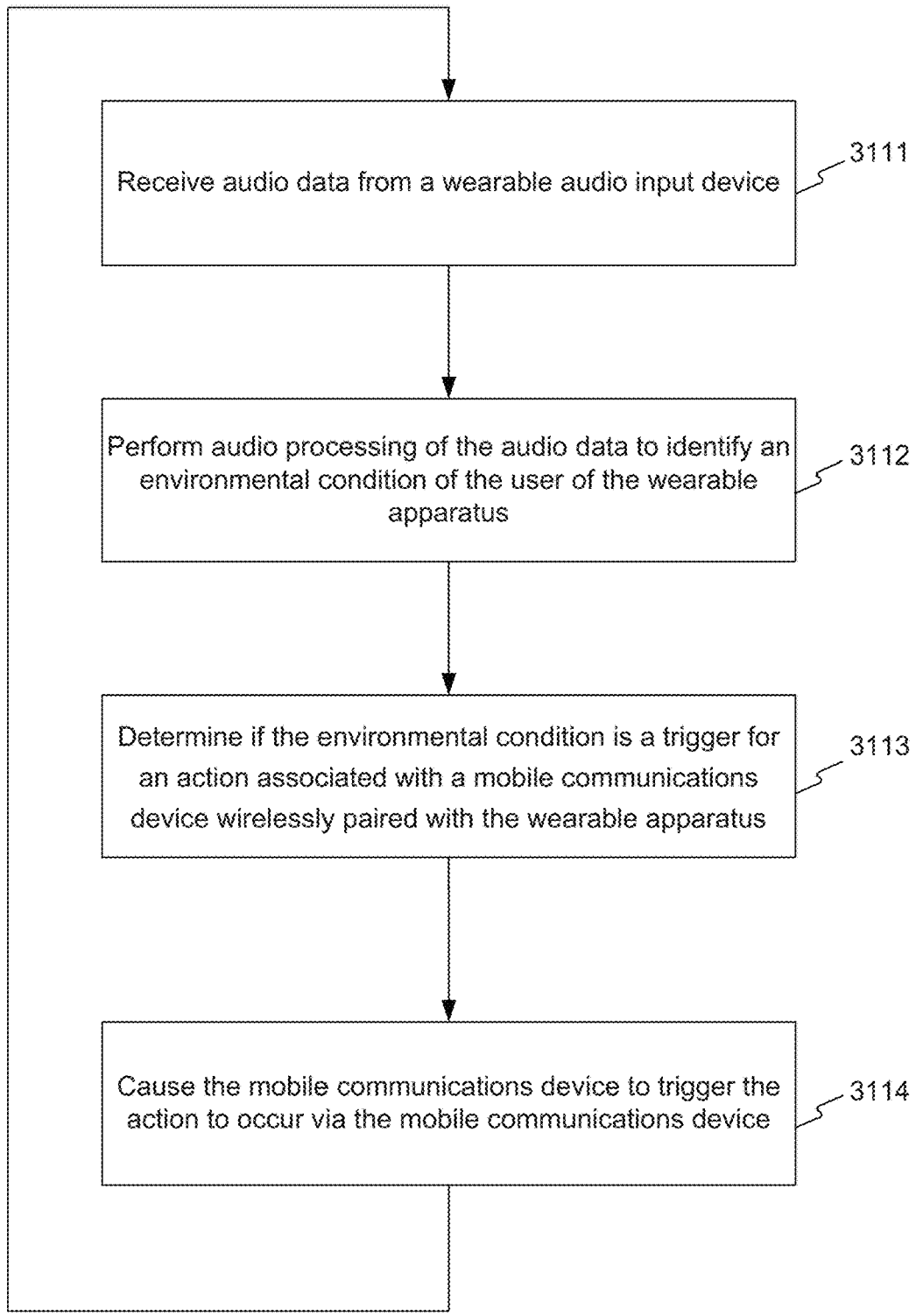
FIG. 31B is a flowchart of a method for detecting a trigger in the environment of a user of the wearable apparatus according to a disclosed embodiment.

FIG. 31B is a flowchart of a method 3110 for identifying triggers based on audio data and executing an action associated with a mobile communications device of the user according to a disclosed embodiment. Method 3110 may be implemented by a general-purpose computer or a special-purpose computer built according to embodiments of the present disclosure. For example, method 3110 may be executed by at least one of processors 210, 210a, 210b, and 540. In some embodiments, the steps of method 3110 may be performed by wearable apparatus 110. In other embodiments, the steps of method 3110 may be performed by wearable apparatus 110 and one or more external devices (e.g., a processor included in an external server that receives data from wearable apparatus 110 over a network and/or a processor included in an external device such as a laptop, smartwatch, smartphone, tablet, or ear phones, etc.).

At step 3111, the processor may receive audio data from a wearable audio input device.

At step 3112, the processor may perform audio processing of the audio data to identify an environmental condition of the user of the wearable apparatus. For example, audio processing module 2905 may receive audio data from an audio input device, such as a microphone, and identify one or more environmental conditions such as another person or other people speaking, music, or an audiovisual presentation, as described with reference to FIG. 29. As previously described, processor 210 may use audio classification techniques to identify the one or more environmental conditions present in the audio data.

At step 3113, the processor may determine if the environmental condition is a trigger for an action associated with a mobile communications device wirelessly paired with the wearable apparatus. As previously described with reference to FIG. 29, trigger database 2904 may store one or more environmental conditions that are triggers, the associated actions, and the parameters of the associated actions. Trigger module 2902 may access trigger database 2904 to retrieve trigger data associated with the environmental conditions identified by audio processing module 2905 at step 3112. In some embodiments, a trigger may be associated with environmental conditions identified by both image and audio data.

At step 3114, the processor may cause the mobile communications device to trigger the action to occur via the mobile communications device. As previously described, action module 2903 may cause the processor to send instructions, via a wired or wireless connection, to the mobile communications device associated with the user. The instructions may cause the mobile communications device to execute an action on itself or may cause the mobile communications device to further send instructions to another device and/or system to execute the action. For example, a mobile communications device may store one or more applications configured to control other devices and/or systems. In another example, the processor 210 may be configured to communicate directly with another device or system without first sending instructions to the mobile communications device. For example, the processor 210 may communicate wirelessly with one or more of a smart home system, security system, or personal computing device.

Figure 31C:
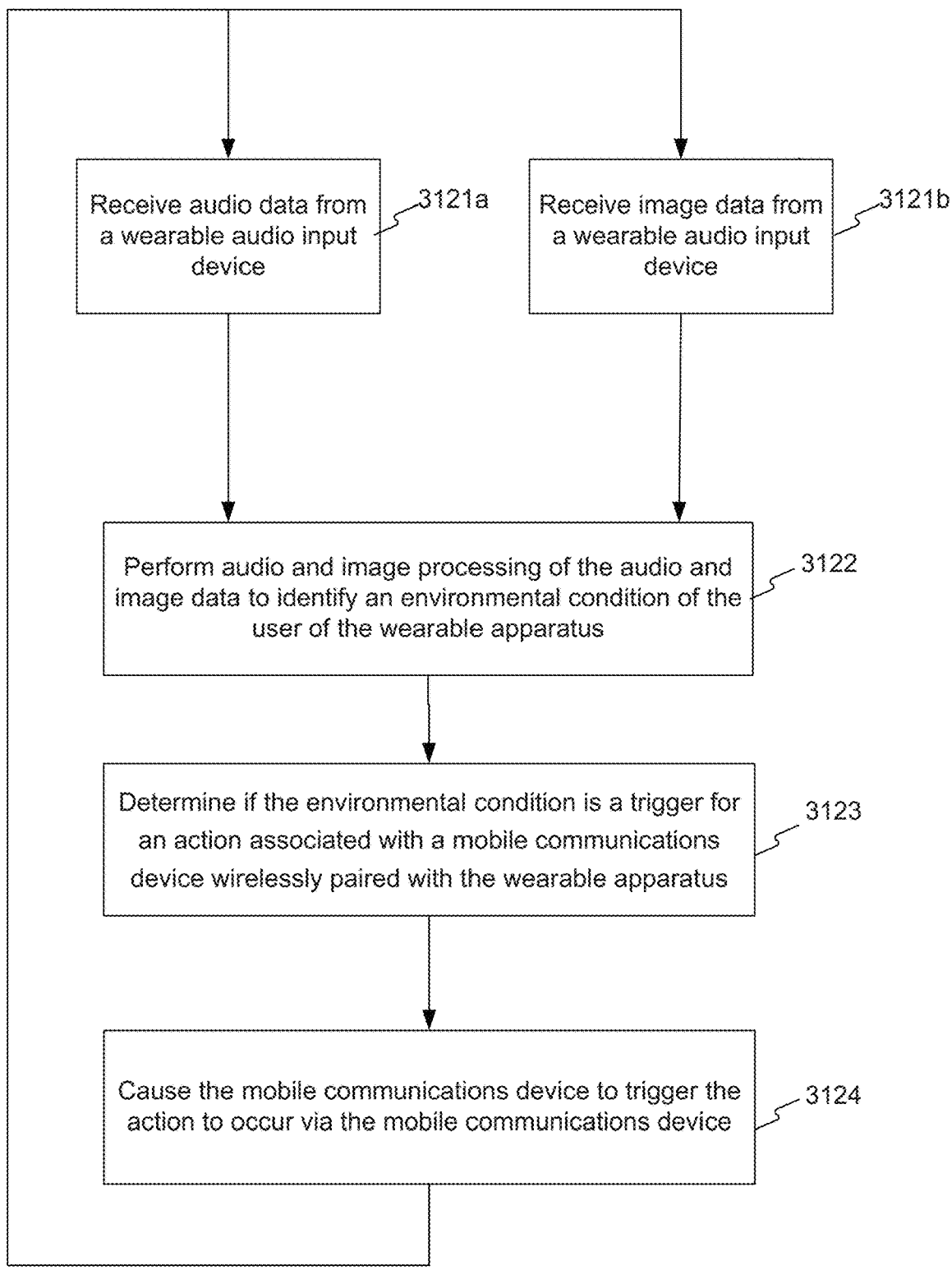
FIG. 31C is a flowchart of a method for detecting a trigger in the environment of a user of the wearable apparatus according to a disclosed embodiment.

FIG. 31C is a flowchart of a method 3120 for identifying triggers based on a combination of audio and image data and executing an action associated with a mobile communications device of the user according to a disclosed embodiment. Method 3120 may be implemented by a general-purpose computer or a special-purpose computer built according to embodiments of the present disclosure. For example, method 3120 may be executed by at least one of processors 210, 210a, 210b, and 540. In some embodiments, the steps of method 3120 may be performed by wearable apparatus 110. In other embodiments, the steps of method 3120 may be performed by wearable apparatus 110 and one or more external devices (e.g., a processor included in an external server that receives data from wearable apparatus 110 over a network and/or a processor included in an external device such as a laptop, smartwatch, smartphone, tablet, or ear phones, etc.).

At step 3121a, the processor may receive audio data from a wearable audio input device. At step 3121b, the processor may receive image data from a wearable image sensor, e.g., image sensor 220. Steps 3121a and 3121b may occur concurrently or in tandem.

At step 3122, the processor may perform audio processing of the audio data and image processing of the image data to identify an environmental condition of the user of the wearable apparatus. For example, audio processing module 2905 may receive audio data from an audio input device, such as a microphone, and identify one or more environmental conditions such as another person or other people speaking, music, or an audiovisual presentation, as described with reference to FIG. 29. Concurrently, or in tandem, image processing module 2901 may receive image data from image sensor 220, and identify one or more objects and/or people in the environment of the user. As previously described, processor 210 may use audio and/or image classification techniques to identify the one or more environmental conditions present in the environment based on the audio and image data.

At step 3123, the processor may determine if the environmental condition is a trigger for an action associated with a mobile communications device wirelessly paired with the wearable apparatus. As previously described with reference to FIG. 29, trigger database 2904 may store one or more environmental conditions that are triggers, the associated actions, and the parameters of the associated actions. Trigger module 2902 may access trigger database 2904 to retrieve trigger data associated with the environmental conditions identified from image and audio data determined by image processing module 2901 and audio processing module 2905 at step 3122. In some embodiments, a trigger may be associated with environmental conditions identified by audio data, image data, or a combination of both audio and image data.

At step 3124, the processor may cause the mobile communications device to trigger the action to occur via the mobile communications device. As previously described, action module 2903 may cause the processor to send instructions, via a wired or wireless connection, to the mobile communications device associated with the user. The instructions may cause the mobile communications device to execute an action on itself or may cause the mobile communications device to further send instructions to another device and/or system to execute the action. For example, a mobile communications device may store one or more applications configured to control other devices and/or systems. In another example, the processor 210 may be configured to communicate directly with another device or system without first sending instructions to the mobile communications device. For example, the processor 210 may communicate wirelessly with one or more of a smart home system, security system, or personal computing device.

Remotely Identifying a Location of a Wearable Apparatus

In some embodiments, wearable apparatus 110 may be paired with a mobile communications device associated with a user. If the user misplaces wearable apparatus 110, the user may initiate an application on a mobile communications device to locate apparatus 110. For example, image sensor 220 may collect information related to the environment of apparatus 110 and may transmit image data and/or location data to the mobile communications device paired with the wearable apparatus 110. Wearable apparatus 110 may use image data of its environment to provide audio and/or spoken directions to the user via the mobile communications device to assist the user in locating apparatus 110. For example, if apparatus 110 is under a piece of furniture, e.g., a sofa, the apparatus 110 may receive image data depicting a low light environment and/or may capture an image with an obscured portion of a field of view, apparatus 110 may process the image data to identify its location and may prompt the user with an audio instruction, such as, "The device is under the sofa," via the mobile communications device. In some embodiments, if the location of apparatus 110 is not able to be determined from image data, i.e., the image sensor 220 is in a dark space and cannot collect image data, the apparatus 110 may send GPS coordinates indicating its location to the mobile communications device.

When a device is misplaced, a user may use a mobile application via a second device to locate the misplaced device. For example, a user may locate a misplaced device based on GPS coordinates or proximity to the second device. However, current devices are not capable of identifying their exact location with reference to other objects in their environment. Because the misplaced device is not aware of other objects and/people in its environments, sufficient information is not available to the device in order to provide precise directions to enable the user to find it.

As described above, in some embodiments, any one of apparatus 110 or computing device 120, via processor 210 or 540, may process captured image data to provide additional functionality to recognize objects in its environment. Apparatus 110 may be paired with a mobile communications device associated with a user via any known wireless standard (e.g., WiFi, Bluetooth®, etc.), as well as near-field capacitive coupling, and other short range wireless techniques. Mobile communications device may be a smartphone, laptop, tablet, or other device capable of communicating via a wireless network. Apparatus 110 may be configured to provide output, for example, via feedback-outputting unit 230, using one or more of a wireless transceiver 530, an audio speaker, a vibrotactile simulator, or a display.

In some embodiments, apparatus 110 may receive, from a mobile communications device wirelessly paired with the wearable apparatus 110, a command to provide location information for the wearable apparatus. For example, the user of wearable apparatus 110 may execute a command, via a mobile application installed on a mobile communications device, for the apparatus 110 to transmit location information. In response to the command received wirelessly from the mobile communications device, apparatus 110 may process image data collected by image sensor 220 and may determine a location of the apparatus 110.

In some embodiments, apparatus 110 may include a motion sensor, e.g., an accelerometer or gyroscope. The motion sensor may gather information about the apparatus' movement. For example, if the apparatus 110 is in a pocket of the user, image sensor 220 may not collect any image data. However, the motion sensor may collect data indicative of a human gait pattern. In this example, mobile communications device may be prompted to alert the user that the apparatus 110 is in a pocket or in a bag that the user is carrying.

Apparatus 110 may transmit location information and/or directions leading from the location of the mobile communications device to the location to the apparatus 110. In some embodiments, the mobile communications device is configured to provide an audible description of the location of the wearable apparatus based on the information about the location of the wearable apparatus. In some embodiments, the audible description includes spoken words specifying the location of the wearable apparatus. For example, via a speaker or a visual display, the mobile communications device may output to the user instructions or directions for finding apparatus 110. In some embodiments, the spoken words include a specification that the wearable apparatus is located under a piece of furniture. For example, mobile communications device may output audio, "Device is under some furniture", or "Device is under the sofa." In other embodiments, the spoken words include a specification that the wearable apparatus is located in a bag or a container. In another embodiment, the spoken words may include a specification that the wearable apparatus is located in a pocket of a user of the mobile communications device. In yet another embodiment, the spoken words may include a specification that the wearable apparatus is located in a direction relative to the user of the mobile communications device.

In other embodiments, the mobile communications device is configured to provide text output of the location of the wearable apparatus based on the information about the location of the wearable apparatus. In some embodiments, the text may include a specification that the wearable apparatus is located under a piece of furniture. In other embodiments, the text may include a specification that the wearable apparatus is located in a bag or a container. In another embodiment, the text may include a specification that the wearable apparatus is located in a pocket of a user of the mobile communications device. In yet another embodiment, the text may specify that the wearable apparatus is located in a direction relative to a user of the mobile communications device.

In another embodiment, locating the apparatus 110 may include establishing a wireless pairing between a wearable apparatus and a mobile communications device. The mobile communications device may be configured for receiving, in a situation when the wearable apparatus is misplaced, a user input for pinging the wearable apparatus, for example, via an application and/or I/O device of the mobile communications device. In response to the user input, locating the misplaced apparatus may include wirelessly transmitting from the mobile communications device a ping to the wearable apparatus. The ping may include an instruction for the wearable apparatus to capture at least one image of surroundings of the wearable apparatus. The apparatus 110 may analyze the at least one image to determine a location of the wearable apparatus and cause the location information to be transmitted to the mobile communications device.

In another embodiment, apparatus 110 may be configured to use audio information in addition to image information. For example, apparatus 110 may detect, via a microphone, the sound of a train. Apparatus 110 may use this audio information instead of, or in addition to, image information to communicate instructions to the mobile communications device that apparatus 110 may be at a train station. In another example, apparatus 110 may be in a bag, restricting data the image sensor 220 may capture. In this example, apparatus 110 may use audio data to determine, for example, that the user is in the same room as the apparatus by using voice recognition.

Figure 32:
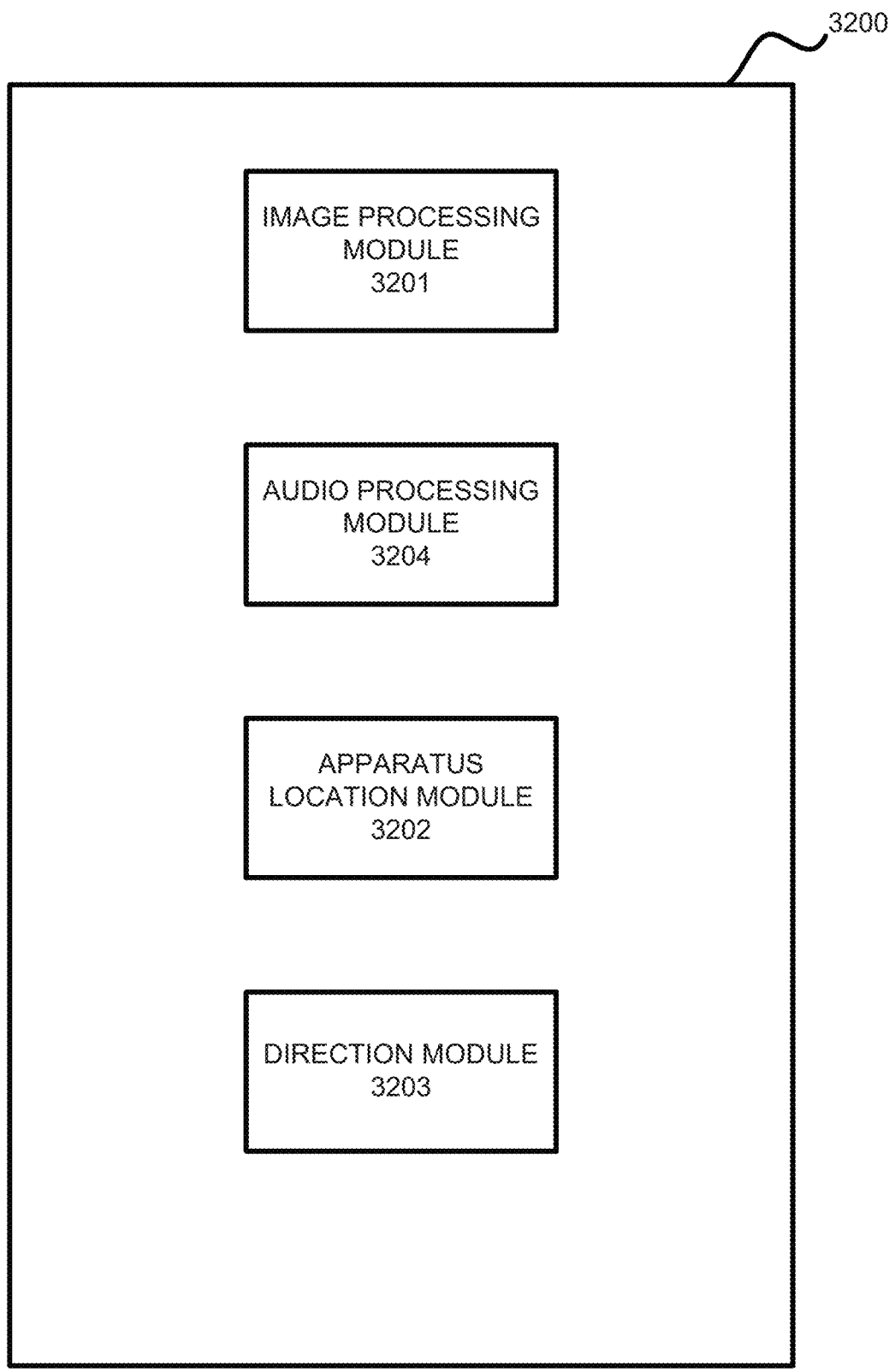
FIG. 32 illustrates an exemplary embodiment of a memory containing software modules consistent with the present disclosure.

FIG. 32 illustrates an exemplary embodiment of a memory 3200 containing software modules consistent with the present disclosure. Included in memory 3200 are an image processing module 3201, an audio processing module 3204, an apparatus location module 3202, and a direction module 3203. Modules 3201, 3202, 3203, 3204 may contain software instructions for execution by at least one processing device, e.g., processor 210, included with a wearable apparatus. In some embodiments, any one or more of image processing module 3201, audio processing module 3204, apparatus location module 3202, and direction module 3203 may be executed by a mobile communications device wirelessly paired with the wearable apparatus. Image processing module 3201, audio processing module 3204, apparatus location module 3202, and direction module 3203 may cooperate to process one or more images from an image sensor, e.g., image sensor 220, and location data, e.g., GPS coordinates of apparatus 110, to generate a set of instructions to assist the user in locating apparatus 110. Memory 3200 may be separate from and/or integrated with memory 550 of FIG. 6, described above. Similarly, orientation identification module 601, orientation adjustment module 602, and motion tracking module 603 of FIG. 6 may operate in tandem or concurrently with image analysis module 3201, audio processing module 3204, device location module 3202, and direction module 3203 of FIG. 32.

Image processing module 3201 may be configured to identify one or more objects in one or more images received from image sensor 220. In some embodiments, objects or people may be identified through the application of one or more image classification techniques. For example, at least one image classification technique may be used to classify at least one feature of an image. In some embodiments, an image classification technique may include one or more of image enhancement, edge detection, image analysis, and data extraction. Specific examples of the methods for identifying one or more objects are exemplary only, and a person of ordinary skill in the art will recognize other methods for identifying objects remain consistent with the present disclosure. In some examples, one or more objects may be detected using an object detection algorithm, using a neural network trained to detect objects and/or objects in images, using a machine learning system, using a pattern recognition system, and so forth.

In some examples, at least one person may be identified in the environment of the user using a facial recognition algorithm, using a neural network trained to detect faces and/or persons in images, and so forth. In other embodiments, the wearable apparatus 110 may capture thermal images, either alone or in combination with visual images, for processing by the thermal signature algorithm. Thermal recognition of at least one person or object may be desirable in implementations in which the wearable apparatus 110 is operating in reduced lighting situations.

In some embodiments, audio processing module 3204 may be configured to identify location information based on audio input received via a microphone of the apparatus 110. In some embodiments, the location information may be identified through the application of one or more audio classification techniques. For example, at least one audio classification technique may be used to classify speech by a person other than the wearer, traffic noises, railroad noises, human noises, etc. In some embodiments, an audio classification technique may include one or more of audio enhancement, natural language processing, speech recognition, and data extraction. Specific examples of the methods for identifying at least one environmental condition are exemplary only, and a person of ordinary skill in the art will recognize other methods for identifying the at least one environmental condition that remains consistent with the present disclosure. Audio processing module 3204 may also have a machine analysis algorithm incorporated such that a library of known environmental conditions may be updated each time audio processing module 3204 may be used.

For example, audio processing module 3204 may identify several voices, indicating that the apparatus is in a room with multiple people. In this example, image processing module 3201 may identify one or more chairs and/or a conference table, indicating that the apparatus is in a conference room. Apparatus 110 may use the information from the audio and image data to cause the mobile communications device to alert the user, via audio or text, that the apparatus 110 is in a conference room.

Apparatus location module 3202 may be configured to receive image data and/or audio data determined by image processing module 3201 and audio processing module 3204. In some embodiments, apparatus location module 3202 may receive location data from one or more apparatus components, e.g., a GPS unit, or from a mobile communications device associated with the user of apparatus 110. Apparatus location module 3202 may determine location information indicating the location of the apparatus 110 based on image information collected by image processing module 3201 and/or audio processing module 3204. For example, objects detected in the environment of the apparatus 110 may indicate its location. Apparatus 110 may use machine learning or other process described above to recognize a collection of one or more objects as being associated with a particular room. In some embodiments, apparatus location module 3202 may also receive motion data from a motion sensor of apparatus 110 and determine the location of the location of the apparatus based on the combination of motion, image, and/or audio data.

For example, upon receiving the command from the user to locate the apparatus 110, mobile communications device may communicate with, or transmit a "ping" to apparatus 110. Apparatus location module 3202 may connect with mobile communications device and may transmit its location data, e.g., GPS coordinates or proximity to the mobile communications device. Location data may include, for example, GPS coordinates, an estimated distance from the mobile communications device, and/or height from a reference point such as the floor. In some embodiments, apparatus location module 3202 may determine the distance from apparatus 110 to the mobile communications device by analyzing GPS coordinates of the apparatus 110 in comparison to GPS coordinates of the mobile communications device.

In other embodiments, if the apparatus 110 is not in the immediate vicinity of the user, e.g., the apparatus is not in the same building, apparatus location module 3202 may access a map on a server and provide directions from the GPS location of the mobile communications device to the GPS location of the apparatus 110. In this example, mobile communications device may provide turn-by-turn audio directions, display a map indicating a route, or may transmit directions and route map to one or more of a GPS unit, a smart vehicle including a GPS unit, and/or another device specified by the user.

Direction module 3203 may receive data from image processing module 3201, audio processing module 3205, and apparatus location module 3202, determine a set of instructions to direct the user to the apparatus 110, and output those directions. The set may or may not be an optimal set of directions. Depending on the distance of the apparatus 110 from the user, mobile communications device may either provide directions to a location or may display and/or provide audio indicating the location of apparatus 110. For example, if apparatus 110 is over 500 feet away from mobile communications device, direction module 3203 may output a listing of turn-by-turn directions to the location of the apparatus 110. In another example, if apparatus 110 is a few feet away, e.g., one or two feet, from the mobile communications device, apparatus 110 may transmit instructions to the mobile communications device to output audio indicating the location of the apparatus 110.

In one example, if the image sensor 220 is on a table, it may capture the table surface and other furniture such as a sofa and armchair. In this example, apparatus location module 3202 may determine the location of the apparatus 110, e.g., that the apparatus 110 is on a table in a living room, and direction module 3203 may generate and transmit instructions for the mobile communications device to provide audio output, "The device is on the table in the living room." In other embodiments, direction module 3203 may generate and image and/or icon indicating the location of apparatus 110. In another embodiment, direction module 3203 may transmit instructions to the user's mobile communications device to alert the user as he gets closer to the misplaced apparatus 110.

In some embodiments, the location information determined by direction module 3203 may be configured to cause the mobile communications device to provide an image representing the location of the wearable apparatus. In some embodiments, a user of the mobile communications device is depicted in the at least one image, and the information includes a position of the user relative to the wearable apparatus. The mobile communications device may be configured to audibly output the position of the user relative to the wearable apparatus based on the information about the location of the wearable apparatus.

In some embodiments, the housing of image sensor 220 may be designed such that the image sensor 220 does not land face down, such that it can always collect an image of its environment. For example, image sensor 220 may have a curved housing such that, if the sensor falls face down on a table, it may still collect some image information. In another example, the apparatus 110 may be configured to change the capturing angle of the image sensor 220, or another parameter, e.g., zoom or brightness, to capture more images if image processing module 3201 cannot extract enough data to locate the apparatus 110 from an initial set of images. In some embodiments, apparatus 110 may use feedback from one or more image processing algorithms to determine areas of the field of view to capture or to determine an amount by which to alter a parameter, e.g., capturing angle.

Modules 3201-3204 may be implemented in software, hardware, firmware, a mix of any of those, or the like. For example, if the modules are implemented in software, they may be stored, for example, in memory 550. However, in some embodiments, any one or more of modules 3201-3204 may, for example, be stored in processor 540 and/or located on server 250, which may include one or more processing devices. Processing devices of server 250 may be configured to execute the instructions of modules 3201-3204. In some embodiments, aspects of modules 3201-3204 may include software, hardware, or firmware instructions (or a combination thereof) executable by one or more processors, alone or in various combinations with each other. For example, modules 3201-3204 may be configured to interact with each other and/or other modules of server 250 and/or a wearable camera system and/or a mobile communications device to perform functions consistent with disclosed embodiments. In some embodiments, any of the disclosed modules may each include dedicated sensors (e.g., IR, image sensors, etc.) and/or dedicated application processing devices to perform the functionality associated with each module.

Figure 33A:
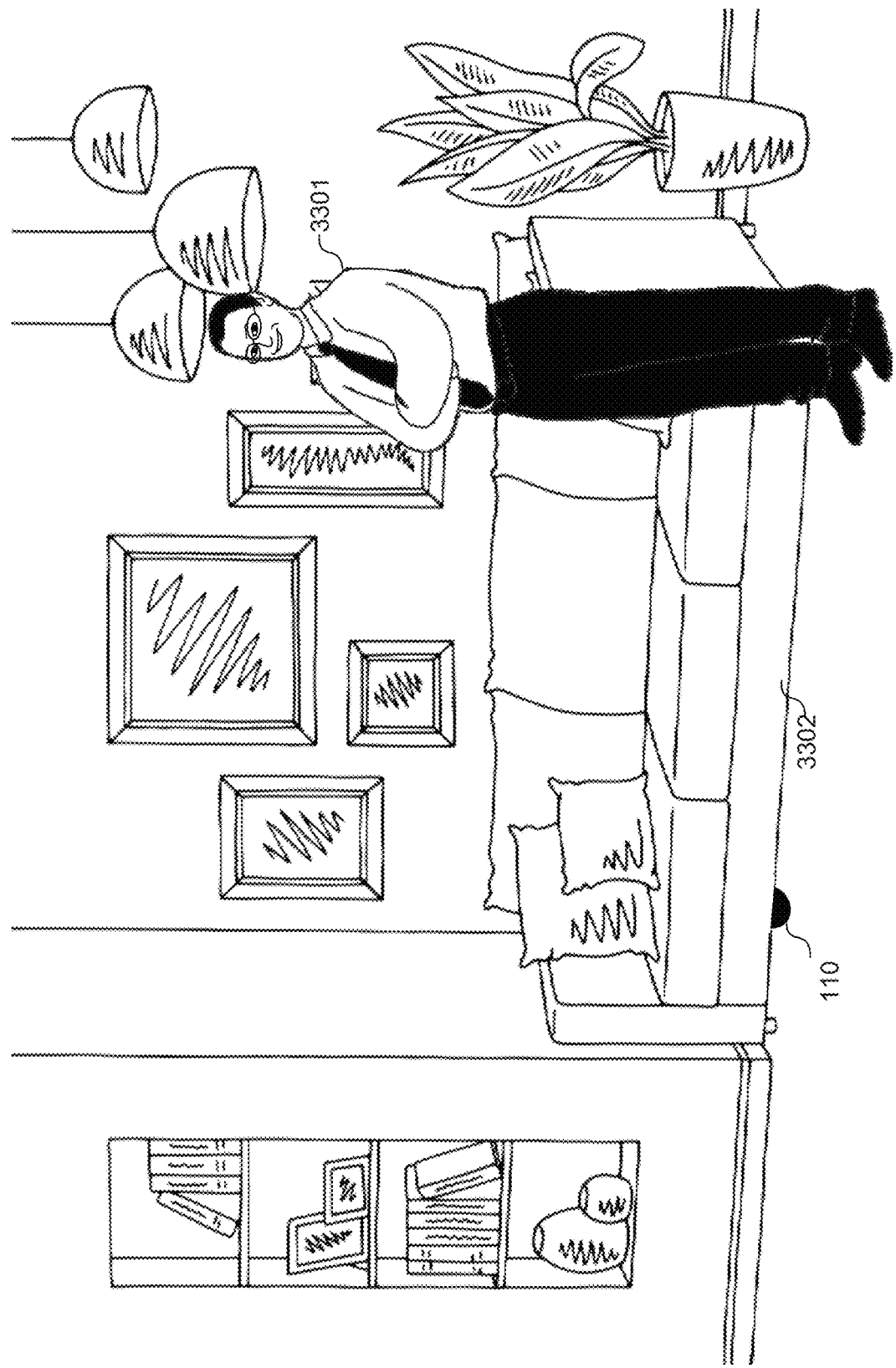
FIGS. 33A, 33B, and 33C are illustrations of exemplary applications of a wearable apparatus consistent with the present disclosure.

FIG. 33A is an exemplary scenario in which a user 3301 is attempting to locate apparatus 110, which has fallen underneath a sofa 3302. To initiate apparatus location, user 3301 may open a mobile application on a mobile communications device (not shown) and input information indicating that he cannot locate the apparatus 110. After receiving a communication, or "ping," from the mobile communications device, apparatus 110 may execute instructions causing image sensor 220 to collect one or more images of the apparatus' environment Image processing module 3201 may process image data to identify one or more objects in the collected one or more images. Objects may include the edge of the sofa 3302, the floor, the feet of the user 3301, etc. Direction module 3203 may analyze these images to determine that the apparatus 110 is on the floor, under a piece of furniture, and to the right of the user 3301. In another example, audio data analyzed by audio processing module 3205 may indicate footsteps and/or the voice of the user. Such audio data may enable the processor 210 to determine that the user 3301 is in the vicinity of the apparatus 110 and may enable the processor 210 to determine the direction and distance of the user 3301 from the apparatus 110.

Direction module 3203 may transmit instructions and/or location information the mobile communications device. For example, direction module 3203 may wirelessly transmit one or more images collected by image sensor 220 and instructions to cause the mobile communications device to display the one or more images, such that a user may also try and find the device based on objects seen in the images. Additionally, direction module 3203 may transmit instructions for the mobile communications device to output spoken audio, for example, "The device is under the furniture to your right."

Figure 33B:
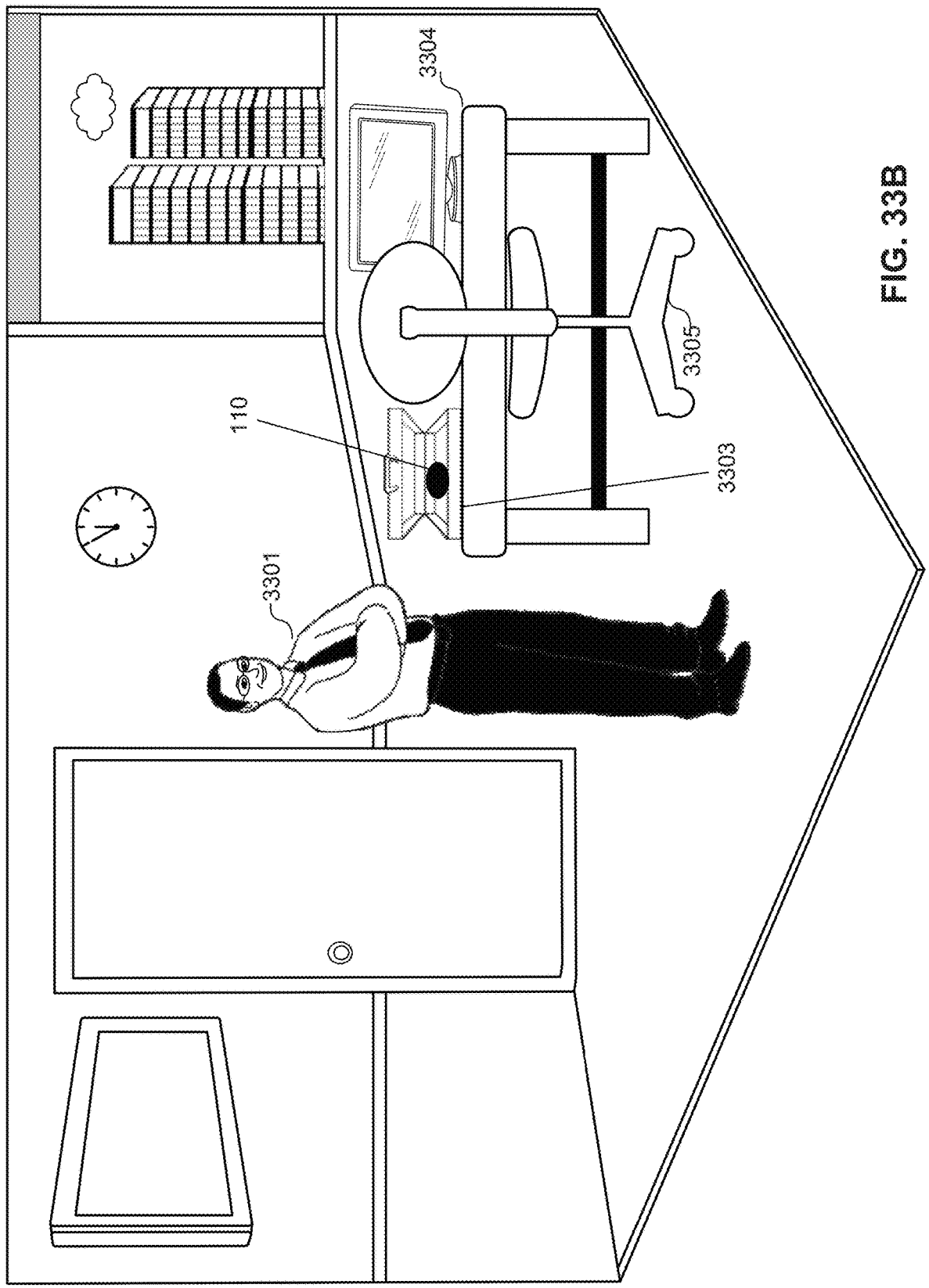

FIG. 33B is an exemplary scenario in which the user 3301 is attempting to locate apparatus 110, which is inside a briefcase 3303 on a desk 3304. To initiate apparatus location, user 3301 may open a mobile application on a mobile communications device (not shown) and input information indicating that he cannot locate the apparatus 110. After receiving a communication, or "ping," from the mobile communications device, apparatus 110 may execute instructions causing image sensor 220 to collect one or more images of the apparatus' environment Image processing module 3201 may process image data to identify one or more objects in the collected one or more images. Objects may include, the edges of the briefcase 3303, a portion of the desk chair 3305, and a portion of user 3301. Audio information may include the voice of the user. For example, audio processing module 3204 may determine how close the user 3301 is to apparatus 110 based on the volume of the user's voice. Direction module 3203 may analyze these images to determine that the apparatus 110 is on the desk inside a container, e.g., the briefcase 3303 and on an elevated surface. Direction module 3203 may determine that apparatus 110 is on a surface based on the detected objects. For example, if image sensor 220 collects images of the top of a chair and the midsection of the user, direction module 3203 may determine that the apparatus 110 is on a table, or other elevated surface.

Direction module 3203 may transmit instructions and/or location information the mobile communications device. For example, direction module 3203 may wirelessly transmit one or more images collected by image sensor 220 and instructions to cause the mobile communications device to display the one or more images. Additionally, direction module 3203 may transmit instructions for the mobile communications device to output spoken audio, for example, "The device is in a container on a table to your left." In some embodiments, mobile communications device may display icons indicating the relative positions and proximity of the apparatus 110 and user 3301.

Figure 33C:
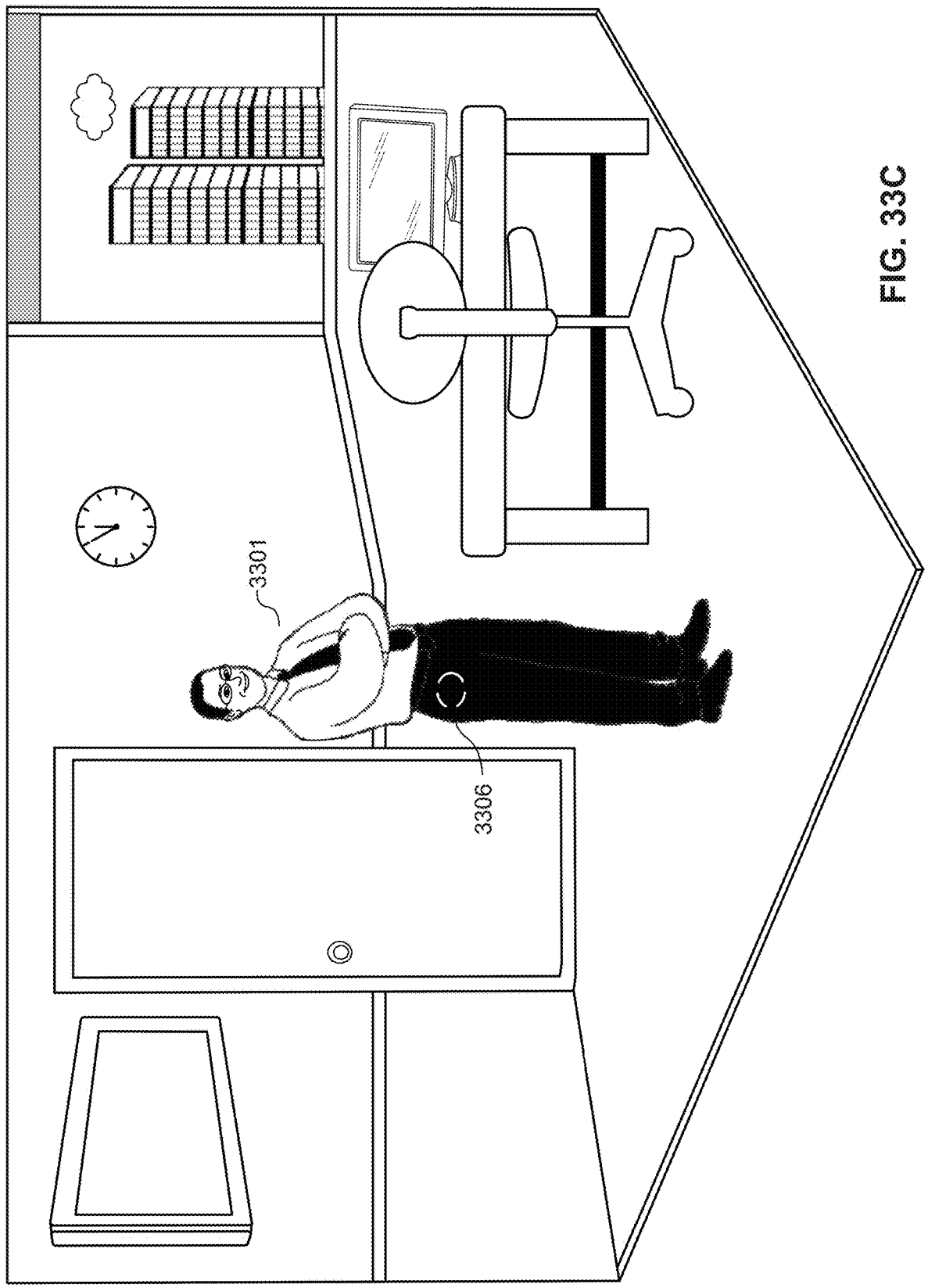

FIG. 33C is an exemplary scenario in which the user 3301 is attempting to locate apparatus 110, which is inside the user's pocket 3306. To initiate apparatus location, user 3301 may open a mobile application on a mobile communications device (not shown) and input information indicating that he cannot locate the apparatus 110. After receiving a communication, or "ping," from the mobile communications device, apparatus 110 may execute instructions causing image sensor 220 to collect one or more images of the apparatus' environment. However, in the user's pocket 3306, image sensor 220 may be unable to collect images since the image sensor 220 may be blocked by fabric. Image processing module 3201 may communicate with direction module 3203 to indicate that the apparatus 110 is inside a container, e.g., a pocket, and cannot provide image data. In this example, direction module 3203 may receive location information, such as proximity to the mobile communications device, from apparatus location module 3202. If the location of the apparatus 110 is close, e.g., one foot, to the location of the mobile communications device, direction module 3203 may instruct the mobile communications device to display or output audio instructing the user that apparatus 110 is in a pocket. In another embodiment, direction module 3203 may execute instructions causing the apparatus 110 to emit a sound to audibly guide the user to the apparatus.

In some embodiments, apparatus 110 may include a motion sensor. For example, if user 3301 is walking and cannot locate apparatus 110, which is in his pocket 3306, the motion sensor may collect motion data indicative of a gait pattern. Apparatus location module 3202 may use the motion data in combination with image and/or audio data to determine that the apparatus 110 is in the user's pocket 3306. In some embodiments, apparatus 110 may be a gait recognition algorithm to determine if the gait pattern detected by the motion sensor matches the user's gait pattern.

Figure 34:
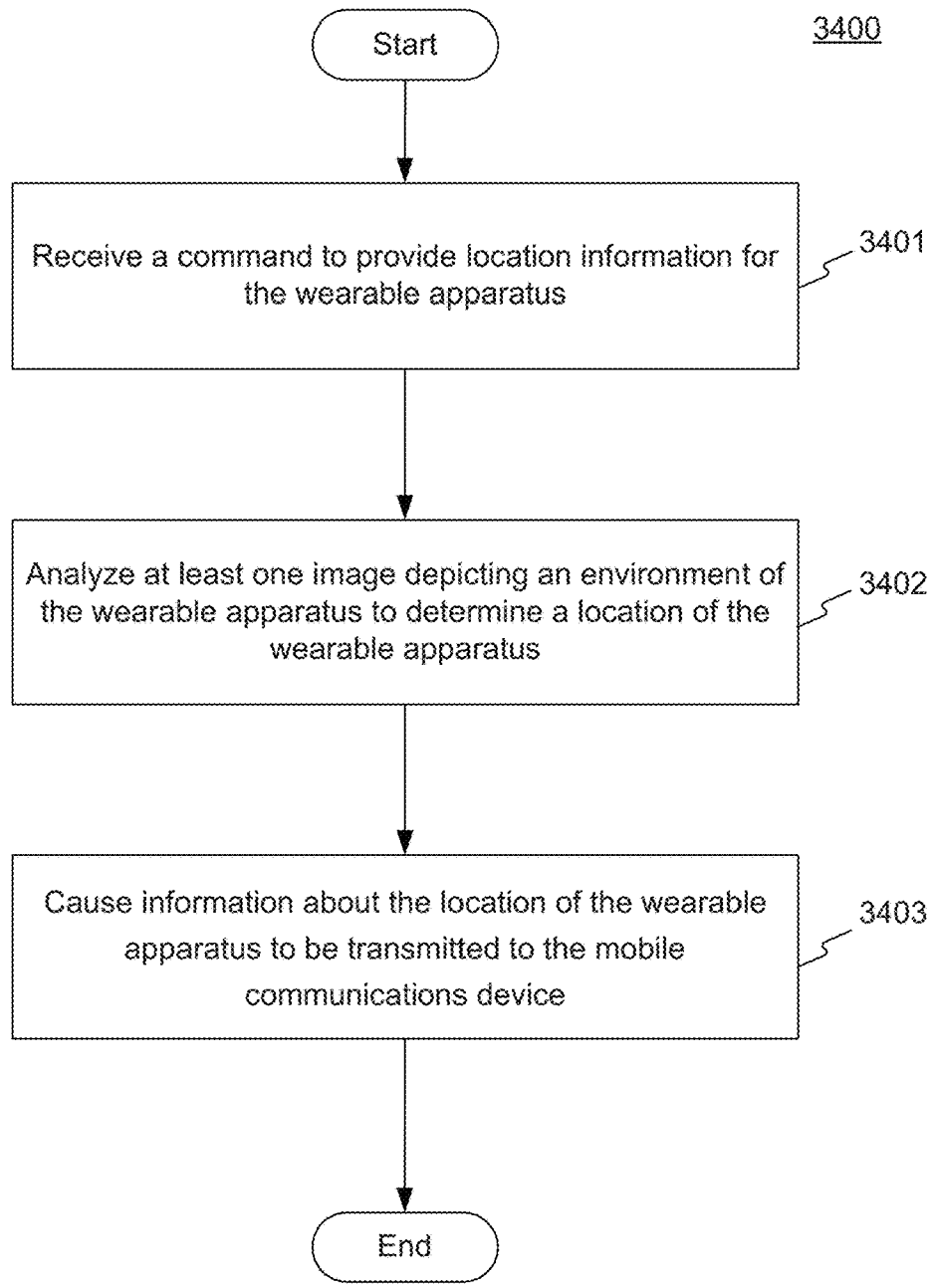
FIG. 34 is a flowchart of a method for providing location information to a user of a wearable apparatus according to a disclosed embodiment.

FIG. 34 is a flowchart of a method 3400 for locating an apparatus and displaying location information on a mobile communications device. Method 3400 may be implemented by a general-purpose computer or a special-purpose computer built according to embodiments of the present disclosure. For example, method 3400 may be executed by at least one of processors 210, 210a, 210b, and 540. In some embodiments, the steps of method 3400 may be performed by wearable apparatus 110. In other embodiments, the steps of method 3400 may be performed by wearable apparatus 110 and one or more external devices (e.g., a processor included in an external server that receives data from wearable apparatus 110 over a network and/or a processor included in an external device such as a laptop, a smartwatch, a smartphone, a tablet, or ear phones, etc.).

At step 3401, the processor may receive, from a mobile communications device wirelessly paired with the wearable apparatus, a command to provide location information of the wearable apparatus. In some embodiments, the processor may establish a wireless pairing between the wearable apparatus and the mobile communications device. If the apparatus is misplaced, the processor may receive user input for pinging the wearable apparatus. In response to the user input, the processor may wirelessly transmit, from the mobile communications device, a ping to the wearable apparatus including an instruction for the wearable apparatus to capture at least one image of the surroundings of the wearable apparatus.

At step 3402, the processor may analyze, in response to the command, at least one image depicting an environment of the wearable apparatus to determine a location of the wearable apparatus. For example, direction module 3203 may receive image information from image processing module 3201 and identify the location of the apparatus 110 based on the image information. In other embodiments, direction module 3203 may additionally receive location data from apparatus location module 3202 and may use the location data in concert with the image information to determine the location of the apparatus.

At step 3402, in some embodiments, the processor may also analyze audio information in combination with image information to determine a location of the wearable apparatus. For example, direction module 3203 may receive image information from image processing module 3201 and audio information from audio processing module 3204, and identify the location of the apparatus 110 based on the combination of image and audio information. In other embodiments, direction module 3203 may additionally receive location data from apparatus location module 3202 and may use the location data in concert with the image and/or audio information to determine the location of the apparatus. One of ordinary skill will recognize that, in some embodiments, the processor may analyze any combination of images and/or audio data to determine a location of the wearable apparatus.

At step 3403, the processor may cause information about the location of the wearable apparatus to be transmitted to the mobile communications device. As previously described, information about the location of the apparatus 110 may include GPS coordinates, images collected by the image sensor 220, and/or directions, location of the apparatus 110 relative to the user. The processor may additionally transmit executable instructions to cause the mobile communications device to display and/or audibly output information about the location of the apparatus 110.

Wearable Apparatus Providing Feedback to Adjust a Field of View

In some embodiments, wearable apparatus 110 may collect information related to the environment of the user of the wearable apparatus 110. Furthermore, in some instances, image sensor 220 of apparatus 110 may be positioned in such a way that it is obstructed from capturing a complete field of view. In other instances, the image sensor 220 may be oriented in such a way that it is unable to capture the complete field of view and/or portions of the field of view containing information about the user's environment. In some embodiments, the apparatus 110 may be configured to detect an obstruction or poor orientation of the image sensor 220 and communicate notification or correction information to the user. For example, apparatus 110 may suggest to the user to reposition or re-orient the image sensor 220.

Currently, wearable devices or apparatuses may include image sensing components. However, the user may be required to ensure the image sensing component is clear of obstruction and/or capable of detecting a required field of view. In some circumstances, the image sensing component may be obstructed unbeknownst to the user, thereby rendering the image sensing component unable to capture images t usable for providing meaningful feedback.

As described above, in some embodiments, any one of apparatus 110 or computing device 120, via processor 210 or 540, may further process captured image data and determine that all or a portion of the field of view of image sensor 220 is obstructed. In some embodiments, apparatus 110 may analyze at least one image captured by the wearable image sensor to determine a positioning issue related to the wearable image sensor 220. Responsive to the determination of a positioning issue, apparatus 110 may determine correction information for resolving the positioning issue and cause the correction information to be provided to the user of apparatus 110.

A positioning issue may arise when image sensor 220 is fully or partially blocked and thus cannot collect image data. In some embodiments, the positioning issue may include an obstruction of the wearable image sensor 220 and/or an impediment to the quality of image capture. In other embodiments, the positioning issue may include an obstruction of the wearable image sensor 220 by the user of apparatus 110. For example, apparatus 110 may be worn by the user in such a manner that image sensor 220 is blocked by the user or by a piece of the user's clothing. In another example, image sensor 220 may be positioned behind a gauzy, or translucent, article of clothing, e.g., a linen scarf. The positioning issue may be the resulting impediment to image quality caused by the scarf. In other embodiments, the positioning issue may include an orientation of the wearable image sensor 220. For example, if the image sensor 220 is mounted on glasses, e.g., glasses 130, the user may remove the glasses and place them on top of his head such that image sensor 220 is oriented toward the sky or ceiling. In this example, image sensor 220 may be unable to capture image information relevant to the user, i.e., information about the user's environment.

In response to the detection of a positioning issue of the image sensor 220, apparatus 110 may provide the user with correction information. In some embodiments, correction information may include a recommendation to move the wearable apparatus. For example, if the image sensor 220 is blocked by the user's scarf, correction information may be to wear the apparatus 110 at a different location on the user's body. In some embodiments, correction information may include a recommendation to remove or reposition the obstruction. In the above example, correction information may include a recommendation to the user to remove and/or reposition the scarf. In embodiments in which the positioning issue is related to the orientation of the image sensor 220, correction information may include a recommendation to change the orientation of the wearable image sensor 220.

In some embodiments, correction information is provided to a mobile communications device wirelessly paired with the wearable apparatus. In some embodiments, the correction information is provided as text output. For example, the correction information may be configured to cause the mobile communications device to output the correction information as text. For example, correction information may be displayed on a screen of the mobile communications device via a mobile application. In another embodiment, the correction information is configured to cause the mobile communications device to audibly output the correction information, via a speaker of the mobile communications device.

In some embodiments, correction information may include a generic recommendation to adjust the wearable apparatus. For example, correction information may cause the user's mobile communications device to alert the user, via a text and/or audio message, that the image sensor is unable to collect sufficient image data. An exemplary message may be, for example, "Image sensor is blocked. Please adjust device."

In another embodiment, correction information may include executable instructions configured to cause the at least one processor to automatically resolve the positioning issue. For example, the positioning issue may be the orientation of the image sensor 220. Correction information may include instructions such that the processor adjusts the orientation and/or angle of the image sensor within the apparatus so the sensor can capture a greater portion of the field of view.

Figure 35:
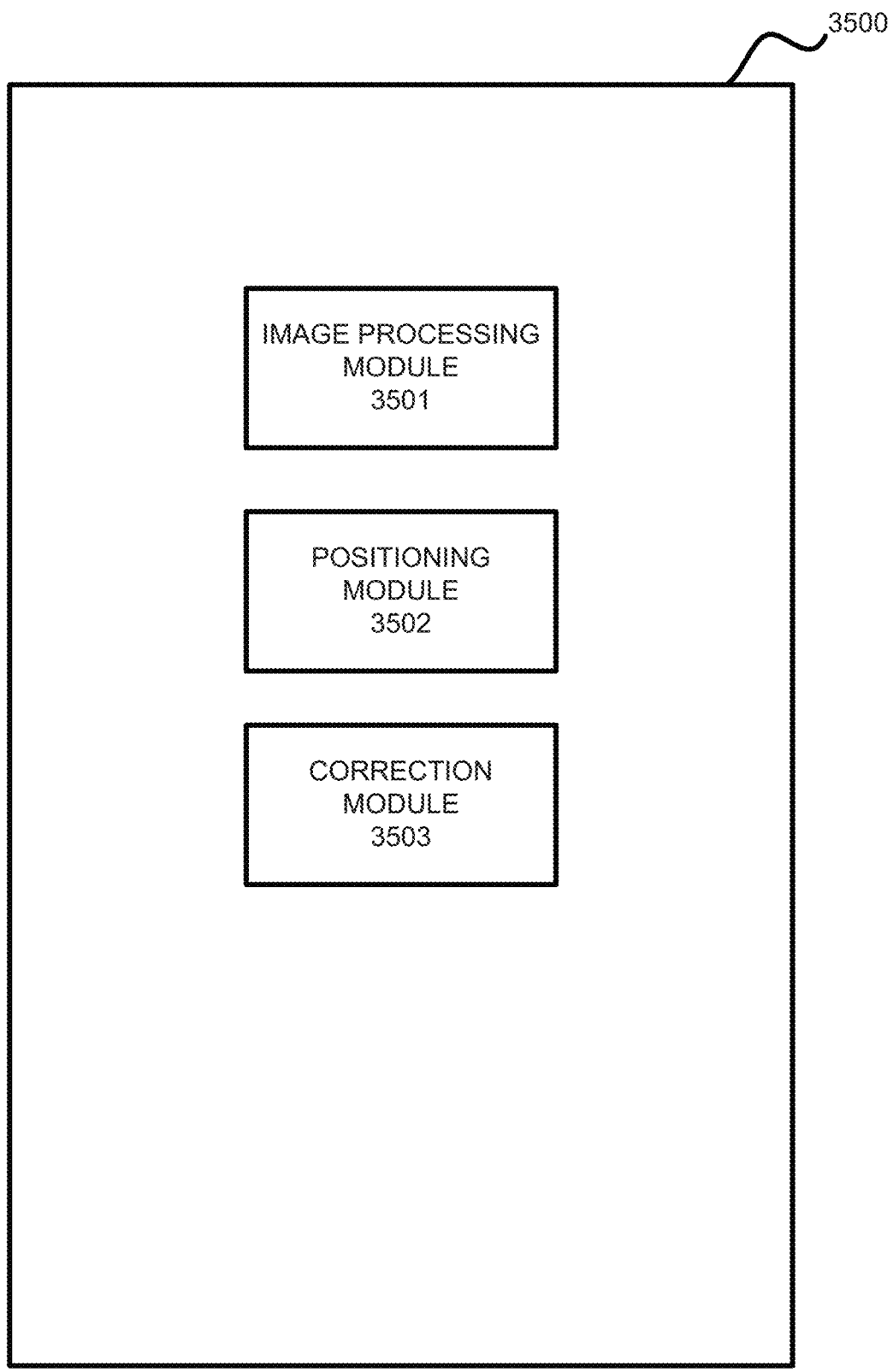
FIG. 35 illustrates an exemplary embodiment of a memory containing software modules consistent with the present disclosure.

FIG. 35 illustrates an exemplary embodiment of a memory 3500 containing software modules consistent with the present disclosure. Included in memory 550 are an image processing module 3501, a positioning module 3502, and a correction module 3503. Modules 3501, 3502, 3503 may contain software instructions for execution by at least one processing device, e.g., processor 210, included with a wearable apparatus. Image processing module 3501, positioning module 3502, and correction module 3503 may cooperate to process an image from an image sensor, e.g., image sensor 220, identify a positioning issue, determine correction information based on the positioning issue, and output the correction information to the user. Memory 3500 may be separate from and/or integrated with memory 550 of FIG. 6, described above. Similarly, orientation identification module 601, orientation adjustment module 602, and motion tracking module 603 of FIG. 6 may operate in tandem or concurrently with image processing module 3501, positioning module 3502, and correction module 3503 of FIG. 35.

Image processing module 3501 may be configured to identify one or more objects and/or lighting levels from one or more images. In some embodiments, objects in the one or more images may be identified through the application of one or more image classification techniques. For example, at least one image classification technique may be used to classify at least one feature of an image. In some embodiments, an image classification technique may include one or more of image enhancement, edge detection, image analysis, and data extraction. Specific examples of the methods for identifying at least one object in an image are exemplary only, and a person of ordinary skill in the art will recognize other methods for identifying the at least one positioning issue that remains consistent with the present disclosure. In some examples, at least one object may be detected using an object detection algorithm, using a neural network trained to detect objects and/or objects in images, using a machine learning system, using a pattern recognition system, and so forth. In some embodiments, image processing module 3501 may identify a lighting level of the environment of the user.

Positioning module 3502 may be configured to receive image data from image processing module 3501 and identify the positioning issue. A positioning issue may be a blockage of the image sensor 220 or orientation of the image sensor 220 such that it is unable to capture relevant image information of the environment of the user. For example, image processing module 3501 may analyze one or more captured images to determine that the image sensor 220 is not collecting image data from a portion of the field of view and positioning module 3502 may associate the lack of data with a partial blockage of the image sensor 220. In this example, positioning module 3502 may determine which side of the image sensor 220 is blocked, e.g., relative to the user, an object is blocking the left portion of the sensor. In another example, image processing module 3501 may not receive any image data, indicating that the image sensor 220 is completely blocked. In another embodiment, if the positioning issue is the orientation of the image sensor 220, image processing module 3501 may identify a flat surface, e.g., a ceiling of the room that the user is in, or the sky. In this example, positioning module 3502 may determine based on information from image processing module 3501, that the positioning issue is that the image sensor is oriented upwards. Positioning module 3502 may also have a machine analysis algorithm incorporated such that a library of known blockages and/or orientations may be updated each time image processing module 3501 and positioning module 3502 may be used.

Correction module 3503 may receive positioning issue information from positioning module 3502 and determine correction information including a recommendation to the user to resolve the positioning issue. Recommendations may include instructions to move, reposition, and/or re-orient the image sensor 220. In other embodiments, a recommendation may be that the user repositions himself and/or an article of clothing. Correction module 3503 may be configured to transmit the correction information as text and/or audio instructions to a mobile communications device wirelessly paired to apparatus 110. The apparatus 110 may transmit the correction information by communicating with a device, via any known wireless standard (e.g., wifi, Bluetooth®, etc.), as well as near-field capacitive coupling, and other short range wireless techniques, or via a wired connection.

In some embodiments, correction module 3503 may receive data indicative of a positioning issue arising from the orientation of the image sensor 220. Correction module 3503 may communicate with one or more orientation modules to automatically modify the orientation of the image sensor to correct the positioning issue identified by positioning module 3502.

Modules 3501-3503 may be implemented in software, hardware, firmware, a mix of any of those, or the like. For example, if the modules are implemented in software, they may be stored, for example, in memory 550. However, in some embodiments, any one or more of modules 3501-3503 may, for example, be stored in processor 540 and/or located on server 250, which may include one or more processing devices. Processing devices of server 250 may be configured to execute the instructions of modules 3501-3503. In some embodiments, aspects of modules 3501-3503 may include software, hardware, or firmware instructions (or a combination thereof) executable by one or more processors, alone or in various combinations with each other. For example, modules 3501-3503 may be configured to interact with each other and/or other modules of server 250 and/or a wearable camera system to perform functions consistent with disclosed embodiments. In some embodiments, any of the disclosed modules may each include dedicated sensors (e.g., IR, image sensors, etc.) and/or dedicated application processing devices to perform the functionality associated with each module.

Figure 36B:
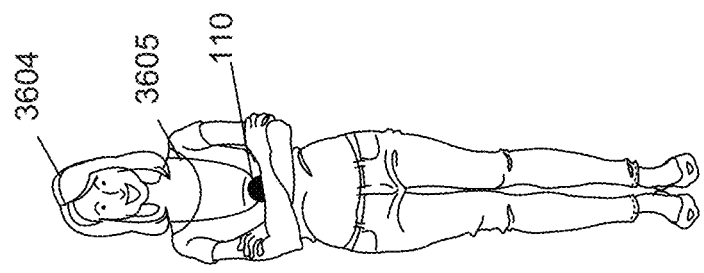
FIGS. 36A, 36B, and 36C are illustrations of exemplary embodiments of image sensor occlusion consistent with the present disclosure.
Figure 36A:
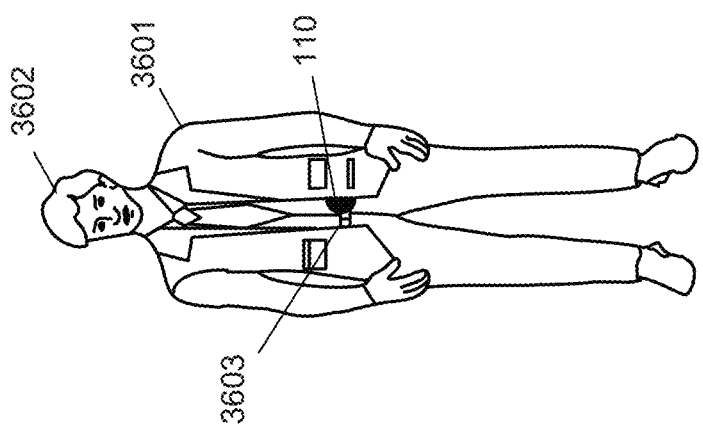

FIG. 36A is an exemplary scenario in which the system may identify a positioning issue in which the image sensor of the apparatus 110 is partially blocked by the jacket 3601 of the user 3602. Apparatus 110 may be worn by the user 3602 on a belt 3603. Belt 3603 may be the same as or similar to belt 150. If the user 3602 is wearing a jacket 3601, the apparatus 110 may become partially obstructed. Images captured by image sensor 220 may lack data corresponding to the obstructed portion of the field of view. Positioning module 3502 may receive this image information from image processing module 3501 and determine that a positioning issue is that the left side (corresponding to the user's left side) of the image sensor is obstructed. Correction module 3503 may determine instructions such as, for example, "Clothing is blocking the device. Please reposition device or clothing." These instructions may be transmitted wirelessly to the user's mobile communications device and displayed on the screen of the mobile communications device and/or audibly output from a speaker of the user's mobile communications device.

FIG. 36B is an exemplary scenario in which the system may identify a positioning issue in which the image sensor of the apparatus 110 is partially blocked by the user 3604. Apparatus 110 may be worn by the user 3604 on a necklace 3605. Necklace 3605 may be the same as or similar to necklace 140. While wearing the device, the user 3604 may block the apparatus 110, for example, by crossing her arms. Image processing module 3501 may analyze one or more images captured by image sensor 220 to determine that the lower portion of the field of view is blocked. Image processing module 3501 may use one or more techniques, as previously described, to characterize objects in the environment of the user, including the object causing the obstruction. Image processing module 3501 may analyze the geometry and/or curvature of the blockage to determine that the blockage is caused by a human body part, e.g., an arm. Positioning module 3502 may receive this information and determine that the lower portion of the field of view is blocked by the user's arm.

In this example, correction information determined by correction module 3503 may be to recommend the user 3604 move her arm. In some embodiments, for example, if correction information is output to the user 3604 who moves her arm, and then the user 3604 assumes a position at a later time such that her arm is again blocking the sensor, correction module 3503 may analyze the sequence of blockages and recommend that the user 3604 move the apparatus 110 to avoid subsequent obstructions. As previously described, correction module 3503 may transmit correction instructions to the user's mobile communications device and display the instructions on the screen of the mobile communications device.

Figure 36C:
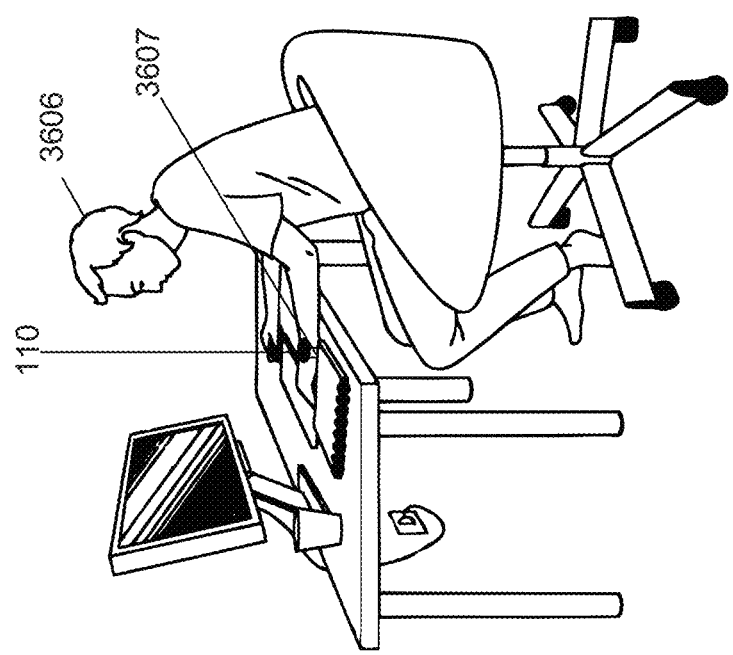

FIG. 36C is an exemplary scenario in which the system may identify a positioning issue in which the image sensor of the apparatus 110 is oriented such that the image sensor 220 cannot collect relevant image information. Apparatus 110 may be worn by the user 3606 on a watch 3607. While wearing the watch, the user 3606 may engage in an activity, such as typing on a keyboard or writing, that causes the apparatus 110 to be oriented upwards. Image processing module 3501 may analyze one or more images captured by image sensor 220 and identify, for example, the chin of the user 3606 and/or the ceiling of the room the user 3606 is in. Image processing module 3501 may use one or more techniques, as previously described, to characterize objects in the environment of the user 3606. Positioning module 3502 may receive this information, e.g., the identification of the chin of the user 3606 and determine that the apparatus 110 is oriented upward.

In this example, correction information determined by correction module 3503 may be to recommend the user 3606 move his arm or to move the apparatus 110 such that the field of view captured by image sensor 220 is consistent with the field of view seen by the user 3606. In some examples, such correction information may recommend that the user remove the apparatus (i.e., no longer wear it as watch), and position the apparatus such that the user may continue an activity (e.g., typing) while the field of view of image sensor 220 may monitor a particular region (e.g., a display). As previously described, correction module 3503 may transmit correction instructions to the user's mobile communications device and display the instructions on the screen of the mobile communications device.

Figure 37:
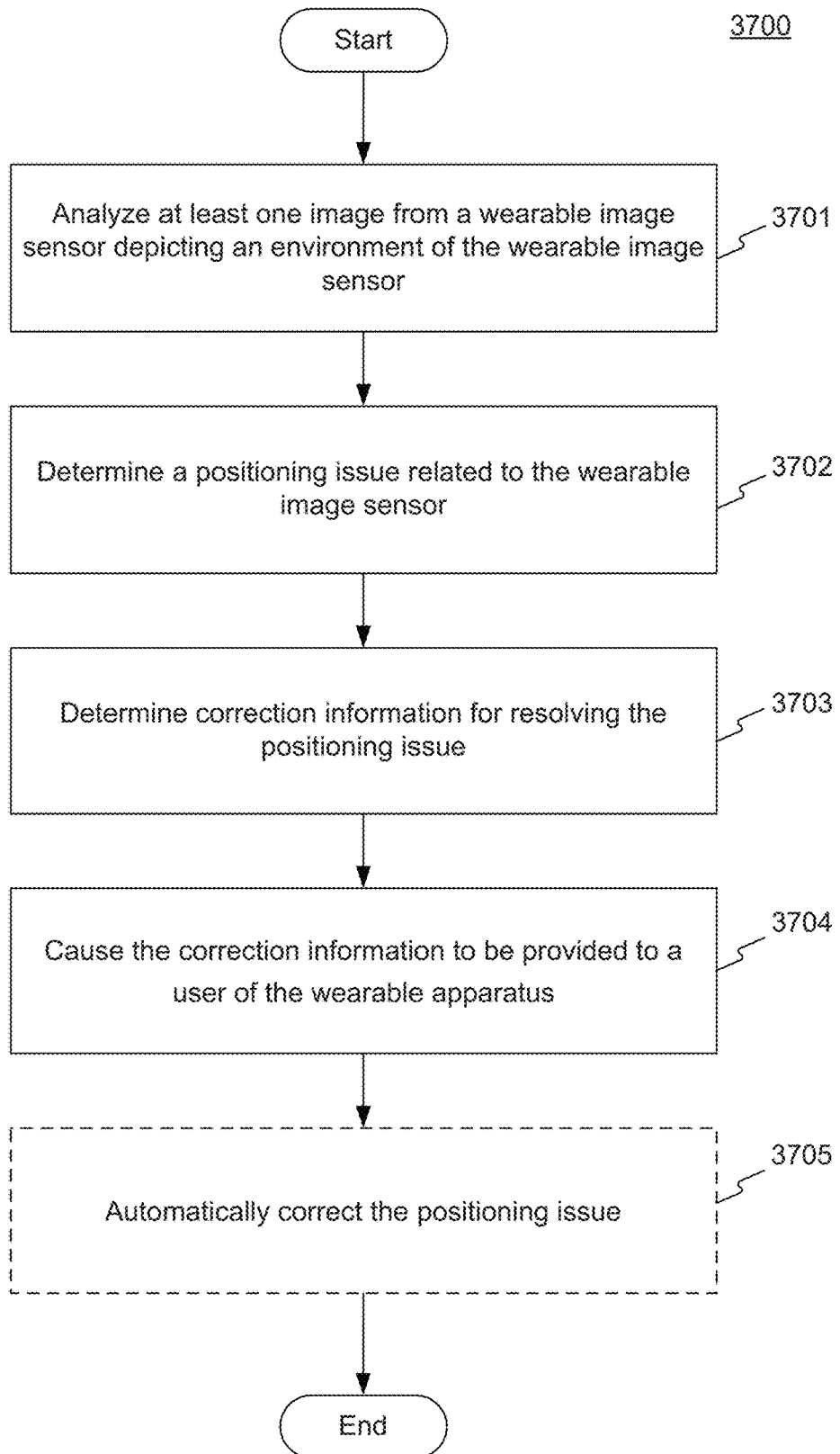
FIG. 37 is a flowchart of a method for detecting and correcting a blockage of the image sensor of the wearable apparatus according to a disclosed embodiment.

FIG. 37 is a flowchart of a method 3700 for determining a positioning issue related to a wearable image sensor and providing correction information, based on the positioning issue, to the user according to a disclosed embodiment. Method 3700 may be implemented by a general-purpose computer or a special-purpose computer built according to embodiments of the present disclosure. For example, method 3700 may be executed by at least one of processors 210, 210a, 210b, and 540. In some embodiments, the steps of method 3700 may be performed by wearable apparatus 110. In other embodiments, the steps of method 3700 may be performed by wearable apparatus 110 and one or more external devices (e.g., a processor included in an external server that receives data from wearable apparatus 110 over a network and/or a processor included in an external device such as a laptop, smartwatch, smartphone, tablet, or ear phones, etc.).

At step 3701, the processor may analyze at least one image from a wearable image sensor, e.g., sensor 220. For example, image sensor 220 may capture one or more images of the environment of the user. Image processing module 3501 may analyze the one or more images to identify one or more objects, a lighting level, and/or a captured field of view. In some embodiments, processor 210 may receive a plurality of images from the wearable image sensor and perform image processing on at least some of the images.

At step 3702, the processor may determine a positioning issue based on the analysis of the at least one image. In some embodiments, processor 210 may determine, based on the image processing, an impediment to quality image capture. As previously described, positioning module 3502 may receive image information from image processing module 3501 and associate the image information with a positioning issue, such as a blockage, impediment, or inefficient orientation of the image sensor 220.

At step 3703, the processor may determine correction information for resolving the positioning issue. In some embodiments, the processor may determine, in response to the determined impediment, correction information for resolving the positioning issue. For example, correction module 3503 may receive information indicating a positioning issue from positioning module 3502 and determine correction information to resolve the positioning issue. As previously described, the correction information may include a recommendation to move or reposition apparatus 110 to resolve the positioning issue.

In some embodiments, correction module 3503 may receive information from positioning module 3202 indicative of a positioning issue, but the positioning information may not indicate a cause of the positioning issue. If a specific cause is not determined by positioning module 3502, correction module 3503 may provide a general message. For example, if the image sensor does not collect any images including extractable data, e.g., if the sensor is completely blocked, positioning module 3502 may be unable to determine the cause of the blockage. In this example, correction module 3503 may cause the mobile communications device to output a generic message such as, "Image sensor is blocked."

At step 3704, the processor may cause the correction information to be provided to a user of the wearable apparatus. Providing the correction information may include transmitting the correction information to a mobile communications device wirelessly paired with the apparatus 110. Correction information may include textual, visual, and/or audio instructions for the user to resolve the positioning issue. The processor may further cause instructions to be transmitted to the mobile communications device to display the text instructions or to output audio instructions using text-to-speech software. In some embodiments, the processor may present the correction information on a display of the pairable mobile communications device.

In some embodiments, method 3700 may include optional step 3705. The positioning issue identified by the positioning module 3502 may not require the user to re-position or re-orient the image sensor 220. If the positioning issue may be resolved by the apparatus 110 itself, at step 3705, the processor may cause the apparatus 110 and/or image sensor 220 to automatically correct the positioning issue. For example, automatically correcting the positioning issue may include modifying one or more of the angle of the sensor, sensitivity of the sensor, or resolution of the images captured.

In one example, a user may wear the apparatus on an article of clothing that is oriented at a slight angle relative to the body of the user. Positioning module 3502 may determine, based on image data, that image sensor 220 is not capturing the full field of view from the same angle as the user. In this example, the processor may resolve the positioning issue by automatically rotating the image sensor 220 such that the sensor is facing away from the user in parallel with the user's line of sight.

Wearable Apparatus for Name Tagging

In some embodiments, the disclosed apparatus and methods may facilitate the association of captured facial images with names by employing natural language processing to extract a name from a conversation, which may be associated with the facial image. To ensure accuracy, the user may be queried for confirmation before the name is stored. The disclosed apparatus and methods may further look-up an identity based on a subsequent facial image, after a subsequent encounter.

Figure 38:
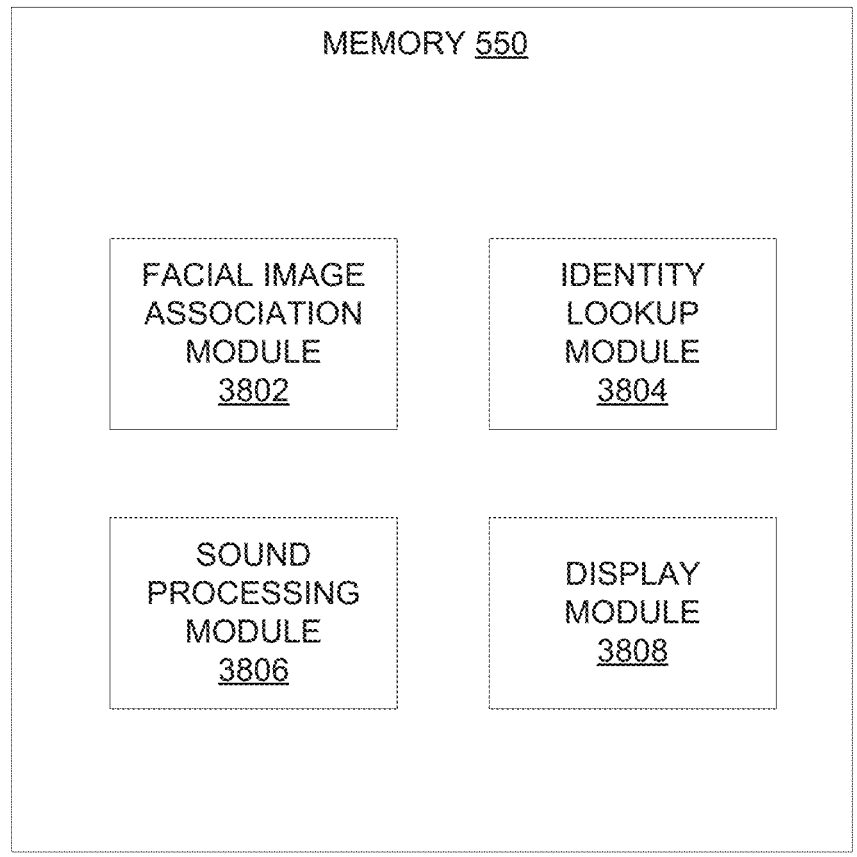
FIG. 38 illustrates an exemplary embodiment of a memory containing software modules consistent with the present disclosure.

As shown in FIG. 38, in combination with other modules discussed above, association of facial images with names may be partitioned into, for example, four modules, including a facial image association module 3802, an identity lookup module 3804, a sound processing module 3806, and a display module 3808. In some embodiments, modules 3802, 3804, 3806, and 3808 may be stored in memory unit 550 of apparatus 110 and/or 120, or modules 3802, 3804, 3806, and 3808 (or portions thereof) may be stored remotely from apparatus 110 (e.g., stored in a server accessible to apparatus 110 via, for example, wireless transceiver 530).

Facial image association module 3802, which may store instructions executable by processor 210, may handle various tasks relating to associating text generated based on a spoken name with a facial image. Such tasks may rely upon input from various sensors and sensing systems associated with the apparatus 110, as described above.

Facial image association module 3802 may receive, from a wearable image sensor (such as image sensor 220), a facial image of an individual with whom a user of the wearable apparatus is interacting. The facial image may be in any suitable still or motion imaging format, and the individual depicted in the facial image may comprise a human person. In an embodiment, the individual depicted in the image may comprise a representation of a person, a rendered, animated, or illustrated depiction of a person, or any other visual subject that may appear in an output of the wearable image sensor.

Facial image association module 3802 may store, in a memory (e.g., memory unit 550), text associated with the individual in a manner associating the text with the facial image. Any form of data structure, file system, or algorithm for associating the text with the facial image may be employed. The text may comprise audio captured during an interaction with the individual. For example, the text may comprise a spoken name of the individual captured in a conversation with the individual and/or related to the individual. In some embodiments, facial image association module 3802 may receive text from sound processing module 3806 (discussed further below). While the description that follows focuses on text related to a name of the individual, the text may comprise any piece of information associated with the individual, for example, a title, common interest, relationship with one or more other individuals, etc.

In some embodiments, prior to storing the text associated with the individual, facial image association module 3802 may prompt the user to confirm a presumed name of the individual. For example, facial image association module 3802 may cause a display to the user of a presumed name of the individual. The display may be carried out at least in part by display module 3808 (described in further detail below). In some embodiments, prior to storing the text associated with the individual, facial image association module 3802 may enable the user to alter the text. Any known means of altering text may be employed. For example, image association module 3802 may prompt display module 3808 to display a cursor to enable editing characters of the text. Additionally or alternatively, image association module 3802 may prompt display module 3808 to display proposed replacement candidates for the text.

In some embodiments, facial association module 3802 may store text associated with an individual in association with a different image than an image received by the wearable image sensor at or near the time that the audio was captured during the interaction with the individual. That is, facial association module 3802 may store the text associated with the spoken name in a manner associating the text with the facial image by storing the text in association with a previously captured facial image.

In some embodiments, facial association module 3802 may receive text from sources other than captured audio and associate the text with a facial image of the individual. For example, facial association module 3802 may be programmed to determine a name based on analysis of text in an image. Facial association module 3802 may determine a name based on a name tag, identification card, etc., which appears in the image. Any suitable process for analyzing the text may be employed in such analysis, such as known optical character recognition (OCR) techniques.

Identity lookup module 3804 may store instructions executable by processor 210 and may handle various tasks relating to looking up an identity of an individual. For example, identity lookup module 3804 may receive, from the wearable image sensor, a facial image of the individual. The received facial image may be a subsequent facial image. That is, the facial image may be received based on an encounter with the individual subsequent to an encounter for which text associated with the individual was stored by facial image association module 3802 in a manner associating the text with a facial image.

Identity lookup module 3804 may perform a look-up of an identity of an individual based on a facial image, such as a subsequent facial image. The look-up may be performed based on any known image matching or facial identification process, or any combination of suitable technologies. Responsive to performing the lookup, identity lookup module 3804 may receive, from a memory (e.g., memory unit 550 of apparatus 110 and/or 120), text of the spoken name of the individual.

Sound processing module 3806 may store instructions executable by processor 210 and may handle various tasks relating to reception and management of audio information. Sound processing module 3806 may receive sound data captured during an interaction with an individual. Sound processing module 3806 may obtain the sound data from a sound sensor in a housing that includes the wearable image sensor, such as that of apparatus 120. Additionally or alternatively, in some embodiments, the sound data may be obtained from a sound sensor included within a computing device 120 in communication with apparatus 110, as described above. In such embodiments, the sound data may be obtained from a mobile communications device such as a smartphone or tablet.

Sound processing module 3806 may process at least a portion of received sound data to determine a spoken name of the individual. Processing may include converting the captured sound data into an appropriate format for storage or further processing. In some embodiments, sound processing module 3806 may convert the spoken name to text, using any known speech-to-text process or technology. Sound processing module 3806 may also access a database of names and compare the names with the at least a portion of received sound data. More specifically, words parsed from the sound data may be compared with names in the database. The database of names may be stored in memory unit 550 of apparatus 110 and/or 120, and additionally or alternatively may be included in a remote server accessible over one or more networks. Sound processing module 3806 may process the portion of the sound data to determine the spoken name of the individual at least in part by accessing the remote server.

Display module 3808 may store instructions executable by processor 210 and may handle various tasks relating to display of identity information related to an individual. For example, display module 3808 may cause a display in text of the name of the individual on a display associated with apparatus 110. In some embodiments, display module 3808 may cause display of text on a display integrated into apparatus 110. Any display technology known in the art and suitable for inclusion in apparatus 110 may be used. In some embodiments, display module 3808 may cause display of text on one or more of a liquid crystal display (LCD), light-emitting diode (LED) display, organic light-emitting diode (OLED) display, etc. Additionally or alternatively, display module 3808 may cause a display of the name of the individual on a device (e.g., computing device 120) paired with, networked with, or otherwise in communication with the wearable apparatus, such as a mobile communications device.

Figure 39A:
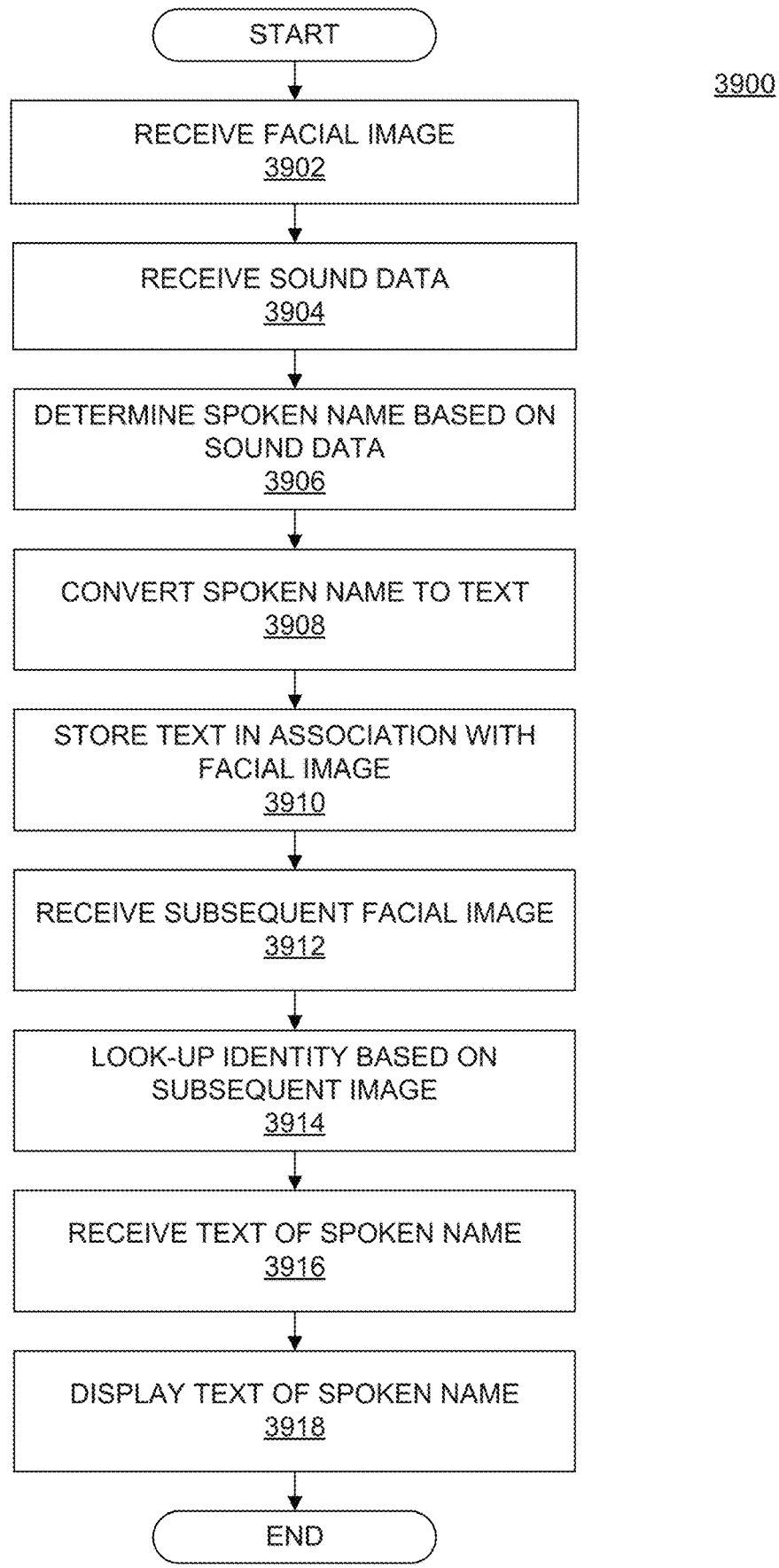

FIG. 39A is an example of a flowchart 3900 representing an example process for association of captured facial images with names, by employing natural language processing to extract a name from the conversation. At step 3902, at least one processing device (e.g., processor 210) of a wearable apparatus may receive, from a wearable image sensor, a facial image of an individual with whom a user of the wearable apparatus is interacting. In some embodiments, the facial image may be received by facial image association module 3802, as described above.

At step 3904, the at least one processing device may receive sound data captured during the interacting. The sound data may be obtained from a sound sensor in a housing that includes the wearable image sensor. For example, as described above, the sound data may be received by sound processing module 3806. As further described above, the sound data may be obtained from a sound sensor included within a mobile communications device.

At step 3906, the at least one processing device may process at least a portion of the sound data to determine a spoken name of the individual. The processing may be performed by sound processing module 3806, as described above. As further described above, processing at least a portion of the sound data at step 3906 may include accessing a database of names and comparing words parsed from the sound data with names in the database, wherein the database may be included in a remote server.

At step 3908, the at least one processing device may convert the spoken name to text. The conversion may be performed by sound processing module 3806, as described above.

At step 3910, the at least one processing device may store, in memory, text associated with the spoken name in a manner associating the text with the facial image. The storing may be performed by facial image association module 3802, as described above. In some embodiments, the storing at step 3910 may include storing the text in association with a previously captured facial image.

At step 3912, the at least one processing device may receive, from the wearable image sensor, a subsequent facial image of the individual. Receiving the subsequent facial image may be performed by identity lookup module 3804, as described above. The subsequent facial image may be received at step 3912, for example, after a subsequent encounter with the individual.

At step 3914, the at least one processing device may perform a look-up of an identity of the individual based on the subsequent facial image. The look-up may be performed by identify lookup module 3804, as described above.

At step 3916, the at least one processing device may receive, from the memory, the text of the spoken name of the individual. The text of the spoken name may be received by identity lookup module 3804, as described above.

At step 3918, the at least one processing device may cause a display in text of the name of the individual on a mobile communications device paired with the wearable apparatus. The display of the name of the individual may be performed by display module 3808, as described above.

Figure 39B:
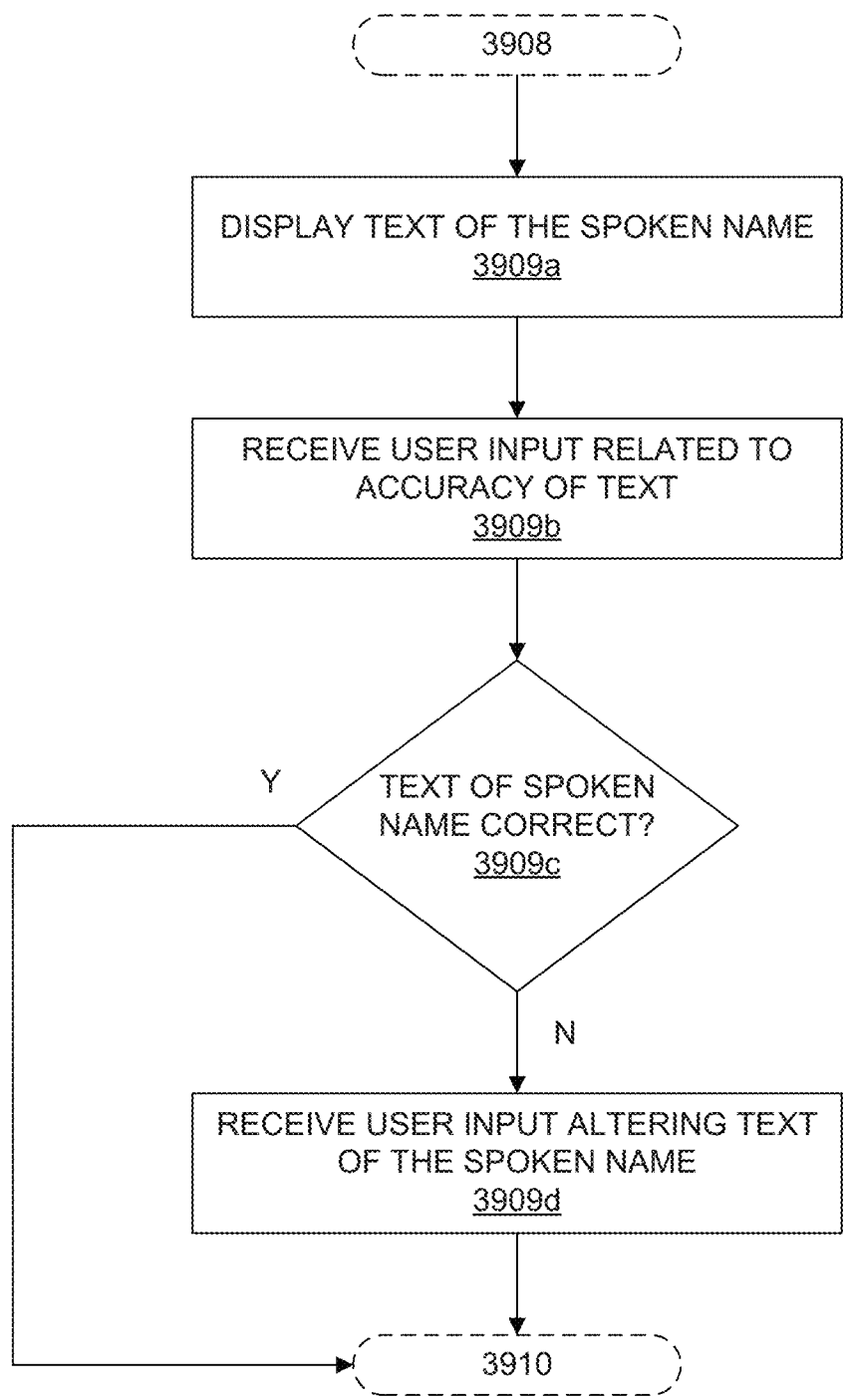

In some embodiments, the at least one processing device may encounter ambiguity or uncertainty in associating captured facial images with names. For example, environmental noise may result in occasional speech to text inaccuracy, or a spoken name may be subject to more than one spelling. To resolve such issues, FIG. 39B is an example of additional steps of flowchart 3900, representing an example process for confirming the accuracy of the text of a name, before and/or as a part of storing the name in association with a facial image.

At step 3909a the at least one processing device may cause a display to the user of a presumed name of the individual. Step 3909a may be performed by facial image association module 3802, as described above. Step 3909a may commence after converting the spoken name to text at step 3908, but may take place prior to storing the text in association with the facial image at step 3910. At step 3909a, the at least one processing device may prompt the user to confirm the displayed presumed name of the individual.

Figure 40:
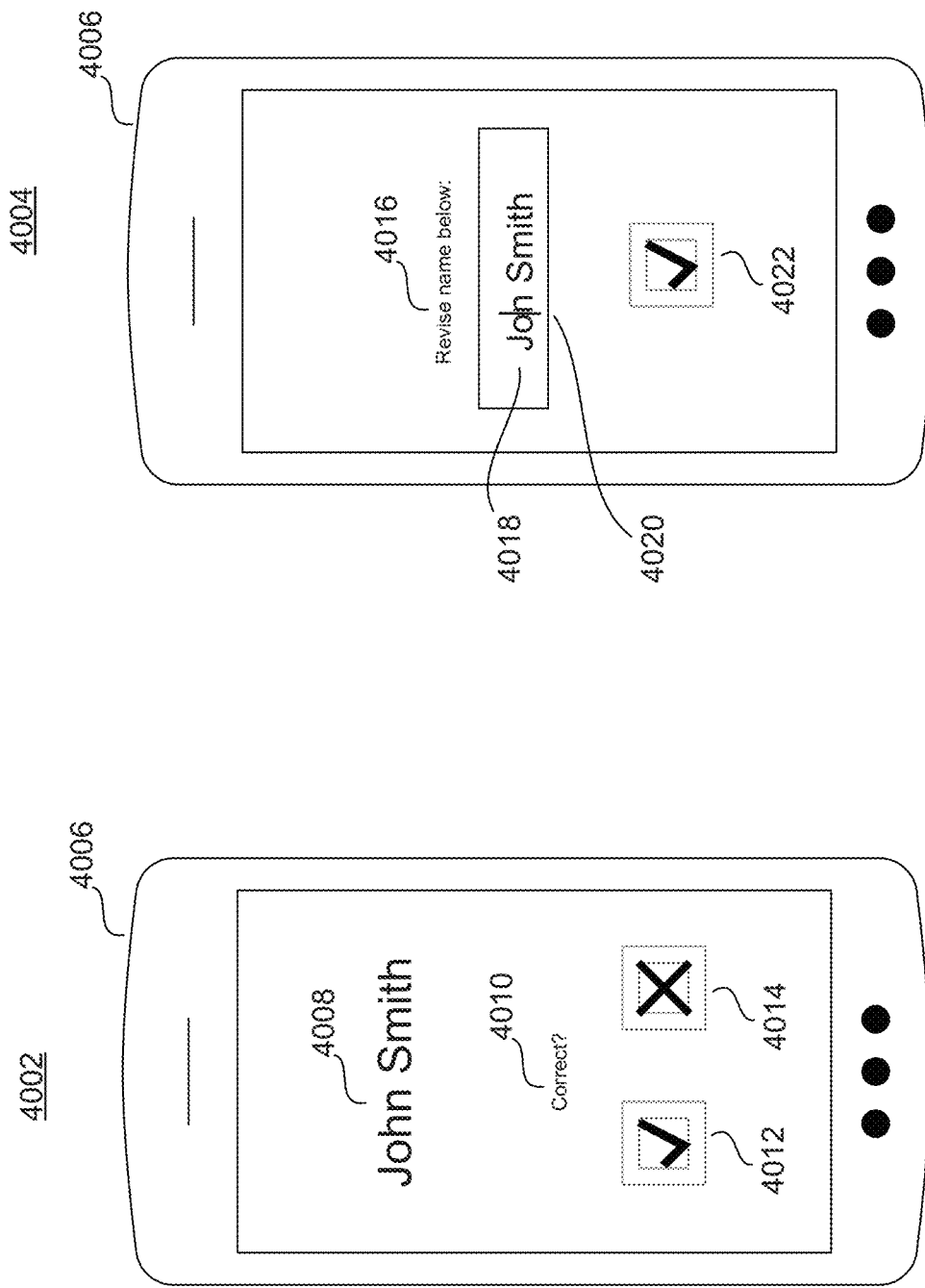
FIG. 40 shows example user interfaces according to disclosed embodiments.

FIG. 40 depicts an example of an interface 4002, displayed on device 4006, which may be configured consistent with step 3909a. The interface may be displayed on a device such as apparatus 110 or computing device 120, as described above in relation to display module 3808. As shown in FIG. 40, interface 4002 may include presumed name 4008, "John Smith." Interface 4002 may also include a message 4010, prompting the user to confirm presumed name 4008.

Returning to FIG. 39B, at step 3909b the at least one processing device may receive user input related to accuracy of the presumed name. Step 3909a may be performed by facial image association module 3802, as described above. Any means of confirmation may be used, such as touch screen input, physical buttons, gestures received by an image sensor or accelerometer, etc. In the example of FIG. 40, interface 4002 depicts interface elements 4012 and 4014, which respectively represent confirmation and rejection of presumed name 4008. Other configurations of confirming or rejecting the presumed name will be apparent to those of skill in the art. For example, in some embodiments, interface element 4014 may be omitted, and a user may be enabled to edit presumed name 4008 by selecting presumed name 4008 itself. If the input received at step 3909b indicates that the presumed name is accurate (step 3909c; YES), flowchart 3900 may proceed to 3910, described above. If, however, the input received at step 3909b indicates that the presumed name is not accurate (step 3909c; NO), flowchart 3900 may proceed to step 3909d.

At step 3909d, the at least one processing device may receive user input altering the text of the spoken name, thereby enabling the user to alter the text prior to storing at step 3910. Step 3909a may be performed by facial image association module 3802, as described above. Returning to the example of FIG. 40, interface 4004 may be configured consistent with step 3909d. Interface 4004 may be configured to provide functionality to allow the user to modify the text of the spoken name. For example, as the names "John" and "Jon" may be pronounced identically, the user may wish to correct the spelling to accurately reflect the name of the individual. Interface 4006 may include a text box 4018 and a cursor 4020, to facilitate such revision. Interface 4006 may also include a message 4016, prompting the user to revise the name shown in text box 4018. After revision of the name, the user may select interface element 4022 to confirm, and flowchart 3900 may proceed to step 3910, described above.

In some embodiments, since it may not be known apriori whether the user is meeting an individual for the first time or the individual's name is already stored, after receiving the individual's facial image at step 3902, flowchart 3900 may proceed to step 3914, and the at least one processing device may look-up the identity of the individual. If an individual is identified based on the look-up, flowchart 3900 may proceed to step 3916, while otherwise flowchart 3900 may proceed to step 3904.

In some embodiments, if an individual is identified based on the lookup at step 3914, the at least one processing device may receive input similar to the input received at step 3909b. The input may represent confirmation or rejection of the identity of the identified individual and/or may allow the user to edit the existing text of the name of the individual identified in the lookup. Furthermore, either automatically or in response to input received from the user, the at least one processing device may associate the received facial image with the identity (e.g., the name) of the individual looked-up at step 3914.

Wearable Apparatus for Prioritizing Tasks

In some embodiments, the disclosed apparatus and methods may facilitate prioritizing tasks based on information identified from captured images. For example, feedback may be provided to a user to alert the user to changes in task priority.

Figure 41:
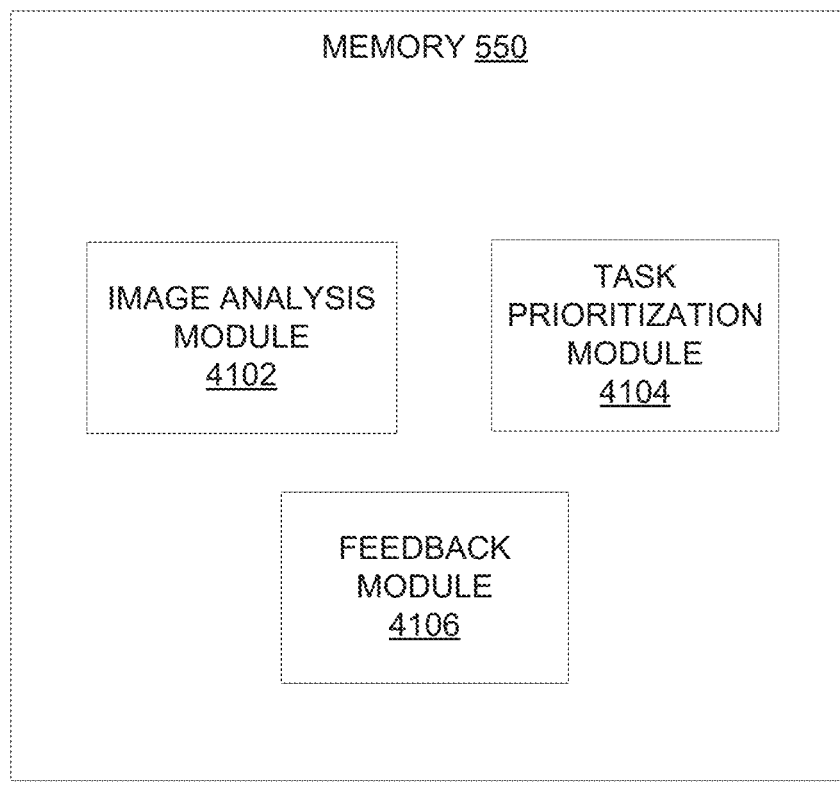
FIG. 41 illustrates an exemplary embodiment of a memory containing software modules consistent with the present disclosure.

As shown in FIG. 41, in combination with other modules discussed above, prioritization of tasks may be partitioned into, for example, three modules, including an image analysis module 4102, task prioritization module 4104, and a feedback module 4106. In some embodiments, modules 4102, 4104, and 4106 may be stored in memory unit 550 of apparatus 110 and/or 120, or modules 4102, 4104, and 4106 (or portions thereof) may be stored remotely from apparatus 110 (e.g., stored in a server accessible to apparatus 110 via, for example, wireless transceiver 530). Further, memory 550 may be configured to store a plurality of tasks.

As described herein, tasks may include any processes or objectives that may be accomplished by or for a user associated with apparatus 110. Tasks may include personal tasks such as appointments, schedule items, chores, shopping lists, exercise goals, health and wellness tasks, etc. Additionally or alternatively, tasks may include tasks involved in satisfying requirements associated with a user's employment. Tasks may be stored in a memory unit configured to store a plurality of tasks, for example, memory unit 550 of apparatus 110 and/or 120, and/or tasks may be stored remotely from apparatus 110 (e.g., stored in a server accessible to apparatus 110 via, for example, wireless transceiver 530).

Image analysis module 4102, which may store instructions executable by processor 210, may handle various operations relating to obtaining information related to a plurality of tasks. Such operations may rely upon input from various sensors and sensing systems associated with the apparatus 110, as described above. For example, image analysis module 4102 may receive images from a wearable image sensor (such as image sensor 220). The wearable image sensor may be configured to capture a plurality of images from an environment of a user of the wearable apparatus. The images may be in any suitable still or motion imaging format, and the subject(s) depicted in the images may comprise anything which may be interpreted to affect priority. In an embodiment, the subject(s) depicted in the image may comprise a representation of a person or object, a rendered, animated, or illustrated depiction of a person or object, or any other visual subject that may appear in an output of the wearable image sensor.

In some embodiments, image analysis module 4102 may additionally or alternatively receive information from sources other than a plurality of images. For example, sound data may be captured and analyzed by image analysis module 4102 and/or another module of apparatus 110. Image analysis module 4102 may obtain sound data from a sound sensor in a housing that includes the wearable image sensor, such as that of apparatus 110. Additionally or alternatively, in some embodiments, sound data may be obtained from a sound sensor included within a computing device 120 in communication with apparatus 110, as described above. In such embodiments, the sound data may be obtained from a mobile communications device such as a smartphone or tablet. Analysis may include converting captured sound data into an appropriate format for storage or further processing.

In some embodiments, sound processing module 3806 may convert sound to text, using any known speech-to-text process or technology.

Image analysis module 4102 may analyze a plurality of images to obtain information related to at least some of a plurality of tasks. Information may be in any appropriate format for use by apparatus 110. Analysis may be performed by any appropriate method or algorithm. For example, comparison with known images may be performed, known traits may be identified from within one or more of the images, optical character recognition may be performed to extract text from an image, etc.

The information related to at least some of the plurality of tasks may comprise an information may be related to an estimated time to complete one or more of the plurality of tasks. In some embodiments, image analysis module 4102 may identify objects in one or more of the images indicative of the expected time to complete the task. For example, image analysis module 4102 may determine that the one or more images indicate that the user is waiting in a line, driving in traffic, or walking in a crowd. The presence of objects associated with such conditions, such as other people, vehicles, etc. may be determined by image analysis module 4102.

In some embodiments, the information related to at least some of the plurality of tasks may comprise information related to a person associated with one or more of the plurality of tasks. For example, image analysis module 4102 may determine an identity of the person, a position of a person, an activity a person is engaged in, whether a person is newly present or absent, etc. As another example, in some embodiments, the information related to at least some of the plurality of tasks may comprise a physical, mental and/or emotional state of a person such as an acute medical problem, an estimated happiness level, patience level, stress level, anger level, etc. Such states may be determined from any appropriate detectable trait of the person, such as by analyzing body or facial features, posture, movement(s), gestures, etc.

In some embodiments, image analysis module 4102 may analyze a plurality of images to obtain information related to a location associated with one or more of a plurality of tasks. For example, image analysis module 4102 may identify text or other identifying information associated with one or more roads, cities, states, other geographic areas. In some embodiments, image analysis module 4102 may identify one or more symbols, landmarks, buildings, organizations, businesses, etc. known to be associated with a particular location or region. Image analysis module 4102 may analyze a plurality of images to obtain information related to a hazardous situation, such as smoke, fire, tides, etc.

Image analysis module 4102 may store obtained information in any appropriate memory, such as memory unit 550 of apparatus 110 and/or 120, or remotely from apparatus 110 (e.g., stored in a server accessible to apparatus 110 via, for example, wireless transceiver 530). Any form of data structure, file system, or algorithm for storing the information may be employed.

Task prioritization module 4104 may store instructions executable by processor 210 and may handle various operations relating to creating a task, or changing or assigning task priority. For example, task prioritization module 4104 may receive, from image analysis module 4102, information related to at least one of a plurality of tasks. Task prioritization module 4104 may prioritize the tasks based on the received information. For example, task prioritization module 4104 may assign a higher priority to a first task over the second task based at least in part on information obtained by image analysis module 4102.

For example, tasks may be ranked by one or more factors such as importance, urgency, duration, etc. Task prioritization module 4104 may prioritize tasks based on a role or relationship between a user and another person or object based on the obtained information. For example, task prioritization module 4104 may prioritize tasks based on a determination that the user is a service provider and another person is a customer or vice versa.

Task prioritization module 4104 may assign or modify a score (such as a numeric score) associated with one or more of the plurality of tasks, based on the obtained information. For example, task prioritization module 4104 may determine at least one score associated with a completeness of one or more of the plurality of tasks and apply the score to relevant tasks. A task that is nearly complete may be prioritized over a task that is not as nearly complete, or vice versa. Assigning a higher priority to a first task over a second task may be based, at least in part, on maximizing an objective function. For example, prioritization module 4104 may assign priority to maximize a number of tasks that may be completed in a particular amount of time or at a particular location. In some embodiments prioritization module 4104 may assign priority to minimize or maximize a cost, risk, and/or other factor associated with completing a task.

Feedback module 4106 may store instructions executable by processor 210 and may handle various operations relating to providing feedback to the user based on the assigned priority. Feedback module 4106 may provide feedback in any appropriate way perceptible to a user, for example via text, graphic display, audio, tactile feedback, etc.

In some embodiments, feedback module 4106 may provide feedback via a display associated with apparatus 110. In some embodiments, feedback module 4106 may cause display of text, graphics, or other information on a display integrated in to apparatus 110. Any display technology known in the art and suitable for inclusion in apparatus 110 may be used. In some embodiments, feedback module 4106 may cause display of information on one or more of a liquid crystal display (LCD), light-emitting diode (LED) display, organic light-emitting diode (OLED) display, etc. Additionally or alternatively, feedback module 4106 may display on a device (e.g., computing device 120) paired with, networked with, or otherwise in communication with the wearable apparatus, such as a mobile communications device.

Figure 42:
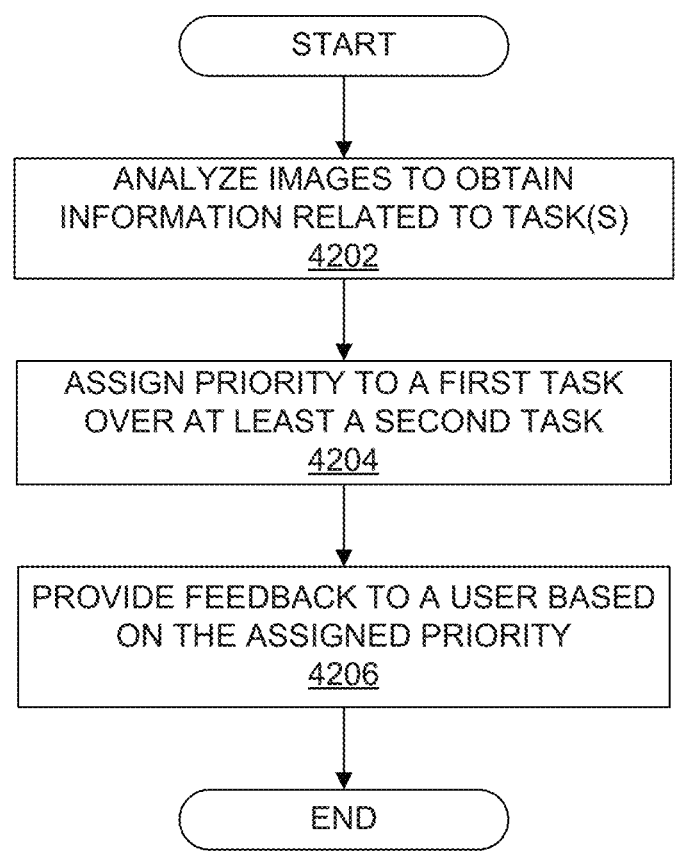
FIG. 42 is a flowchart of a method for prioritizing tasks according to disclosed embodiments.

FIG. 42 is an example of a flowchart 4200 representing an example process for prioritizing tasks.

At step 4202, at least one processing device (e.g., processor 210) of a wearable apparatus may analyze a plurality of images to obtain information related to at least some of the plurality of tasks. As discussed earlier, the wearable apparatus may include a memory unit (e.g., memory 550) configured to store a plurality of tasks. In some embodiments, the plurality of tasks may comprise at least a first task and a second task. The memory unit may store various information regarding the tasks, including an indicator or description of the task, and may further include any other information related to or relevant to the task (e.g., names, locations, due dates, goals, etc.).

Figure 43A:
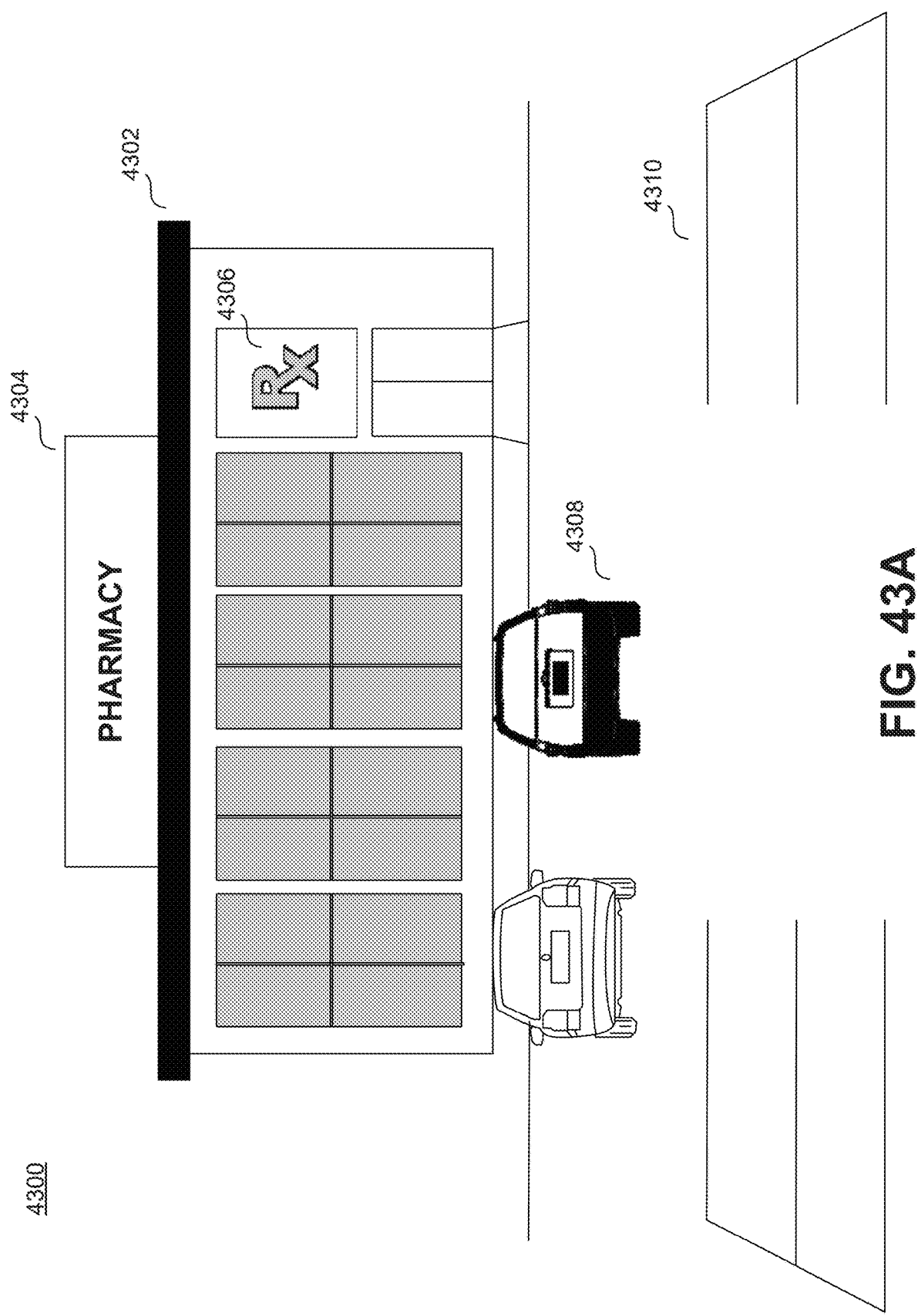
FIGS. 43A and 43B show example captured images according to disclosed embodiments.

FIG. 43A depicts an example of an image 4300 that may be analyzed by the at least one processing device at step 4202. In some embodiments, the images may be analyzed by image analysis module 4102, as described above. For example, image 4300 depicts a pharmacy 4302. The at least one processing device may analyze the image at step 4202 to identify, for example, the text of "pharmacy" sign 4304 or pharmacy symbol 4306 (e.g., information related to a location associated with one or more of a plurality of tasks). The at least one processing device may also identify information such as the presence or number of vehicles 4308 and/or parking spaces 4310 (e.g., information related to an estimated time to complete one or more of the plurality of tasks).

Figure 43B:
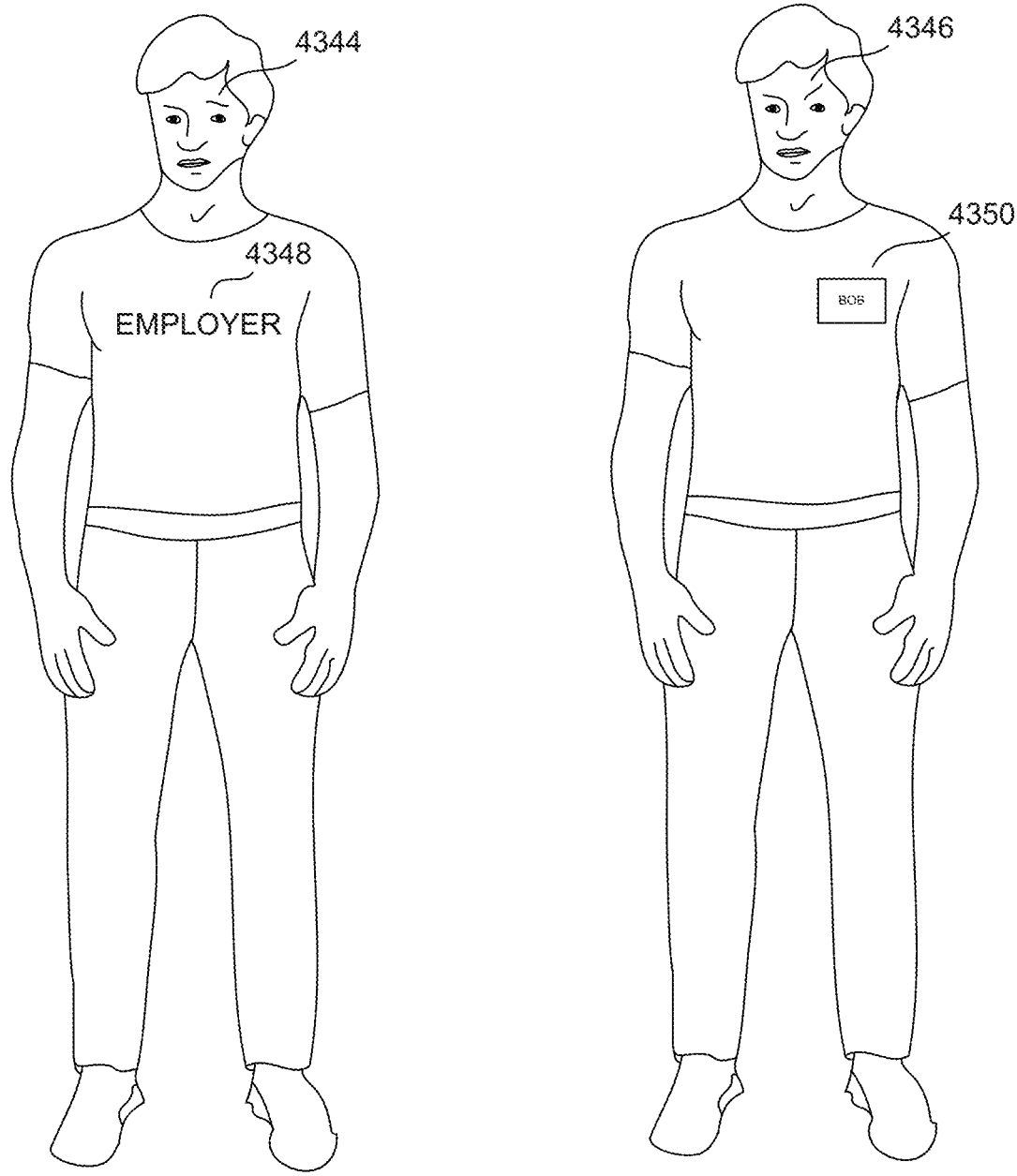

Information obtained at step 4202 may comprise information related to a person associated with one or more of the plurality of tasks. For example, FIG. 43B depicts another example of an image 4340 that may be analyzed by the at least one processing device at step 4202. Image 4340 depicts two people, 4341 and 4342. The at least one processing device may identify person 4341 and/or person 4342 based on any trait or other information that may be determined based on an analysis of image 4340, such as by facial analysis, OCR of a name tag 4350 or other text information such as the text 4348 displayed on person 4341's apparel, etc.

The at least one processing device may determine relationship information between people or objects at step 4202. For example, the at least one processing device may determine based on any of the traits shown in image 4340 that the user is a service provider and that person 3431 and/or person 3432 is a customer or vice versa.

In some embodiments, the at least one processing device may determine a physical, mental or emotional state of a person in an image. For example, the at least one processing device may identify traits such as wounds, the relative position of eyebrows 4344 and 4346 as indicating that the estimated patience level of person 4341 is higher than that of person 4342 or that the estimated stress level of person 4342 is higher than that of person 4341.

Referring back to FIG. 42, at step 4204, the at least one processing device may prioritize tasks based on the obtained information. For example, at step 4204 the at least one processing device may assign a higher priority to a first task over a second task. The prioritization may be performed by prioritization module 4104, as described above.

For example, referring back to FIG. 43A, based on a determination at step 4202 that image 4300 includes pharmacy 4302, the at least one processing device may assign a higher priority to a task associated with a pharmacy, such as picking up a prescription, than a task unrelated to a pharmacy.

The at least one processing device may take into account completeness of a task at step 4204. For example, upon the presence of information indicating that image 4300 includes pharmacy 4302, the at least one processing device may prioritize a task of picking up a prescription based on an amount of time that has elapsed since the prescription was dropped off at the pharmacy.

At step 4204, the at least one processing device may assign priority based, at least in part, on maximizing an objective function. For example, based on information related to a number of vehicles 4308 and/or vacant parking spaces 4310, the at least one processing device may determine an estimated amount of time expected to be spent carrying out a task at pharmacy 4302. The at least one processing device may, for example, prioritize a task related to pharmacy 4302 based on this estimated amount of time (e.g., to minimize time spent carrying out the task). However, if a user is late for a meeting, the priority of picking up a prescription from the pharmacy may be reduced.

Referring back to FIG. 43B, the at least one processing device may assign priority based on relationship information between people or objects determined at step 4202. For example, the at least one processing device may prioritize tasks based on a physical, mental or emotional state of a person in an image. For example, person 4341 and person 4342 may both be customers and the user a service provider. Based on the estimated patience level of person 4341 being higher than 4342 and/or the estimated stress level of person 4342 being higher than that of person 4341, the at least one processing device may prioritize a task of providing service to person 4342 over a task of providing service to person 4341.

At step 4206, the at least one processing device may provide feedback to the user based on assigned priority. Providing the feedback may be performed by feedback module 4106, as described above.

Figure 43C:
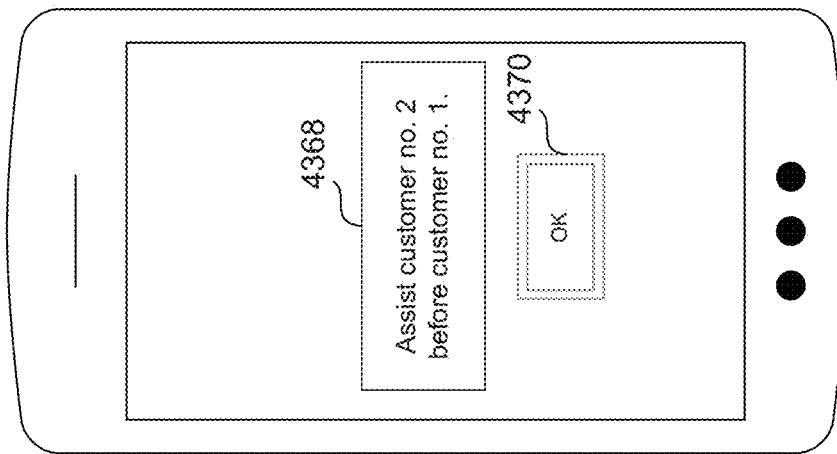
FIG. 43C shows example user interfaces according to disclosed embodiments.
Figure 43C:
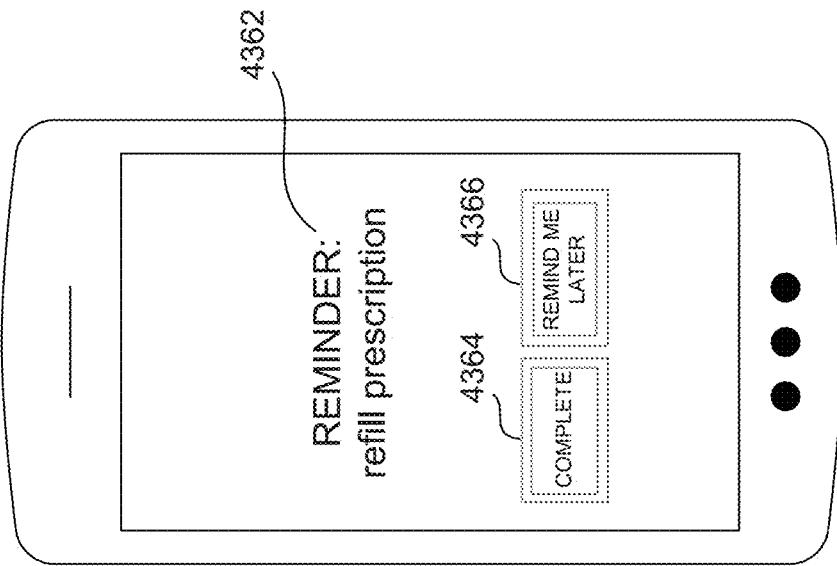

FIG. 43C depicts example interfaces 4360 and 4361. In an embodiment, interfaces 4360 and/or 4361 may be generated by feedback module 4106. Interface 4360 may be generated based on an increase in priority of a task to refill a prescription over one or more other tasks, for example in response to analysis of and prioritization based on image 4300 of FIG. 43A. Interface 4360 may include a message 4362 identifying the task. In some embodiments, interface 4360 may include interface elements 4364 and 4366. As shown in FIG. 43C, interface elements such as 4364 and 4366 may provide options allowing a user to manipulate task status and/or priority. In the example of FIG. 43C, interface element 4364 may provide functionality to mark the task complete. Interface element 4366 may provide "remind me later" functionality. For example, selection of interface element 4366 may reduce the priority of the task, in effect assigning the task a lower priority than another task.

Interface 4361 may be generated based on a change in priority of a task based on image 4340 of FIG. 43B. For example, based on an assignment of priority at step 4204 of a task providing service to person 4342 over a task providing service to person 4341, interface 4361 may display a message 4368 indicating the assignment of priority. Interface 4360 may also include an interface element 4370. As shown in FIG. 43C, interface element 4370 may provide an option to confirm message 4368.

Wearable Apparatus for Analyzing Group Dynamics

In some embodiments, apparatus 110 may capture and analyze images to determine group dynamics of detected persons in the environment of user 100 of apparatus 110. For example, apparatus 110 may analyze images to detect two or more persons and analyze the images to determine association information related to the detected persons. Association information may comprise information related to a relationship between two or more persons based on an identity, a characteristic, or a social system of an individual. The characteristic may relate to intrinsic characteristics such as age, gender, marital status, employment status, or extrinsic characteristics related to the surroundings of the persons, activities that that persons may be engaged in, emotional states of an individuals in an environment, or relationships with third parties. Information for a first detected individual may be compared to information for a second detected individual to determine association information. The association information may be analyzed to develop an understanding of a group dynamic. Data representing the association information may be transmitted to a computing device (e.g., a smartphone, tablet, watch, computer, etc.) and/or a server for analysis and/or reporting to the user. The association information may also be used to update a social representation. The social representation may take the form of a graphical representation showing changes in association information over time. The social representation update may also include displaying a captured image on a social network associated with user 100 through a smartphone application for user 100.

Figure 44:
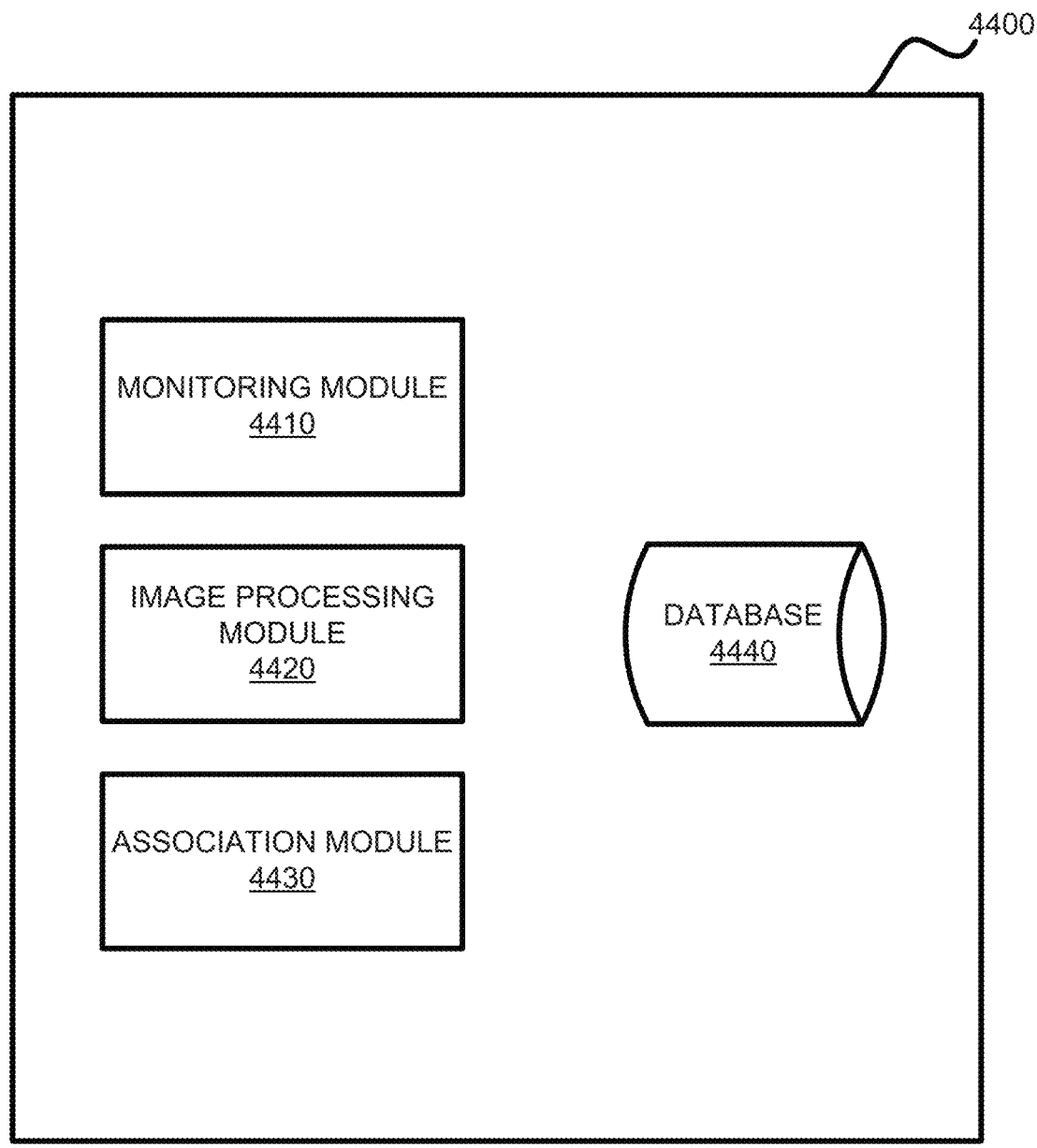
FIG. 44 is an exemplary embodiment of a memory containing software modules consistent with the present disclosure.

FIG. 44 illustrates an exemplary embodiment of a memory 4400 containing software modules consistent with the present disclosure. Included in memory 4400 are a monitoring module 4410, image processing module 4420, association module 4430, and database 4440. Modules 4410, 4420, and 4430 may contain software instructions for execution by at least one processing device, e.g., processor 210, included with apparatus 110. In some embodiments, memory 4400 may comprise a non-transitory computer readable medium that resides on a mobile communications device (e.g., a smart phone) configured to be wirelessly paired with wearable image sensor 220 of capturing unit 710.

Monitoring module 4410 may provide for continuous, periodic, or on demand monitoring. For example, monitoring may include tracking a movement of at least one detected person included in one or more images captured by image sensor 220. For example, in one embodiment, apparatus 110 may track a person as long as the object remains substantially within the field-of-view of image sensor 220. In additional embodiments, monitoring module 4410 may continually orient image sensor 220 towards a detected person. For example, in one embodiment, monitoring module 4410 may cause image sensor 220 to adjust an orientation to ensure that a detected person remains within the field-of view of image sensor 220. In another embodiment, monitoring module 4410 may continuously monitor an area of interest included in one or more images captured by the image sensor. For example, a user may be occupied by a certain task, for example, delivering a speech to a large room, while image sensor 220 remains oriented in a particular direction of a predetermined person of interest, such as a guest of honor or host of an event, and continuously monitors a portion of each image from a series of images to detect a trigger or other event. For example, image sensor 220 may be oriented towards the person of interest and monitoring module 4410 may be configured to monitor the person's reaction to the speech while the user's attention is directed to a piece of paper on placed on a lectern or a different area of the room. Monitoring module 4410 may operate in tandem or concurrently with image processing module 4420 and association module 4430 of FIG. 44.

Image processing module 4420 may be configured to identify at least two detected persons from one or more images. In some embodiments, the at least two detected persons may be identified through one or more image processing techniques. For example, at least one image processing technique may be used to identify at least one feature of an image. In some embodiments, an image processing technique may include one or more of image enhancement, edge detection, image analysis, and data extraction. Specific examples of the methods for identifying at least one feature are exemplary only, and a person of ordinary skill in the art will recognize other methods for identifying the at least one feature that remains consistent with the present disclosure. In some examples, at least one feature may be detected using an object detection algorithm, using a neural network trained to detect objects and/or objects in images, using a machine learning system, using a pattern recognition system, and so forth.

In some examples, at least one person may be identified in the surroundings of the user using a facial recognition algorithm, using a neural network trained to detect faces and/or persons in images, and so forth. For example, a detected person may be identified by analyzing one or more images for a characteristic of the detected person. The characteristic of the individual may be any physical characteristic of the detected person including eye color, hair color, face shape, tattoos, piercings or others. The characteristics may be used to identify the detected person as a person that user 100 has previously encountered and relate the present interaction with interactions stored in database 4440. Image processing module 4420 may also detect that the detected person is unidentifiable based on no previous encounter and may generate a profile for the detected person, to be populated with information collected by image processing module 4420. Image processing module 4420 may additionally identify other objects in the surroundings of user 100, for example, a book, a name tag, indicia of an activity etc. and populate the profile with data for the detected person with information to be used to determine group dynamics.

Association module 4430 may be configured to identify association information based on features of two or more detected persons identified by image processing module 4410. Parameters for analyzing association information may be configured and/or defined by user 100 and stored in database 4440. For example, user 100 may configure association module 4430 to determine a category of information via a mobile application on a mobile communications device. For example, user 100 may plan to attend a professional event and configure image processing module 4420 to identify and store employment information for each detected person based on information identified from a name tag. Association module 4430 may be configured to compare information for two or more detected persons to determine association information. For example, image processing module 4420 may communicate with database 4440 to identify a detected person based on an online profile or social network of the detected person. Association module 4430 may then query the profile to acquire data related to each of the two detected persons. Association module 4430 may compare the acquired data to determine association information for the two detected persons. For example, association module 4430 may determine that the two detected persons are in the same professional industry, work for the same organization, or the like.

Monitoring module 4410, image processing module 4420 and association module 4430 may be configured to transfer or receive data to/from database 4440 via network 240. In the disclosed embodiments, the data being received from database 4440 may include numerous different types of information based on the previously analyzed image data, stored representational data, information related to a person, an identified landmark, and any other information capable of being stored in or accessed by database 4440. In some embodiments, data may be received and transferred via computing device 120. Database 4440 and/or computing device 120 may retrieve information from different data sources (e.g., a user specific database, a user's social network account or other account, the Internet, and other managed or accessible databases) and provide information to apparatus 110 related to the analyzed image data according to the disclosed embodiments. In some embodiments, calendar-related information retrieved from the different data sources may be analyzed to provide certain time information or a time-based context for providing certain information based on the analyzed image data.

FIGS. 45A-45D illustrate exemplary captured images for determining association information. For example, in FIG.

45A, association information may be based on a physical distance between two or more persons in a group. Apparatus 110 may be configured to measure a distance between individuals. Continuous monitoring of distances between individuals may also be used to detect changes in body language. For example, processor 210 may capture a plurality of images of two detected persons. Analysis of the plurality of images may result in a measured average distance between two of more detected individuals. Distance 4510a may be of a smaller magnitude than distance 4510b. Processor 210 may determine that persons separated by the smaller distance 4510a are associated, while persons separated by a distance 4510b, which may be larger than a predetermined threshold, are not associated. Association information based on physical distance may also include a determination that the two or more persons have had a previous encounter, are colleagues, or have a familial bond. Association information may also provide information about group dynamics including information about how frequently a person is in close proximity to other people or how sociable a detected person is. For example, apparatus 110 may determine that person 4520 is frequently within a close physical distance of person 4530. Apparatus 110 may determine that distance 4510b between person 4530 and a third-party changes at approximately the same rate and approximately the same relative time as the distance between person 4520 and the third-party. Based on this association information, processor 210 may determine that person 4520 and person 4530 are attending an event together (as professional partners, dates, etc.)

Association information based on a physical distance for analyzing group dynamics may also be based on changes in physical distance between two detected persons. Apparatus 110 may determine distance 4510a and distance 4510c between person 4520 and 4530. Changes in distance 4510c may correlate with a body language indicator stored in a database. For example, apparatus 110 may detect that distance 4510a is constant, while distance 4510c increases. This may correlate with a stored body language indicating that person 4520 is leaning away from person 4530. Leaning away may suggest to processor 210 that person 4520 is experiencing situational discomfort. Alternatively, a decrease in distance 4510c followed by an increase may relate to an embrace between person 4520 and 4530.

Figure 45A:
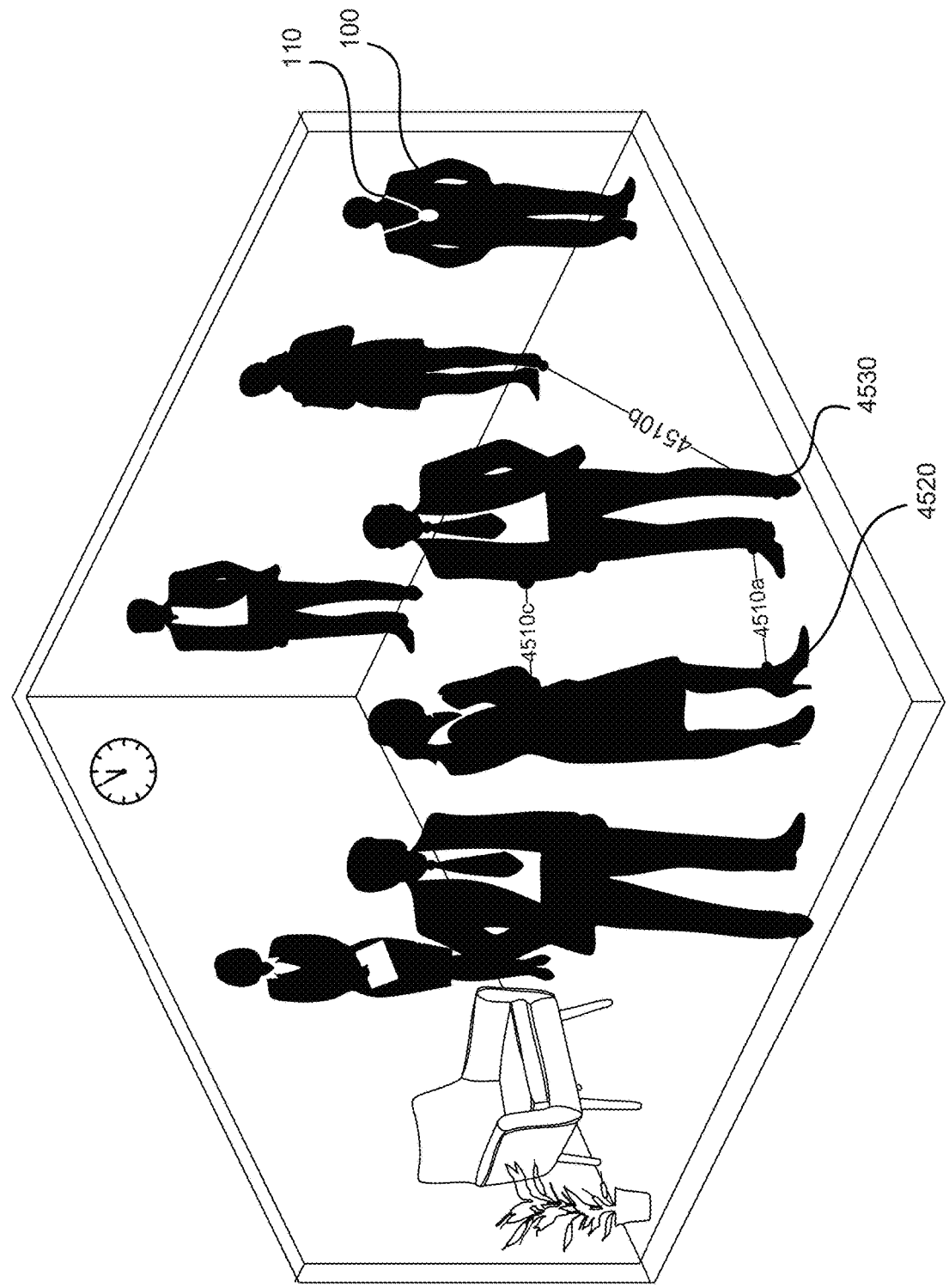
FIG. 45A is a schematic illustration for determining association information based on a physical distance.
Figure 45B:
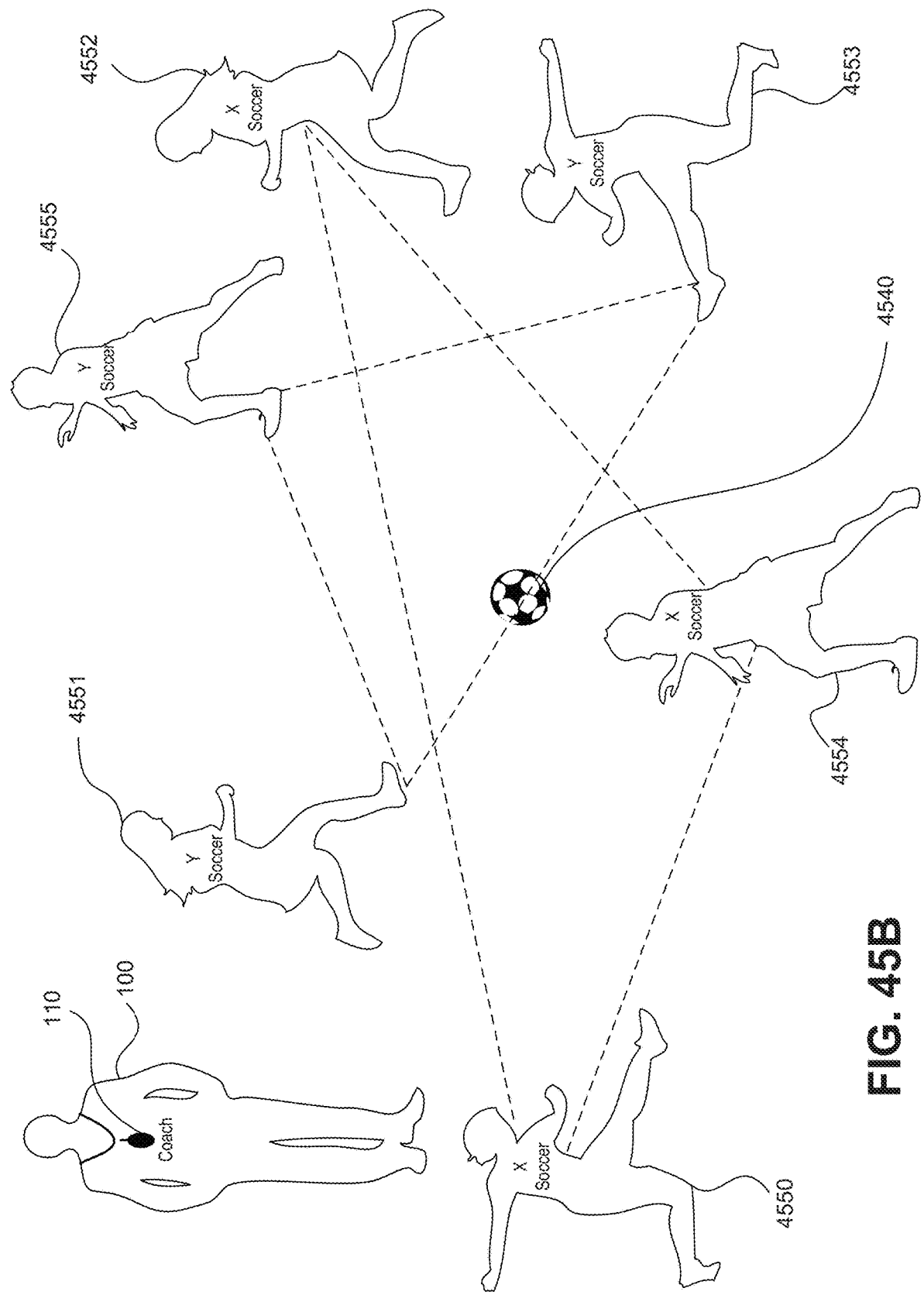
FIG. 45B is a schematic illustration for determining association information based on a joint activity.

As illustrated in FIG. 45B, association information may also be based on a joint activity the at least two detected persons are engaged in. Apparatus 110 may detect an activity based on indicia of the activity that is involved. The plurality of images captured by apparatus 110 may be analyzed by comparing detected indicia of the activity with exemplary indicia stored in a database. For example, apparatus 110 may capture a plurality of images representing an activity that two or more persons are engaged in, such as a sport, travel, attending a movie, etc. FIG. 45B illustrates a plurality of persons engaged in a soccer game, as observed by user 100 wearing apparatus 110. The plurality of images may determine that indicia 4540 is a soccer ball based on characteristics of the ball including shape, size, pattern, and color. Based on this information, processor 210 may determine that the two or more detected persons are engaged in a soccer game. Apparatus 110 may also determine association information based on a team that a detected person is playing for and identify the detected person's teammates. For example, apparatus 110 may determine that two or more detected persons play for the same team based on a determination that the ball is frequently passed between the two or more detected persons. The determination may also be based on a determination that a first group of persons frequently kick the ball in a first direction, while a second group of persons frequently kick the ball in the second direction, opposite to the first direction.

Figure 45C:
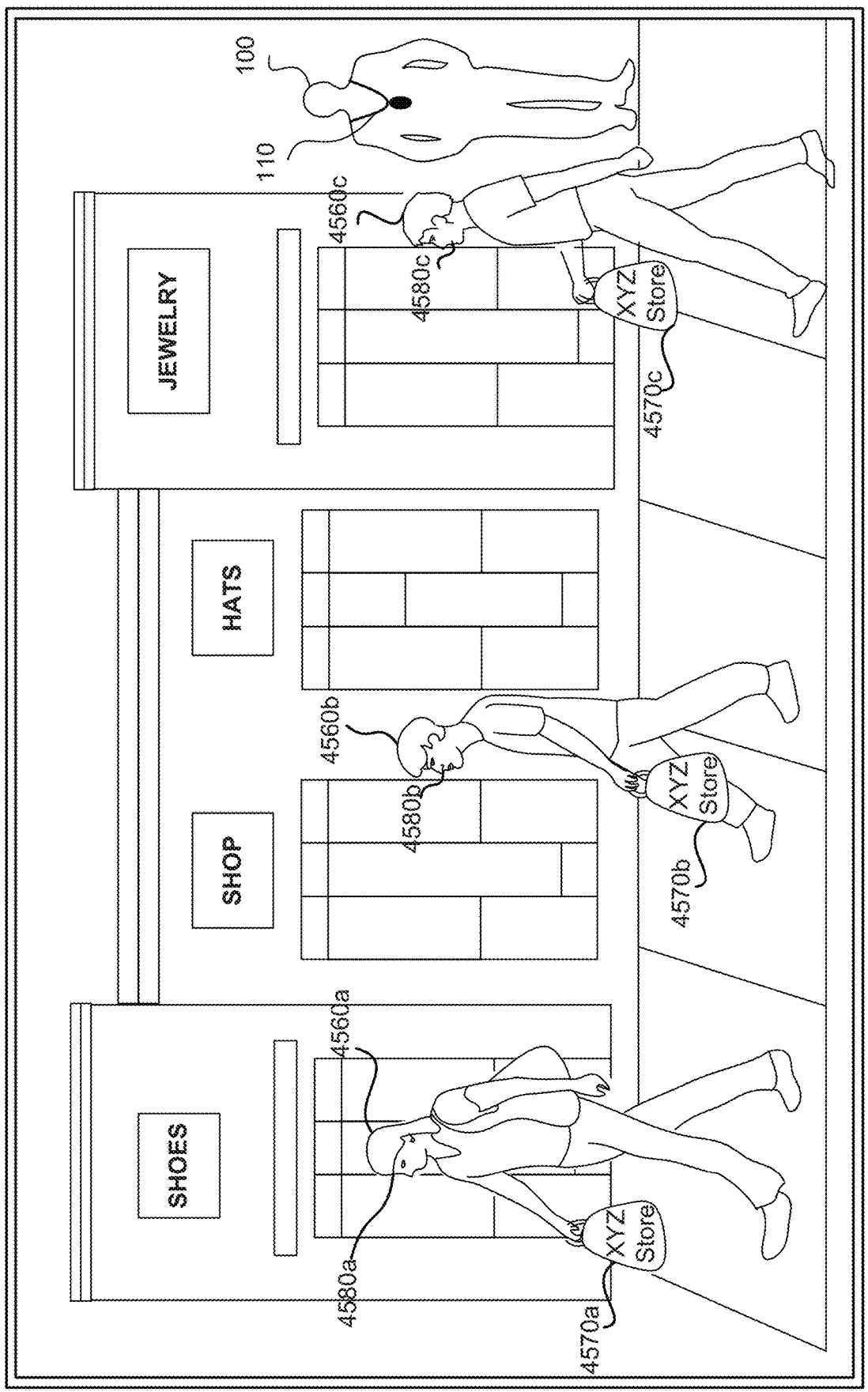
FIG. 45C is a schematic illustration for determining association information based on a shared characteristic.

As illustrated in FIG. 45C, association information may be based on a shared characteristic of the two detected persons. The shared characteristic may include a detected intrinsic characteristic such as hair color, facial structure, height, etc. The shared characteristic may provide information relating to group dynamics. For example, apparatus 110 may capture a plurality of images. Processor 210 may analyze the captured images and detect that the two or more persons in the captured image share a characteristic such as hair color or a unique nose shape. From this information, processor 210 may determine that detected persons are relatives. Processor 210 may detect that two of more detected persons share an intrinsic characteristic based on an analysis of the captured image.

The shared characteristic may also include situational characteristics. A detected situational characteristic may relate to a characteristic associated with a given environment. For example, apparatus 110 may capture a plurality of images. Processor 210 may analyze the captured images and detect that the two or more persons in the captured image share a situation characteristic such as a common article of clothing, a similar accessory, or similar behaviors (e.g., laughing at the same time, becoming agitated in response to a stimulus, etc.).

Shared characteristics may be used to analyze group dynamics. For example, processor 210 may determine that when a particular shared characteristic is detected, a particular group dynamic is applied. This determination may be based on a set of rules for analyzing group dynamics. For example, apparatus 110 may capture a plurality of images of a political rally. Processor 210 may detect two or more individuals with a shared characteristic, such as a similar pin or shirt worn by persons with a political affiliation at the rally. The shared characteristic may also include a facial reaction to a rallying cry. Processor 110 may also detect shared characteristics of a second group dynamic. Two or more detected persons may become agitated in response to a rallying cry. This may indicate to processor 210 that members sharing that characteristic may be protestors of the rally.

As illustrated in FIG. 45C, apparatus 110 of user 100 may capture a plurality of images of two or more persons. Upon detecting persons 4560a, 4560b, and 4560c, processor 210 may analyze the images to identify shared characteristics. Processor 210 may determine similarities between facial features 4580a, 4580b, and 4580c. Similar facial features may include a distinctive nose shape or eye color. Processor 210 may also determine that persons 4560a, 4560b, and 4560c all share a similar hair color. Other shared characteristics may include an identical shopping bag 4570a, 4570b, and 4570c, held by each detected person 4560a, 4560b, and 4560c. Based on these shared characteristics, processor 210 may determine that detected persons 4560a, 4560b, and 4560c are family members shopping together. Processor 210 may also detect other shared characteristics including departure from a store at the same time, walking in a similar direction and remaining within a predetermined distance of each other. The shared characteristics may provide information about a group dynamic such as family members engaged in shopping.

Association information may also be based on a reaction of one of the two persons to an action of the other of the two persons. For example, user 100 of apparatus 110 may be engaged in a conversation or activity with at least one other person. Apparatus 210 may capture a plurality of images representing different reactions of the detected persons to an action of user 100. A reaction may include a departure of a detected person from the group, a facial reaction depicting an emotion, or body language indicators such as leaning in for an embrace.

Figure 45D:
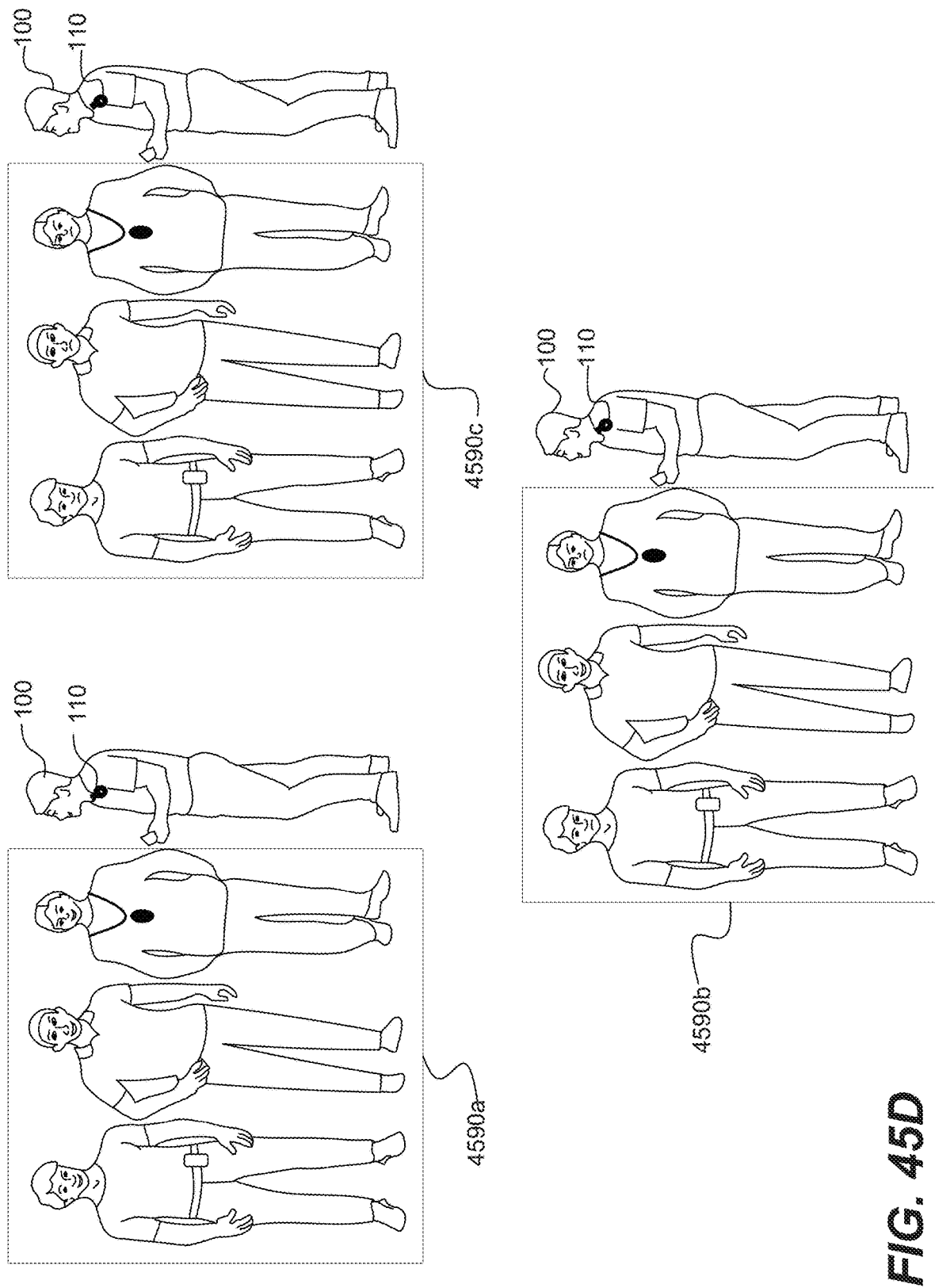
FIG. 45D is a schematic illustration for determining association information based on a reaction to an action.

As illustrated in FIG. 45D, user 100 of apparatus 110 may be engaged in a conversation with a group. Apparatus 110 may capture a plurality of images 4590a, 4590b, and 4590c illustrating different reactions of the members of the group to an action by user 100. Image 4590a shows the detected person having a positive reaction to an action of user 100. Processor 210 may detect the positive reaction based on an analysis of the image showing that all detected persons are smiling. Alternatively, an analysis of image 4590b may show that some of detected persons have a positive reaction to user 100. Still alternatively, an analysis of image 4590c may show that all of the detected persons have a negative reaction to an action by user 100. This analysis may be used to understand a group dynamic, particularly in response to another person. The group dynamic may indicate how well-liked a person is, how responsive a group of persons are to a concept communicated to the group, or a general mood of the group.

Figure 46:
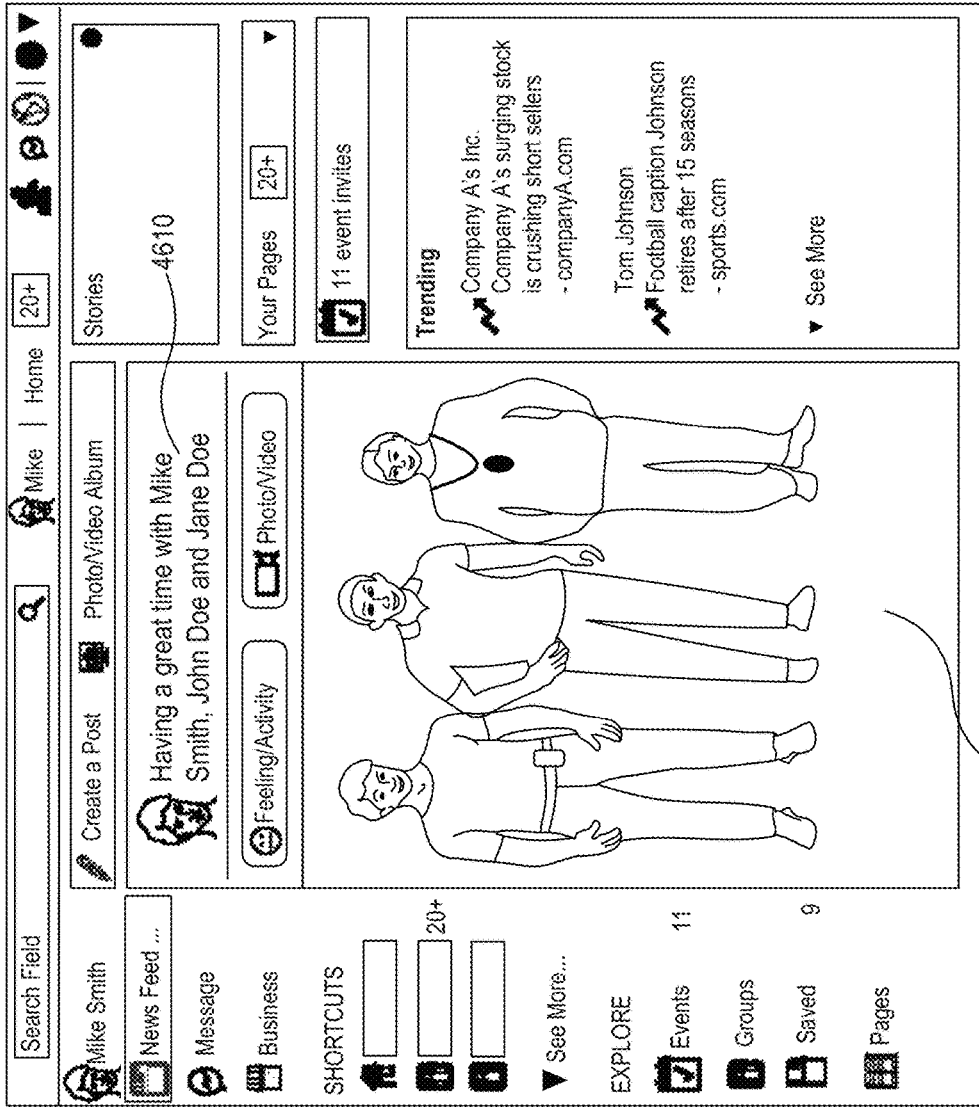
FIG. 46 is a schematic illustration of an update to a social representation based on a group dynamic.

FIG. 46 illustrates updating a social representation 4600 based on determined association information. Image 4590a captured by apparatus 110 may be analyzed to determine association information including a positive reaction to an action by user 100. In one embodiment, update to social representation 4600 includes a status update to a social network associated with user 100. Caption 4610 may be suggested based on the group dynamic detected by processor 210. Image 4590a may be analyzed to determine that the detected persons are smiling and thus have a positive reaction to user 100. Thus, the updated social representation may embody the determined association information to illustrate a group dynamic. Updated social representation may also include expanding an online social network of user 100. For example, data representing the association information may be transmitted to an external computing device for analysis. The analysis may result in identifying an online social network account (e.g., Facebook, Twitter, LinkedIn, etc.) of the detected person and transmit a request to user 110 to connect with the detected person.

Figure 47:
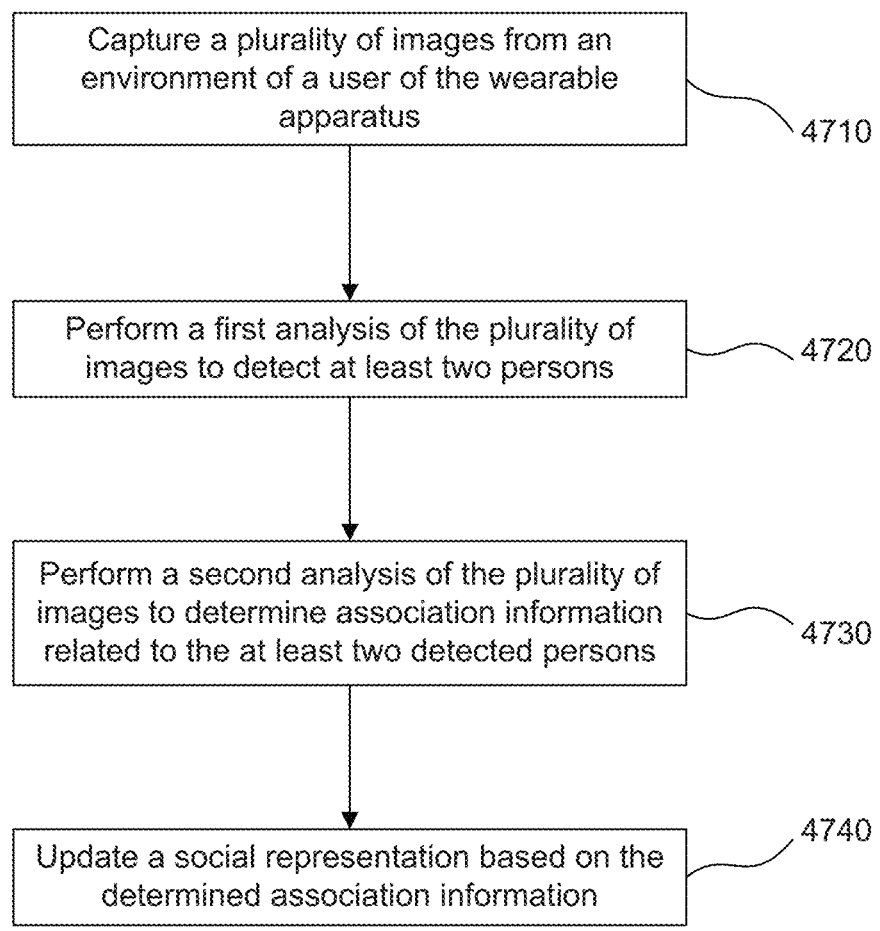
FIG. 47 is a flowchart showing an exemplary process for analyzing a group dynamic.

FIG. 47 illustrates a flowchart showing an exemplary process 4700 for analyzing group dynamics related to user 100, consistent with disclosed embodiments. Apparatus 110 may implement one or more steps of process 4700 to determine group dynamic information, illustrated in, for example FIGS. 45A-45D.

As illustrated in FIG. 47, at step 4710, apparatus 110 may capture a plurality of images from an environment of user 100. For example, capturing unit 710 may match the field-of-view of user 100 and image sensors 220 of capturing unit 710 may capture images of one or more detected persons in the field-of-view of user 100. Image sensors 220 may also capture images of the detected persons even when the attention of user 100 is directed away from the detected person. For example, monitoring module 4410 may continuously monitor one of the detected persons relative to the environment of the detected persons and user 100. The environment of user 100 may include a room that user 100 has entered or a path that user 100 is traveling. The environment may also include a maximum field-of-view of image sensor 220 in a direction that it is pointed.

At step 4720, a processing device (e.g., processor 210) may perform a first analysis of the plurality of images to detect at least two persons from the environment of the user. A person may be detected by apparatus 110 using any one of various image processing techniques including object recognition, pattern recognition, or edge detection. Once a person is detected in the environment, the person may be identified by comparing the captured image with images stored in database 4440. Based on the comparison, processor 210 may identify the person using image processing module 4420 based on a previous stored encounter of the identified person with user 100. For example, user 100 may be in a room with a plurality of persons. Apparatus 110 may capture a plurality of images of the room and using an image processing technique, detect one or more persons in the room. Processor 210 may then use facial recognition techniques to determine that user 100 has previously encountered the detected person based on a facial match to a stored image of the detected person.

At step 4730, processor 210 may perform a second analysis of the plurality of images to determine association information related to the at least two detected persons. Association information may be based on characteristic information about the two or more detected persons identified through facial recognition or biographical data stored on a database. The characteristic information may also be based on information about the environment of the detected persons. Further, image processing techniques may be used to detect environment information. For example object identification may be used to identify objects within a predetermined proximity of detected persons. An object in a portion of an image may be captured and analyzed by comparing the detected object to stored images of representative objects in database 4440. The characteristic information for a first detected individual may be interrelated with characteristic information for a second detected individual to detect similarities or differences between the first and second detected persons. The similarities and differences between characteristic information for the two or more detected persons may be used to determine association information. Association information may also be based on information obtained from a social network, or one or more directories, such as a listing on a webpage. For example, processor 210 may query social networks of the first and second detected person and determine that both are listed as "attending" an event hosted by a third detected person. Other information obtained from the social network of the detected persons may include a relationship status, employment status, a name of an employer, political affiliations, listing of other persons as family members, and biographical data. Thus, information about detected persons may be based on an online presence of the detected persons and may be used to determine association information.

At step 4740, processor 210 may update a social representation based on the determined association information. The social representation may include providing an update to a user's social network account for lifelogging an event or updating stored data about the detected person. Social representations may also include information stored in database 4440 regarding the detected persons. The information may include profiles for one or more detected persons and may be updated to include association information from an encounter with user 100. For example, user 100 may attend a social event. Apparatus 110 may detect that two or more persons maintained a physical distance from each other greater than a predetermined threshold value. Processor 210 may determine that previously stored association data includes information that the detected persons were regularly engaged in activity together, such as attending a movie and dining together. Processor 210 may update a social representation for each of the two detected person with new association information indicating that the relationship between the two persons may be strained. The updated social representation may also be a graphical representation of changes in association information over time. The association information from a first event may be aggregated with association information from a second event to provide composite association information for analysis.

Apparatus 110 may also transmit data to a computing device (e.g., a smartphone, tablet, watch, computer, etc.) over one or more networks via any known wireless standard (e.g., cellular, Wi-Fi, Bluetooth®, etc.), or via a wired connection. The data transmitted by apparatus 110 may include images, portions of images, identifiers related to information appearing in analyzed images, association information, or group dynamic information. For example, an image may be analyzed and a group dynamic related to an activity occurring in the image may be identified. The image may then be transmitted to the computing device (e.g., a "paired device"). In the embodiments described herein, apparatus 110 may analyze images locally (on board the wearable apparatus) and/or remotely (via a computing device). Further, a paired device may execute one or more applications (apps) to process, display, and/or analyze data (e.g., identifiers, text, images, etc.) received from apparatus 110.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A wearable apparatus, the wearable apparatus comprising:
    a wearable image sensor configured to capture a plurality of images; and
    at least one processor programmed to:
        receive, from a mobile communications device wirelessly paired with the wearable apparatus, a command to provide location information for the wearable apparatus, the command having been transmitted in response to a user input at the mobile communications device to ping the wearable apparatus;
        analyze, in response to the command, at least one image depicting an environment of the wearable apparatus to determine a location of the wearable apparatus; and
        cause information about the location of the wearable apparatus to be transmitted to the mobile communications device.

2. The wearable apparatus of claim 1, wherein the mobile communications device is configured to provide an audible description of the location of the wearable apparatus based on the information about the location of the wearable apparatus.

3. The wearable apparatus of claim 2, wherein the audible description includes spoken words specifying the location of the wearable apparatus.

4. The wearable apparatus of claim 3, wherein the spoken words include a specification that the wearable apparatus is located under a piece of furniture.

5. The wearable apparatus of claim 3, wherein the spoken words include a specification that the wearable apparatus is located in a bag or a container.

6. The wearable apparatus of claim 3, wherein the spoken words include a specification that the wearable apparatus is located in a pocket of a user of the mobile communications device.

7. The wearable apparatus of claim 3, wherein the spoken words include a specification that the wearable apparatus is located in a direction relative to a user of the mobile communications device.

8. The wearable apparatus of claim 1, wherein the mobile communications device is configured to provide text output of the location of the wearable apparatus based on the information about the location of the wearable apparatus.

9. The wearable apparatus of claim 8, wherein the text includes a specification that the wearable apparatus is located under a piece of furniture.

10. The wearable apparatus of claim 8, wherein the text includes a specification that the wearable apparatus is located in a bag or a container.

11. The wearable apparatus of claim 8, wherein the text includes a specification that the wearable apparatus is located in a pocket of a user of the mobile communications device.

12. The wearable apparatus of claim 8, wherein the text includes a specification that the wearable apparatus is located in a direction relative to a user of the mobile communications device.

13. The wearable apparatus of claim 1, wherein the location information is configured to cause the mobile communications device to provide at least one image representing the location of the wearable apparatus.

14. The wearable apparatus of claim 1, wherein a user of the mobile communications device is depicted in the at least one image, and the information includes a position of the user relative to the wearable apparatus.

15. The wearable apparatus of claim 14, wherein the mobile communications device is configured to audibly output the position of the user relative to the wearable apparatus based on the information about the location of the wearable apparatus.

16. A non-transitory computer-readable medium containing instructions that when executed by at least one processor cause the at least one processor to perform steps, comprising:
- establishing a wireless pairing between a wearable apparatus and a mobile communications device;
- receiving, in a situation when the wearable apparatus is misplaced, a user input for pinging the wearable apparatus;
- in response to the user input, wirelessly transmitting from the mobile communications device, a ping to the wearable apparatus, wherein the ping includes an instruction for the wearable apparatus to capture at least one image of surroundings of the wearable apparatus;
- analyzing the at least one image to determine a location of the wearable apparatus; and
- causing, based on the location of the wearable apparatus, the location information to be transmitted to the mobile communications device.

17. A method for locating a wearable apparatus, the method comprising:
- receiving, from a mobile communications device wirelessly paired with the wearable apparatus, a command to provide location information for the wearable apparatus, the command having been transmitted in response to a user input at the mobile communications device to ping the wearable apparatus;
- analyzing, in response to the command, at least one image depicting an environment of the wearable apparatus to determine a location of the wearable apparatus; and
- causing information about the location of the wearable apparatus to be transmitted to the mobile communications device.

18. The method of claim 17, further comprising analyzing, in response to the command, audio data indicative of the environment of the wearable apparatus to determine the location of the wearable apparatus.

19. The method of claim 17, further comprising providing, by the mobile communications device, an audible description of the location of the wearable apparatus based on the information about the location of the wearable apparatus.

20. The method of claim 17, further comprising providing, by the mobile communications device, text output of the location of the wearable apparatus based on the information about the location of the wearable apparatus.

* * * * *

UNITED STATES PATENT AND TRADEMARK OFFICE
CERTIFICATE OF CORRECTION

| | | |
|---|---|---|
| PATENT NO. | : 11,039,053 B2 | Page 1 of 1 |
| APPLICATION NO. | : 16/659190 | |
| DATED | : June 15, 2021 | |
| INVENTOR(S) | : Yonatan Wexler et al. | |

It is certified that error appears in the above-identified patent and that said Letters Patent is hereby corrected as shown below:

On the Title Page

Item (57), in the ABSTRACT, delete the existing Abstract in its entirety and substitute therefor:
--A wearable apparatus is provided. The wearable apparatus may include: a wearable image sensor configured to capture a plurality of images; and at least one processor programmed to: receive, from a mobile communications device wirelessly paired with the wearable apparatus, a command to provide location information for the wearable apparatus; analyze, in response to the command, at least one image depicting an environment of the wearable apparatus to determine a location of the wearable apparatus; and cause information about the location of the wearable apparatus to be transmitted to the mobile communications device.--.

Signed and Sealed this
Twenty-third Day of November, 2021

Drew Hirshfeld
*Performing the Functions and Duties of the
Under Secretary of Commerce for Intellectual Property and
Director of the United States Patent and Trademark Office*